United States Patent [19]
Aszodi et al.

[11] Patent Number: 5,763,617
[45] Date of Patent: Jun. 9, 1998

[54] CEPHALOSPORINS

[75] Inventors: Jozsef Aszodi, Pontault Combault; Jean-Francois Chantot, Gressy en France; Patrick Fauveau, Livry Gargan; Solange Gouin D'Ambrieres, Paris; Daniel Humbert, Fonenay Sous Bois; Christophe Dini, Le Plessis Pate, all of France

[73] Assignee: Roussel Uclaf, France

[21] Appl. No.: 769,488

[22] Filed: Dec. 18, 1996

Related U.S. Application Data

[62] Division of Ser. No. 453,923, May 30, 1995, which is a division of Ser. No. 167,192, Dec. 13, 1993, Pat. No. 5,587,372, which is a continuation-in-part of Ser. No. 989,235, Dec. 11, 1992, Pat. No. 5,455,238.

[30] Foreign Application Priority Data

Dec. 12, 1991 [FR] France ................... 91 15416
Sep. 28, 1992 [FR] France ................... 92 11520

[51] Int. Cl.$^6$ ............ C07D 417/12; C07D 409/12
[52] U.S. Cl. .............. 548/128; 548/130; 548/465; 548/475; 548/194; 540/227; 540/225; 540/222; 540/228; 549/65; 549/66; 549/61; 549/64
[58] Field of Search ................... 548/465, 130, 548/128

[56] References Cited

FOREIGN PATENT DOCUMENTS 376724  7/1990  European Pat. Off. .

*Primary Examiner*—Mukund J. Shah
*Assistant Examiner*—King Lit Wong
*Attorney, Agent, or Firm*—Bierman, Muserlian and Lucas LLP

[57] ABSTRACT

A syn isomer in (R) or (S) form or a mixture thereof of a compound of the formula

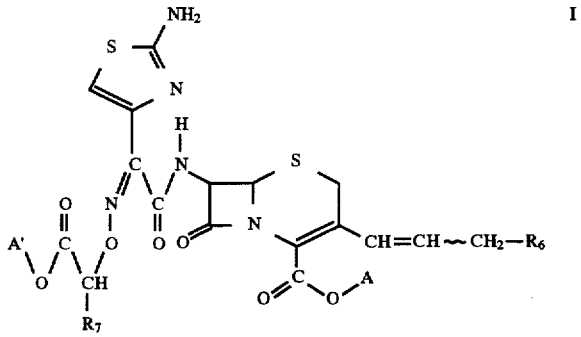

syn isomer, in the (R) or (S) form or in the form of an (R,S) mixture, in the form of an integral salt or their salts with organic or mineral acids wherein the substituents are as defined in the application and having antibacterial properties.

1 Claim, No Drawings

CEPHALOSPORINS

PRIOR APPLICATION

This application is a division of U.S. patent application Ser. No. 453,923 filed May 30, 1995 which is a division of U.S. patent application Ser. No. 167,192 filed Dec. 13, 1993, now U.S. Pat. No. 5,587,372, which is a Continuation-in-Part of U.S. patent application Ser. No. 989,235 filed Dec. 11, 1992, now U.S. Pat. No. 5,455,238.

STATE OF THE ART

Related prior art includes EP application No. 0,266,060 and U.S. Pat. Nos. 4,436,586 and 5,075,298.

OBJECTS OF THE INVENTION

It is an object of the invention to provide the novel compounds of formula I and their non-toxic, pharmaceutically acceptable acid addition salts and a process and intermediates for their preparation.

It is another object of the invention to provide novel anti-bacterial compositions and a novel method of combatting bacterial infections in warm-blooded animals.

These and other objects and advantages of the invention will become obvious from the following detailed description.

THE INVENTION

The novel compounds of the invention are the syn isomer in (R) or (S) form or a mixture thereof of a compound of the formula

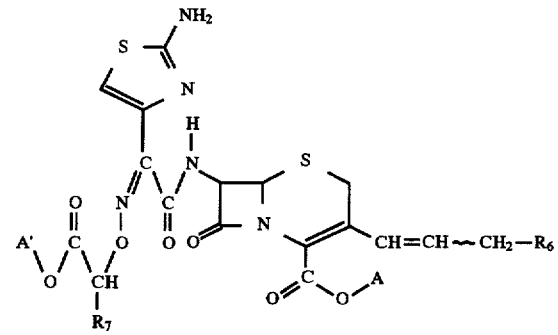

I syn isomer, in the (R) or (S) form or in the form of an (R,S) mixture, in the form of an internal salt or their salts with organic or mineral acids wherein $R_7$ is selected from the group consisting of

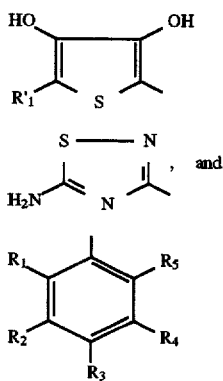

K

L

M $R'_1$ is selected from the group consisting of alkyl of 1 to 4 carbon atoms, —CN, carboxy and alkoxy carbonyl of 1 to 4 alkoxy carbon atoms, $R_1$, $R_2$, $R_3$ and $R_5$ are individually selected from the group consisting of hydrogen, halogen, hydroxy, alkyl of 1 to 4 carbon atoms optionally substituted with at least one member of the group consisting of halogen, alkoxy and alkylthio of 1 to 4 carbon atoms, —NO₂, —CN, —NH₂, mono- and dialkylamino of 1 to 4 carbon atoms, carbamoyl, (alkylamino) carbonyl of 2 to 5 carbon atoms, (dialkylamino) carbonyl of 3 to 9 carbon atoms, carboxy, alkoxycarbonyl of 2 to 5 carbon atoms, acyloxy of 1 to 8 carbon atoms and

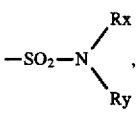

Rx and Ry are individually hydrogen or alkyl of 1 to 4 carbon atoms, $R_4$ is —OH or acyloxy of 1 to 8 carbon atoms, A and A' are individually selected from the group consisting of hydrogen, an equivalent of an alkali metal or alkaline earth metal, magnesium, ammonium and an organic amine, or one or two of —COOA or —COOA' are —CO₂⁻, the wavy line means —CH₂R₆ can be in the E or Z position. $R_6$ in the quaternary ammonium form is selected from the group consisting of

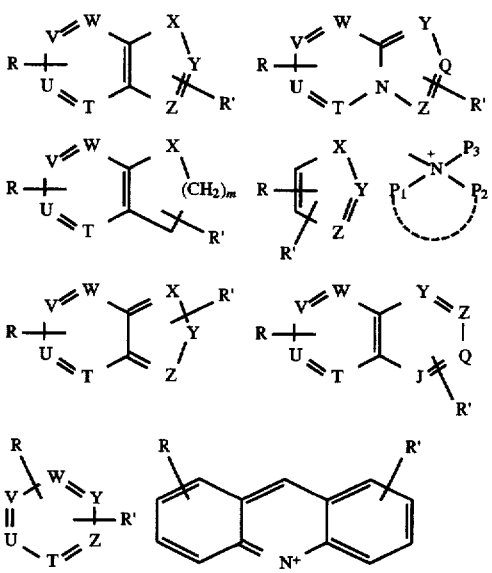

X is selected from the group consisting of —CH₂—, —NH—, —O— and —S—; Q, J, Y, T, U, V, W and Z are individually =N— or —CH=, each of cyclics containing 1 to 5 heteroatoms of which at least one is =N— and optionally substituted by at least one R or R'. R and R' are individually selected from the group consisting of halogen, alkyl and alkoxy of 1 to 4 carbon atoms, halogen, —CN, —COOQ₁, —CONQ₁Q₂, —NQ₁Q₂, —SO₂NQ₁Q₂, —CSNH₂, —NHCOQ₁, —CH=NOH, —CH=N—O—Q₁, —CH₂CN and —CH₂—S—Q₁, Q₁ and Q₂ are individually hydrogen or alkyl of 1 to 4 carbon atoms, P₁, P₂ and P₃ are individually alkyl of 1 to 4 carbon atoms optionally substituted with a substituent of R or R' or P₁ and P₂ taken together with the nitrogen to which they are attached form a 5 or 6 ring heterocyclic with the proviso that when R₃ is —OH or alkoxy of 1 to 8 carbon atoms, at least one of R₁, R₂ and R₅ is other than hydrogen.

Examples of alkyl and alkoxy of 1 to 4 carbon atoms are methyl, ethyl, propyl, isopropyl, butyl, isobutyl, sec.-butyl, tert.-butyl, methoxy, ethoxy, propoxy, isopropoxy, butoxy, isobutoxy, sec.-butoxy and tert.-butoxy. Examples of alkylthio of 1 to 4 carbon atoms are methylthio, ethylthio, propylthio, isopropylthio, butylthio, isobutylthio, sec.-butylthio and tert.-butylthio.

Examples of alkylamino of 1 to 4 carbon atoms are methylamino, ethylamino, propylamino, isopropylamino, butylamino, isobutylamino, sec.-butylamino and tert.-butylamino while examples of dialkylamino of 2 to 8 carbon atoms are dimethylamino, diethylamino, dipropylamino, diisopropylamino, dibutylamino, diisobutylamino, ethyl methylamino, propyl methylamino, butyl methylamino and propyl ethylamino.

Examples of (alkylamino) carbonyl of 2 to 5 carbon atoms are (methylamino) carbonyl, (ethylamino) carbonyl, (propylamino) carbonyl, (isopropylamino) carbonyl and (butylamino) carbonyl. Examples of alkoxycarbonyl of 2 to 5 carbon atoms are methoxycarbonyl and ethoxycarbonyl. Examples of (dialkylamino) carbonyl or 3 to 9 carbon atoms are (dimethylamino) carbonyl, (diethylamino) carbonyl, (dipropylamino) carbonyl.

Examples of acyloxy of 1 to 8 carbon atoms are acetoxy, propionyloxy and benzoyloxy while examples of halogen are fluorine, chlorine, bromine or iodine.

When $P_1$ and $P_2$ form a heterocycle with the nitrogen atom to which they are attached, it may be pyrrolidine, morpholine or piperidine. When $R_4$ is alkoxy, it is preferably acetoxy, propionyloxy or benzoyloxy.

Among the values of A' and A are an equivalent of sodium, potassium, lithium, calcium, magnesium or ammonium and organic bases such as methylamine, propylamine, trimethylamine, diethylamine, triethylamine, N,N-dimethylethanolamine, tris[(hydroxymethyl)-amino]-methane, ethanolamine, pyridine, picoline, dicyclohexylamine, morpholine, benzylamine, procaine, lysine, arginine, histidine and N-methylglucamine.

The products of formula I can also appear in the form of a pure internal salt, in salified form or in a combined form with the acids of the solution. Among the acids with which the products of formula I can be salified include acetic acid, trifluoroacetic acid, maleic acid, tartaric acid, methanesulfonic acid, benzenesulfonic acid, p-toluenesulfonic acid, phosphoric acid, sulfuric acid, hydrochloric acid, hydrobromic acid, hydroiodic acid.

In the invention, more preferably A' is hydrogen and CO2A is $CO_2^-$.

The expression in the form of quaternary ammonium indicates that $R_6$ is linked by one of the nitrogen atoms that it contains. Preferably $R_6$ is one of the following:

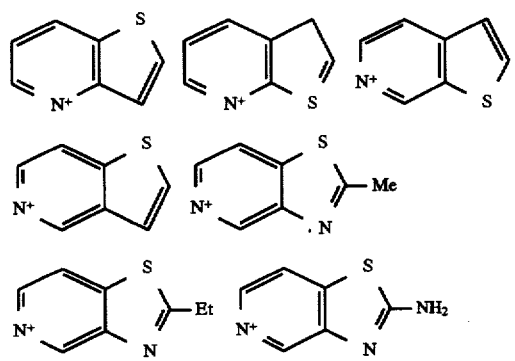

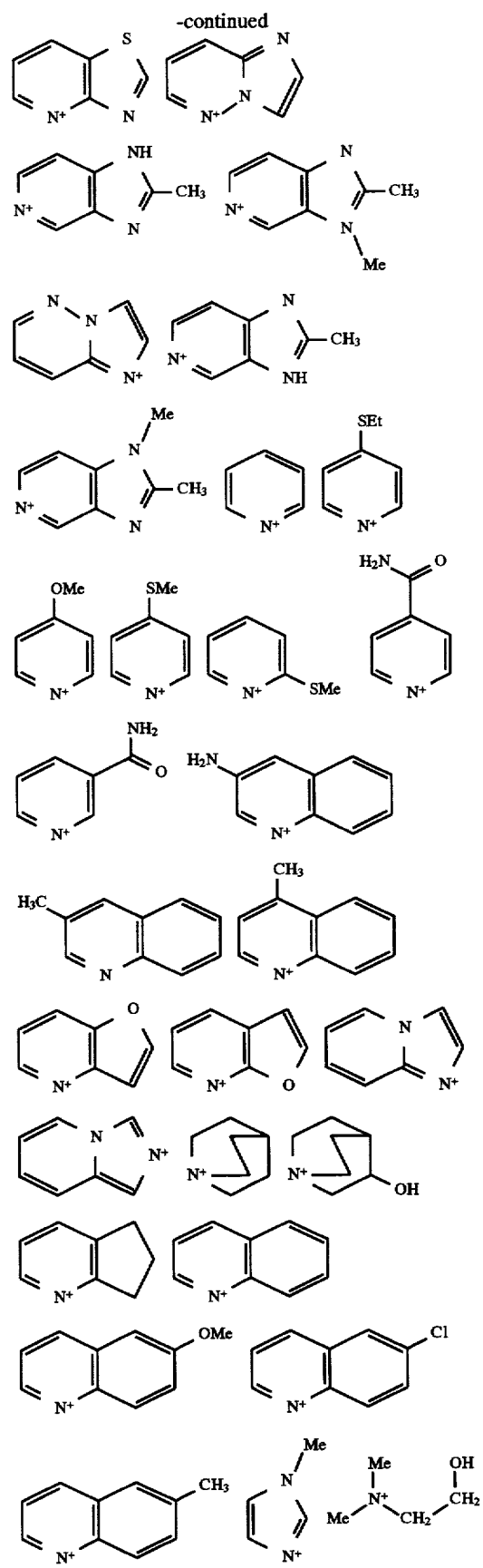

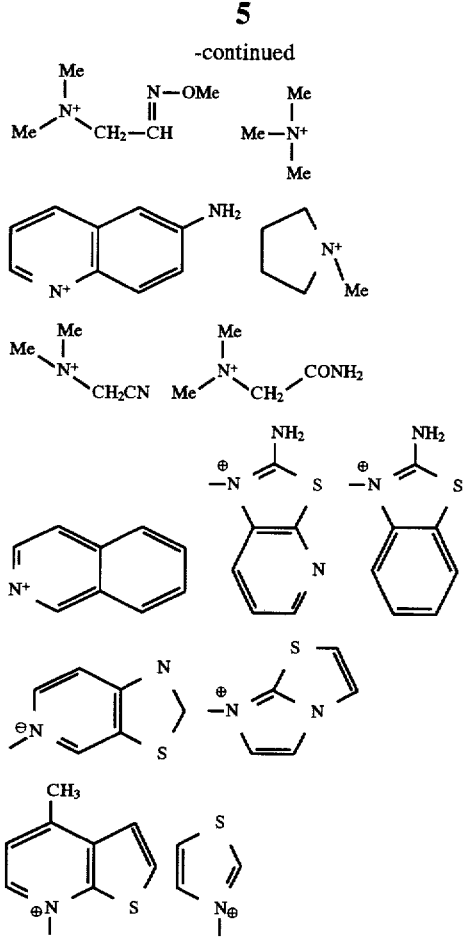

Preferred compounds are those wherein:

$R_6$ is quinolinium, isoquinolinium, 4-(methylthio)-pyridinium, thieno[2,3-b]pyridinium, imidazo(1,2-a) pyridinium or 6,7-dihydro-5H-pyrindinium, those in which $R_3$ and $R_4$ individually are hydroxy and those in which $R_2$ and $R_5$ are chlorine or fluorine, those in which $R_1$ and $R_2$ are fluorine and those in which $R_2$ is methoxy and one of $R_1$ or $R_5$ is chlorine and those wherein $R'_1$ is —CN, —COOH or alkoxycarbonyl.

Specific compounds of the invention are the internal salt of (6R-(3-(E) 6α,7β (Z)))-1-(3-(7-(((2-amino-4-thiazolyl) (carboxy-(2,3-difluoro-4,5-dihydroxy-phenyl)-methoxy)-imino)-acetamido)-2-carboxy-8-oxo-5-thia-1-azabicyclo[4,2,0]oct-2-en-3-yl)-2-propenyl)imidazo(1,2-a) pyridinium, the internal salt of (6R-(3-(E) 6α,7β (Z)))-1-(3-(7-(((2-amino-4-thiazolyl) (carboxy-(2,5-difluoro-3,4-dihydroxy-phenyl)methoxy)-imino)-acetamido)-2-carboxy-8-oxo-5-thia-1-azabicyclo[4,2,0]oct-2-en-3-yl)-2-propenyl)-imidazoa)pyridinium, the internal salt of (6R-(3-(E) 6α,7β (Z)))-1-(3-(7-(((2-amino-4-thiazolyl) (carboxy-(2-chloro-4,5-dihydroxy-3-methoxy-phenyl)methoxy)-imino)-acetamido)-2-carboxy-8-oxo-5-thia-1-azabicyclo[4,2,0]oct-2-en-3-yl)-2-propenyl)quinolinium, the internal salt of (6R-(3-(E) 6α,7β (Z)))-1-(3-(7-(((2-amino-4-thiazolyl) (carboxy-(2,5-dichloro-3,4-dihydroxy-phenyl)methoxy)-imino)-acetamido)-2-carboxy-8-oxo-5-thia-1-azabicyclo[4,2,0]oct-2-en-3-yl)-2-propenyl)-6,7-dihydro-5H-pyrindinium, the internal salt of (6R-(3-(E) 6α,7β (Z(S*))))-1-(3-(7-((2-amino-4-thiazolyl)(carboxy-(3,4-dihydroxy-5-fluorophenyl)-methoxy)-imino)-acetamido)-2-carboxy-8-oxo-5-thia-1-azabicyclo[4,2,0]oct-2-en-3-yl)-2-propenyl)-quinolinium, the internal salt of [6R-[3(E), 6α,7β (Z)]]-1-[3-[7-[[(2-amino-4-thiazolyl) [carboxy-(2-chloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-quinolinium (R) or (S) or an (R+S) mixture, the internal salt of [6R-[3(E), 6α,7β (Z)]]-1-[3-[7-[[(2-amino-4-thiazolyl) [carboxy-(3-cyano-4,5-dihydroxy-phenyl)-methoxy]-imino]-acetamido]-2-carboxy-8-oxo-5-thia-1-azabicyclo[4,2,0]oct-2-en-3-yl]-2-propenyl]-quinolinium (R) or (S) or an (R+S) mixture, the internal salt of [6R-[3(E), 6α,7β (Z)]]-1-[3-[7-[[(2-amino-4-thiazolyl) (carboxy-(3-fluoro-4,5-dihydroxy-phenyl)-methoxy]-imino]-acetamido]-2-carboxy-8-oxo-5-thia-1-azabicyclo[4,2,0]oct-2-en-3-yl]-2-propenyl]-quinolinium (R) or (S) or an (R+S) mixture, the internal salt of [6R-[3(E), 6α,7β (Z)]]-2-[3-[7-[[(2-amino-4-thiazolyl) [carboxy-(2,5-dichloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-quinolinium (R) or (S) or an (R+S) mixture, the internal salt of [6R-[3(E), 6α,7β (Z)]]-1-[3-[7-[[(2-amino-4-thiazolyl) (carboxy-(2,5-dichloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-thieno[2,3-b]pyridinium (R) or (S) or an (R+S) mixture, the internal salt of [6R-[3(E), 6α,7β [Z(S*)]]]-1-[3-[7-[[(2-amino-4-thiazolyl) [carboxy-(3-cyano-4,5-dihydrophenyl)-methoxy]-imino]-acetamido]-2-carboxy-8-oxo-5-thia-1-azabicyclo[4,20]-oct-2-en-3-yl]-2-propenyl]-thieno[2,3-b]pyridinium, the internal salt of [6R-[3(E), 6α,7β (Z)]]-3-1-[3[-7-[[(2-amino-4-thiazolyl) [carboxy-2,5-dichloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-2-propenyl]-isoquinolinium (R) or (S) or an (R+S) mixture, and the internal salt of [6R-[3(E), 6α,7β (Z)]]-1-[3-[7-[[(2-amino-4-thiazolyl) [carboxy-(2,5-dichloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-4-(methylthio)-pyridinium (R) or (S) or an (R+S) mixture the internal salt of [6R-[3-(E)-6α,7β-[Z,(S*)]]-1-[3-7-[[(2-amino-4-thiazolyl)-[carboxy-(2,3-difluoro-4,5-dihydroxy-phenyl)-methoxy]-imino]-acetamido]-2-carboxy-8-oxo-5-thia-1-azabicyclo[4,2,0]oct-2-en-3-yl]-2-propenyl]-quinolinium.

the internal salt of [6R-[3-(E)-6α,7β-[Z,(S*)]]-1-[3-7-[[(2-amino-4-thiazolyl)-[carboxy-(2,5-difluoro-3,4-dihydroxy-phenyl)-methoxy]-imino]-acetamido]-2-carboxy-8-oxo-5-thia-1-azabicyclo[4,2,0]oct-2-en-3-yl]-2-propenyl]-quinolinium.

the internal salt of [6R-[3-(E) 6-α,7-β-(Z)]] 1-[3-[7-[[(2-amino 4-thiazolyl) [[carboxy 5-cyano 3,4-dihydroxy 2-thienyl) methoxy] imino] acetyl] amino] 2-carboxy 8-oxo 5-thia 1-azabicyclo[4,2,0]oct-2-en-3-yl] 2-propenyl] quinolinium.

The novel process of the invention for the preparation of a compound of formula I wherein $R_7$ is M comprises reacting a compound of the formula

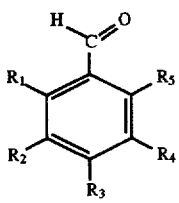

in which $R_1$, $R_2$, $R_3$, $R_4$ and $R_5$ are as defined above optionally with necessary protection of its reactive functions to form an aromatic aldehyde of formula $II_p$:

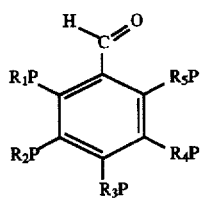

in which $R_{1p}$, $R_{2p}$, $R_{3p}$, $R_{4p}$ and $R_{5p}$ represent $R_1$, $R_2$, $R_3$, $R_4$ and $R_5$ as defined previously or a protected reactive function, the latter is homologated into an α-hydroxy acid of the formula

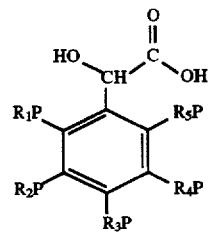

esterifying the latter to form an α-hydroxy ester of the formula

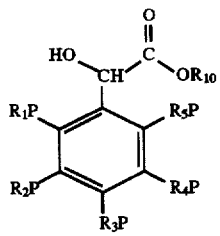

wherein $R_{10}$ is the remainder of an easily-cleaveable ester, reacting the latter with N-hydroxy phthalimide to obtain a compound of the formula

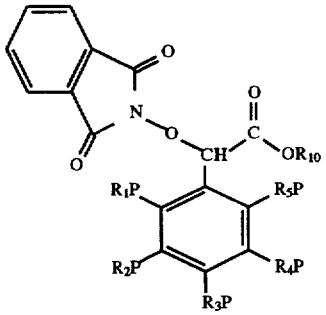

hydrolysing the latter to form an O-substituted hydroxy-lamine of the formula

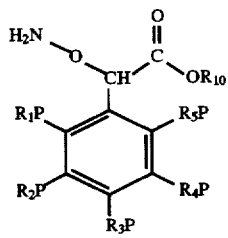

condensing the latter with a derivative of (2-amino-thiazolyl)-glyoxylic acid of the formula

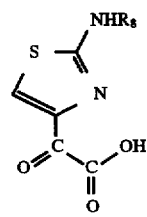

wherein $R_8$ is hydrogen or a protective group of the amine function to form a compound of the formula

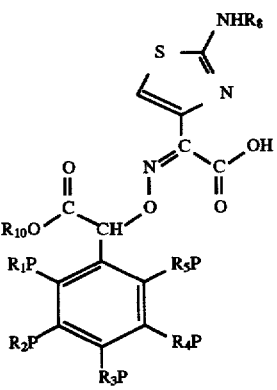

amidifying the latter with an ester of 7-amino-3-(3-chloro-1-propenyl)-8-oxo-5-thia-1-azabicyclo[4.2.0]oct-2-en-2- carboxylic acid hydrochloride of the formula
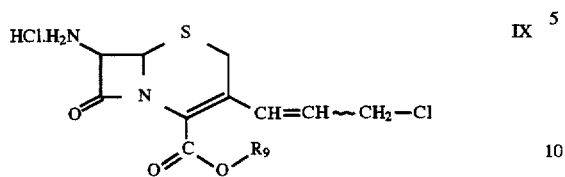
or its salts wherein $R_9$ is the remainder of an easily-cleavable ester to obtain a compound of the formula
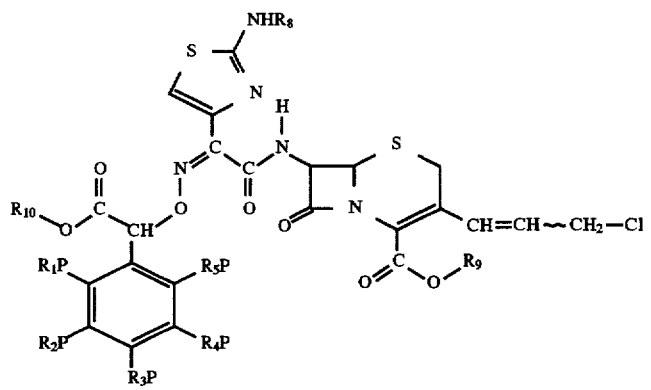
converting the latter into an 3-(3-iodo-propenyl) of the formula
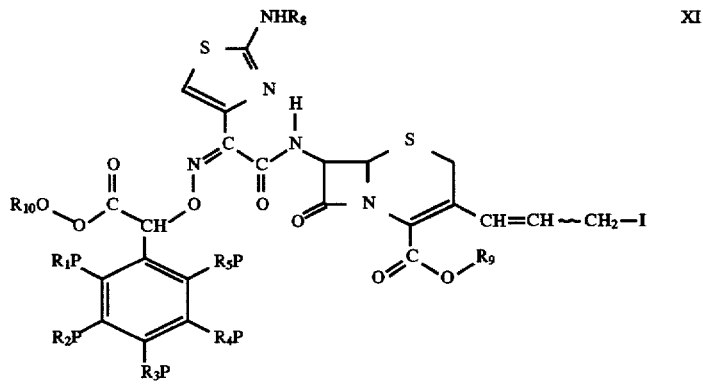
treating the latter with a base of $R_6$ to obtain a compound of the formula

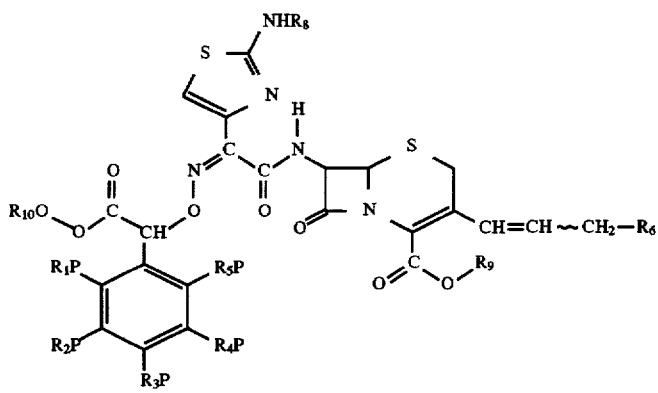

optionally separating the (E) or (Z) isomers or the (Z) isomers are converted into (E) isomers and subjecting the compound of formula XII to one or more of the following reactions in any order:

a) cutting by hydrolysis or by the action of thiourea of all or part of the ester groups or the protective groups of the amino or hydroxy, b) esterification or salification of the carboxylic by a base, c) salification of amino by an acid, d) separation of the products in the form of an R,S mixture into R or S.

In a variant of the process, the O-substituted hydroxylamine of formula VI is condensed with a compound of the formula

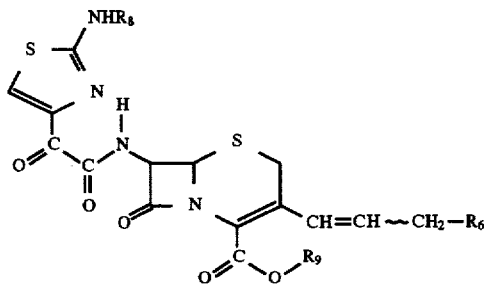

to obtain the product of formula XII as defined previously.

The protected hydroxy functions of $R_{1p}$, $R_{2p}$, $R_{3p}$, $R_{4p}$ and $R_{5p}$ are chosen from acyloxy groups such as formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy. Other groups include ethoxycarbonyloxy, methoxycarbonyloxy, propoxycarbonyloxy, 2,2,2-trichloro ethoxycarbonyloxy, benzyloxycarbonyloxy, tert.-butoxycarbonyloxy, 1-cyclopropyl ethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, capryloyloxy, acryloyloxy, methylcarbamoyloxy, phenylcarbamoyloxy, naphthylcarbamoyloxy.

Other protective groups are phenoxy, 4-chloro phenoxy, tolyloxy or tert.-butyl phenoxy, tetrahydropyrannyloxy, tetrahydrothiopyrannyloxy, methoxytetrahydropyrannyloxy, trityloxy, benzyloxy, 4-methoxy benzyloxy, benzhydryloxy, trichloroethoxy, 1-methyl-1-methoxyethoxy, or alkoxy alkoxy-methyl such as methoxy ethoxy methyl.

Two adjacent hydroxyls can be protected by forming a methylenedioxy, isopropylenedioxy, 1,1-cyclohexyl bis (oxy), diphenylmethylenedioxy, carbonate or hydroxy borannylbis(oxy).

The protected hydroxy functions of $R_{1p}$, $R_{2p}$, $R_{3p}$, $R_{4p}$ and $R_{5p}$, are preferably chosen from methoxyethoxymethoxy, propionyloxymethoxy, acetoxymethoxy, butoxy, isobutoxy, tert.-butoxy, pentoxy, hexyloxy, butyryloxymethoxy, valeryloxymethoxy, pivaloyloxymethoxy, 2-acetoxy ethoxy, 2-propionyloxy ethoxy, 1-butyryloxy ethoxy, 2-iodoethoxy, 2,2,2-trichloro ethoxy, vinyloxy, allyloxy, ethynyloxy, propynyloxy, benzyloxy, 4-methoxy, benzyloxy, 4-nitro benzyloxy, phenylethoxy, trityloxy, diphenylmethyloxy or 3,4-dimethoxyphenoxy. The 2-methoxy ethoxymethoxy (MEM-O) group is particularly preferred.

The remainders of the easily-cleavable ester groups of $R_{10}$ and $R_9$ are chosen from butyl, isobutyl, tert.-butyl, pentyl, hexyl, methoxymethyl, ethoxymethyl, isopropoxymethyl, α-methoxy ethyl, α-ethoxy ethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert.-butylcarbonyloxymethyl, hexadecanoyloxymethyl, pivaloyloxymethyl, propionyloxyethyl, isovaleryloxyethyl, 1-acetoxy ethyl, 2-acetoxy ethyl, 1-propionyloxy ethyl, 2-propionyloxy ethyl, 1-butyryloxy ethyl, 2-butyryloxy ethyl, 1-(tert.-butylcarbonyloxy)ethyl, 1-acetoxy propyl, 1-hexadecanoyloxy ethyl, 1-propionyloxy propyl, 1-methoxycarbonyloxy ethyl, methoxycarbonyloxymethyl, 1-acetoxy butyl, 1-acetoxy hexyl, 1-acetoxy heptyl, phthalidyl, 5,6-dimethoxy phthalidyl, tert-butylcarbonylmethyl, vinyl, allyl, 2-chloro allyl, ethynyl, propynyl, methoxycarbonylmethyl, benzyl, 4-methoxy benzyl, 4-nitro benzyl, phenethyl, trityl, diphenyl methyl, phenyl, 4-chloro phenyl, tolyl, tert.-butyl phenyl, 3,4-dimethoxy phenyl, methoxyethoxymethyl, dimethylaminoethyl, cyanomethyl, tert-butoxycarbonylmethyl, 2,2-ethylenedioxy ethyl, cyanoethyl, 2,2-dimethoxy ethyl; 2-chloro ethoxymethyl, (2-hydroxy ethoxy) ethyl, 2,3-epoxy propyl 3-dimethylamino 2-hydroxy propyl, 2-hydroxy ethyl, 2-methylaminoethoxymethyl, (2-amino ethoxy)methyl, 3-methoxy 2,4-thiadiazol-5-yl, tetrahydropyrann-2-yl, 1-methoxy 1-methyl ethyl, 2-hydroxy 1-methyl ethyl, isopropyl, carbamoylmethyl, chloromethyl, 2-chloro ethyl, 2,2,2-trichloro ethyl, 2-iodo ethyl, acetyl, methyl, 2-methylthio ethyl, thiocyanatomethyl, 2-chloro-1-acetoxy ethyl, 2-bromo 1-acetoxy ethyl, 2-fluoro 1-acetoxy ethyl, 2-methoxy 1-acetoxy ethyl, 2-methyl 1-acetoxy propyl, 1-methyl 1-acetoxy ethyl, 1-(methoxyacetoxy) ethyl, 1-acetyl carbonyloxyethyl, 1-hydroxy acetoxyethyl, 1-(2-thienyl)carbonyloxyethyl, 1-(2-furyl)carbonyloxyethyl, 1-(5-nitro-2-furyl) carbonyloxy-ethyl, 1-(2-pyrrolyl) carbonyloxyethyl, 1-(propionyloxycarbonyloxy) ethyl, 1-(propoxycarbonyloxy) ethyl, 1-(isopropoxycarbonyl) ethyl, 1-(methoxyethoxy-carbonyloxy) ethyl, 1-(allyloxycarbonyloxy) ethyl, isopropoxycarbonyl methyl, 1-[(2,3-epoxy propyl) oxycarbonyloxy]ethyl, 1-[(2-furyl) methoxycarbonyloxy ethyl, 1-[(2-fluoro ethoxy)-carbonyloxy] ethyl, 1-(methoxy-carbonyloxy) propyl, 1-(methoxycarbonyloxy) 1-methyl ethyl, (methoxycarbonyloxy) chloromethyl, 1-(methoxycarbonyloxy)-2-chloro ethyl, 1-(methoxy carbonyloxy) 2-methoxy ethyl, 1-(methoxycarbonyloxy) allyl or a 5-methyl 2-oxo 1,3-dioxol-4-yl remainder.

Diphenylmethyl is preferred for $R_{10}$ and 4-benzyl methoxy or diphenylmethyl are preferred for $R_9$.

The protective group of the amino $R_8$ can be for example carbamoyl, methyl carbamoyl, phenylcarbamoyl, naphthylcarbamoyl, as well as the corresponding thiocarbamoyls, alkyl of 1 to 6 carbon atoms substituted or non-substituted, such as preferably, trichloroethyl, tert.-butyl or tert-amyl, aralkyl such as benzyl, 4-methoxy benzyl, phenethyl, trityl, 3,4-dimethoxy benzyl or benzhydryl, a substituted or non-substituted aliphatic, aromatic or heterocyclic acyl such as formyl, acetyl, propionyl, butyryl, isobutyryl, valeryl, isovaleryl, chloroacetyl, dichloroacetyl, trichloroacetyl, bromoacetyl, trifluoroacetyl benzoyl, toluolyl, naphthoyl, chlorobenzoyl, para-nitro benzoyl, para-tert-butyl benzoyl, phenoxyacetyl, caprylyl, decanoyl, acryloyl, phthaloyl, mesyl, phenyl-acetyl, phenylpropionyl, oxalyl, succinyl, pivaloyl, lower alkoxycarbonyl or cycloalkoxycarbonyl such as methoxycarbonyl, ethoxycarbonyl, propoxycarbonyl, 1-cyclopropylethoxycarbonyl, isopropoxycarbonyl, butoxycarbonyl, tert-butoxycarbonyl, pentoxycarbonyl, hexyloxycarbonyl, trichloroethoxy carbonyl, aralkoxycarbonyl such as benzyloxycarbonyl. The trityl is preferred.

The above list is not limitative and it is evident that other amine protective groups, groups known in particular in the chemistry of the peptides, can also be used.

The hydrolysis of the compound of formula V can be made by methods known in the art.

The functional derivative of the acid of formula VIII may be for example a halide, a symmetrical or mixed anhydride, amide, azide or an activated ester. An example of a mixed anhydride is that formed with isobutyl chloroformate or that formed with pivaloyl chloride and the carboxylic-sulfonic mixed anhydrides formed for example with p-toluene sulfonyl chloride.

An example of an activated ester is the ester formed with 2,4-dinitrophenol or that formed with hydroxybenzothiazole. An example of a halide is the chloride or bromide.

The anhydride can be formed in situ by the action of N,N'-disubstituted carbodiimide, for example, N,N-dicyclohexylcarbodiimide. The acylation reaction is preferably carried out in an organic solvent such as methylene chloride but other solvents can be used such as tetrahydrofuran, chloroform or dimethylformamide.

When an acid halide is used and in a general manner when a hydrohalic acid molecule is released during the reaction, the reaction is preferably carried out in the presence of a base such as sodium hydroxide, potassium hydroxide, sodium or potassium carbonates and bicarbonates, sodium acetate, triethylamine, pyridine, morpholine or N-methylmorpholine. The reaction temperature is generally lower than or equal to ambient temperature.

A product of formula VIII can also be reacted directly with a product of formula IX in the presence of a carbodiimide such as diisopropylcarbodiimide or 1-(3-dimethylamino propyl)-3-ethyl carbodiimide (EDC).

The action of the reagent capable of introducing $R_6$ into the product of formula XI is carried under the following conditions: When Hal is chlorine, a substitution of chlorine by iodine in the presence of sodium iodide can be carried out in situ or separately, then the desired reagent is added in the optional presence of an organic solvent such as dichloromethane, acetonitrile or tetrahydrofuran. The desired reagent of $R_6$ can also be reacted directly on the product of formula X in the presence of silver tetrafluoroborate.

The isomerism of the products of formula XII can be different from that of the products of formula X or XI used at the start. When the Z isomer is isolated, this isomer can be converted into the E isomer by the usual methods, notably by the action of iodine.

Depending upon $R_8$, $R_{10}$, $R_9$, $R_{1p}$, $R_{2p}$, $R_{3p}$, $R_{4p}$ and $R_{5p}$, the action of one or more of hydrolysis, hydrogenolysis agents or of thiourea on the product of formula XII is intended to eliminate $R_8$ when the latter is a protective group of the amino to convert $R_{1p}$, $R_{2p}$, $R_{3p}$, $R_{4p}$ and $R_{5p}$ into $R_1$, $R_2$, $R_3$, $R_4$ and $R_5$ respectively when these are a protective group of hydroxyls and/or to eliminate $R_{10}$ and $R_9$ when these are easily-cleavable ester groups, one of those that it is desired to eliminate.

It is possible to eliminate $R_8$ and to convert $R_{1p}$, $R_{2p}$, $R_{3p}$, $R_{4p}$ and $R_{5p}$ into $R_1$, $R_2$, $R_3$, $R_4$ and $R_5$ respectively when these are a protective group of hydroxyls without affecting $R_{10}$ and $R_9$ when these have to be preserved. The nature of the reagents to be used in such a case is well known to one skilled in the art. Examples of such reactions are given further on in the experimental part. A description of the methods for eliminating the different protective groups will be found in French Patent Application No. 2,499,995.

Given the nature of the preferred protective groups used: trityl for $R_8$, 2-methoxyethoxymethyl to protect hydroxy functions of $R_1$, $R_2$, $R_3$, $R_4$ and $R_5$, diphenylmethyl for $R_{10}$ and 4-methoxy benzyl or diphenylmethyl for $R_9$, trifluoroacetic acid is preferably used without a solvent or in a solvent such as anisole or a mixture of solvents such as anisole/methylene chloride. A salt is then obtained with trifluoroacetic acid and the free base can be obtained by the action of a base such as triethylamine carbonate.

The salification of the products can be carried out by the usual methods. For example, by the action, on a product in the acid form or on a solvate, for example the ethanolic solvate or a hydrate of this acid, of a mineral base such as sodium or potassium hydroxide, sodium or potassium carbonate or bicarbonate. Mineral acid salts such as trisodium phosphate can also be used. Organic acid salts can also be used such as, for example, sodium salts of saturated or unsaturated, linear or branched aliphatic carboxylic acids of 1 to 18 and preferably 2 to 10 carbon atoms. The aliphatic chains of these acids can be interrupted by one or more heteroatoms such as oxygen or sulfur or substituted by aryl such as phenyl, thienyl or furyl, by one or more hydroxyl or by one or more halogens such as fluorine, chlorine or bromine, preferably chlorine, by one or more lower carboxylic or alkoxycarbonyl, preferably methoxycarbonyl, ethoxycarbonyl or propyloxycarbonyl, by one or more aryloxy, preferably phenoxy.

Moreover, sufficiently soluble aromatic acids can be used as the organic acids such as benzoic acid substituted preferably by lower alkyl.

Examples of such organic acids are formic acid, acetic acid, acrylic acid, butyric acid, adipic acid, isobutyric acid, n-caproic acid, isocaproic acid, chloropropionic acid, crotonic acid, phenyl acetic, (2-thienyl) acetic acid, (3-thienyl) acetic acid, (4-ethyl phenyl) acid, acetic acid, glutaric acid, monoethylic ester of adipic acid, hexanoic acid, heptanoic, acid, decanoic acid, oleic acid, stearic acid, palmitic acid, 3-hydroxy propionic acid, 3-methoxy propionic acid, 3-methylthio butyric acid, 4-chloro butyric acid, 4-phenyl butyric acid, 3-phenoxy butyric acid, 4-ethyl benzoic acid, 1-propyl benzoic acid.

Sodium acetate, sodium 2-ethyl hexanoate or sodium diethyl acetate are preferably used as sodium salts.

The salification can also be obtained by the action of an organic base such as triethylamine, diethylamine, trimethylamine, propylamine, N,N-dimethylethanolamine; tris[(hydroxymethyl)-amino]methane, methylamine, ethanolamine, pyridine, picoline, dicyclohexyl amine, morpholine and benzylamine or by the action of arginine, lysine, procaine, histidine, N-methyl glucamine. This salification is preferably carried out in a solvent or a mixture of solvents such as water, ethyl ether, methanol, ethanol or acetone.

The salts are obtained in amorphous or crystallized form according to the reaction conditions used. The crystallized salts are preferably prepared by reacting the free acids with one of the salts of the aliphatic carboxylic acids mentioned above, preferably with sodium acetate. The salification of the products by mineral or organic acids is carried out under the usual conditions.

The optional esterification of the products is carried out under standard conditions. The operation is generally carried out by reacting the acid of formula I or a functional derivative of the acid with a derivative of the formula Z—Re wherein Z is hydroxyl or halogen such as chlorine, bromine, iodine and Re is the ester group to be introduced, a non-exhaustive list of which group is given above. In certain cases, it may be advantageous to carry out an esterification on a product of which the amine and/or reactive groups present on the oxyimino are blocked before removing the protective group of the same amine and of the reactive group present on the oxyimino.

The novel process for the preparation of the compounds of formula I wherein $R_7$ is K or L comprises reacting an ester of the formula

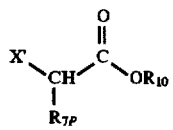

wherein X' is a leaving group or a radical capable of generating a leaving group in situ, $R_{7P}$ is $R_7$ as defined above in which the hydroxy or the amino are protected and $R_{10}$ is the remainder of an easily cleavable ester with N-hydroxy phtalimide optionally in the presence of an activating agent to obtain a compound of the formula

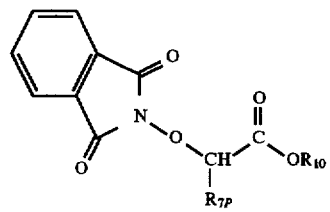

hydrolyzing the latter into the O-substituted hydroxylamine of the formula

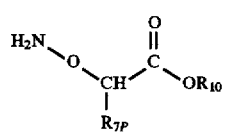

condensing the latter with a derivative of (2-amino thiazol-4-yl)-2-oxoacetic acid of the formula

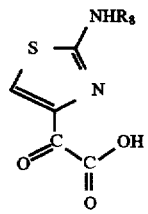

wherein $R_8$ is hydrogen or a protective group of the amine function to obtain the derivative of the α-alkoxy imino acetic acid of the formula

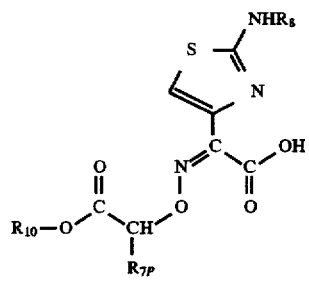

optionally preparing a functional -derivative of the latter, amidifying the product of formula VI or functional derivative with an ester of the hydrochloride of 7-amino-3-(3-halogeno-1-propenyl)-8-oxo-5-thia-1-azabicyclo[4,2,0]oct-2-en-2-carboxylic acid of the formula

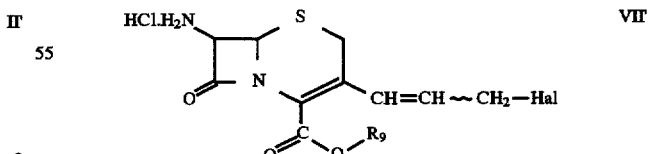

or its salts, wherein Hal is halogen and $R_9$ is the remainder of an easily cleavable ester to obtain a derivative of 7-(N-substituted amido)3-(3-halo-1-propenyl)-8-oxo-5-thia-1-azabicyclo [4,2,0]oct-2-en-2-carboxylic acid of the formula

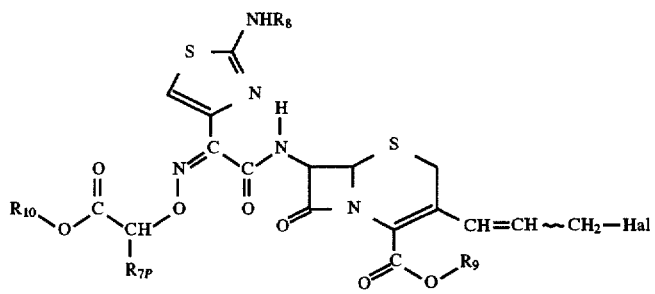

VIII' optionally converting the latter into the analogous 3-(3-iodopropenylated) product of the formula

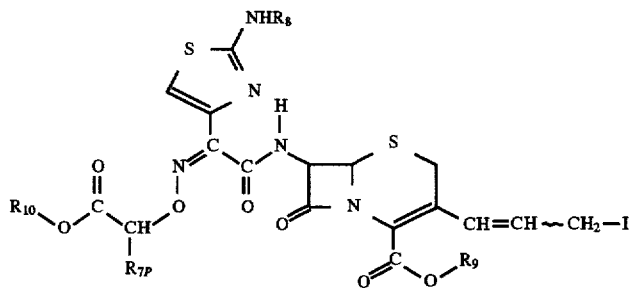

IX' with a base of treating the latter formula $R_6$ to obtain a product of the formula

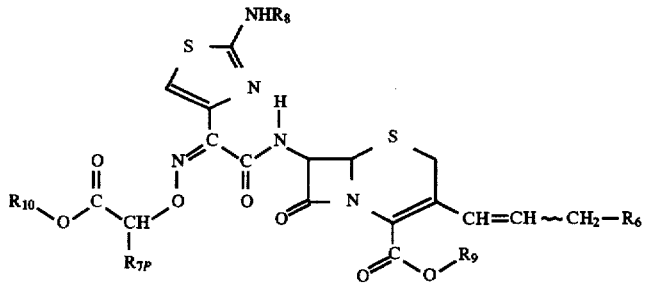

X' from which product of formula X' optionally isolating the (E) or (Z) isomers or the Z isomers are converted into the E isomer and which product of formula X' is subjected to one or more of the following reactions, in any order:

a) cutting by hydrolysis or by the action of thiourea of all or part of the ester groups or protective groups of the amino or the hydroxyl, b) esterification or salification by a base of the carboxylic, c) salification by an acid of the amino, d) separation of the products in the form of an R,S mixture into R or S.

A variant of the process described above comprises condensing O-substituted hydroxylamine of formula IV' with a product of the formula

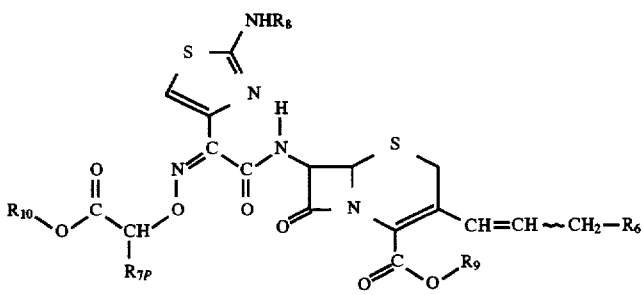

to form a compound of formula X'.

In the above process and in its variant, the protecting groups of the hydroxy and amino functions contained in $R_{7P}$ are chosen from the same groups as those mentioned above for $R_{1P}$, $R_{2P}$, $R_{3P}$, $R_{4P}$, $R_{5P}$ and $R_8$.

Diphenylmethyl is preferred for $R_{10}$ and 4-methoxybenzyl or diphenylmethyl is preferred for $R_9$.

Trityl is preferred for $R_8$ and benzyloxycarbonyl is preferred for $R_{7P}$.

The X group can be a hydroxy radical, an alkylsulfonyloxy radical such as methylsulfonyloxy, an arylsulfonyloxy radical such as phenyl or tolylsulfonyloxy, or a halogen atom such as chlorine, bromine or iodine. The hydroxy and chloro values are more particularly preferred. The hydrolysis of III', the preparation of the functional derivative of the acid VI', the acylation reaction, the introduction of the $R_6$ radical, the optional transformation of an obtained isomer, the action of a hydrolysis reagent or of the thiourea, the elimination of the $R_8$ group, the transformation of the $R_{7P}$ group into $R_7$ group, the salification of the products, the optional esterification, the resolution of the diastereoisomers:

can be made in the same conditions and preferred conditions as those mentioned above for the preparation of the compounds of formula I wherein $R_7$ is M.

The products of formula I contain several asymetrical carbons. In the cephem nucleus which contains two asymetrical carbons, the two carbons are in R configuration. Furthermore, the substituent present on the oxyimino function also contains an asymetrical carbon which can be in R or S form or in the form of an R+S mixture. The separation of the two diastereoisomers can be carried out by means of a man skilled in the art, for example by chromatography.

The compounds of formula II' are new and can be prepared by reacting a compound of the formula $$R'_7\text{—CHO} \qquad XII$$

of which the reactive functions are if necessary protected to obtain a compound of the formula $$R'_{7P}\text{—CHO} \qquad XIII$$

converting the derivative of formula XII or XIII into the α-hydroxy acid derivative of the formula

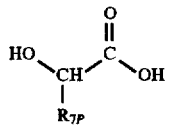

which can be optionally converted into a corresponding halogenated or alkyl- or arylsulfonylated derivative, which is then esterified.

The derivatives of formula II' in which X' is halogen can in a preferential manner be obtained by a process according to which an aldehyde of formula XII' or XIII' is treated with malonodinitrile to obtain a compound of the formula

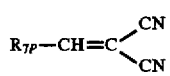

which is subjected to the action of an oxidizing agent to obtain an epoxide of the formula

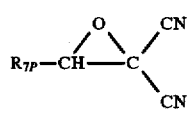

which is treated with a hydrohalic acid to obtain the acid of the formula

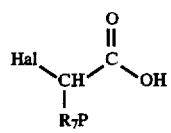

which is esterified.

The derivatives of formulae III', IV', VI', VIII', IX' and X', as well as the derivatives of formulae XIV, XV, XVI and XVII are also new.

The compounds of formula II' in which X' hydroxy can also be prepared by a process in which a compound of the formula

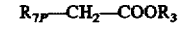

is subjected to the action of an oxidizing agent to obtain a ketonic derivative of the formula

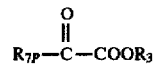

which is reduced to the corresponding secondary alcohol of formula II'.

The compounds of formula XII' are known, for example, from the C.A. Vol. 111,P194772, Vol. 108,P150482, Vol.

101,P38342, Vol. 97P215983, Vol. 95P203734 or also J. Am. Chem. Soc., Vol. 73, p. 2956 (1951), or can be prepared by methods known to an average man skilled in the art, starting with the compounds described in these references.

As for the compounds of formula XVIII and the corresponding acid, they are described in European Patent Application No. 136,721, as well as J. of Antibiotics, Vol. 36, No. 8, p. 1020 (1983). In a general manner, the compounds of formula XVIII can be prepared from the acid by methods known to an average man skilled in the art.

The antibacterial compositions of the invention are comprised of an antibactericidally effective amount of at least one compound of formula I or its non-toxic, pharmaceutically acceptable acid addition salts and an inert pharmaceutical carrier. The compositions may be in the form of tablets, dragees, capsules, granules, suppositories, ointments, creams, gels and injectable solutions.

Examples of inert pharmaceutical carriers are talc, arabic gum, lactose, starch magnesium stearate, cocoa butter, aqueous or non-aqueous vehicles, fatty derivatives of animal or vegetable origin, paraffin derivatives, glycols, various wetting agents, dispersants and emulsifiers and preservatives.

When in the form of a powder, the compositions are dissolved extemporaneously in a vehicle such as apyrogenic water.

The compositions have a very good antibiotic activity on gram (+) bacteria such as staphylococci, streptococci and notably on penicillin-resistant staphylococci. Their effectiveness on gram (−) bacteria, particularly on coliform bacteria, klebsiella, salmonella, proteus and pseudomonas, is particularly remarkable.

These properties make the compositions suitable for use as medicaments in the treatment of germ-sensitive diseases and particularly in that of staphylococci, such as staphylococci septicemias, malignant staphylococcia of the face or skin, pyodermititis, septic or suppurative sores, anthrax, phlegmon, erysipelas, acute primary or post-influenzal staphylococcia, bronocho-pneumonia, pulmonary suppurations. These compositions can also be used as medicaments in the treatment of colibacilloses and associated infections, of proteus, klebsiella and salmonella infections and of other diseases caused by gram (−) bacteria.

The compositions wherein A is a cleavable ester are preferred for oral administration and when in the form of a powder, the compositions are dissolved extemporaneously in a vehicle such as apyrogenic water.

The novel method of combatting bacterial infections in warm-blooded animals, including humans, comprises administering to warm-blooded animals an antibacterially effective amount of at least one compound of formula I or its non-toxic, pharmaceutically acceptable acid addition salts. The compounds may be administered orally, rectally, parenterally or topically on skin and mucous membranes. The usual daily dose is 3 to 50 mg/kg depending on the condition treated, specific compound used and the method of administration. The method can also be used for disinfecting surgical instruments.

The novel intermediates of the invention are those compounds of formulae III, III', IV, IV', V, V', VI, VI', VIII, VIII', IX', X, X', XI, XII, XIII as well as the derivatives of the formulae XIV, XV, XVI and XVII.

The compound of formula VI in which $R_{1p}$ and $R_{2p}$ are fluorine and $R_{3p}$ and $R_{4p}$ are a hydroxy protected by a methoxyethoxymethyl (M.E.M.) (hereafter) product of formula VI$_A$ may be prepared by reacting a compound of the formula

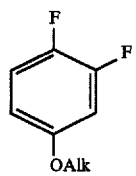

wherein Alk is alkyl, preferably methyl, with butyllithium and trimethylborate and then oxygenated water to obtain a compound of the formula

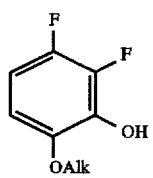

reacting the latter with dimethylamine in the presence of formic anhydride to obtain a compound of the formula

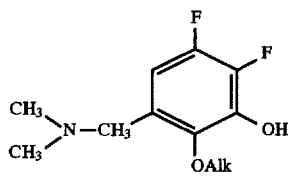

reacting the latter with methyl iodide and hexamethylenetetramine in the presence of acetic acid to obtain a compound of the formula

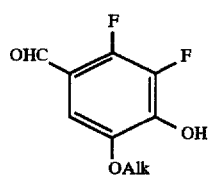

reacting the latter to eliminate the alkyl in the presence of borontribromine to obtain the compound of the formula

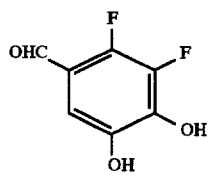

reacting the latter with a protecting agent to protect the hydroxyl function by a MEM group for example to obtain a compound of the formula

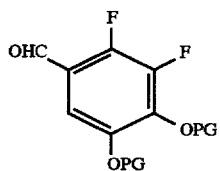

wherein PG represents a protective group of the hydroxyls, reacting the latter with a organophosphorated derivative of the formula

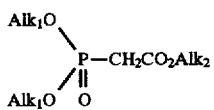

wherein Alk$_1$ and Alk$_2$ are individually alkyl of 1 to 4 carbon atom to obtain a compound of the formula

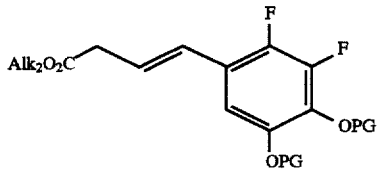   G reacting the latter with a reducing agent i.e. diisobutyl-aluminium hydride to obtain a compound of the formula

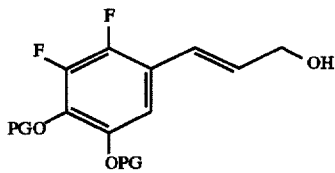   H reacting the latter with an epoxidation reagent, i.e. with m-chloroperbenzoic acid to obtain a compound of the formula

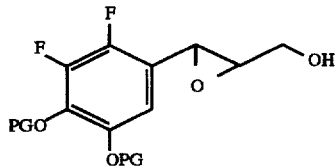   J reacting the latter with cuprous chloride in the presence of lithium chloride to obtain a compound of the formula

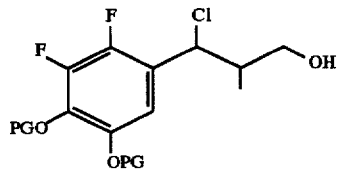   N reacting the latter with an oxidation reagent i.e. sodium metaperiodate then with an esterifying reagent to obtain a compound of the formula

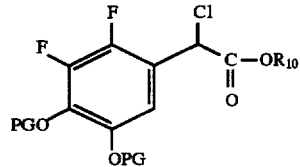   P wherein R$_{10}$ has the above definition and reacting the latter with N-hydroxyphthalimide to obtain a compound of the formula

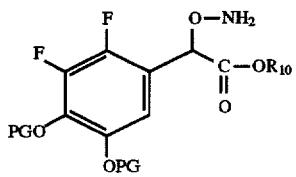   VI$_A$

The products of formulae II and A are known in a general manner and most are commercially available. Others can be prepared from commercially-available products by the methods described in the preparations below for the preparation of the compound of formula II. The methods described in the literature can also be used, notably the so-called Rosemund reduction, the reduction of benzoic acid or the formylation of aromatic rings such as the Vilsmeier-Haack reaction, the Gatterman-Koch reaction, the Reimer-Tiemann reaction or the reaction with formyl fluoride (J. Am. Chem. Soc., Vol. 82, p. 2380 (1960)).

The products of formulae VII and IX are also known in the literature, notably in Belgian Patent Application No. 864,828 and European Patent Application EP 0,333,154.

In the following examples, there are described several preferred embodiments to illustrate the invention. However, it should be understood that the invention is not intended to be limited to the specific embodiments.

PREPARATION 1

2-chloro-3,4-bis[(2-methoxy-ethoxy)-methoxy]-benzaldehyde

STEP A: 2-chloro-3,4-dihydroxy benzaldehyde 27.62 g of 3,4-dihydroxy benzaldehyde (commercial) were dissolved in 450 ml of acetic acid and chlorine was bubbled through the solution at an ordinary temperature until 4.48 ml of the gas had been consumed. The mixture was stirred for 16 hours and then the solution was concentrated and cooled to 0° C. The precipitate was filtered, washed and dried to obtain 7.5 g of the expected product which after it was crystallized from ethyl acetate melted at 196° C.

STEP B: 2-chloro-3,4-bis[(2-methoxy-ethoxy)-methoxy]-benzaldehyde 46 ml of diisopropyl ethylamine were added to a suspension of 11.42 g of the product of Step A in 120 ml of methylene chloride and the mixture was cooled to −10° C. Then, 30.14 ml of chloro-(2-methoxy-ethoxy)-methane were added and the mixture was stirred for one hour. The mixture was diluted with 100 ml of water, separated and then the organic phase was washed, dried and concentrated to obtain 22.6 g of the expected product with a Rf=0.6 (eluant: ethyl acetate).

NMR analysis of the proton (CDCl$_3$ 250 MHz in ppm): 3.36 (s), and 3.38 (s): —OCH$_3$ 3.58 (m) (4H), 3.84 (m) (2H) and 4.06 (m) (2H): —O—CH$_2$—CH$_2$—O 5.29 (s) (2H) and 5.38 (s) (2H): —O—CH$_2$—O 7.21 (d) and 7.71 (d): aromatic protons (Ar—H) 10.36 (s): —CH=O.

PREPARATION 2

3-formyl-5,6-bis[(2-methoxy-ethoxy)-methoxy]-benzonitrile

STEP A: 3-formyl-6-hydroxy-5-methoxy benzonitrile

A mixture of 23.1 g of 3-bromo-4-hydroxy-5-methoxy benzaldehyde, 9.3 g of cuprous cyanide and 140 ml of dimethyl acetamide (DMA) was refluxed for 2 hours with stirring. After cooling, the mixture was poured over ice and extracted with an ethyl acetate-methanol mixture (90-10). The organic phase was washed and dried and the solvents were eliminated to obtain 18 g of crude product which was used as is for the following step. It melted at 180° C.

STEP B: 3-formyl-5,6-dihydroxy benzonitrile 18 g of the product of Step A and 400 ml of dichloromethane were mixed together under nitrogen and the mixture was cooled to 0° C. 150 ml of a molar solution of boron tribromide in dichloromethane were added and the mixture stood for one night at ambient temperature. It was concentrated, cooled again to 0° C. and 250 ml of a normal solution of hydrochloric acid were added. The crystallized product was separated out, washed with water, dried then crystallized from an isopropanol-water mixture (1-2) to obtain 12 g of the expected product.

Infrared analysis (Nujol):
Strong and complex absorption in the —NH/OH region
2245 cm$^{-1}$: C≡N
1700 cm$^{-1}$: C=O
1602, 1597 1520 cm$^{-1}$: aromatic nucleus
NMR analysis of the proton (DNSO 250 MHz in ppm):
7.45 (d) (J=2): Ar—H
7.73 (d) (J=2): Ar—H
9.74: CH=O
11.15: mobile absorption STEP C: 3-formyl-5,6-bis[(2-methoxy-ethoxy)-methoxy]-benzonitrile 53.6 ml of diisopropyl ethylamine were added to a suspension of 12.6 g of the product of Step B in 500 ml of dichloromethane and the mixture was cooled to –1° C. Then 35.3 ml of chloro-(2-methoxy-ethoxy)-methane were added and the mixture was stirred for one hour. The medium was diluted with 100 ml of water, separated and then the organic phase was washed, dried and concentrated to obtain 21.4 g of the expected product.

Infrared analysis (CHCl$_3$):
Absence of OH
2235 cm$^{-1}$: C≡N
1702 and 2730 cm$^{-1}$: CH=O
1592, 1582 and 1485 cm$^{-1}$: aromatic nucleus
NMR analysis of the proton (CDCl$_3$ 250 MHz in ppm):
3.37 (s): —OCH$_3$
3.58 (m) (4H), 3.85 (m) (2H) and 4.06 (m) (2H): O—CH$_2$—CH$_2$—O
5.39 (s) (2H) and 5.49 (s) (2H): —O—CH$_2$—O
7.76(d) (1H) and 7.92 (d) (1H): Ar—H
9.90 (s): —CH=O

PREPARATION 3

3-fluoro-4,5-bis[(2-methoxy-ethoxy)-methoxy] benzaldehyde

STEP A: 3-fluoro-4-hydroxy-5-methoxy benzaldehyde

A mixture of nitrogen containing 10% of fluorine was bubbled for two and a half hours through a mixture of 30.4 g of 4-hydroxy-5-methoxy benzaldehyde (vanillin) 100 ml of acetonitrile and 250 ml of Freon at 0° C. under nitrogen. After treatment with thiosulfate, acidification with a solution of 2N hydrochloric acid and extraction with ethyl acetate, the organic phase was washed, dried, concentrated and chromatographed on silica eluting with dichloromethane to obtain 2.1 g of the desired product with a Rf=0.3.

Analysis: C$_7$H$_7$FO$_3$ Calculated: %C 56.47 %H 4.14 %F 11.16 Found: 56.4 4.1 11.0

STEP B: 3-fluoro-4,5-dihydroxy benzaldehyde 3.72 g of the product of Step A and 60 ml of dichloromethane were mixed together under nitrogen and the mixture was cooled to 0° C. 32 ml of a molar solution of boron tribromide in dichloromethane were added and the mixture stood for one hour at ambient temperature and then was concentrated, cooled again to 0° C. and acidified. The crystallized product was separated out, washed with water and dried to obtain 2.83 g of the expected crude product which is used as is for the following step. It had a Rf=0.2 [eluant: acetone-dichloromethane (1-9)].

STEP C: 3-fluoro-4,5-bis[(2-methoxy-ethoxy)-methoxy] benzaldehyde 17 ml of diisopropyl ethylamine were added to a suspension of 2.8 g of the product of Step B in 5.6 ml of dichloromethane. The mixture was cooled to 10° C. and then 6.5 ml of chloro-(2-methoxy-ethoxy)-methane were added. The mixture was stirred for one hour and was then diluted with 100 ml of water and separated. Then, the organic phase was washed, dried and concentrated to obtain 5.5 g of the expected product with a Rf=0.55 [eluant: dichloromethane-acetone (9-1)].

Infrared analysis (CHCl$_3$):
Absence of OH
1696 and 2730 cm$^{-1}$: conjugated CH=O
NMR analysis of the proton (CDCl$_3$ 200 MHz in ppm):
3.36 (s) and 3.37 (s): —OCH$_3$
3.60 (m) (4H), 3.85 (m) (2H) and 3.96 (m) (2H): O—CH$_2$—CH$_2$—O
5.33 (s) and 5.36 (s): O—CH$_2$—O
7.32 (dd) 7.51 (m): Ar—H
9.90 (m): —CH=O

PREPARATION 4

3-chloro-4,5-bis[(2-methoxy-ethoxy)-methoxy]-benzaldehyde

STEP A: 3-chloro-4,5-dihydroxy benzaldehyde 37.2 g of commercial 5-chloro vanillin and 800 ml of dichloromethane were mixed together under nitrogen and cooled to 0° C. 300 ml of a molar solution of boron tribromide in dichloromethane were added and the mixture stood for one night at ambient temperature. It was concentrated, cooled again to 0° C. and acidified. The crystallized product was separated, washed with water, dried and crystallized from an isopropanol-water mixture (1-2 by volume) to obtain 26.6 g of the expected product melting at >260° C.

Infrared analysis (Nujol):
3425 cm$^{-1}$: —OH+general absorption
1672–1660 cm$^{-1}$: C=O
1595, 1588, 1534, 1500 cm$^{-1}$: aromatic ring
NMR analysis of the proton (DMSO 250 MHz in ppm):
7.24 (d J=2 Hz) and 7.44 (d J=2 Hz): Ar—H
9.90 (m): —CH=O
10.40: mobile absorption STEP B: 3-chloro-4,5-bis[(2-methoxy-ethoxy)-methoxy] benzaldehyde 60.5 ml of diisopropyl ethylamine were added to a suspension of 15 g of the product of Step A in 150 ml of dichloromethane and the mixture was cooled to −10° C. Then, 39.7 ml of chloro-(2-methoxy-ethoxy)-methane were added over 45 minutes and the mixture was stirred for half an hour and diluted with 100 ml of water and separated. Then, the organic phase was washed, dried, concentrated and chromatographed on silica, eluting with a dichloromethane-methanol mixture (99-1) to obtain 15.9 g of the expected product.

Infrared analysis (CHCl$_3$):
1698 and 2735 cm$^{-1}$: conjugated CH=O
1591, 1579, 1498 cm$^{-1}$: aromatic ring
NMR analysis of the proton (CDCl$_3$ 250 MHz in ppm):
3.38 (s): —OC$\underline{H}_3$
3.57 (m) (4H), 3.87 (m) (2H) and 4.03 (m) (2H): O—C$\underline{H}_2$—C$\underline{H}_2$—O
5.36 (s) and 5.38 (s): O—C$\underline{H}_2$—O
7.59 (d) 7.62 (d): Ar—$\underline{H}$
9.85: —C$\underline{H}$=O

PREPARATION 5

3-nitro-4 5-bis[(2-methoxy-ethoxy)-methoxy] benzaldehyde

STEP A: 3-nitro-4,5-dihydroxy benzaldehyde 35 g of 5-nitro vanillin (commercial) and 1200 ml of dichloromethane were mixed together under nitrogen and the mixture was cooled to 0° C. 533 ml of a molar solution of boron tribromide in dichloromethane were added and the mixture stood for 2 days at ambient temperature and then was concentrated. The residue was taken up cold (ice bath+methanol) in 300 ml of 2N hydrochloric acid and the mixture was stirred for two to three hours at this temperature, then left for 16 hours at ambient temperature. Extraction was carried out with ethyl acetate and the organic phase was washed, dried and concentrated to obtain 18 g of the expected product melting at>260° C.

Infrared analysis (Nujol):
general absorption NH/OH
1602 cm$^{-1}$: C=O
1620, 1590, 1580, 1548 and 1525 cm$^{-1}$: aromatic ring+—NH$_2$

STEP B: 3-nitro-4,5-bis[(2-methoxy-ethoxy)-methoxy] benzaldehyde 13.6 ml of diisopropyl ethylamine were added to a suspension of 18 g of the product of Step A in 50 ml of dichloromethane and the mixture was cooled. Then, 39.6 ml of chloro-(2-methoxy-ethoxy)-methane were added over 45 minutes and was then stirred for two hours at 0° C. and diluted with 100 ml of water and separated. The organic phase was washed, dried, concentrated and chromatographed on silica, eluting with a dichloromethane-acetone mixture (9-1) to obtain 22.1 g of the expected product with a Rf=0.3.

Infrared analysis (CHCl$_3$):
1704 cm$^{-1}$: CH=O
1608, 1578, 1546, 1196 cm$^{-1}$: aromatic ring+—NO$_2$
NMR analysis of the Proton (CDCl$_3$ 300 MHz in ppm):
3.36 and 3.38: —OC$\underline{H}_3$
3.55 (m), 3.87 (m): O—C$\underline{H}_2$—C$\underline{H}_2$—O
5.41: O—C$\underline{H}_2$—O
7.92: Ar—$\underline{H}$
9.93: —C$\underline{H}$=O

PREPARATION 6

3-iodo-4,5-bis[(2-methoxy-ethoxy)-methoxy] benzaldehyde

STEP A: 3-iodo-4,5-dihydroxy benzaldehyde 37.2 g of 5-iodo vanillin (commercial) and 360 ml of dichloromethane were mixed together under nitrogen and the mixture was cooled to 0° C. 135 ml of a molar solution of boron tribromide in dichloromethane were added and the mixture stood for 16 hours at ambient temperature and was then concentrated, cooled to 0° C. and acidified. The crystallized product was separated out, washed with water, dried and crystallized from an isopropanol-water mixture (1-2 by volume) to obtain 23.4 g of the expected product.

Infrared analysis (Nujol):
general absorption NH/OH
1662 (m) 1640 (F) cm$^{-1}$: C=O
1588, 1578, 1516 cm$^{-1}$: aromatic ring
NMR analysis of the proton (DMSO 250 MHz in ppm):
7.25 (sl) and 7.44 (sl): Ar—$\underline{H}$
9.68 (m): —C$\underline{H}$=O
10.46, 1043 cm$^{-1}$: mobile absorption

STEP B: 3-iodo-4,5-bis[(2-methoxy-ethoxy)-methoxy] benzaldehyde 67 ml of diisopropyl ethylamine were added to a suspension of 25.4 g of the product of Step A in 640 ml of dichloromethane and the mixture was cooled to 10° C. Then, 44 ml of chloro-(2-methoxy-ethoxy)-methane were added over 45 minutes and the mixture was stirred for half an hour, diluted with 100 ml of water and was separated. Then, the organic phase was washed, dried, concentrated and chromatographed on silica, eluting with an ethyl acetate-hexane mixture (1/1) to obtain 25.5 g of the expected product.

Infrared analysis (CHCl$_3$):
Absence of OH
1698 and 2730 cm$^{-1}$: CH=O
1588, 1562, cm$^{-1}$: aromatic ring
NMR analysis of the proton (CDCl$_3$ 250 MHz in ppm):
3.38 (sl) (6H): —OC$\underline{H}_3$
3.58 (m) (4H), 3.84 (m) (2H) and 4.05 (m) (2H): O—C$\underline{H}_2$—C$\underline{H}_2$—O
5.33 (sl) and 5.39 (sl): O—C$\underline{H}_2$—O
7.68 (sl) and 7.96 (sl): Ar—$\underline{H}$
9.82: —C$\underline{H}$=O

PREPARATION 7

3,4,5-tris[(2-methoxy-ethoxy)-methoxy) benzaldehyde 52 ml of diisopropyl ethylamine were added to a suspension of 8 g of 3,4,5-trihydroxy benzaldehyde (commercial) in 160 ml of dichloromethane and the mixture was cooled to 0° to 5° C. Then, 35 ml of chloro-(2-methoxy-ethoxy)-methane were added over one and a half hours and the mixture was stirred, diluted with 100 ml of water and separated. The organic phase was washed, dried and concentrated to obtain 21.75 g of crude product which was used as is for what follows.

Infrared analysis (CHCl$_3$):
Absence of OH
1696 cm$^{-1}$: CH=O
1590, 1498 cm$^{-1}$: aromatic ring
NMR analysis of the proton (CDCl$_3$ 250 MHz in ppm):
3.36 and 3.38 (9H): —OC$\underline{H}_3$
3.57 (m) (6H), 3.85 (m) (4H) and 3.99 (m) (2H): —O—C$\underline{H}_2$—C$\underline{H}_2$—O
5.31 (w) (2H) and 5.34 (s) (4H): O—C$\underline{H}_2$—O
7.43 (s): Ar—$\underline{H}$
9.82: —C$\underline{H}$=O
5.31 (w) (2H) and 5.34 (s) (4H): O—C$\underline{H}_2$—O
7.43 (s): Ar—$\underline{H}$
9.82: —C$\underline{H}$=O

PREPARATION 8

2,5-dichloro-3,4-bis[(2-methoxy-ethoxy)-methoxy] benzaldehyde

STEP A: 2,5-dichloro-3,4-dihydroxy benzaldehyde 27.6 g of 3,4-dihydroxy benzaldehyde (commercial) were dissolved in 300 ml of acetic acid and chlorine was bubbled through the solution at an ordinary temperature until 31.24 g of the gas had been consumed. The mixture was stirred for 42 hours and then was concentrated, cooled to 0° C. The precipitate was filtered, washed and dried to obtain 13.7 g of the expected product melting at 176° to 178° C. with a Rf=0.1 [eluant: ethyl acetate-cyclohexane (5-5)].

NMR analysis of the proton (DMSO 250 MHz in ppm):
7.24 (d J=2 Hz) and 7.44 (d J=2H): Ar—H
9.90 (m): —CH=O
10.40: mobile absorption STEP B: 2,5-dichloro-3,4-bis[(2-methoxy-ethoxy)-methoxy] benzaldehyde 60.5 ml of diisopropyl ethylamine and then 11.27 ml of chloro(2-methoxy-ethoxy)-methane were added to a solution of 6.83 g of the product of Step A in 265 ml of acetonitrile. The mixture was stirred for two hours at 35° C. and was evaporated to dryness. The residue was taken up in dichloromethane, washed, dried and the solvent was evaporated. Chromatography was carried out on silica, eluting with an ethyl acetate-cyclohexane mixture (6-4) to obtain 10.9 g of the expected product melting at 50° C. with a Rf=0.3.

Infrared analysis (PE 580):
1690 cm⁻¹: CH=O
1572, 1551 cm⁻¹: aromatic ring

NMR analysis of the proton (CDCl₃ 250 MHz in ppm):
3.37 and 3.38: —OCH₃
3.58 and 4.01 (m) (2H): O—CH₂—CH₂—O
5.29 and 5.36 (s): O—CH₂—O
7.78 (s): Ar—H
10.36 (s): —CH=:

PREPARATION 9

3-methoxy-4,5-bis[(2-methoxy-ethoxy)-methoxy] benzaldehyde 34 ml of diisopropyl ethylamine were added to a suspension of 8 g of 3,4-dihydroxy-5-methoxy benzaldehyde (commercial) in 80 ml of dichloromethane and the mixture was cooled to −5° C. to −10° C. Then, 23 ml of chloro-(2-methoxy-ethoxy)-methane were added over half an hour and the mixture was stirred for 16 hours. The organic phase was washed, dried, filtered, concentrated and chromatographed on silica, eluting with a hexane-ethyl acetate mixture (50-50) to obtain the expected product with a Rf=0.4 [eluant: hexane-ethyl acetate (30-70)].

Infrared analysis (CHCl₃ on PE 580):
Absence of OH
1696 cm⁻¹: CH=O
1558, 1498 cm⁻¹: aromatic ring NMR analysis of the proton (CDCl₃ 250 MHz in ppm):
3.36 (s) (3H) and 3.38 (s) (3H): O—CH₂—CH₂—OCH₃
3.57 (m) (4H), 3.87 (m) (2H) and 4.00 (m) (2H): O—C H₂—CH₂—O
3.90 (s) (3H): Ar—OCH₃
5.31 (s) (2H) and 5.35 (s) (2H): O—CH₂—O
7.19 (d J=2 Hz) (1H) and 7.38 (d J=2 Hz) (1H): Ar—H in the meta position
9.80 (s) (1H): —CH=O

PREPARATION 10

1-[3-[7β-[oxo-[2-[(triphenylmethyl)-amino]-thiazol-4-yl]-acetamido]-2-[(4-methoxy-benzyloxy)-carbonyl]-8-oxo-5-thia-1-azabicyclo[4,2,0] [oct-2-en-3-yl]-2-propenyl]-thieno-[2,3-b] pyridinium iodide STEP A: 4-methoxy-benzyl 7β-[oxo-[2-[(triphenylmethyl)-amino]-thiazol-4-yl]-acetamido]-3-[(Z+E)-3-chloro-1-propenyl]-8-oxo-5-thia-1-azabicyclo-[4,2,0]-oct-2-en-2-carboxylate 5 g of 4-methoxy benzyl 7β-amino-3-[(Z)-3-chloro-1-propenyl]-8-oxo-5-thia-1-azabicyclo-[4,2,0]-oct-2-en-2-carboxylate hydrochloride (European Patent Application No. 0,333,154) and 0.72 g of oxo-[2-[(triphenylmethyl)-amino]-thiazol-4-yl] acetic acid (Belgian Patent Application No. 864,828) in 200 ml of dichloromethane were stirred under nitrogen and the mixture was cooled to 0° C. Then, 2.315 g of 1-(3-dimethylamino-propyl)-3-ethyl carbodiimide (EDC) were added, followed by stirring for 40 minutes, washing and drying. The solvents were evaporated and the residue was chromatographed, eluting with a dichloromethane-isopropyl ether mixture (9-1) to obtain 5.51 g of the expected product with a Rf=0.3.

STEP B: 4-methoxy benzyl 7β-[oxo-[2-[(triphenylmethyl)-amino]-thiazol-4-yl]-acetamido]-3-[(Z+E)-3-iodo-1-propenyl]-oxo-5-thia-1-azabicyclo-[4 2.0]-oct-2-en-2-carboxylate 5.5 g of the product of Step A were dissolved in 110 ml of acetone and 3.094 g of sodium iodide were added. The mixture was stirred for one and a half hours at 20° C. and the solvent was evaporated. The residue was taken up in 350 ml of dichloromethane, washed, dried, filtered and brought to dryness. The foam was filtered and the residue was chromatographed, eluting with a dichloromethane-isopropyl ether mixture (90-10) to obtain 3.93 g of the expected iodine with a Rf=0.3.

Infrared analysis (CHCl₃)
1786, 1721, 171 and 1633 cm⁻¹: C=O and β-lactam
1613, 1586, 1535, 1516 cm⁻¹: aromatic+conjugated system
NMR analysis of the proton (CDCl₃ 300 MHz in ppm):
3.57: —S—CH₂—C(C=CH—)=C—3.82 (s): Ar—OC H₃, 3.98 (d, J=8): —CH=CH—CH₂—I
5.03 (d J=5) ppm: CO—NH—CH(C=O)—C H—(N—)—S—
5.25 (AB, J=12): CO—O—CH₂—Ar
5.75: CO—NH—CH(C=O)—CH(N—)—S—
6.14 (dt, J=16 and 8) ppm: —C=CH—CH₂—I E isomerism
6.8 to 7.4 (m): —S—CH=C(C=N—)—N=C(NH-trityl)- and Ar—H of trityl
8.19 (d): CO—CO—NH—CH(C=O)—CH(N—)—S—

STEP C: 1-[3-[7β-[oxo-[2-[(triphenylmethyl)-amino]-thiazol-4-yl]- acetamido]-2-[(4-methoxy-benzyloxy)-carbonyl]-8-oxo-5-thia-1-azabicyclo-[4, 2,0]-[oct-2-en-3-yl]-2-propenyl]-thieno-[2,3-b]-pyridinium iodide 3.93 g of the iodine derivative of Step B mixed with 6 g of thieno-[2,3-b]-pyridine were stirred for one and a half hours at 20° C. and the mixture was precipitated from 400 ml of ether, filtered and dried under vacuum to obtain 4.12 g of the desired product with a Rf=0.1 [eluant: dichloromethane-methanol (92-8)].

Analysis: $C_{49}H_{40}IN_5O_6S_3$ Calculated: %C 57.81 %H 3.96 %I 12.46 %N 6.87 % 9.44 Found: 57.3 3.9 11.7 6.7 9.6

NMR analysis of the proton ($CDCl_3$, 300 MHz in ppm):
5.02 (d): CO—NH—CH(C=O)—C$\underline{H}$—(N—)—S—
5.27 (s): —CO—O—C$\underline{H}_2$—Ar
5.6 (dd): —C$\underline{H}$=CH—C$\underline{H}_2$—N$^+$
5.74 (dt): CO—NH—C$\underline{H}$(C=O)—CH(N—)—S—
6.56 (d): —CH=C$\underline{H}$—CH$_2$—N$^+$ E isomerism
7.3: Ar—$\underline{H}$ of the trityl
8.3 : —S—C$\underline{H}$=C(C=N—)—N=C(NH$_2$)—
7.89 (d): $\underline{H}$ in position 2 of thieno-[2,3-b]-pyridinium 7.71 (d): $\underline{H}$ in position 3 of thieno-[2,3-b]-pyridinium 8.8 (d): $\underline{H}$ in position 4 of thieno-[2,3-b]-pyridinium 8.10 (m): $\underline{H}$ in position 5 of thieno-[2,3-b]-pyridinium.

PREPARATION 11

[4-fluoro-(2,3-bis-hydroxy)-phenyl]-hydroxy acetic acid 51.2 g of 3-fluorocatechol and 36.8 g of glyoxylic acid were dissolved at 20° C. in 160 ml of water and 34.8 g of sodium hydroxide in solution in 400 ml of water were added to this solution cooled to 0° C. The mixture was heated for 4 hours at 46° C., then cooled to 0° C. and the pH was brought to 4.6 by the addition of concentrated hydrochloric acid. Extraction was carried out with ethyl ether (after evaporation 14.7 g of the starting 9-fluorocatechol were collected) and the aqueous phase was acidified with concentrated hydrochloric acid until a pH of 1.8 was obtained. Extraction was carried out with ethyl acetate and after evaporation of the solvent, 47.7 g of the desired product were obtained (mixture of isomers, 2,3-bis-hydroxy-4-fluoro; 3,4-bis-hydroxy-5-fluoro; 2-fluoro-3,4-bis-hydroxy) which was used as is in Step A of Example 16.

PREPARATION 12

3-bromo-4,5-bis-[(2-methoxyethoxy)-methoxy] benzaldehyde

Using the procedure of preparation 4,5-bromo-vanillin was reacted to obtain the expected compound which was used in Example 15.

EXAMPLE 1

Internal salt of [6R-[3(E), 6α,7β (Z)]]-1-[3-[7-[[2-amino-4-thiazolyl) [carboxy-(2-chloro-3,4-dihydroxy-phenyl]-methoxy]-imino]acetamido]-2-carboxy-8-oxo-5-thia-1-azabicyclo-[4,2,0]-oct-2-en-3-yl]-2-propenyl]-quinolinium STEP A: [2-chloro-3,4-bis-[(2-methoxy-ethoxy)-methoxy]-phenyl]-hydroxy acetic acid 2.42 g of lithium chloride and 7.02 g of potassium hydroxide were dissolved in 30 ml of water at 0° C. and a solution of 10 g of 2-chloro-3,4-bis-[(2-methoxy-ethoxy)-methoxy] benzaldehyde (synthesized in Preparation 1), 2.8 ml of bromoform and 38 ml of dioxane were added to this mixture. The mixture was stirred for 24 hours at 0° C. and then another 2.8 ml of bromoform were added. The mixture stood for 16 hours and after dilution with 100 ml of water, the solution was washed with ether, decanted, cooled to 0° C. and acidified until the pH was 2.5–3. Extraction was carried out with ether and the organic phase was washed with water and dried. The solvent was driven off to collect 11.4 g of the desired product in the form of an oil with a Rf=0.1 [eluant: methylene chloride-methanol-acetic acid (89-10-1)].

Infrared analysis ($CHCl_3$):
General absorption in the —OH region (acid+associated OH)
1726 cm$^{-1}$ complex: C=O of the acid function 1598–1489 cm$^{-1}$: aromatic nucleus NMR analysis of the proton ($CDl_3$ 250 MHz in ppm):
3.37 (1) (6H): —OC$\underline{H}_3$
3.57 (m) (4H), 3.81 (m) (2H) and 4.01 (m) (2H): O—C$\underline{H}_2$—O
5.25 (m) (4H) and 5.52 (sl) (1H): —O—C$\underline{H}_2$—O and Ar—C$\underline{H}$—CO
7,.11 (sl) (2H): Ar—$\underline{H}$.

STEP B; Diphenylmethyl [2-chloro-3,4-bis-[(2-methoxy-ethoxy)-methoxy]-phenyl]-hydroxy acetate 11.4 g of the acid of Step A were dissolved at ambient temperature under nitrogen in 120 ml of dichloromethane and then 120 ml of a 0.3 molar solution of diphenyl diazomethane in dichloromethane were added at 15° C. The mixture was stirred for 16 hours at ambient temperature and then 30 ml of water were added, followed by decanting and acidifying with 309 ml of acetic acid, washing with a saturated solution of sodium bicarbonate, drying and evaporating the solvents. After chromatography on silica, eluting with an ethyl acetate-hexane mixture (60-40), 8.1 g of the desired product were obtained.

Infrared analysis ($CHCl_3$):
3528 cm$^{-1}$: non-phenolic —OH
1734 cm$^{-1}$: C=O of the ester function
1597, 1496, 487 cm$^{-1}$: aromatic nucleus NMR analysis of the proton ($CDCl_3$ 300 MHz in ppm):
3.36 (s): —OC$\underline{H}_3$
3.55 (s) (4H), 3.82 (s) (2H) and 4.03 (s) (2H): —O—C$\underline{H}_2$—C$\underline{H}_2$—O
5.27 (s) and 5.29 (s): —O—C$\underline{H}_2$—O
5.67 (d after exchange): Ar—C$\underline{H}$(C=O)—OH
6.88 (s): CO—O—C$\underline{H}$Ar$_2$
7.0 (masked) and 7.08 (d): coupled Ar—$\underline{H}$ (ortho of the tetra-substituted ring 7.00 (2H), 7.18 (3H) and 7.30 (s) (5H): Ar—$\underline{H}$ STEP C: Diphenylmethyl [2-chloro-3,4-bis-[(2-methoxy-ethoxy)-methoxy]-phenyl]-phthalimidoxy acetate 2.47 g of N-hydroxy phthalimide and 7.55 g of triphenyl phosphine were added to a solution of 8.1 g of the ester of Step B in 90 ml of tetrahydrofuran and the mixture was cooled to 10° C. Then 3.88 ml of diethyl azodicarboxylate (DEAD) were poured into it and the mixture was stirred for 16 hours. After concentration of the solvents and chromatography on silica, eluting with an ethyl acetate-hexane mixture (60-40), 6.27 g of the desired product were obtained in the form of an oil with a Rf=0.25.

Infrared analysis ($CHCl_3$):
1739, 1755 (sh) and 1795 cm$^{-1}$: C=O
1597, 1489 cm$^{-1}$: aromatic nucleus NMR analysis of the proton ($CDCl_3$ 300 MHz in ppm):
3.33 and 3.37: —OC$\underline{H}_3$
3.54 (m) (4H), 3.82 (m) (2H) and 3.92 (m) (2H): O—C$\underline{H}_2$—CH$_2$—O—
5.22 (AB sys.) and 5.30 (AB sys.): —O—CH$_2$—O 6.50: Ar—CH(C=O)—O—
6.93 (s) ppm: CO—O—CH—Ar₂
7.09 (d), 7.41 (d): coupled Ar—H (ortho of the tetra-substituted ring)
7.44 (d) (4H): Ar—H of the phthalimido
7.05 to 7.33 ppm: Ar—H aromatics STEP D: Diphenylmethyl aminoxy (2-chloro-3,4-bis-[(2-methoxy-ethoxy)-methoxy]-phenyl] acetate 6.27 g of the product of Step C were dissolved in 65 ml of ethanol and the solution was cooled to 5° C. Then 0.47 ml of hydrazine hydrate were added and the mixture stood at 5° C. for half an hour and then was returned to ambient temperature for 2 hours. After filtration, evaporation of the solvent and chromatography on silica, eluting with ethyl acetate, 3.64 g of the desired product were obtained in the form of an oil with a Rf=0.3.

Analysis: $C_{29}H_{34}ClNO_9$ Calculated: %C 60.46 %H 5.95 %N 2.43 Found: 60.1 6.1 2.6

Infrared analysis ($CHCl_3$):
3235 cm⁻¹: —NH₂
1738 cm⁻¹: C=O of the ester function
1598, 1572, 1490 cm⁻¹: aromatic nucleus+NH₂

STEP E: [[[1-[2-chloro-3,4-bis-[(2-methoxy-ethoxy)-methoxy]-phenyl]-2-oxo-2-(diphenylmethoxy)-ethyl]-oxy]-imino] [2-[(triphenylmethyl)-amino]-thiazol-4-yl] acetic acid 0.69 g of the product of Step D and 0.496 g of oxo-[2-[(triphenylmethyl)-amino]-thiazol-4-yl] acetic acid (Belgian Patent Applicaton No. 864,828) were stirred for 3 hours under nitrogen and at ambient temperature in the presence of 7 ml of methanol and then the solvent was eliminated. The residue was chromatographed on silica, eluting with a methylene chloride-methanol mixture (95-5) to obtain 0.726 g of the expected product with a Rf=0.3 [eluant: $CHCl_2$—MEOH (90-10)].

Analysis: $C_{53}H_{50}ClN_3O_{11}S$ Calculated: %C 65.45 %H 5.18 %N 4.32 %S 3.29 %Cl 3.64 Found: 3 3.7 5.1 4.2 3.2 3.1

STEP F: 4-methoxy-benzyl 7β-[[[[1-[2-chloro-3,4-bis-[(2-methoxy-ethoxy)-methoxy]-phenyl]-2-oxo-2-(diphenylmethoxy)-ethyl]-oxy]-imino]-[2-[(triphenylmethyl)-amino]-thiazol-4-yl]-acetamido]-3-[(Z)-3-chloro-1-propenyl]-8-oxo-5-thia-1-azabicyclo-[4,2,0]-oct-2-en-2-carboxylate 0.322 g of 4-methoxy-benzyl 7β-amino-3-[(Z)-3-chloro-1-propenyl]-8-oxo-5-thia-1-azabicyclo-[4,2,0]-oct-2-en-2-carboxylate hydrochloride (European Patent Application No. 0,333,154) and 0.72 g of the product of Step E were stirred in 10 ml of dichloromethane and the mixture was cooled to 5° C. Then, 0.1803 g of 1-(3-dimethylamino-propyl)-3-ethyl carbodiimide (EDC) were added, and the mixture was stirred for half an hour. Then, the mixture was treated with 10 ml of potassium hydrogenophosphate in 10 ml of methylene chloride, followed by decanting, washing and drying and evaporating the solvents to obtain 0.670 g of the expected product with a Rf=0.43 [eluant: methylene chloride-ethyl acetate (80-20)].

STEP G: 4-methoxy-benzyl 7β-[[[[1-[2-chloro-3,4-bis-[(2-methoxy-ethoxy)-methoxy]-phenyl]-2-oxo-2-(diphenylmethoxy)-ethyl]-oxy]-imino] 2-[(triphenylmethyl)-amino]-thiazol-4-yl]-acetamido]-3-[(Z)-3-iodo-1-propenyl]-8-oxo-5-thia-1-azabicyclo[1-4,2,0]-oct-2-en-2-carboxylate 0.67 g of the product of Step F in 10 ml of acetone and 0.223 g of sodium iodide were stirred for one hour at ambient temperature in the presence of an iodine crystal. After elimination of the solvent, the residue was taken up in methylene chloride and the organic phase was washed and dried. The solvent was eliminated and crystallization was carried out from isopropyl ether to obtain 0.579 g of the iodated product with a Rf=0.27 [eluant: methylene chloride-methanol (90-10)].

STEP H: 1-[3-[7-[[[[1 [2-chloro-3,4-bis-[(2-methoxy- ethoxy)-methoxy]-phenyl]-2-oxo-2-(diphenylmethoxy)-ethyl]-oxy]-imino] [2[(triphenylmethyl)-amino]-thiazol-4-yl]-acetamido]-2-[(4-methoxy-benzyloxy)-carbonyl]-8-oxo-5-thia-1-azabicyclo[4,2,0] [oct-2-en-3-yl]-2-propenyl]-quinolinium iodide 0.572 g of the product of Step G were dissolved in 6 ml of methylene chloride and 0.234 g of quinoline were added. The mixture was stirred for one hour and the solvent was evaporated. The residue was taken up in ether, followed by crystallization and separation, and chromatography was carried out on silica, eluting with a methylene chloride-methanol mixture (9-1) to obtain 0.235 g of the expected product with a Rf=0.27 [eluant: methylene chloride-methanol (90-10)].

NMR analysis of the proton ($CDCl_3$ 250 MHz; ppm):
3.31 to 3.34: —OCH₃
3.73 (s): Ar—O—CH₂
3.42 to 4.01: CH₂—S and O—CH₂—CH—O
4.92 (m): —CH(N—)—S—
5.84 (m): —NH—CH—C—
5.20 to 5.30: —O—CH₂—O and COO—CH₂—Ar
5.93 to 6.15: =C—CH₂—N⁺
6.40 to 6.55: =CH—CH₂— E isomerism and O—C H—Ar resolved 6.76: H in position 5 of the thiazole ring
6.86 to 7.42: —CH—Ar, COO—CHAr₂, =C—C H=CH— E isomerism
8.05 to 8.25 (3H), 8.37 (m) (1H), 8.92 (d (resolved)) (1H), and
10.4 (d): hydrogens of the quinoline ring
7.83 and 8.27: —CO—NH—

STEP I: Internal salt of [6R-[3(E), 6α,7β-(Z)]]-1-[3-[7-[[(2-amino-4-thiazolyl)-[carboxy-(2-chloro-3,4-dihydroxy-phenyl)-methoxy]-imino]-acetamido]-2-carboxy-8-oxo-5-thia-1-azabicyclo[4,2,0] oct-2-en-3-yl]-2-propenyl]-quinolinium isomer (R) and isomer (S)

A mixture of 0.235 g of the product of Step H and 5 ml of trifluoroacetic acid containing 10% anisole was stirred for 90 minutes at ambient temperature. After the addition of ether, the mixture was subjected to ultrasonics, followed by filtration, washing and drying for 16 hours under vacuum at ambient temperature to obtain 0.118 g of the desired internal salt.

Analysis: $C_{32}H_{25}ClN_6O_9S_2+1.5$ $C_2HF_3O_2+0.5$ HI; molecular weight=1014 Calculated: %C 43.81 %H 2.88 %N 8.28 %Cl 3.49 %S 6.32 %F 8.42 %I 6.25 Found: 44.1 2.7 8.5 4.1 6.7 8.5 6.0

NMR analysis of the proton (DMSO 300 MHz in ppm):
—S—CH₂—C(C=CH—)=C— masked by the water of DMSO
5.15 (resolved d) ppm: CO—NH—CH(C=O)—C H—(N—)—S—
5.72 to 5.89 (4H): CO—NH—C H(C=O)—CH(N—)—S—, Ar—CH(CO—O—)—O— and —CH=CH—CH₂—N⁺

6.38 (m) ppm: —CH=CH—CH₂—N⁺ E isomerism
6.7 to 6.82: —S—CH=C(C=N—)—N=C(NH₂)— and Ar—H of the catechol
6.98 ppm (d J=15.5): —CH=CH—CH₂—N⁺ E isomerism
7.30: NH₂
8.06 (t) (1H), 8.25 (m) (2H), 8.54 (m) (2H) and 9.34 (d) (1H):
Ar—H of the quinoline
9.29 (sl) and 9.94 (sl): mobile H's
9.47 (d) and 9.58 (d): Ar—H and —CO—N H—CH(C=O)—CH(N—)—S—

EXAMPLE 2

The internal salt of [6R-[3(E), 6α,7β-((Z)]]-1-[3-[7-[[(2-amino-4-thiazolyl) [carboxy-(3-cyano-4,5-dihydroxy-phenyl)-methoxy]-imino]-acetamido]-2-carboxy-8-oxo-5-thia-1-azabicyclo-[4,2,0] oct-2-en-3-yl]-2-propenyl]-quinolinium (R) or (S) or an (R+S) mixture

STEP A: [3-cyano-4,5-bis[-(2-methoxy-ethoxy)-methoxy]-phenyl]-hydroxy acetic acid Using the procedure of Step A of Example 1, 6.2 g of the product of Step C of preparation 2, 4.4 g of potassium hydroxide, 3.15 g of lithium bromide, 1.7 ml of bromoform and 15 ml were reacted and after stirring for 48 hours at –5° C., 7.2 g of crude acid were obtained which, after chromatography on silica eluting with a dichloromethane-methanol-acetic acid mixture (90-7-3), yielded 3.42 g of the desired product with a Rf=0.3 [eluant: methylene chloride-methanol-acetic acid (91-07-3)].

Infrared analysis (CHCl₃):
General absorption in the —OH region (acid+associated OH)
1721 cm⁻¹ max+1750 cm⁻¹ sh.: C=O of the acid function
2235 cm⁻¹
1602–1586–1489 cm⁻¹: aromatic nucleus

STEP B: Diphenylmethyl [3-cyano-4,5-bis-[(2-methoxy-ethoxy)-methoxy]-phenyl]-hydroxy acetate 8.5 g of the acid of Step A were dissolved at ambient temperature under nitrogen in 100 ml of dichloromethane and then 75 ml of a 0.3 molar solution of diphenyl diazomethane in ether were added at 15° C. The mixture was stirred for 16 hours at ambient temperature and then 30 ml of water were added, followed by decanting and acidifying with 30 ml of acetic acid, washing with a saturated solution of sodium bicarbonate, drying and evaporating the solvents. After chromatography on silica and eluting with an ethyl acetate-hexane mixture (50-50), 4.2 g of the desired product with a Rf=0.3 were obtained.

Infrared analysis (CHCl₃):
3525 cm⁻¹: non-phenolic —OH
2235 cm⁻¹: C=N
1732 and 1750 cm⁻¹: C=O of the ester function
1600, 1535, 1495, 1490 cm⁻¹: aromatic nucleus NMR analysis of the proton (CDCl₃ 300 MHz in ppm):
3.32 to 3.47: —OCH₃
3.58 and 3.72: O—CH₂—CH₂—O
5.15 to 5.40: —OCH₂—O and Ar—CH(C=O)—OH
6.89 (s): CO—O—CHAr₂
7.24 to 7.50: Ar—H

STEP C: Diphenylmethyl [3-cyano-4,5-bis-[(2-methoxy-ethoxy)-methoxy-phenyl]-phthalimidoxy acetate 0.134 g of N-hydroxy phthalimide and 0.409 g of triphenyl phosphine were added to a solution of 0.430 g of the ester of Step B in 10 ml of tetrahydrofuran and the mixture was cooled to –10° C. Then, 0.21 ml of diethyl azodicarboxylate (DEAD) was poured in and the mixture was stirred for 16 hours. After concentrating the solvents and chromatography on silica eluting with a dichloromethane-acetone mixture (95-5), 0.2 g of the desired product in the form of an oil and with a Rf=0.25 [eluant: dichloromethane-acetone (97-3)] were obtained.

Infrared analysis (CHCl₃):
1792 (m), 1775 (sh) 1760 (sh) and 1738 (max) cm⁻¹: C=O
2230 cm⁻¹: C=N
1604, 1586, 1490 cm⁻¹: aromatic nucleus

STEP D: Diphenylmethyl-aminoxy [3-cyano-4,5-bis-[(2-methoxy-ethoxy)-methoxy]-phenyl] acetate 2.7 g of the product of Step C were dissolved under nitrogen in 80 ml of ethanol and the solution was cooled to –2° C. Then, 0.20 ml of hydrazine hydrate were added and the mixture was held at –2° C. for half an hour, then returned to ambient temperature for one hour. After filtration, evaporation of the solvent and chromatography on silica eluting with an ethyl acetate-hexane mixture (7-3) yielded 1.8 g of the desired product in the form of an oil with a Rf=0.25.

Analysis: C₃₀H₃₄N₂O₉ Calculated: %C 63.53 %H 6.04 %N 4.94 Found: 63.3 6.4 4.6

Infrared analysis (CHCl₃):
3335 cm⁻¹: O—NH₂
2230 cm⁻¹: C=N
1748 cm⁻¹: C=O of the ester function
1600, 1588, 1488 cm⁻¹: aromatic nucleus+NH₂

STEP E: [[[1-[3-cyano-4,5-bis-[(2-methoxy-ethoxy)-methoxy]-phenyl]-2-oxo-2-(diphenylmethoxy)-ethyl]-oxy]-imino] [2-[(triphenylmethyl)-amino]-thiazolyl] acetic acid 0.650 g of the product of Step D and 0.428 g of oxo-[2-[(triphenylmethyl)-amino]-thiazol-4-yl]-acetic acid (Belgium Patent Application No. 864,823) were stirred for 2 hours under nitrogen at ambient temperature in the presence of 6 ml of methanol. The solvent was eliminated and the residue was taken up in ether. Filtration was carried out and the filtrate was chromatographed on silica, eluting with a methylene chloride-methanol mixture (95-5) to obtain 0.841 g in total of the expected product melting at 158° C.

Infrared analysis (CHCl₃):
3402 cm⁻¹: =C—NH
General absorption OH/NH
2235 cm⁻¹: C=N
1755 (sh), 1740 (max) and 1717 (sh) cm⁻¹: C=O
1587, 1531 1509 and 1490 cm⁻¹: aromatic, heterocycle, conjugated system NMR analysis of the proton (in ppm):
3.36 (s) and 3.43 (s): —OCH₃
3.55 to 3.90 (m) (6H) and 4.05 (m) (2H): O—CH₂—CH₂—O
5.03 (d), 5.12 (d) and 5.33 (d): —O—CH₂—O
5.85 (S): Ar—CH(C=O)—O—
6.68 (s): CO—O—CHAr₂,
6.87 (s): —S—CH=C(C=N)—N
7.10 to 7.36 (massive) (27H), 7.67 (d) (1H): Ar—H

STEP F: 4-methoxy benzyl 7β-[[[[1-[3-cyano-4,5-bis-[(2-methoxy-ethoxy)-methoxy]-phenyl]-2-oxo-2-(diphenyl methoxy)-ethyl]-oxy]-imino] [2-(triphenyl methyl)-amino]-thiazol-4-yl]-acetamido]-3-[(Z)-3-chloro-1-propenyl]-8-oxo-5-thia-1-azabicyclo-[4,2,0]-oct-2-en-2-carboxylate 0.160 g of 4-methoxy-benzyl 7β-amino-3-[(Z)-3-chloro-1-propenyl]-8-oxo-5-thia-1-azabicyclo-[4,2,0]-oct-2-en-2- carboxylate hydrochloride (European Patent Application No. 0.333,154) and 0.36 g of the product of Step E in 5 ml of dichloromethane were stirred and cooled to 5° C. Then, 0.0893 g of EDC were added and the mixture was stirred for 15 minutes, then treated with 15 ml of potassium hydrogenophosphate in 8 ml of dichloromethane, decanted, washed and dried. The solvents were evaporated and after chromatography on silica, eluting with a dichloromethane-ethyl acetate mixture (8-2) yielded. 0.349 g of the expected product with a Rf=0.4 [eluant: dichloromethane-ethyl acetate (8-2)].

STEP G: 4-methoxy-benzyl 7β-[[[[1-[3-cyano-4,5-bis-[(2-methoxy-ethoxy)-methoxy]-phenyl]-2-oxo-2-(diphenyl methoxy)-ethyl]-oxy]-imino] 2-[(triphenylmethyl)-amino]-thiazol-4-yl]-acetamido]-3-[(Z)-3-iodo-1-propenyl]-8-oxo-5-thia-1-azabicyclo-[4,2,0]-oct-2-en-2-carboxylate 0.573 g of the product of Step F in 7 ml of actone and 0.192 g of sodium iodide were stirred for one hour at ambient temperature in the presence of an iodine crystal. After elimination of the solvent, the residue was taken up in dichloromethane and the organic phase was washed and dried. The solvent was eliminated and the residue was crystallized from isopropyl ether to collect 0.463 g of the iodated product with a Rf=0.30 [eluant: dichloromethane methanol (9-2)].

STEP H: 1-[3-[7-β-[[[[1-[3-cyano-4,5-bis-[(2-methoxy-ethoxy)-methoxy]-phenyl]-2-oxo-2-(diphenylmethoxy)-ethyl]-oxy]-imino] [2-(triphenylmethyl)-amino]thiazol-4-yl]-acetamido]-2-[(4-methoxy-benzyloxy)-carbonyl]-8-oxo-5-thia-1-azabicyclo-[4,2,0] [oct- 2-en-3-yl]-2-propenyl]-quinolinium iodide 0.463 g of the product of Step G were dissolved in 4 ml of dichloromethane and 0.191 g of quinoline was added. The mixture was stirred for one hour, and the solvent was evaporated. The residue was taken up in ether and crystallized and separation was carried out followed by chromatography on silica. Elution with a dichloromethane-methanol mixture (97-3) yielded. 0.241 g of the expected product with a Rf=0.27.

NMR analysis of the proton (CDCl₃ 400 MHz in ppm): 3.25 (s), 3.27 (s) and 3.34: —OC$\underline{H}_3$
3.26 to 4.04: C$\underline{H}_2$—S and O—C$\underline{H}_2$—C$\underline{H}_2$—O
3.98 (s) Ar—O—C$\underline{H}_3$
4.90 to 5.08 and 5.15 to 5.40: —C$\underline{H}$(N—)—S—, =C—C$\underline{H}_2$—N⁺, —O—C$\underline{H}_2$—O and COO—C$\underline{H}_2$—Ar
5.75 to 6.05: N—C$\underline{H}$(C=O)—CH—(N—)—S— and —O—C$\underline{H}$(C=O)—Ar
6.38 (m) and 6.56 (m): =C$\underline{H}$—CH— E isomerism
6.73 (m): L —S—C$\underline{H}$—C(C=N)—N
6.80 to 7.50: trityl's, COO—C$\underline{H}$Ar₂,
7.9 to 8.56 (5H), 8.56 (d) and 8.87 (d) resolved in (1H), 10.27 (d) and 10.83 (d): hydrogens of the quinoline ring and —N$\underline{H}$—

STEP I: Internal salt of [6R-[3-(E), 6α,7β (Z)]]-1-[3-[7-[[(2-amino-4-thiazolyl) [carboxy-(3-cyano-4,5-dihydroxy-phenyl)-methoxy]-imino]-acetamido]-2-carboxy-8-oxo-5-thia-1-azabicyclo-[4,2,0] oct-2-en-3-yl]-2-propenyl]-quinolinium isomer (R) and isomer (S).

A mixture of 0.241 g of the product of Step H and 5 ml of trifluoroacetic acid containing 10% anisole was stirred for one and a half hours at ambient temperature. After the addition of ether, crystallizing, filtering, washing and drying for 16 hours under vacuum at ambient temperature, 0.128 g of the sought internal salt were obtained.

Analysis: $C_{33}H_{25}N_7O_9S_2$+1.4 $C_2HF_3O_2$+0.4 HI Calculated: %C 45.8 %H 2.87 %N 10.43 %S 6.83 %F 8.5 %I 5.4 Found: 44.1 2.7 8.5 7.0 8.0 4.1

NMR analysis of the proton (DMSO 300 MHz in ppm): 3.53 (d) and 3.74 (d): —S—C$\underline{H}_2$—C(C=CH—)=C—
5.14 (resolved d) ppm: CO—NH—CH—(C=O)—C$\underline{H}$—(N—)—S—
5.40 (s): Ar—C$\underline{H}$(CO—O—)—O—
5.76 (m) CO—NH—C$\underline{H}$—(C=O)—CH(N—)—S— to 5.89 (m): —CH=CH—C$\underline{H}_2$—N⁺,
6.34 (m) ppm: —CH=C$\underline{H}$—C$\underline{H}_2$—N⁺ E isomerism
6.76 (s) and 6.79 (s): —S—C$\underline{H}$=C(C=N—)—N=C(NH₂)—
6.98 ppm (d J=16): —C$\underline{H}$=CH—CH₂—N⁺ E isomerism
7.11 to 7.15 (m) (2H): Ar—$\underline{H}$
7.30 (m) and 10.38 (m): mobile H's
8.06 (t) (1H), 8.26 (m) (2H), 8.53 (m) (2H), 9.33 (d) and 9.58 (d): Ar—$\underline{H}$
9.60 (d) and 9.65 (d): —CO—NH—CH(C=O)—CH(N—)—S—

EXAMPLE 3

The internal salt of [6R-[3(E), 6α,7β-(Z)]]-1-[3-[7-[[(2-amino-4-thiazolyl) [carboxy-(3-fluoro-4,5-dihydroxy-phenyl)-methoxy]-imino]-acetamido]-2-carboxy-8-oxo-5-thia-1-azabicyclo-[4,2,0]-oct-2-en-3-yl]-2-propenyl]-quinolinium (R) or (S) or an (R+S) mixture STEP A: [3-fluoro-4,5-bis-[(2-methoxy-ethoxy)-methoxy]-phenyl]-hydroxy-acetic acid 0.662 g of lithium bromide and 3.6 g of potassium hydroxide were dissolved in 13 ml of water at 0° C. and a solution of 5.5 g of 3-fluoro-4,5-bis-[(2-methoxy-ethoxy)-methoxy benzaldehyde (synthesized in Preparation 3), 2.85 ml of bromoform and 13 ml of dioxane were added to this mixture. The mixture stood with stirring for 24 hours at 0° C. and then another 2.85 ml of bromoform were added. The mixture stood for one night and after dilution in water and washing with ether, decanting took place, followed by cooling to 0° C., acidifying until the pH was 2.5–3 and extracting with ether. The organic phase was washed with water, dried and the solvent was evaporated to obtain 5.3 g of the desired product in the form of an oil.

Infrared analysis (CHCl₃):

3600 cm⁻¹: —OH region (acid+associated OH)
1715 cm⁻¹ complex: C=O of the acid function
1616, 1595 and 1510 cm⁻¹: aromatic nucleus STEP B: Diphenylmethyl [3-fluoro-4,5-bis-[(2-methoxy-ethoxy)-methoxy]-phenyl]-hydroxy-acetate 5.3 g of the acid of Step A were dissolved in 66 ml of dichloromethane and then 46 ml of a solution of diphenyl diazomethane at 6.5 g in ether were added at 15° C. The mixture was stirred for 16 hours at ambient temperature and then water was added, followed by decanting and acidifying with acetic acid. Washing with a saturated solution of sodium bicarbonate, drying and evaporating the solvents yielded after chromatography on silica and eluting with an ethyl acetate-hexane mixture (50-50) 4.0 g of the desired product with a Rf=0.17.

Infrared analysis (CHCl$_3$):
3520 cm$^{-1}$: non-phenolic —OH
1735 cm$^{-1}$: C=O of the ester function
1615, 1595 and 1509 cm$^{-1}$: aromatic nucleus
NMR analysis of the proton (CDCl$_3$ 2500 MHz in ppm):
3.33 (s) and 3.37 (s): —OCH$_3$
3.46 (m), 3.57 (m), 3.78 (m) and 3.98 (m): O—CH$_2$—CH$_2$—O
5.19 to 5.30: —O—CH$_3$—O— and Ar—CH(C=O—O)—O—
6.87 (s): CO—O—CHAr$_2$
6.87 (m) (1H), 6.97 (m) (2H), 7.07 (m) (1H), 7.21 (m) (3H) and 7.32 (m) (5H): Ar—H STEP C: Diphenylmethyl [3-fluoro-4,5-bis-[(2-methoxy-ethoxy)-methoxy]-phenyl]-phthalimidoxy-acetate 0.77 g of N-hydroxy phthalimide and 2.42 g of triphenyl phosphine were added to a solution of 2.6 g of the ester of Step B in 28 ml of tetrahydrofuran, and after cooling to −10° C., 1.4 ml of diethyl azodicarboxylate (DEAD) were added dropwise into the resultant mixture. The mixture was stirred at 0° C. for one and a half hours. After concentration of the solvents and chromatography on silica, elution with a dichloromethane-acetone (95-5) mixture yielded 2.56 g of the desired product in the form of an oil with Rf=0.6 [eluant: dichloromethane-acetone (85-15)].

Infrared analysis (CHCl$_3$):
1794, 1752 and 1738 (max) cm$^{-1}$: C=O
NMR analysis of the proton (CDCl$_3$ 250 MHz in ppm):
3.34 (s) and 3.33 (s): —OCH$_3$
3.48 (m) (2H), 3.56 (m) (2H) 3.77 (m) (2H) and 3.96 (m) (2H):
O—CH$_2$—CH$_2$—O
5.22 (m) (4H): —O—CH$_2$—O
5.92 (s): Ar—CH(C=O—O)—O—
6.92 (s): CO—O—CHAr$_2$
7.00 to 7.35 (m): Ar—H
7.75 (m) (4H): Ar—H of the phthalimide STEP D: Diphenylmethyl aminoxy-[3-fluoro-4,5-bis-[(2-methoxy-ethoxy)-methoxy]-phenyl]-acetate 2.4 g of the product of Step C were dissolved under nitrogen in 25 ml of ethanol and the mixture was cooled to −5° C. Then, 0.38 ml of hydrazine hydrate were added and the mixture was held at −5° C. for two hours. After filtration, the solvent was evaporated and the residue was chromatographed on silica, eluting with a mixture of ethyl acetate-hexane (7-3) to obtain 1.67 g of the desired product in the form of an oil with a Rf=0.3.

Infrared analysis (CHCl$_3$):
3340 cm$^{-1}$: O—NH$_2$
1747 cm$^{-1}$: C=O of the ester function
1616, 1596, 1581, 1508 and 1497 cm$^{-1}$: aromatic nucleus+ NH$_2$
NMR analysis of the proton (CDCl$_3$ 300 MHz in ppm):
3.34 and 3.36: —OCH$_3$
3.48, 3.56, 3.77 and 3.97: O—CH$_2$—CH$_2$—O
5.17 (s): Ar—CH(C=O—O)—O—
5.20 and 5.21: —O—CH$_2$—O
5.79 (s): O—NH$_2$
6.82 (dd): Ar—H in ortho position of F
6.91 (s): CO—O—CHAr$_2$
7.02: Ar—H in para position of F
7.05 to 7.40: Ar—H STEP E: [[[1-[3-fluoro-4,5-bis-[(2-methoxy-ethoxy)-methoxy]-phenyl]-2-oxo-2-(diphenylmethoxy)-ethyl]-oxy]-imino]-[2-[(triphenylmethyl)-amino]-thiazol-4-yl]-acetic acid 0.640 g of the product of Step D and 0.474 g of oxo-[2-[(triphenylmethyl)-amino]-thiazol-4-yl]-acetic acid (Belgian Patent Application No. 864,828) were stirred for 4 and a half hours under nitrogen and at ambient temperature in the presence of 20 ml of methanol. Then, the solvent was eliminated, and the residue was chromatographed on silica, eluting with a dichloromethane-methanol (95-5) mixture to obtain 0.612 g of the expected product with a Rf=0.35 [eluant: dichloromethane-methanol (9-1)].

Infrared analysis (CHCl$_3$):
3400 cm$^{-1}$: =C—NH
1755 (shoulder), 1736 (max) cm$^{-1}$: C=O
1695, 1527, 1509 and 1496 cm$^{-1}$: aromatic, heterocycle,
1635 cm$^{-1}$: C=0
NMR analysis of the proton (CDCl$_3$ in ppm):
3.09 (s) and 3.22 (s): —OCH$_3$
3.30 (m), 3.55 (m), 3.60 (m), 3.92 (m).: O—CH$_2$—CH$_2$—O
5.15 (s), 5.10 (d) and 5.20 (d): —O—CH$_2$—O
5.81 (s): Ar—CH(C=O)—O—
6.56 (s): CO—O—CHAr$_2$.
6.74 (s): —S—CH=C(C=N)—N
7.10 to 7.33 (m): Ar—H STEP F: 4-methoxy-benzyl 7β-[[[[[1-[3-fluoro-4,5-bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z)-3-chloro-1-propenyl]-8-oxo-5-thia-1-azabicyclo-[4.2.0]-oct-2-en-2-carboxylate 0.289 g of 4-methoxy-benzyl 7β-amino-3-[(Z)-3-chloro-1-propenyl]-8-oxo-5-thia-1-azabicyclo-[4.2.0]-oct-2-en-2-carboxylate hydrochloride (European Patent Application No. 0.333,154), and 0.641 g of the product of Step E in 6 ml of dichloromethane were stirred and cooled to 5° C. Then 0.160 g of EDC was added and the mixture was stirred for half an hour. Then, the mixture was treated with potassium hydrogen phosphate in dichloromethane, followed by decanting, washing, drying and evaporating the solvents. After chromatographing on silica eluting with a dichloromethane-ethyl acetate (8-2) mixture, 0.678 g of the expected product with a Rf=0.4 [eluant: dichloromethane-ethyl acetate (8-2)] were obtained.

STEP G: 4-methoxy-benzyl 7β-[[[[[1-[3-fluoro-4,5-bis-[(2-methoxy-ethoxy)-methoxy]-phenyl]-2-oxo-2-(diphenylmethoxy)-ethyl]-oxy]-imino[-[2-(triphenylmethyl)-amino]-thiazol-4-yl]-acetamido]-3-[(Z)-3-iodo-propenyl]-8-oxo-5-thia-1-azabicyclo-[4.2.0]-oct-2-en-2-carboxylate 0.678 g of the product of Step F in 7 ml of acetone and 0.228 g of sodium iodide were stirred for one hour at ambient temperation in the presence of an iodine crystal. After eliminating of the solvent, the residue was taken up in dichloromethane and the organic phase was washed and dried. The solvent was eliminated and the residue was separated to obtain 0.501 g of the iodated product with a Rf=0.2 (eluant: dichloromethane-methanol (97-3)].

STEP H: 1-[3-[7β-[[[[[1-[3-fluoro-4,5-bis-[(2-methoxy-ethoxy)-methoxy]-phenyl]-2-oxo-2-(diphenyl methoxy)-ethyl]-oxy]-imino]-[2-(triphenylmethyl)-amino]-thiazol-4-yl]-acetamido]-2-[(4-methoxy-benzyloxy)-carbonyl]-8-oxo-5-thia-1-azabicyclo-[4.2.0]-oct-2-en-3-yl]-2-propenyl]-quinolinium iodide 0.500 g of the product of Step G dissolved in 2 ml of dichloromethane and 0.226 ml of quinoline were added and the solvent was concentrated. The mixture was stirred for one hour at ambient temperature and 2 ml of dichloromethane were added. Then precipitation was carried out with ether and chromatography took place on silica eluting with a dichloromethane-methanol (97-3) mixture to obtain 0.220 g of the expected product with a Rf=0.20.

STEP I: Internal salt of [6R-[3(E), 6α,7β-(Z)]]-1-[3-[7-[[(2-amino-4-thiazolyl)-[[carboxy-(3-fluoro-4,5-dihydroxy-phenyl)-methoxy]-imino]-acetamido]-2-carboxy-8-oxo-5-thia-1-azabicyclo-[4.2.0]-oct-2-en-3-yl]-2-propenyl]-quinolinium (R) isomer and (S) isomer A mixture of 0.220 g of the product of Step H and 5 ml of trifluoroacetic acid containing 10% anisole was stirred at ambient temperature for one and a half hours. After 15 ml of ether were added, the precipitate was washed and dried to obtain 0.0994 g of the desired internal salt.

Analysis: $C_{32}H_{25}FN_6O_9S_2+1.2\ C_2HF_3O_2+0.5$ HI Calculated: %C 44.8 %H 2.89 %n 9.12 %S 6.95 %F 9.48 %I 6.88 Found: 44.7 2.8 8.8 6.6 9.1 6.6

NMR analysis of the proton (DMSO 300 MHz in ppm):
3.5 and 3.8: (masked by the water of the solvent)
5.14 (d resolved) ppm: CO—NH—CH(C=O )—C H—(N—)—S—
5.34 (s resolved): Ar—CH(CO—O—)—O—
5.77 (dd resolved d resolved): CO—NH—CH(C=O)—CH(N—)—S—
5.80 to 6.0: —CH=CH—CH$_2$—N$^+$,
6.37 (m): —CH=CH—CH$_2$—N$^+$ E isomerism
6.7 to 6.8: —S—CH=C(C=N—)—N=C(NH$_2$)— and Ar—H in ortho and para position of F.
6.98 ppm (d resolved): —CH=CH—CH$_2$—N$^+$ E isomerism
8.07 (t), 8.29 (t): H in positions 6 and 7 of the quinolinium
8.24(dd): H in position 3 of the quinolinium
3.53: H in positions 5 and 8 of the quinolinium
9.34 (d): H in position 4 of the quinolinium
9.58 (d): F in position 2 of the quinolinium
7.31–9.19 and 9.5 to 9.7: mobile H's

EXAMPLE 4

The internal salt of [(±) (cis) (Z)] 7-[3-[7-[[(2-amino-4-thiazolyl)-[[carboxy-(3-chloro-4,5-dihydroxy-phenyl]-methoxy]-imino]-acetamido]-2-carboxy-8-oxo-5-thia-1-azabicyclo-[4.2.0]-oct.2-en-3-yl] 2(E)-propenyl]-thieno-[2.3-b]-pyridinium (R) or (S) or an (R+S) mixture STEP A: [3-chloro-4,5-bis-[(2-methoxy-ethoxy)-methoxy]-phenyl]-hydroxy acetic acid 3.34 g of lithium chloride and 9.64 g of potassium hydroxide were dissolved in 36 ml of water at 0° C. and a solution of 13.77 g of 3-chloro-4,5-bis-[(2-methoxy-ethoxy)-methoxy benzaldehyde (synthesized in Preparation 3). 3.74 ml of bromoform and 34 ml of dioxane were added to this mixture. The mixture was stirred for 24 hours at 0° C. and then another 3.74 ml of bromoform were added. The resultant mixture was stirred for 16 hours and after dilution in 100 ml of water and washing with ether. Decanting took place, followed by cooling to 0° C., acidifying to a pH of 2.5–3 and extracting with ether. The organic phase was washed with water, dried and the solvent was evaporated to obtain 13.95 g of the desired product in the form of a yellow oil.

Infrared analysis (CHCl$_3$):
1700 (max) and 1730 (shoulder) cm$^{-1}$: C=O
1599, 1578, 1489 cm$^{-1}$: aromatic nucleus
NMR analysis of the proton (CDCl$_3$ 250 MHz in ppm):
3.38 (m) (6H): —OCH$_3$
5.09 to 5.35 (m): —O—CH$_2$—O and Ar—CH(C=O)—O
7.05 to 7.78 ppm (m) (2H): Ar—H STEP B: Diphenylmethyl [3-chloro-4,5-bis-[(2-methoxy-ethoxy)-methoxy]-phenyl]-hydroxy acetate 13.95 g of the acid of Step A were dissolved in 150 ml of ether at ambient temperature and under nitrogen and then 150 ml of a 0.3 molar solution of diphenyl-diazomethane in dichloromethane were added at 15° C. The mixture was stirred for 16 hours at ambient temperature and then, 30 ml of water were added, followed by decanting and acidifying with 30 ml of acetic acid. Washing took place again with a saturated solution of sodium bicarbonate, followed drying and evaporating the solvents. After chromatographing on silica eluting with a dichloromethane-methanol (99-1) mixture, 10 g of the desired product were obtained.

Infrared analysis (CHCl$_3$):
3535 cm$^{-1}$: non-phenolic —OH
1738 cm$^{-1}$: C=O of the ester function
1600, 1580, 1489 cm$^{-1}$: aromatic nucleus
NMR analysis of the proton (CDCl$_3$ 250 MHz in ppm):
3.59 (m) and 3.47 (m) (4H), 3.75 (m) (2H) and 4.04 (m) (2H): O—CH$_2$—CH$_2$—O
3.38, 3.33 and 3.25 (m) (6H): —OCH$_3$
5.02 to 5.30 (m): O—CH$_2$—O and Ar—CH(C=O)—O
6.8 to 7.35 (m): Ar—H STEP C: Diphenylmethyl [3-chloro-4,5-bis-[(2-methoxy-ethoxy)-methoxy]-phenyl]-phthalimidoxy acetate 1 g of N-hydroxy phthalimide and 1.54 g of triphenyl phosphine were added to a solution of 1 g of the ester of Step B in 35 ml of tetrahydrofuran, followed by cooling to 10° C. Then, 1.58 g of diethyl azodicarboxylate (DEAD) were added dropwise and the mixture was stirred for 16 hours. After concentration of the solvents, chromatography on silica and eluting with a dichloromethane-methanol (99-1) mixture yielded, 3.09 g of the desired product in the form of a colorless oil (Rf=0.3).

Infrared analysis (CHCl$_3$):
1738, 1755 (shoulder) and 1795 cm$^{-1}$: C=O
1600, 1578, 1488 cm$^{-1}$: aromatic nucleus
NMR analysis of the proton (CDCl$_3$ 250 MHz in ppm):
3.34 (s), and 3.36 (s): —OCH$_3$
3.49 (m) (2H),3.57 (m) (2H), 3.77 (m) (2H) and 4.02 (m) (2H) ppm: O—CH$_2$—CH$_2$—O
5.22 (s) and 5.27 (s) ppm: —O—CH$_2$—O
5.91 (s) and 5.92 (s) ppm: Ar—CH(C=O)—O
6.92 (s) ppm: CO—O—CH—Ar$_2$
7.75 ppm (m) (4H): Ar—H of the phthalimido
7.11 (m) and 7.21 to 7.33 ppm: the other aromatic H's STEP D: Diphenylmethyl aminoxy [3-chloro-4,5-bis-[(2-methoxy-ethoxy)-methoxy]-phenyl] acetate 3 g of the product of Step C were dissolved under a nitrogen atmosphere in 40 ml of ethanol and the mixture was cooled to 5° C. Then, 0.224 ml of hydrazine hydrate were added and the mixture was stirred at 5° C. for half an hour, then returned to ambient temperature for 2 hours. After filtration and evaporation of the solvent, the desired product was obtained in the form of an oil with a Rf=0.3 [eluant: acetone-cyclohexane (3-7)].

Infrared analysis (CHCl$_3$):
3330 cm$^{-1}$: —NH$_2$
1745 cm$^{-1}$: C=O
1600, 1578, 1488 cm$^{-1}$: aromatic nucleus+NH$_2$
NMR analysis of the proton (CDCl$_3$ 250 MHz in ppm):
3.34 (s) and 3.38 (s): —OCH$_3$
3.48 (m), 3.58 (m), 3.76 (m) and 4.02 (m): O—CH$_2$—CH$_2$—O
5.17: Ar—CH(C=O)—O
5.80: mobile NH$_2$
6.91 (s): CO—O—CH—Ar$_2$
7.10 (m) (4H) and 7.21 to 7.33 (8H): Ar—H STEP E: 7-[3-[7β-[[[[[1-[3-chloro-4,5-bis-[(2-methoxy-ethoxy)-methoxy]-phenyl]-2-oxo-2-(diphenyl methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo-[4.2.0]-[oct-2-en-3-yl]-2-propenyl]-thieno-[2,3-b]-pyridinium iodide 0.441 g of the product of Step D, 24 ml of methanol and 145 ml of p-toluene sulfonic acid were mixed under a nitrogen atmosphere for 5 minutes and a solution of 0.65 ml of 1-[3-[7β-[oxo-[2-[(triphenylmethyl)-amino]-thiazol-4-yl]-acetamido]-2-[(4-methoxy-benzyloxy)-carbonyl]-8-oxo-5-thia-1-azabicyclo-[4,2,0]-[oct-2-en-3-yl]-2-propenyl]-thieno-[2,3-b]-pyridinium iodide (preparation 10) were added. Then, the mixture was stirred for 16 hours and after evaporation of the solvent, the residue was taken up in ether. The precipitate was filtered, washed and dried to obtain 0.730 g of the desired product with a melting point of 135° C. (gum) and a Rf=0.3 [eluant: dichloromethane-methanol (9-1)].

STEP F: The internal salt of [(±) (cis (Z)] 7-[3-[7-[[(2-amino-4-thiazolyl)-[carboxy-(3-chloro-4,5-dihydroxy-phenyl)-methoxy]-imino]-acetamido]2-carboxy-8-oxo-5-thia-1-azabicyclo-[4,2,0]-oct-2-en-3-yl]-2(E)-propenyl]-thieno-[2,3-b]-pyridinium (R) or (S) or an (R+S) mixture A solution of 31 ml of trifluoroacetic acid in 8.5 ml of dichloromethane was poured at 0° C. into a mixture at 0° C. of 0.69 ml of the product of Step E, 17 ml of dichloromethylene and 3 ml of anisole and the mixture was stirred at this temperature for one hour. The solvents were eliminated, followed by crystallizing, filtering, washing and drying, chromatography and elution with an acetonitrile-water (1-1) mixture yielded 0.22 g of the desired product.

NMR analysis of the proton (DMSO 300 MHz in ppm):
3.19: C=C—CH$_2$—S—
5.01 (d) and 5.07 (d): CO—NH—CH (C=O)—CH—(N—)—S—
5.12 (s) and 5.17 (s): Ar—CH(CO—O—)—O—
5.52 (l): —CH=CH—CH$_2$N$^+$,
5.60: CO—NH—CH(C=O)—CH—(N—)—S— (cis/H in position 6)
5.87 (m): —CH=CH—CH$_2$—N$^+$ E isomerism
6.78 to 6.86: —S—CHC(C=N—)—N=C(NH$_2$)— and Ar—H in ortho and para position of the Cl
7.21 and 7.41: —NH$_2$ $_{7.87}$ (d): H in position 3 of the thieno-[2,3-b]-pyridinium 8.10 (1): H in position 5 of the thieno-[2,3-b]-pyridinium 8.26 (d): H in position 2 of the thieno-[2,3-b]-pyridinium 9.03 (1): H in position 4 of the thieno-[2,3-b]-pyridinium 9.23: (1) H in position 6 of the thieno-[2,3-b]-pyridinium 9.74 (d): CO—NH—CH(C=O)—CH(N—)—S—

Using the procedure of Example 4, the products of preparations 1 to 12 were reacted to obtain the following compounds:

EXAMPLE 5

The internal salt of [[6R-[3(E), 6α,7β (Z)]]7-[3-[7-]](2-amino-4-thiazolyl)-[carboxy-(3,4-dihydroxy-5-nitro-phenyl)-methoxy]-imino]-acetamido]-2-carboxy-8-oxo-5-thia-1-azabicyclo-[4, 2,0]-oct-2-en-3-yl]-2-propenyl]-thieno-[2,3-b]-pyridinium (R) or (S) or an (R+S) mixture NMR analysis of the proton 9DMSO 300 mHz in ppm):
3.49 to 3.9 (m) (C=C—CH$_2$—S—
3.14 (d) and 5.18 (d): CO—NH—CH(C=O)—CH—(N—)—S—
5.47 (s), 5.50 (s), 5.60 (s), 5.63 (s): Ar—CH—(CO—O—)—O—
6.67 (d): —CH=CH—CH$_2$—N$^+$,
5.77 (m): CO—NH—CH(C=O)—CH—(N—)—S—
6.29 (m): —CH=CH—CH$_2$—N$^+$
6.80 (s), 6.83 (s), 7.64 (s) and 7.66 (s): —S—CH=C(C=N—)—N=C(NH$_2$)—
7.42 (d) and 7.47 (d): Ar—H in ortho position of the nitro
7.1 to 7.2 (m): —CH=CH—CH$_2$—N$^+$ and Ar—H in para position of the nitro
7.89 (d): H in position 3 of the thieno-[2,3-b]-pyridinium
8.15 (dd): H in position 5 of the thieno-[2,3-b]-pyridinium
8.29 (d): H in position 2 of the thieno-[2,3-b]-pyridinium
9.09 (d): H in position 4 of the thieno-[2,3-b]-pyridinium
9.23 (d): H in position 6 of the thieno-[2,3-b]-pyridinium
9.54 (d res.), 9.65 (d) and 9.69 (d): CO—NH—CH—(C=O)—CH—(N—)—S—
10.42 (m) mobile H's

EXAMPLE 6

The internal salt of [(±) (cis) (Z)] 7-[3-[7-[[(2-amino-4-thiazolyl)-[carboxy-(3,4-dihydroxy-5-iodo-phenyl)-methoxy]-imino]-acetamido]-2-carboxy-8-oxo-5-thia-1-azabicyclo-[4,2,0]-oct-2-en-3-yl]-2-(E)-propenyl]-thieno-[2,3-b]-pyridinium (R) or (S) or an (R+S) mixture Analysis: C$_{30}$H$_{23}$IN$_6$O$_9$S$_3$+1 C$_2$HF$_3$O$_2$+1 APTS Calculated: %C 41.78 %H 2.85 %N 7.5 %S 11.43 %I 11.3 Found: 46.6 2.8 7.8 12.0 10.9

NMR analysis of the proton (DMSO 300 MHz in ppm):
3.70: C=C—CH$_2$—S—
5.11 (s) and 5.17 (s) (1H): CO—NH—CH(C=O)—CH—(N—)—S—5.29 (s) and 5.32 (s): Ar—CH(CO—O—)—O—
5.67 (d): —CH=CH—CH$_2$—N$^+$,
5.75 (m): CO—NH—CH(C=O)—CH(N—)—S—
6.29: —CH=CH—CH$_2$—N$^+$ E isomerism
6.77 (resolved) (1H): —S—CH=C(C=N—)—N=C(NH$_2$)—
6.90 (2H): Ar—H in ortho and para position of I
7.89 (d): H in position 3 of the thieno-[2,3,-b]-pyridinium
8.15 (dd): H in position 5 of the thieno-[2,3-b]-pyridinium
8.29 (d): H in position 2 of the thieno-[2,3-b]-pyridinium
9.09 (d): H in position 4 of the thieno-[2,3-b]-pyridinium
9.13 (d): H in position 6 of the thieno-[2,3-b]-pyridinium
9.37 (sl): CO—NH—CH(C=O)—CH(N—)—S—

EXAMPLE 7

The internal salt of [(±) (cis) (Z)] 7-[3-[7-[[(2-amino-4-thiazolyl)-[carboxy-(3,4,5-trihydroxy-phenyl)-methoxy]-imino]-acetamido]-2-carboxy-8-oxo-5-thia-1-azabicyclo-[4 2.0]-oct-2-en-3-yl]-2(E)-propenyl]-thieno-[2,3-b]-pyridinium (R) or (S) or an (R+S) mixture NMR analysis of the proton (DMSO 300 MHz in ppm):
5.15 (d) and 5.17 (d) (1H): CO—NH—CH(C=O)—CH—(N—)—S—[2/5 (R/S) 3/5]
5.22 and 5.34 (2H): Ar—C$\underline{H}$(CO—O—)—O—
5.67 (d): —CH=CH—C$\underline{H}_2$—N$^+$.
5.76 (m), 6.20 to 6.49 (m): CO—NH—C$\underline{H}$(C=O)—CH(N—)—S—,
C$\underline{H}$=CH—CH$_2$—N$^+$ and Ar—$\underline{H}$ of the triphenol
6.75, 6.77, 6.87 and 6.90 (1H): —S—C$\underline{H}$=C(C=N—)—N=C(NH$_2$)—
7.74 (d): $\underline{h}$ in position 5 of the thieno-[2,3-b]-pyridinium
7.89 (d) and 8.28 (d): $\underline{H}$ in positions 4 and 3 of the thieno-[2,3-b]-pyridinium
8.10 to 8.27, 9.09 and 9.23: $\underline{H}$ in positions 2 and 6 of the thieno-[2,3-b]-pyridinium
9.6 to 9.85: CO—N$\underline{H}$—CH(C=O)—CH(N—)—S—

EXAMPLE 8

The internal salt of [(±) (cis) (Z)] 7-[3-[7-[[(2-amino-4-thiazolyl)-[carboxy-(2-chloro-3,4-dihydroxy-phenyl)-methoxy]-imino]-acetamido]-2-carboxy-8-oxo-5-thia-1-azabicyclo-[4,2,0]-oct-2-en-3-yl]-2(E)-propenyl]-thieno-[2,3-b]-pyridinium (R) or (S) or an (R+S) mixture Analysis: C$_{30}$H$_{23}$IN$_6$O$_9$S$_3$+2 APTS Found: %C 46.8 %H 2.55 %N 8.53 %S 9.76 %Cl 3.59

NMR analysis of the proton (DMSO 300 MHz in ppm):
3.5 to 3.9 (m): C=C—CH$_2$—S—
5.17 (m) (1H): CO—NH—CH(C=O)—C$\underline{H}$—(N—)—S—
5.67 (d): —CH=CH—C$\underline{H}_2$—N$^+$.
5.70 to 5.90 (2H): CO—NH—C$\underline{H}$(C=O)—CH(N—)—S—+other $\underline{H}$
6.33 (m): —C$\underline{H}$=CH—CH$_2$—N$^+$ E isomerism
6.79 (m) and 6.96 (m) (4H): 4$\underline{H}$
7.89 (d) and 8.29 (d): $\underline{H}$ in positions 2 and 3 of the thieno-[2,3-b]-pyridinium
8.14 (m): $\underline{H}$ in position 5 of the thieno-[2,3-b]-pyridinium
9.08 (d): $\underline{H}$ in position 4 of the thieno-[2,3-b]-pyridinium
9.26 (d): $\underline{H}$ in position 6 of the thieno-[2,3-b]-pyridinium

EXAMPLE 9

The internal salt of [[6R-[3(E), 6α,7β (Z)]] 7-[3-[7-[[(2-amino-4-thiazolyl)-[carboxy-(2,5-dichloro-3,4-dihydroxy-phenyl)-methoxy]-imino]-acetamido]-2-carboxy-8-oxo-5-thia-1-azabicyclo-[4 2,0]-oct-2-en-3-yl]-2-propenyl]-thieno-[2,3-b]-pyridinium (R) or (S) or an (R+S) mixture NMR analysis of the proton (DMSO 300 MHz in ppm):
5.20: Ar—$\underline{H}$ in ortho position of the Cl
5.79: Ar—C$\underline{H}$(CO—O—)—O—
5.78 (m): —CH=CH—C$\underline{H}_2$—N$^+$,
6.31: —CH=CH—C$\underline{H}_2$—N$^+$
7.88 (d): $\underline{H}$ in position 3 of the thieno-[2,3-b]-pyridinium
8.15 (m): $\underline{H}$ in position 5 of the thieno-[2,3-b]-pyridinium
8.98 (d): $\underline{H}$ in position 2 of the thieno-[2,3-b]-pyridinium
9.09 (d): $\underline{H}$ in position 4 of the thieno-[2,3-b]-pyridinium
9.12 (d): $\underline{H}$ in position 6 of the thieno-[2,3-b]-pyridinium

EXAMPLE 10

The internal salt of [[6R-[3(E), 6α,7β (Z)]] 7-[3-[7-[[(2-amino-4-thiazolyl)-[carboxy-(3-cyano-4,5-dihydroxy-phenyl)-methoxy]-imino[-acetamido[-2-carboxy-8-oxo-5-thia-1-azabicyclo-[4,2,0]-oct-2-en-3-yl]-2-propenyl]-thieno-[2,3-b]-pyridinium (R) or (S) or an (R+S) mixture NMR analysis of the Proton (DMSO 300M MHz in ppm):
3.19: C=C—CH$_2$—S—
5.15 (D) and 5.20 (d): CO—NH—CH(C=O)—C$\underline{H}$—(N—)—S—
5.40 (s): Ar—C$\underline{H}$(CO—O—)—O—
5.67 (d): —CH=CH—C$\underline{H}_2$—N$^+$.
5.81 (m): CO—NH—C$\underline{H}$(C=O)—CH(N—)—S—
6.67 (S): —S—C$\underline{H}$=C(C=N—)—N=C(NH$_2$)—
7.10 to 7.20 (m) (3H): Ar—$\underline{H}$ and C$\underline{H}$=
7.34 (m), 10.27 to 10.42 (m): mobile $\underline{H}$'s
7.89 (d): $\underline{H}$ in position 3 of the thieno-[2,3-b]-pyridinium
8.15 (dd): $\underline{H}$ in position 5 of the thieno-[2,3-]-pyridinium
8.28 (d): $\underline{H}$ in position 2 of the thieno-[2,3-b]-pyridinium
9.09 (d): $\underline{H}$ in position 4 of the thieno-[2,3-b]-pyridinium
9.23 (d): $\underline{H}$ in position 6 of the thieno-[2,3-b]-pyridinium
9.52 (d) and 9.62 (d): CO—N$\underline{H}$—CH(C=O)—CH—(N—)—S—

EXAMPLE 11

The internal salt of [[6R-[3(E), 6α,7β (Z)]] 7-[3-[7-[[(2-amino-4-thiazolyl)-[carboxy-(3,4-dihydroxy-5-methoxy-phenyl)-methoxy]-imino]-acetamido]-2-carboxy-8-oxo-5-thia-1-azabicyclo-[4,2,0] oct-2-en-3-yl]-2-propenyl]-thieno-[2,3-b]-pyridinium (R) or (S) or an (R+S) mixture The (R) and (S) isomers were separated by HPLC (Microbonda-pack column C18), solvent: Water/acetonitrile (85/15)

(S) Isomer

NMR analysis of the proton (DMSO 300 MHz in ppm):
3.71 (s): Ar—OC$\underline{H}_3$
5.16 (d J=5): CO—NH—CH(C=O)—C$\underline{H}$—(N—)—S—
5.32 (s): Ar—C$\underline{H}$(CO—O—)—O—
5.68 (d): —CH=CH—C$\underline{H}_2$—N$^+$,
5.79 (dd J=5 and 7.5): CO—NH—C$\underline{H}$(C=O)—CH(N—)—S—
6.28 (m): —CH=C$\underline{H}$—CH$_2$—N$^+$,
6.55 (s) (2H): Ar—$\underline{H}$ in ortho and para position of the —OMe
6.78 (s): —S—C$\underline{H}$=C(C=N—)—N=C(NH$_2$)—
7.11 (d): —C$\underline{H}$=CH—CH$_2$—N$^+$,
7.29 (m), 8.38 (m), 8.99 (m): mobile $\underline{H}$'s
7.88 (d): $\underline{H}$ in position 3 of the thieno-[2,3-b]-pyridinium
8.15 (dd): $\underline{H}$ in position 5 of the thieno-[2,3-b]-pyridinium
8.29 (d): $\underline{H}$ in position 2 of the thieno-[2,3-b]-pyridinium
9.08 (d): $\underline{H}$ in position 4 of the thieno-[2,3-b]-pyridinium
9.22 (d): $\underline{H}$ in position 6 of the thieno-[2,3-b]-pyridinium
9.55 (d): CO—N$\underline{H}$—CH(C=O)—CH(N—)—S—

(R) Isomer

NMR analysis of the proton (DMSO 300 MHz in ppm):
3.50 (s) (partly masked): C=C—CH$_2$—S—
3.72 (s): Ar—OC$\underline{H}_3$
5.19 (d J=5): CO—NH—CH(C=O)—C$\underline{H}$—(N—)—S—
5.32 (s): Ar—C$\underline{H}$(CO—O—)—O—
5.68 (d J=6): —CH=CH—C$\underline{H}_2$—N$^+$
5.76 (dd J=5 and 7.5): CO—NH—C$\underline{H}$(C=O)—CH(N—)—S—,
6.29 (m) —CH—C$\underline{H}$—CH$_2$—N$^+$,
6.55 (s) and 6.57 (s) (2H): ar—$\underline{H}$ in ortho and para position of the —OMe 6.74 (s): —S—CH=C(C=N—)—N=C(NH$_2$)—
7.15 (d): —CH=CH—CH$_2$—N$^+$.
7.30 (m) (2H), 8.39 (s) (1H), 8.96 (s) (1H): mobile H's
7.89 (d): H in position 3 of the thieno-[2,3-b]-pyridinium
8.15 (dd): H in position 5 of the thieno-[2,3-b]-pyridinium
8.29 (d): H in position 2 of the thieno-[2,3-b]-pyridinium
9.08 (d): H in position 4 of the thieno-[2,3-b]-pyridinium
9.23 (d): H in position 6 of the thieno-[2,3-b]-pyridinium
9.62 (d): CO—NH—CH(C=O)—CH(N—)—S—

EXAMPLE 12

The internal salt of [[6R-[3(E), (6α,7β (Z)]]1-[3-[7-[[(2-amino-4-thiazolyl)-[carboxy-(2,5-dichloro-3,4-dihydroxy-phenyl]-methoxy]-imino]-acetamido]-2-carboxy-8-oxo-5-thia-1-azabicyclo-[4.2.0]-oct-2-en-3-yl]-2-propenyl]-quinolinium (R) or (S) or (R+S) mixture

EXAMPLE 13

The internal salt of [[6R-[3(E), 6α,7β (Z)]] 2-[3-[7-[[(2-amino-4-thiazolyl)-[carboxy-(2,5-dichloro-3,4-dihydroxy-phenyl)-methoxy]-imino]-acetamido]-2-carboxy-8-oxo-5-thia-1-azabicyclo-[4.2.0]-oct-2-en-3-yl]-2-propenyl] isoquinolinium (R) or (S) or an (R+S) mixture Rf=0.6 (eluant: acetone-water (8-2))

EXAMPLE 14

The internal salt of [[6R-[3(E), 6α,7β-(Z)]] 1-[3-[7-[[(2-amino-4-thiazolyl)-[carboxy-(2,5-dichloro-3,4-dihydroxy-phenyl)-methoxy]-imino]-acetamido -2-carboxy-8-oxo-5-thia-1-azabicyclo-[4.2.0]-oct-2-en-3-yl]-2-propenyl]-4-(methylthio) pyridinium (R) or (S) or an (R+S) mixture Rf=0.6 (eluant: acetone-water (8-2))

EXAMPLE 15

The internal salt of [(+) (cis (Z)] 7-[3-[7-[[(2-amino-4-thiazolyl)-[carboxy-(3-bromo-4,5-dihydroxy-phenyl)-methoxy]-imino]-acetamido]-2-carboxy-8-oxo-5-thia-1-azabicyclo-[4.2.0]-oct-2-en-3-yl]-2-(E)-propenyl]-thieno-[2,3-b]-pyridinium (R) or (S) or an (R+S) mixture

EXAMPLE 16

Internal salt of (6R (3(E), 6α,7β (Z))) 1-(3-(7-((((2-amino-4-thiazolyl)-(carboxy-(2,3-dihydroxy-4-fluorophenyl)-methoxy)-imino)-acetamido)-2-carboxy-8-oyo-5-thia-1-azabicyclo-(4.2.0)-oct-2-en-3-yl)-2-propenyl) quinolinium

STEP A: Diphenylmethyl [4-fluoro-(2,3-bis-hydroxy)-phenyl]-hydroxy-acetate 480 ml of a 0.3M solution of diphenyl diazomethane were added over 2 hours to a solution of 417.7 g of the product of Preparation 11 in 500 ml of ethyl ether cooled to −10° C. The temperature was taken to −5° C. and 10 ml of acetic acid were added and the solution was used as is in the following steps.

STEP B: Diphenylmethyl [4-fluoro-[2,3-bis-[(2-methoxyethoxy)-methoxy]-phenyl]-hydroxy-acetate 238 ml of diisopropylethylamine were added to the solution of Step A and the ether was replaced by 500 ml of methylene chloride. Then, the mixture was cooled to 6° to 10° C. and 53 ml of methoxyethoxymethyl chloride were added over 75 minutes. The mixture was stirred for 75 minutes and 500 ml of water were added, followed by decanting. The organic phase was washed with N hydrochloric acid, then with N sodium hydroxide and with water, followed by drying and evaporating to dryness. The residue was chromatographed on silica and eluted with an ethyl acetate-hexane (1-1) mixture to obtain 26.1 g of crude product which was chromatographed again on silica, eluant: methylene chloride-acetone (97-3) to obtain 14.58 g of the desired product.

NMR Spectrum: CDCl$_3$ 300 MHz in ppm:
3.34–3.36: the C—O—Me's; 3.52–3.80-3.91: the O—CH$_2$—CH$_2$—O's; 4.06 (dJ=6.5); mobile H; 5.17 to 5.27; the O—CH$_2$—O's; 5.49 (dJ=7.5): the C$_6$H$_5$—CH—O's; 6.84 (dd: J=9 and 10): H$_6$; 6.96 (dd J=9 and 6): H$_5$; 7.20 to 7.40 and 6.94 (sl): the aromatics.

STEP C: Diphenylmethyl [4-fluoro-2,3-bis-[(2-methoxyethoxy)-methoxy]-phenyl]-phthalimidoxy acetate Using the procedure of Step C of Example 4, 14.42 g of the product of Step B were reacted to obtain after chromatography on silica, eluant methylene chloride-methanol (99-1), 11.89 g of the desired product.

IR Spectrum CHCl$_3$ 1792–1756–1734 cm$^{-1}$: C=O; 1600–1492 cm$^{-1}$: aromatic.

NMR Spectrum: CDCl$_3$ 250 MHz: for 2 OMEM groups: 3.30 (s), 3.34 (s): OCH$_3$; 3.47 (m) 3.84 (m): O—CH$_2$—CH$_2$—O; 5.10–5.27; O—CH$_2$O ; then 6.39 (s): AR—CH(ON=)—CO$_2$; 6.95 (s) CO$_2$CH(C$_6$H$_5$)$_2$; 6.84 (t): H$_5$; 7.15 (2H) 7.19–7.32 (9H) 7.74 (4H): aromatic H's.

STEP D: Diphenylmethyl aminoxy [4-fluoro-2,3-bis-[2-methoxy-ethoxy)-methoxy]-phenyl]-acetate 0.88 ml of hydrazine hydrate were added over one hour at −10° C. to a solution or 11.27 g of the product of Step C, 112.7 ml of tetrahydrofuran and the mixture was stirred for 90 minutes. The insoluble part was filtered off and the filtrate was concentrated to dryness. The residue was chromatographed on silica (eluant: methylene chloride-ethyl acetate (80-20)) to obtain 4.72 g of the desired product.

NMR Spectrum: CDCl$_3$ 200 MHz: 3.35 (s): 3.36 (s): OCH$_3$; 3.54 (m) (4H) 3.93 (m) (4H): O—CH$_2$—CH$_2$O; 5.20 (s) 5.27 (s): OCH$_2$O; 6.78 (dd J=9.5 and 9): H$_5$; 6.89 (m): H$_6$; 5.73 (s): Ar—CH(ONH$_2$)—CO$_2$; 6.94 (s): CO$_2$—CH—(C$_6$H$_5$)$_2$; 7.10 (m) (5H): 10 aromatic H's (C$_6$H$_5$)$_2$.

STEP E: [[[1-[4-fluoro-2,3-bis-[(2-methoxy-ethoxy)-methoxy]-phenyl]-2-oxo-2-(diphenylmethoxy)-ethyl]-oxy]-imino]-[2-[(triphenylmethyl)-amino)-amino]-thiazol-4-yl]-acetic acid Using the procedure of Step E of Example 1, 4.65 g of the product of Step D and 3.45 g of oxo-[2-[(triphenylmethyl)-amino]-thiazol-4-yl]-acetic acid (Belgium Patent Application No. 864,828) were reacted to obtain after chromatography on silica (eluant: methylene chloride-methanol (96-4)) 6.5 g of the desired product.

IR Spectrum (CHCl$_3$): 3410 cm$^{-1}$; =CH—NH—; 1781 cm$^{-1}$: C=O; 1618, 1607, 1528, 1496 cm$^{-1}$: CO$_2$, aromatic and heteroaromatic.

NMR Spectrum: DMSO 300 MHz: 3.18 (s)–3.20 (s): OCH$_3$; 3.43 (m) (4H) 3.81 (m) 4H): O—CH$_2$—CH$_2$—O; 5.17 (s) (2H) 5.21 (s) (2H): O—CH$_2$—O; 5.87 (s) (3/4H):

ArCH(O—NH$_2$) —CH$_2$—; 6.68 (s) (3/4H): H$_5$ thiazole; 6.84 (s) (3/4H): CO$_2$CH(C$_6$H$_5$)$_2$; approx. 6.95–7.0: H$_5$ H$_6$ approx. 7.18–7.50: other aromatics; 8.65 (sl): =C—NH.

STEP F: 4-methoxy-benzyl 7β-[[[[1-[4-fluoro-2,3-bis-[(2-methoxy-ethoxy)-methoxy]-phenyl]-2-oxo-2-(diphenyl-methoxy)-ethyl]-oxy]-imino-[2-(triphenyl-methyl)-amino]-thiazol-4-yl]-acetamido]-3-[(Z)-3-chloro-1-propenyl]-8-oxo-5-thia-1-azabicyclo-[4.2,0]-oct-2-en-2-carboxylate Using the procedure of Step F of Example 1 but at a temperature of −10° C., 6.44 g of the product of Step E were reacted to obtain after chromatography on silica [eluant: methylene chloride-ethyl acetate (90-10)], 5.35 g of the desired product were obtained.

NMR Spectrum: (CDCl$_3$ 400 MHz): 3.05 (d, 1H)–3.20 (d,1H): CH$_2$S; [3.24 (s), 3.26 (s)] (3H) 3.35 (s, 3H): OCH$_3$; 3.43 (m, 2H)–3.55 (m, 2H)–3.70–4.15: (CH$_2$CH$_2$O and =CH—CH$_2$Cl; 3.81 (s): CH$_3$OAr; 4.96 (d)–4.97 (d): H$_6$ cephalo; 5.12 5.31 (6-7H): OCH$_2$O, CO$_2$CH$_2$Ar, ArCH(ONH$_2$)—CO$_2$—; 5.81 (m): H$_7$ cephalo; 5.75 (m): CH=CH—CH$_2$Cl (Z); 6.26 (d, J=11)–6.29 (d, J=11): —CH=CH—CH$_2$Cl (Z); approx. 6.77: H$_5$ thiazole; approx. 6.85–7.45: aromtic H's+CO$_2$CH(c$_6$h$_5$)$_2$; 7.85–8.20: NH.

STEP G: 4-methoxy-benzyl 7β-[[[[1-[4-fluoro-2,3-bis [(2-methoxy-ethoxy)-methoxy]-[phenyl]-2-oxo-2-(diphenyl-methoxy)-ethyl]-oxy]-imino]-2-(triphenyl-methyl)-amino]-thiazol-4-yl]-acetamido]-3-[(Z)-3-iodo-1-propenyl]-8-oxo-5-thia-1-azabicyclo-[4.2,0]-oct-2-en-2-carboxylate Using the procedure of Step G of Example 1, 1.2 g of the product of Step F were reacted to obtain 1.05 g of the desired product.

NMR Spectrum: 3.23 (s) 3.26 (s) 3.35 (s): CH$_3$O; approx. 3.50 to 3.95: O—CH$_2$—CH$_2$—O of which 3.81: CH$_3$OAr; approx. 4.0: =CH—CH$_2$—I; 4.92 (m): H$_6$ cephalo; 5.16–5.30: OCH$_2$O, CO$_2$CH$_2$Ar; 5.50 (m): H$_7$ cephalo; 6.12 (m): =CH—CH$_2$I (E); 6.42 (s) 6.44 (s): Ar—CH(ONH$_2$)CO$_2^-$; 6.66 (t,J=9, approx.=0.5H): aromatic H in ortho position of F; 6.76 (s resolved): H$_5$ thiazole; 6.77–7.45: aromatic H's; 7.95 (d) 8.25 (d): NH.

STEP H: 1-[3-[7β-[[[[1-[4-fluoro-2,3-bis-[(2-methoxy-ethoxy)-methoxy]-phenyl]-2-oxo-2-(diphenylmethoxy)-ethyl]-oxy]-imino]-2-triphenylmethyl)-amino]-thiazol-4-yl]acetamido]-2-[(4-methoxy-benzyloxy)carbonyl]-8-oxo-5-thia-1-azabicyclo-[4.2,0]-[oct-2-en-3-yl]-2-propenyl quinolinium iodide Using the procedure of Step H of Example 1, 1.02 g of the product of Step G and 0.46 g of quinoline were reacted to obtain after chromatography on silica, eluant: methylene chloride-methanol (97-3), 347 mg of the desired product (50/50 mixture of the two R and S isomers of expected product).

NMR Spectrum: (CDCl$_3$ 400 MHz): 3.20 (s) 3.26 (s) 3.34 (s) 3.35 (s) CH$_3$O; 3.79 (s) 3.80 (s): CH$_3$OAr; 3.42 (m) 3.54 (m) 3.79 (m) 3.90 (m): OCH$_2$CH$_2$O; 4.89 (d): H$_6$ cephalo; 5.12 to 5.28: OCH$_2$O, CO$_2$CH$_2$Ar; 5.77 (dd resolved) H$_7$ cephalo; 6.00 (dd) 6.13 (dd): =CH—CH$_2$—N$^+$=: $^{6.38}$ (s) 6.44 (s): Ar—CH—(O—)CO$_2^-$; 6.51 (m): =CHCH$_2$ (E) 6.72 (resolved) H$_5$ thiazole; 6.70 to 7.15 H$_5$–H$_6$ fluorophenyl, CH=CH—CH$_2$, CO$_2$CH(C$_6$H$_5$)$_2$; approx. 7.30: aromatic H's (C$_6$H$_5$)$_3$—C.

STEP I: Internal salt of (6R(3(E), 6α,7β (Z))) 1-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo[4.2,0]-oct-2-en-3-yl)-2-propenyl)-quinolinium Using the procedure of Step I of Example 1, 339 mg of the product of Step H and 5 ml of a solution of trifluoroacetic acid with 10% anisole to obtain 180 mg of the desired product.

NMR Spectrum: DMSO 300 MHz: 5.15 (d resolved) H$_6$ cephalo; 5.75 (dd) approx. 5.811–5.95: H$_7$ cephalo, =CH—CH$_2$N$^+$=, Ar—CH(—O—)CO$_2$; 6.38 (m): CH=CH—CH$_2$ (E); 6.99 (d resolved J=16): CH=CH—CH$_2$ (E); 6.59 (d resolved J=10): H$_5$ fluorophenyl; 6.75–6.81: H$_6$ and H$_5$ thiazole; 7.35 (wide): NH$_2$ and/or C$_6$H$_5$; 8.07 (t, 1H) 8.26 (m, 2H), 8.52 (d, 1H) 8.56 (dd, 1H) 9.30 (d, 1H) 9.58 (sl, 1H): quinoline; approx.=10.50: OH; 9.46 (d): CONH.

EXAMPLE 17

Internal salt of (6R(3(E), 6α,7β-(Z))) 7-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4.2,0) oct-2-en-3-yl)-2-propenyl)-thieno-(2,3,-b) pyridinium STEP A: 1-[3-[7β-[[[[-[4-fluoro-2,3-bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy-carbonyl]-8-oxo-5-thia-1-azabicyclo-[4.2,0]-[oct-2-en-3-yl]-2-propenyl-thieno-(2,3-b) pyridinium iodide Using the procedure of Step H of Example 16, 944 mg of the product of Step G of Example 16 and 0.45 g of thieno-[2.3-b] pyridine were reacted to obtain 339 mg of the desired product after chromatographing on silica (eluant: methylene chloride-methanol (95-5)).

NMR Spectrum: CDCl$_3$ 300 MHz: 3.20 ( ) 3.27 (s) 3.34 (s) 3.35 (s): OCH$_3$; 3.40–3.60 and 3.77–4.00: OCH$_2$CH$_2$O, CH$_2$S; 3.79 (s) 3.80 (s): ArOCH$_3$; 4.92 (d, J=5) 4.99 (d, J=5): H$_6$ cephalo; approx. 5.18–5.30: OCH$_2$O, CO$_2$CH$_2$Ar; approx. 5.77 (m): H$_7$ cephalo; 5.68 (m) 5.96 (m): =CH—CH$^+$N$^+$=: $^{6.39}$ (s) 6.45 (s): ArCH(—O—CO$_2^-$; 6.73 (s) 6.74 (s): H$_5$ thiazole; approx. 6.77 (t, resolved): H$_5$ fluorophenyl; 6.90 to 7.40: benzene H's, CO$_2$CH(C$_6$H$_5$)$_2$, CH=CH—CH$_2$(E); 6.92 (m): CH=CH—CH$_2$(E); 7.54 (d) 7.66 (d): H$_3$' and 7.83–7.87: H$_2$, and 8.06 (m): H$_5$' and 8.80 (d): H$_4$' and 10.05 (m): H$_6$' and 8.23 (d): CONH of the thieno [2,3-b] pyridine.

STEP B: Internal salt of (6R(3(E), 6α,7β (Z)))-7-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo-[4,2,0]-oct-2-en-3-yl)-2-propenyl)-thieno (2,3,-b) pyridinium Using the procedure of Step I of Example 16, 332 mg of the product of Step A were reacted to obtain 164 mg of the desired product.

NMR Spectrum DMSO 300 MHz: 5.18 (d) resolved: H$_6$ cephalo; 5.67 (d) =CH—CH$_2$—N=; 5.77–5.90: H$_7$ cephalo, Ar—CH(—O—)CO$_2^-$; 6.31 (m): CH=CH—CH$_2$ (E); 7.14 (d, J=15): CH=CH—CH$_2$(E); approx. 6.80 (m): H$_5$ thiazole, H$_5$ fluorophenyl; 7.36 (wide): NH$_2$; 6.59 (t, J=9): $H_6$; 7.89 9d, J=6) 8.15 (dd) 8.28 (d, J=6) 9.09 (d) 9.23 (d): $H_3'$ $H_5'$ $H_2'$ $H_4'$ $H_6'$ of the thieno [2,3-b] pyridine.

EXAMPLE 18

Internal salt of (6R(3(E), 6α,7β (Z)))-1-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4,2,0) oct-2-en-3-yl)-2-propenyl)-4-(methylthio) pyridinium STEP A: 1-[3-[7β-[[[[1-[4-fluoro-2,3-bis-[(2-methoxy-ethoxy)-methoxy]-phenyl]-2-oxo-2-(diphenyl-methoxy)-ethyl]-oxy]-imino][2-(triphenylmethyl)-amino]-thiazol-4-yl]-acetamido]-2-[(4-methoxybenzyloxy-carbonyl]-8-oxo-5-thia-1-azabicyclo-[4,2,0]-oct-2-en-3-yl]-2-propenyl-4-(methylthio) pyridinium iodide Using the procedure of Step H of Example 16, 1.052 g of the product of Step G of Example 16 and 462 mg of 4-thiomethyl pyridine were reacted to obtain 536 mg of the desired product after chromatography on silica (eluant: methylene chloride-methanol (95-5)).

NMR Spectrum: $CDCl_3$ 400 MHz: 2.61 (s): $CH_3S$; 3.21 (s) 3.26 (s) 3.34 (s) 3.35 (s): $OCH_3$; 3.79 (s) 3.88 (s): $CH_3OAr$; 3.43 (m) 3.54 (m) 3.80–4.00: $CH_2S$, $OCH_2CH_2O$; 4.92 (d): $H_6$ cephalo; 5.70 (dd)+5.77 (dd) $H_7$ cephalo; 533 (m) 5.54 (m): $CH_2N^{+=:\ 5.17\ 5.30}$; $OCH_2O$, $CO_2CH_2Ar$; 6.33 (m): CH=C$\underline{H}$—$CH_2$ (E); 6.35 (s): ArC$\underline{H}$(—O—)$CO_2$—; 6.741 (s) 6.75 (w): $H_5$ thiazole; 6.72 to 7.18: $H_5$, $H_6$ fluorophenyl, $CO_2C\underline{H}C_6H_5$, rH aromatic, C$\underline{H}$=CH—$CH_2$ (E); 7.20 to 7.38: aromatic H C—$(C_6H_5)_3$, $(C_6H_5)_2$—$CH_2$—$CO_2$; 7.61 (d, 2H) 8.8 (m, 2H): $H_3'$, $H_5'$ and $H_2'$, $H_6'$ of the pyridinium; 7.83 (d), 8.15 (d): —CONH.

STEP B: Internal salt of (6R(3(E), 6α,7β-(Z)))-1-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4,2,0) oct-2-en-3-yl)-2-propenyl)-4-(methylthio) pyridinium Using the procedure of Step I of Example 16, 500 mg of the product of Step A were reacted to obtain 251 mg of desired product.

NMR Spectrum DMO 300 MHz: 3.50–3.70: $CH_2S$; 2.72 (s): $CH_3S$; 5.18 (m): $H_6$ cephalo; approx.=5.77 (m): $H_7$ cephalo; 5.24 (m): =CH—$\underline{CH}_2$—N=; 5.83 (s), 5.87 (s): $OCH_2O$, $ArCO_2CH_2$; 6.28 (m): CH=C$\underline{H}$—$CH_2$(E); 6.98 (d, J=16): C$\underline{H}$=CH—$CH_2$; 6.61 (t, resolved): $H_6$ fluorophenyl; 6.77 6.82: $H_5$ and $H_6$ thiazole; 7.32: $NH_2$; 7.96 (d) 8.71 (d): $H_3'$ $H_5'$ and $H_2'$ $H_6'$ of the pyridinium.

EXAMPLE 19

Internal salt of (6r(3(E), 6α,7β (Z)))-2-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4,2,0) oct-2-en-3-yl)-2-propenyl) isoquinolinium STEP A: 1-[3-[7β-[[[[1-[4-fluoro-2,3-bis-[(2-methoxy-ethoxy)-methoxy]-phenyl]-2-oxo-2-(diphenyl-methoxy)-ethyl]-oxy]-imino]-2-(triphenyl methyl)-amino]-thiazol-4-yl]-acetamido]-2-[(4-methoxybenzoyloxy-carbonyl]-8-oxo-5-thia-1-azabicyclo-[4,2,0]-[oct-2-en- 3-yl]-2-propenyl isoquinolinium iodide Using the procedure of Step H of Example 16, 917 mg of the product of Step G of example 16 and 416 mg of isoquinoline were reacted to obtain 473 mg of desired product after chromatography on silica (eluant: methylene chloride-methanol (96,4)).

NMR Spectrum: $CDCl_3$ 300 MHz: 3.20 (s) 3.26 (s) 3.34 (s) 3.35 (s): $CH_3O$; 3.76 (s) 3.78 (s): $ArOCH_3$; 3.40–4.00: OCH—$CH_2O$, $CH_2S$; $H_6$ cephalo; 5.80 (m): $H_7$ cephalo; approx. 5185.30: $OCH_2O$, $ArCO_2CH_2$; approx. 6.48 (m): $CH_2$—CH(E); 6.38 (s) 6.44 ( ): Ar—C$\underline{H}$(—O—)$CO_2$—; 6.73 (s) 6.75 (s): $H_5$ thiazole; approx.=6.76 to 7.49: aromatic H's (phenyl groups), $CO_2C\underline{H}(C_6H_5)_2$; 7.96 (m, 1H) 8.10 (m, 2H) 8.26 (m, 2H) 8.49 (m, 1H) 8.69 (m, 1H) 10.90 (s resolved, 1h): of the isoquinoline.

STEP B: Internal salt of (6R(3(E), 6α,7β (Z))) 2-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4, 2,0) oct-2-en-3-yl)-2-propenyl) isoquinolinium Using the procedure of Step I of Example 16, 460 mg of the product of Step A were reacted to obtain 176 mg of the expected product.

NMR Spectrum: DMSO 400 MHz: 3.72 (m): $CH_2S$; 5.18 (d, resolved): $H_6$ cephalo; 5.77 (dd,d after exchange) —$H_7$ cephalo; 5.52 (m): $CH_2$—$N^{+=:\ 5.83}$ (s), 5.87 (s): Ar—C$\underline{H}_2$(—O—)$CO_2^-$; 6.39 (m): CH=C$\underline{H}$—$CH_2$(ΔE); 7.10 (d, J=10): C$\underline{H}$CH—$CH_2$ (E); 6.59 (m), 6.80 (m) $H_6$, $H_5$ fluorophenyl; 6.77 (s) 6.80 (s): $H_5$ thiazole; 8.09 (t) 8.28 (t) and 8.37 (d) 8.53 (d) 8.61 (d) 8.74 (m) 10.06 (s): $H_6'$–$H_7'$ and $H_3'$ $H_4'$ and $H_5'$ and $H_8'$ and $H_1'$ of the isoquinoline.

EXAMPLE 20

Internal salt of (6R(E(E) 6α,7β (Z))) 1-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4,2,0)oct-2-en-3-yl)-2-propenyl)-imidazo(1,2-a) pyridinium STEP A: 1-[3-[7β-[[[[1-[4-fluoro-2,3-bis-[(2-methoxy-ethoxy)-methoxy]-phenyl]-2-oxo-2-diphenyl-methoxy)-ethyl]-oxy]-imino][2-(triphenylmethyl)-amino]-thiazol-4-yl]-acetamido]-2-[(4-methoxy-benzyloxy-carbonyl]-8-oxo-5-thia-1-azabicyclo-[4,2,0]-[oct-2-en-3-yl]-2-propenyl-imidazo-(1,2-a) pyridinium iodide Using the procedure of Step H of Example 16, 955 mg of the product of Step G of Example 16 and 401 mg of imidazo [1,2-a] pyridine were reacted to obtain 486 mg of expected product after chromatography on silica, eluant: methylene chloride-methanol (95,5).

NMR Spectrum: $CDCl_3$ 399 MHz 3.20 (w) 326 (s) 3.34 (s) 3.35 (s): $CH_3O$; 3.40–3.95: $OCH_2$—$CH_2O$, $CH_2S$; 4.89 (d): $H_6$ cephalo; 5.74 (m): $H_7$ cephalo; 5.20–5.42 (9H, excess): $ArCO_2CH_2$—$OCH_2O$, CH—$\underline{CH}_2$—$N^{+=:\ 6.28}$ (m): =C$\underline{H}$—$CH_2$(E); 6.38 (s) 6.44 (s): Ar—C$\underline{H}$(—O—)$CO_2^-$; 6.88 (s) 6.90 (s): $CO_2C\underline{H}(C_6H_5)_2$; approx. 6.75 to 7.35: aromatic H's (phenyl groups)+nitrogenous bicyclic H's; 7.85 (m, 1H) 8.03 (d, 1H) 8.36 (d, 1H) 9.09 (m, 1H); other nitrogenous bicycle H's; 7.94 (d), 8.25 (d): CONH.

STEP B: Internal salt of (6R(3(E), 6α,7β (Z))) 1-(3-(7-(((2-amino-4-thiazolyl)-(carboxy-(2,3-dihydroxy-4-fluorophenyl)-methoxy)-imino)-acetamido)-2-carboxy-8-oxo-5-thia-1-azabicyclo (4, 2,0)oct-2-en-3-yl)-2-propenyl)imidazo (1,2-a) pyridinium Using the procedure of Step I of Example 16, 476 mg of the product of Step A were reacted to obtain 215 mg of desired product.

NMR Spectrum: (DMSO, 400 MHz 3.70 (m): $CH_2S$; 5.15 (d, resolved): $H_6$ cephalo; 5.74 (dd, d after exchange) 5.82 (dd, d after exchange): $H_7$ cephalo; 5.28 (m): $CH_2$—$N^{+=}$ 5.83 (s), 5.86 (s): Ar—C$\underline{H}$(—O—)$CO_2^-$; 6.25 (m): CH=C $\underline{H}$—$CH_2$ (E); 6.89 (d, resolved, J=15.5): C $\underline{H}$=CH—$CH_2$(E); 6.60 (m), 6.78 (m): $H_6$, $H_5$ fluorophenyl; 6.76 (s) 6.80 (s): $H_5$ thiazole; 7.57 (m) 8.05 (m) 8.19 (m) and 8.28 (d, resolved, J=2.5) 8.44 (d, resolved, J=2.5) 8.96 (d, J=6.5): $H_51'$, $H_6'$, $H_7'$, $H_4'$ and $H_2'$, $H_3^{-1}$ of the imidazo (1,2-a)pyridinium; 9.44 (d) 9.56 (d) CON$\underline{H}$—C; 7.32 (m) 9.40 (m): mobile H's.

EXAMPLE 21

Internal salt of (6R-(3-(E) 6α,7β (Z))1-(3-(7-(((2-amino-4-thiazolyl)-(carboxy-(2,3-dihydroxy-phenyl)-methoxy-imino)-acetamido)-2-carboxy-8-oxo-5-thia-1-azabicyclo[4,2,0]oct-2-en-3-yl)-2-propenyl)-4-(methylthio) pyridinium STEP A: Ethyl [(2,3-dihydroxy)-phenyl]-hydroxy acetate 10 ml of a molar solution of titanium chloride in methylene chloride were added to a solution of 1.1 g of pyrocatechol in 20 ml of methylene chloride cooled to −20° C. and the mixture was stirred for 30 minutes at −20° C. Then, a solution of 1.02 g of ethyl glyoxylate in 10 ml of methylene chloride was added over 5 minutes and the mixture was stirred for 2 hours at −20° C. The mixture was allowed to return to ambient temperature and then was poured into 50 ml of a saturated solution of ammonium chloride, extracted with methylene chloride. The extracts were washed, dried and evaporated to dryness under reduced pressure. The residue was chromatographed on silica (eluant: methylene chloride-ethyl acetate (7-3)), to obtain 860 mg of the desired product melting at 86° C.

IR Spectrum: $CHCl_3$ 3595 $cm^{-1}$, 340 $c.^{-1}$ OH complex+ associated, 1730 $cm^{-1}$ C=O, 1602–1402 $cm^{-1}$: aromatic.

NMR Spectrum: $CDCl_3$ 250 MHz ppm 5.33 (s): C—C $\underline{H}$(OH)COOEt; 1.26 (t)–4.27 (m): COOEt; 3.75–5.86–7.45: mobile H; 6.7 to 6.95: aromatic H's.

STEP B: Ethyl [2,3-bis-((2-methoxy ethoxy)-methoxy]-phenyl]-hydroxy acetate 15.69 g of methoxy ethoxy methyl chloride and 16.35 g of N-ethyl diisopropylamine were added to a solution of 8.1 g of the product of Step A in 750 ml of acetonitrile and the mixture was stirred for 16 hours at 0° C. Then, the mixture was poured into 100 ml of water and the acetonitrile was evaporated off, followed by taking up in methylene chloride, washing with 1N hydrochloric acid, with water, then with a 10% solution of sodium carbonate. After drying and evaporating to dryness under reduced pressure, the 12.3 g of product was chromatographed on silica (eluant: cyclohexane-ethyl acetate (5-5)) to obtain 6.7 g of the desired product.

IR Spectrum: $CHCl_3$ 3315–3440 $cm^{-1}$: OH complex; 1735 $cm^{-1}$: C=O; 1601–1590 $cm^{-1}$: aromatics.

NMR Spectrum: $CDCl_3$ 250 MHz 1.21 and 4.22: $CO_2Et$; 3.37: $OCH_3$; 3.57–3.83–3.93: $CH_2$—$CH_2$—O; 5.25–5.28: O—$CH_2$—O; 4.07: OH; 5.39; C—CH(OH)—$CO_2Et$.

STEP C: Diphenylmethyl [2,3-bis-[(2-methoxy-ethoxy)-methoxy]-phenyl]-hydroxy acetate a) Saponification 22 ml of 2N sodium hydroxide were added to a solution of 8.54 g of the product of Step B in 400 ml of ethanol and the mixture was stirred for 3 hours at ambient temperature, followed by acidifying to pH 2 with a N hydrochloric acid, concentrating to ½ volume under reduced pressure, diluting with 200 ml of water and extracting with methylene chloride and ethyl acetate. The extracts were dried and after evaporating to dryness under reduced pressure, 8.2 g of [2,3-bis-[(2-methoxy-ethoxy)-methoxy]-phenyl]-hydroxy acetic acid were obtained.

b) Esterification 109 ml of diphenyl diazomethane in a 0.3M solution in ethyl ether were added to a solution of 8.2 g of the above acid in 300 ml of methylene chloride cooled to 0° C. and the mixture was stirred for 16 hours at ambient temperature. Acetic acid was added at 0° C. followed by evaporation to dryness under reduced pressure to obtain 13 g of product which was chromatographed on silica, eluant: cyclohexane-ethyl acetate (6-4) to obtain 10.2 g of the desired product.

IR Spectrum: $CHCl_3$ 3530–3520 $cm^{-1}$: OH complex; 1742 $cm^{-1}$: C=O; 1600–1585–1495 $cm^{-1}$: aromatics.

NMR Spectrum $CDCl_3$ 300 MHz 3.34–3.37: $CH_3$; 3.54–3.83: O—$CH_2$—$CH_2$; 4.08: 5.18–5.28: $OCH_2O$; 5.53: C—C$\underline{H}$(OH)C—$(C_6H_5)_2$.

STEP D: Diphenylmethyl [2,3-bis-[(2-methoxy-ethoxy)-methoxy]-phenyl]-phthalimidoxy acetate 226 mg of triphenyl phosphine and 77 mg of N-hydroxy phthalimide were added at ambient temperature to a solution of 227 mg of the product of Step C in 25 ml of tetrahydrofuran. The mixture is cooled to −5° C. and 136 ul (150 mg) of diethylazodicarboxylate were added over 2 hours. The mixture was stirred for 2 hours while allowing the temperature to rise to ambient and was then poured into 25 ml of ice-cooled water, extracted with methylene chloride then with ethyl acetate. The extracts were dried and evaporated to dryness under reduced pressure to obtain 760 mg of residue which was chromatographed on silica (eluant: methylene chloride-acetone (97-3)) to obtain 230 mg of the desired product.

IR Spectrum: $CHCl_3$ 1794–1738 $cm^{-1}$: C=O; 1602–1588–1488 $cm^{-1}$: aromatics.

NMR Spectrum: $CDCl_3$ 300 MHz 3.31 3.36: $CH_3$; 3.46–3.52–3.79–3.89: $CH_2$—$CH_2O$; 5.24: O—$CH_2$—O; 6.43: C—C$\underline{H}$(ON=)$CO_2C$—$(C_6H_5)_2$; 6.95: C $\underline{H}$—$(C_6H_5)_2$; 7.72: Ar—$\underline{H}$ phthalimido; 7.0–7.35: Ar—H aromatic.

STEP E: Diphenylmethyl aminoxy [2,3-bis-[(2-methoxy-ethoxy)-methoxy]-phenyl] acetate 1.42 ml of (1.47 g) of hydrazine hydrate were added to a solution of 6.2 g of the product of Step D in 400 ml of ethanol and 20 ml of methylene chloride and the mixture was stirred for 3 hours at ambient temperature. After evaporating to dryness under reduced pressure, the dry extract was taken up in methylene chloride and the insoluble part was filtered out. The filtrate was evaporated to dryness under reduced pressure to obtain 5.0 g of desired product.

IR Spectrum $CHCl_3$: 3335 $cm^{-1}$: $ONH_2$; 1745 $cm^{-1}$: C=O; aromatics 1602, 1589, 1577, 1495 $cm^{-1}$ aromatics.

NMR Spectrum: $CDCl_3$ 250 MHz 3.35–3.37: $OCH_3$; 3.54–3.83–3.95: O—$CH_2CH_2$—O; 5.26–5.29: O—$CH_2$—O; 5.75: —C—C$\underline{H}$($ONH_2$)$CO_2C$—$(C_6H_5)_2$; 5.86: O—$NH_2$; 6.95: COO—C$\underline{H}$$(C_6H_5)_2$.

STEP F: [[[1-[2,3-bis-[(methoxy-ethoxy)-methoxy]-phenyl-2-oxo-2-(diphenyl-methoxy)-ethyl]-oxy]-imino]-[2-triphenyl-methyl)-amino]-thiazol-4-yl] acetic acid A mixture of 5.0 g of the product of Step E in solution in 60 ml of methanol with 4.016 g of [2-[(triphenyl-methyl)- amino]-thiazol-4-yl] acetic acid described in Belgian Patent Application No. 864,828) was stirred for 6 hours. After evaporating to dryness, the residue was chromatographed on silica, eluant: ethyl acetate-ethanol (7-3) to obtain 5.55 g of desired product.

IR Spectrum: $CHCl_3$ =C—NH, 3405 $cm^{-1}$; C=O: 1735 $cm^{-1}$; C=N, aromatic and $CO_2^-$: 1619–1602–1529–1494 $cm^{-1}$ NMR Spectrum: $CDCl_3$ 250 MHz 3.13–3.31: $CH_3$; 3.34–3.49–3.76: O—$CH_2$—$CH_2$O; 5.14–5.18 O—$CH_2$—O; 6.11: —C—CH(ON=)$CO_2$C—; 6.46: —$CO_2$—CH($C_6H_5$)$_2$; 6.81: CH thiazol; 6.75 to 7.3 aromatic H's.

STEP G: 4-methoxy-benzyl 7β-[[[[[1-[2,3-bis-[(2-methoxy-ethoxy)-methoxy]-phenyl]-2-oxo-2-(diphenyl-methoxy)-ethyl]-oxy]-imino]-[2-[(triphenyl-methyl)-amino]-thiazol-4-yl]-acetamido]-3-[(Z)-3-chloro-1-propenyl]-8-oxo-5-thia-1-azabicyclo-[4,2,0]-oct-2-en-2-carboxylate 3.55 g of 4-methoxy benzyl 7β-amino-3-[(Z)-3-chloro-1-propenyl]-8-oxo-5-thia-1-azabicyclo[4,2,0]oct-2-en-2-carboxylate hydrochloride (described in EP Application No. 0,333,154) and 1.6 g of N-ethyl dimethylaminopropyl carbodiimide (EDAC) were added to a solution of 6.18 g of the product of Step F in 150 ml of methylene chloride and cooled to 0° C. The mixture was stirred for 10 minutes at 0° C., then for 2 hours while allowing the temperature to rise 20° C. The mixture was poured into a molar solution of potassium hydrogen phosphate and extraction took place with methylene chloride, then with ethyl acetate followed by drying and evaporating to dryness. After chromatography on silica and eluting with methylene chloride-ethyl acetate (9-1), 5.1 g of the desired product were obtained.

IR Spectrum: $CDCl_3$ 3040 $cm^{-1}$: =C—NH; 1790–1731–1684 $cm^{-1}$: C=O; aromatics heteroatom, amide II: 1613, 1597–1526–1517–1496 $cm^{-1}$.

NMR Spectrum: $CDCl_3$ (300 MHz) 3.24 to 3.37: $CH_2$—O—$CH_3$ and C—s—$CH_2$—; 3.44 to 4.0: $CH_2Cl$ and $C_6H_5OCH_3$; 3.44 to 4.0: O—$CH_2$—$CH_2$—; 5.15 to 5.28: —O—$CH_2$—O; 5.67 to 5.88, 6.29: C—CH—$CH_2Cl$; 6.77: CH thiazol; 6.7 to 7.4: aromatics; 8.01–8.37: NH.

STEP H: 4-methoxy-benzyl 7β-[[[[[1-[2,3-bis-[(2-methoxy-ethoxy)-methoxy]-phenyl]-2-oxo-2-(diphenyl-methoxy)-ethyl]-oxy]-imino]-[2-(triphenyl-methyl)-amino]-thiazol-4-yl]-acetamido]-3-[(Z)-3-iodo- 1-propenyl]-8-oxo-5-thia-1-azabicyclo-[4 2,0]-oct-2-en-2 carboxylate 0.57 g of sodium iodide and 1 crystal of iodine were added to a solution of 1.25 g of the product of Step G in 5 ml of acetone and the mixture was stirred for 90 minutes at ambient temperature. After evaporating to dryness under reduced pressure, the dry extract was taken up in methylene chloride, washed with a 10% solution of sodium thiosulfate, then with salt water, followed by drying and evaporating to dryness under reduced pressure to obtain 1.28 g of the expected product which is used as is for the following step.

STEP I: 1-[3[7β-[[[[[1-[2,3-bis-[(2-methoxy-ethoxy) -methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo-[4,2,0]-[oct-2-en-3-yl]-2-propenyl]-4-methyl-thio pyridinium iodide 1.28 g of the product of Step H, 1.15 g of thiomethyl pyridine and 3 ml of methylene chloride were mixed together and after evaporating to dryness under reduced pressure, the residue was chromatographed on silica (eluant: methylene chloride-methanol (97-3), then (96-4) and (95-5)) to obtain 415 mg of the desired product.

NMR Spectrum: $CDCl_3$ 250 MHz 2.6: S—$CH_3$; 3.21, 3.25, 3.35, 3.36, 3.37: —$OCH_3$; 3.4 to 3.9: —O—$CH_2$—$CH_2$—O; 3.77, 3.79 $C_6H_5$—$OCH_3$ STEP J: Internal salt of (6R-(E) 6α,7β-(Z))) 1-3-(7-(((2-amino-4-thiazolyl)-(carboxy-(2,3-dihydroxy-phenyl)-methoxy)-imino)-acetamido)-2-carboxy-8-oxo-5-thia-1-azabicyclo-[4,2,0]-oct-2-en-3-yl)-2-propenyl)-4-(methylthio) pyridinium 400 mg of the product of Step I, 4.5 ml of trifluoroacetic acid and 0.5 ml of anisole were stirred for 2 hours at ambient temperature and then, 0.5 ml of water were added. The mixture was stirred for 2 hours at ambient temperature, followed by filtering, rinsing twice with 3 ml of trifluoroacetic acid and 15 ml of ethyl ether were added. The mixture was stirred for 15 minutes, followed by separating and drying under reduced pressure to obtain 222 mg of the desired product.

MR Spectrum: DMSO (300 MHz) ppm 2.71: $SCH_3$; 3.72: C—S—$CH_2$—C; 5.19, 5.76, 5.83; —S—CH—(—N=)—CH—NH—; 5.22: —C=C—$CH_2$—$N^+$; 5.91, 5.95: H imino-carboxybenzyl; 6.28: —CH=C H—$CH_2$—$N^+$; 6.98: —CH=CH—$CH_2$—$N^+$; 6.59, 6.79: aromatic H's; 6.79 6.83: H thiazol; 9.49: NH.

EXAMPLE 22

Internal salt of (6R-(3-(E) 6α,7β-(Z))) 7-(3-(7-(((2-amino-4-thiazolyl)-(carboxy-( 2,3-dihydroxyphenyl) -methoxy)-imino)-acetamido)-2-carboxy-8-oxo-5-thia-1-azabicyclo-[4,2,0]-oct-2-en-3-yl)-2-propenyl)-thieno-(2,3-b]-pyridinium STEP A: 1-[3-[7β-[[[[[-[2,3-bis-[(1-methoxy)-ethoxy)-methoxy]-phenyl]-2-oxo-2-(diphenyl-methoxy)-ethyl]-oxy]-imino]-[2-[(triphenylmethyl)-amino]-thiazol[4-yl]-acetamido]-2-[(4-methoxy-benzyloxy)-carbonyl]-8-oxo-5-thia-1-azabicyclo[4,2,0]-[oct-2-en-3-yl]pyridinium iodide Using the procedure of Step I of Example 21, 1.24 g of the product of Step H of Example 21 and 1.28 of thieno (2,3-b) pyridine were reacted to obtain after chromatography on silica, eluant: methylene chloride-methanol (97-3 then 96-4 and 95-5), 450 mg of the desired product.

IR Spectrum: $CHCl_3$ =C—NH: 3404 $cm^{-1}$; C=O: 1790, 1731, 1684 $cm^{-1}$; C=C, aromatics, heteroatoms, amide II: 1613, 1587, 1526, 1517, 1496 $cm^{-1}$; thieno pyridine: 1599 $cm^{-1}$.

NMR Spectrum: $CDCl_3$ 300 MHz 3.21, 3.26, 3.34, 3.37: $CH_2$—O—$CH_3$; 3.43, 3.55, 3.82: —O—$CH_2$—O—CH$_2$—$CH_2$; 3.80: $C_6H_5O$—$CH_3$; 5.2 to 5.3: O—CH$_2$—O—$CH_2$—, $CO_2CH_2C_6H_5$—O—; 5.90: —CH—$CH_2$—$N^+$; 6.45 to 6.6: C—CH=CH—$CH_2$—$N^+$; 6.51 to 6.56: $CO_2$—CH($C_6H_5$)$_2$; 6.73: H thiazol; 6.85 to 8.78: aromatic H's.

STEP B: Internal salt of (6R-(3-(E) 6α,7β-(Z)))-7-(3-(7-(((2-amino-4-thiazolyl)-(carboxy-(2,3-dihydroxy-phenyl)-methoxy)-imino)-acetamido)-2-carboxy-8-oxo-5-thia-1-azabicyclo[4,2,0]oct-2-en-3-yl)-2-propenyl)-thieno(2,3-b) pyridinium Using the procedure of Step J of Example 21, 430 mg of the product of Step A were reacted to obtain 206 mg of desired product.

IR Spectrum: Nujol C=O: 1775 cm⁻¹ (β-lactam) 1670 cm⁻¹ (complex); conjugated system, aromatic, NH₂, amide: 1599, 1580, 1520 cm⁻¹.

NMR Spectrum: CDCl₃ 400 MHz 3.69: —S—C$\underline{H}_2$—C—; 5.18, 5.78, 5.86: —NH—C$\underline{H}$—C$\underline{H}$—S—; 5.67: =CH—C$\underline{H}_2$—N⁺; 5.91, 5.95: —C—CH(O—N=)CO₂H; 6.31 and 7.15: the H's of the propylene; 6.59 and 6.79: aromatic H's; 6.78 and 6.82: H thiazol; 7.89 to 9.22: thieno pyridine; 9.49 and 9.61: amide.

EXAMPLE 23

Internal salt of (6R-(3-(E) 6α,7β-(Z)))-7-(3-(7-(((2-amino-4-thiazolyl)-(carboxy-(2,3-dihydroxy-phenyl)-methoxy)-imino)-acetamido)-2-carboxy-8-oxo-5-thia-1-azabicyclo[4.2.0]oct-2-en-3-yl)-2-propenyl)-imidazo (1,2-a) pyridinium STEP A: 1-[3-[7β-[[[[1-[2,3-bis-[(2-methoxy-ethoxy)-methoxy]-phenyl]-2-oxo-2-(diphenyl-methoxy)-ethyl]-oxy]-imino]-[2-[(triphenylmethyl)-amino]-thiazol-4-yl]-acetamido]-2-[(4-methoxybenzyloxy)-carbonyl]-8-oxo-5-thia-1-azabicyclo[4.2.0][oct-2-en-3-yl]-2-propenyl]-imidazo(1,2-a) pyridinium iodide Using the procedure of Step I of Example 21, 1.24 g of the product of Step H of Example 21 and 1.28 g of imidazopyridine were reacted to obtain 270 mg of expected product.

NMR Spectrum CDCl₃ 400 MHz 3.25, 3.20, 3.35, 3.37: CH₂OCH₃; 3.30 to 3.90: OCH₂—C$\underline{H}_2$—OCH₃; 3.30 to 390: —S—C$\underline{H}_2$—C—; 3.78, 3.79: —C₆H₅OCH₃; 4.88 and 5.72: NH—C$\underline{H}$—C$\underline{H}$—S; 5.10 to 5.50: C—O—C$\underline{H}_2$—OCH₂—, =C—C$\underline{H}_2$—N⁺; 6.28: C—CH=C$\underline{H}$—CH₂—; 6.51 to 6.56: —C—C$\underline{H}$(O—N=)CO₂CH; 6.7 to 7.4: aromatic H, H thiazol, H propylene; 7.93, 8.20: NH.

STEP B: Internal salt of (6R-(3-(E) 6α,7β-(Z))) 7-(3-(7-(((2-amino-4-thiazolyl)-(carboxy-(2,3-dihydroxy-phenyl)-methoxy-imino)-acetamido)-2-carboxy-8-oxo-5-thia-1-azabicyclo[4.2.0]oct-2-en-3-yl]-2-propenyl)-imidazo(1,2-a) pyridinium Using the procedure of Step J of Example 21, 280 mg of the product of Step A were reacted to obtain 140 mg of desired product.

IR Spectrum: C=O: 1775, 1670 cm⁻¹; conjugated system, aromatic, amide II: 1598, 1530, 1510 cm⁻¹.

NMR Spectrum: DMSO 300 MHz 3.45 to 4.20: —S—C$\underline{H}_2$—; 5.16, 5.76, 5.82: —NH—C$\underline{H}$—C$\underline{H}$—S—; 5.29: —CH₂—N⁺—; 5.91, 5.94: C—C$\underline{H}$(—O—N=)CO₂H; 6.26: 1H propylene; 6.58, 6.70 to 6.95: H thiazol, aromatic, 1H propylene; 9.47, 9.58: NH; 7.58, 8.06, 8.20, 8.96, 8.29, 8.44: bicycle.

EXAMPLE 24

Internal salt of (6R-(3-(E) 6α,7β-(Z))) 7-(3-(7-(((3-amino-4-thiazolyl)-(carboxy-(2,3-dihydroxy-phenyl)-methoxy)-imino)-acetamido)-2-carboxy-8-oxo-5-thia-1-azabicyclo[4.2.0]oct-2-en-3-yl)-2-propenyl)-quinolinium STEP A: 1-[3-[7β-[[[[1-[2,3-bis-[(2-methoxy-ethoxy)-methoxy]-phenyl]-2-oxo-2-(diphenyl-methoxy)-ethyl]-oxy]-imino]-[2-[(triphenylmethyl)-amino]-thiazol-4-yl]-acetamido]-2-[(4-methoxybenzyloxy)-carbonyl]-8-oxo-5-thia-1-azabicyclo[4.2.0][oct.2-en-3-yl]-2-propenyl]-quinolinium iodide Using the procedure of Step I of Example 21, 1.33 g of the product of Step H of Example 21 and 1.2 g of quinoline were reacted to obtain 475 mg of the desired product after chromatography on silica (eluant: methylene chloride-methanol (97-3 then 95-5)).

NMR Spectrum: 3.42 to 3.95: OCH₂—CH₂—OCH₃; 3.78, 3.79: —C₆H₄—OCH₃; 5.13 to 5.28: —OC$\underline{H}_2$—O—CH₂—, =C—C$\underline{H}$—(O—N=); 5.96, 6.11: —CH₂—N⁺; 6.49, 6.55: —CO₂—C$\underline{H}$—(C₆H₅)₂; 6.85, 8.93: aromatics.

STEP B: Internal salt of (6R-(3-(E) 6α,7β (Z))) 7-(3-(7-(((2-amino-4-thiazolyl) (carboxy-(2,3-dihydroxy-phenyl)-methoxy)-imino)-acetamido)-2-carboxy-8-oxo-5-thia-1-azabicyclo[4.2.0]oct-2-en-3-yl)-2-propenyl quinolinium Using the procedure of Step J of Example 21, 465 mg of the product of Step A were reacted to obtain 255 mg of the desired product.

NMR Spectrum: DMSO 300 MHz 3.3 to 3.8: —S—CH₂—; 5.15 and 5.78: —NH—C$\underline{H}$—C$\underline{H}$—S—; 5.91: —C—C$\underline{H}$(O—N=)CO₂H and CH₂—N⁺—; 6.39: =C—CH=C$\underline{H}$—; 6.99: =C—C$\underline{H}$—CH— 6.7 to 6.9: aromatic H's; 8.08 to 9.58: bicyclic H.

EXAMPLE 25

Internal salt of (6R-(3-(E) 6α,7β (Z))) 1-(3-(7-(((2-amino-4-thiazolyl) (carboxy-(2,5-dichloro-3,4-dihydroxy-phenyl)-methoxy)-imino)-acetamido)-2-carboxy-8-oxo-5-thia-1-azabicyclo[4.2.0]oct-2-en-3-yl)-2-propenyl)-N,N-dimethyl benzenaminium STEP A: [[[1-[2,5-dichloro-3,4-bis-[(2-methoxy ethoxy)-methoxy]-phenyl]-2-oxo-2-(diphenyl methoxy)-ethyl]-oxy]-imino]-[2-[(triphenylmethyl)-amino]-thiazol-4-yl] acetic acid Using the procedure of Step E of Example 1, 3.5 g diphenyl methyl aminoxy [2,5-dichloro-3,4-bis-[(2-methoxy-ethoxy)-methoxy]-phenyl]-acetate in Step E of Example 9) and 2.37 g oxo [2-[(triphenyl-methyl)-amino]-thiazol-4-yl]-acetic acid in Belgian Patent Application No. 864,828 were reacted to obtain after chromatography on silica (eluant: ethyl acetate-ethanol (9-1)) 5.14 g of the desired product.

NMR Spectrum: 300 MHz CDCl₃ 3.30 (s): OCH₃; 3.51, 3.92 (m) —O—C$\underline{H}_2$—OCH₃; 5.16 (s) 5.18 (s) O—CH₂—O; 6.25: C$\underline{H}$—CO—CHφ₂. H₆; 7.20 to 7.30: aromatic H's.

STEP B: 4-methoxy-benzyl 7β-[[[[1-[2,5-dichloro-3,4-bis-[(2-methoxy-ethoxy)-methoxy]-phenyl]-2-oxo-2-(diphenyl-methoxy)-ethyl]-oxy]-imino]-[2-[(triphenylmethyl)-amino]-thiazol-4-yl]-acetamido]-3-[(Z)-3-chloro-1-propenyl]-8-oxo-5-thia-1-azabicyclo[4.2.0]oct-2-en-2-carboxylate Using the procedure of Step F of Example 1, 4.8 g of the product of Step A and 2.26 g of 4-methoxy-benzyl 7β-amino-3-[(Z)-3-chloro-1-propenyl]-8-oxo-5-thia-1-azabicyclo[4.2.0]oct-2-en-2-carboxylate hydrochloride (EP Patent No. 0,333,154) were reacted to obtain after chromatography on silica (eluant: methylene chloride-ethyl-ether (9-1)), 4.6 g of desired product.

NMR Spectrum: 300 MHz CDCl₃ 3.05 (m) 3.45 (m): —CH₂—Cl; 3.36, 3.37 (s): —O—CH₃; 3.57 (m) 3.97 (m): O—C$\underline{H}_2$—O—; 3.81 (s,d): —o—OC$\underline{H}_3$; 4.99, 5.02 (d): NH—CH—C$\underline{H}$—S; 5.86, 5.90: NH—C$\underline{H}$CH—S; 5.15 to 5.26: O—C$\underline{H}_2$—O—; 5.75 (m): H₂ propylene; 6.26 (J=11.5)

(d) 6.35 (J=11.5) (d): $H_1$ propylene; 6.47 to 6.50 (s) —$CO_2$—CH—$o_2$; 6.85 to 7.40 the aromatic H's.

STEP C: 4-methoxy-benzyl 7β-[[[[1-[2,5-dichloro-3,4-bis-[(2-methoxy-ethoxy)-methoxy]-phenyl]-2-oxo-2-(diphenyl-methoxy)-ethyl]-oxy]-imino]-[2-[(triphenylmethyl)-amino]-thiazol-4-yl]-acetamido]-3-[(Z)-3-iodo-1-propenyl]-8-oxo-5-thia-1-azabicyclo[4.2.0]oct-2-en-2 carboxylate Using the procedure of Step G of Example 1, 150 mg of the product of Step B were reacted to obtain 160 mg of the desired product.

STEP D: 1-[3-[7β-[[[[1-[2,5-dichloro-3,4-bis-[(2-methoxyethoxy)-methoxy]-phenyl]-2-oxo-2-(diphenyl-methoxy)-ethyl]-oxy]-imino]-2-[(triphenylmethyl)-amino]-thiazol-4-yl]-acetamido]-2-[(4-methoxy-benzyloxy)-carbonyl]-8-oxo-5-thia-1-azabicyclo[4.2.0]oct-2-en-3-yl]-2-propenyl]-N,N-dimethyl benzene aminium iodide Using the procedure of Step H of Example 1, 155 mg of the product of Step C and 64 mg of N,N-dimethylaniline were reacted to obtain after chromatography on silica (eluant: methylene chloride-methanol (96-4)), 55 mg of the desired product.

NMR Spectrum: $CDCl_3$ 300 MHz 2.95 (s):

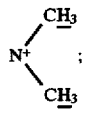

3.30 to 3.45: —S—$CH_2$—, 3.35, 3.36, 3.37 (s): O—$CH_3$; 3.82 (s,d) φ—$OCH_3$; 3.90 to 4.05: —O—$CH_2CH_2$—O—, =C—$CH_2$—N($CH_3$)$_2$o; 4.94 (d)-4.98 (d): NH—CH—CH—S; 5.87 (m): NH—CH—CH—S; 5.18 to 5.30 (m): O—$CH_2$—O and O—$CH_2$—o; 6.14 (m) (E) C—CH=CH—$CH_2$—; 6.70 to 7.40 (m) C—CH—CH—$CH_2$—, H thiazole, aromatic H's; 8.17, 8.25 (d): NH.

STEP E: Internal salt of (6R-(3-(E) 6α,7β-(Z)))-1-(3-(7-(((2-amino-4-thiazolyl)-(carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-N,N-dimethyl benzene aminium Using the procedure of Step I of Example 1, 50 mg of the product of Step D were reacted to obtain 22 mg of the desired product.

EXAMPLE 26

Internal salt of (6R-(3-(E) 6α,7β-(Z)))-1-(3-(7-(((2-amino-4-thiazolyl)-(carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-imidazo (1,2-a) pyridinium STEP A: 1-[3-[7β-[[[[1-[2,5-dichloro-3,4-bis-[(2-methoxyethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl]-imidazo (1,2-a)pyridinium iodide Using the procedure of Step H of Example 1, 1.24 g of the product of Step C of Example 25 and 0.497 g of imidazo (1,2-a) pyridine were reacted to obtain after chromatography on silica (eluant: methylene chloride-methanol (95-5)), 625 mg of the desired product.

NMR Spectrum: $CDCl_3$ 400 MHz 3.34, 3.36: —$CH_2$—O—$CH_3$; 3.50, 3.87: O—$CH_2$—$CH_2$—OMe; 3.80 (s) —o—$OCH_3$; 4.94 (d,d): —NH—CH—CH—S—; 5.20, 5.24: —O—$CH_2$—O—, $CO_2$—$CH_2$—φ—; 5.86: NH—CH—CH—S; 6.15, 6.35: H propylene; 6.47, 6.51: =N—O—CH—; 6.77: H thiazole; 6.90 to 7.40: the aromatic H's; 7.88, 8.04: H of the imidazole; 7.88: —N HCφ$_3$.

STEP B: Internal salt of (6R-(3-(E) 6α,7β-(Z)))-1-(3-(7-(((2-amino-4-thiazolyl)-(carboxy-(2,5-dichloro-3,4-dihydroxy-phenyl)-methoxy-imino)-acetamido)-2-carboxy-8-oxo-5-thia-1-azabicyclo[4,2,0]oct-2-en-3-yl)-2-propenyl)-imidazo (1,2-a) pyridinium Using the procedure of Step I of Example 1, the product of Step A were reacted to obtain 327 mg of desired product.

NMR Spectrum: $CDCl_3$300 MHZ 3.50 to 3.75: —S—$CH_2$—C=; 5.16: —NH—CH—CH—S—; 5.79 (m): —NH—CH—CH—S—; 6.24 (m): =C—CH=CH—C—; 6.91 (dd): =C—CH=CH—C—; 6.83 (dd): H thiazole; 7.58, 8.06 (t) and 8.21, 8.96 (d): H pyridine; 8.29, 8.45: H imidazole; 9.62: NH; 993: $NH_2$, $CO_2H$.

EXAMPLE 27

Internal salt of (6R-(3-(E) 6α,7β-(Z))) 1-(3-(7-(((2-amino-4-thiazolyl)-(carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-6,7-dihydro-5H-pyrindinium STEP A: 1-[3-[7β-[[[[1-[2,5-dichloro-3,4-bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl]-6,7-dihydro-5H-pyrindinium iodide Using the procedure of Step H of Example 1) 1.13 g of the product of Step C of Example 25 and 457 mg of cyclopentano [2,3-a] pyridine were reacted to obtain after chromatography on silica (eluant: methylene chloride-methanol (9-1)) 460 mg of the desired product.

NMR Spectrum: $CDCl_3$ 300 MHz ppm 2.41, 3.23, 3.45: —S—$CH_2$ and $CH_2$ of the cyclopentane; 3.34 to 3.37: O—$CH_3$; 3.57 to 3.98: —O—$CH_2$—$CH_2$—O—; 3.81: O—O—ch$_3$; 4.97, 5.88: NH—CH—CH—S—; 5.12 to 5.25: —O—$CH_2$—O—; 6.22 and 6.45 (ΔE) =C—CH—CH—$CH_2$—; 6.85 t 7.35: =C—CH=CH—$CH_2$—; 6.46, 6.50 (s) =N—O—CH—$CO_2$—; 6.72: H thiazole; 6.85 to 7.35: aromatic H's 7.97, 8.23 (d): NH; 7.79, 9.20: H pyridine.

STEP B: Internal salt of (6R-(3-(E) 6α,7β-(Z)))-1-(3-(7-(((2-amino-4-thiazolyl)-(carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-6,7-dihydro-5H-pyrindinium Using the procedure of Step I of Example 1, 447 mg of the product of Step A were reacted to obtain 194 mg of the desired product.

NMR Spectrum: DMSO 300 MHz 2.23 (m): the central CH$_2$'s; 3.19 (t) the =C—CH$_2$'s; 5.17 (d): H$_6$; 5.33 (m): =CH—CH$_2$—N$^+$; 5.78 (m) (2H): the H$_7$'s and O—CH—φ's; 6.23 (m): CH$_2$—CH= E; 6.82 (s) (d): H$_5$, thiazole's; 6.89 (d)d) the =C—CH=CH (ΔE)'s; 7.01 (s.d) aromatic H; 7.91 (t): H$_5$'; 8.42 (d): H$_4$'; 8.76 (d): H$_6$'; 7.35 (1): NH$_2$; 9.56 to 10.0 the mobile H's.

EXAMPLE 28

Internal salt of (6R-(3-(E) 6α.7β-(Z))) 1-(3-(-(((2-amino-4-thiazolyl) carboxy-(2.5-dichloro-3,4-dihydroxy-phenyl)-methoxy)-imino)-acetamido)-2-carboxy-8-oxo-5-thia-1-azabicyclo[4.2.0]oct-2-en-3-yl)-2-propenyl)-1-methyl-pyrrolidinium STEP A: 1-[3-[7β-[[[[1-[2,5-dichloro-3,4bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]acetamido]-2-[(4-methoxy-benzyloxy)-carbonyl]-8-oxo-5-thia-1-azabicyclo[4.2.0]oct-2-en-3-yl]-2-propenyl]-1-methyl pyrrolidinium iodide Using the procedure of Step H of Example 1, 605 mg of the product of Step C of Example 25 and 174 mg of N-methyl pyrrolidine were reacted to obtain after chromatography on silica (eluant: methylene chloride-methanol (9-1)), 210 mg of the desired product.

NMR Spectrum: 400 mHz in CDCl$_3$ 3.49 to 3.72 and 3.97: the central CH$_2$'s and N$^+$CH$_3$; 3.20, 3.33, 3.34: the OCH$_3$'s 2.6: pyrrolidine; 4.01, 4.28, 4.52; N$^+$—CH$_2$; 5.25: CO$_2$—CH$_2$—φ and O—CH$_2$—O; 6.09 and 6.17 =C—CH=CH—CH$_2$—; 6.85 to 7.42; =C—C H=CH$_2$— and CO$_2$—CH—φ$_2$.

STEP B: Internal salt of (6R (3-(E) 6α.7β-(Z)))-1-(3-(7-(((2-amino-4-thiazolyl)-(carboxy-(2.5-dichloro-3,4-dihydroxy-phenyl)-methoxy)-imino)-acetamido)-2-carboxy-8-oxo-5-thia-1-azabicyclo[4, 2.0]oct-2-en-3-yl)-2-propenyl)-1-methyl pyrrolidinium Using the procedure of Step I of Example 1, 200 mg of the product of Step A were reacted to obtain 93 mg of the desired product.

NMR Spectrum: DMSO 300 MHz ppm 2.09 (sl): CH$_2$ in position 3', 4'; approx.=3.45 (sl) CH$_2$ in position 2', 5'; 2.99 (s): N$^+$CH$_3$; 3.61 (d,d) and 3.80 (d) 3.86 (d): CH$_2$—S; 4.10 (d): =CH—CH$_2$—N$^+$; 5.21 (d): H$_6$; 5.84 (m): H$_7$; 5.78 (s) 5.81 (s) =C—CH—O; 6.16 (m): CH=CH—CH$_2$ (ΔE); 7.03 (d, J=15) CH=CH—CH$_2$; 7.01 (s) 7.06 (s) 6.83 (s) 6.84 (s): H$_5$ of the thiazole and aromatic 1H; 9.60 (d) 9.66 (d) CONH—CH; 9.95 (m) 7.40 (m): mobile H's.

EXAMPLE 29

Internal salt of (6R-(3-(E) 6α.7β-(Z))) 1-(3-(7-(((2-amino-4-thiazolyl)-(carboxy-(2,5, -dichloro-3,4-dihydroxy-phenyl)-methoxy)-imino)-acetamido)-2-carboxy-8-oxo-5-thia-1-azabicyclo[4.2.0]oct-2-en-3-yl)-2-propenyl)-thieno(2,3-c) pyridinium STEP A: 1-[3-[7β-[[[[1-[2,5-dichloro-3,4-bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxy-benzyloxy)-carbonyl]-8-oxo-5-thia-1-azabicyclo[4.2.0]oct-2-en-3-yl]-2-propenyl]-thieno-(2,3-c) pyridinium iodide Using the procedure of Step H of Example 1, 1 g of the product of Step C of Example 25 and 458 mg of thieno-[2, 3-c]-pyridine were reacted to obtain after chromatography on silica (eluant: methylene chloride-methanol (9-1)) 520 mg of the desired product.

NMR Spectrum: CDCl$_3$ 300 MHz 3.56 (s) 3.98 (s): the central CH$_2$'s and S—CH$_2$; 3.79 (s): φ—OCH$_3$; 5.20 to 5.30: O—CH$_2$—O and CO$_2$—CH$_2$—φ; 4.95, 5.26 (m): NH—C H—CH—S; 6.33, 6.48 (m) E: C—CH=CH—; 6.80 to 7.40: =C—CH=CH; 5.59 (m) to 5.80 (m): =CH—C H$_2$—N=; 6.80 to 7.40: aromatic H; 6.77 (sd): H thiazole; 11.50 (sl.d) NH, —N=CH—.

STEP B: Internal salt of (6R-(3-(E) 6α.7β-(Z)))-1-(3-(7-(2-amino-4-thiazolyl)-(carboxy-(2.5-dichloro-3,4-dihydroxy-phenyl)-methoxy)-imino)-acetamido) -2-carboxy-8-oxo-5-thia-1-azabicyclo[4.2.0]oct-2-en-3-yl)-2-propenyl)-thieno-(2,3-c) pyridinium Using the procedure of Step I of Example 1, the product of Step A was reacted to obtain 114 mg of the desired product.

NMR Spectrum: DMSO 300 MHz 5.19 (d): H$_6$; 5.46 (d) N$^+$CH$_2$—CH=; 5.79 (m): —O—CH-o, H$_7$; 6.35 (m): =CH—CH$_2$ (E); 6.81 (s) d: H$_5$ thiazole; 7.00 (s): H of the phenyl; 7.07 (dJ=16): =C—CH=CH (E); 7.34 (1): NH$_2$; 7.94 (dJ=5.5) H$_3$' 8.76 (dJ=5.5): H$_2$'; 8.53 (d, J=6.5) 8.73 (d, J=6.5): H$_4$' and H$_5$'; 9.91 (s.l): H$_6$'; 9.59 (d,d) =C—NH—CH; 9.88: mobile H.

EXAMPLE 30

Internal salt of (6R-(3-(E) 6α.7β-(Z)))-7-(3-(7-(((2-amino-4-thiazolyl) (carboxy-(4-cyano-2,3-dihydroxy-phenyl)-methoxy)-imino)-acetamido)-2-carboxy-8-oxo-5-thia-1-azabicyclo[4.2.0]oct-2-en-3-yl)- 2-propenyl)-thieno-(2,3-b)-pyridinium STEP A: [4-cyano-2,3-bis-[(2-methoxy-ethoxy)-methoxy]-phenyl]bromoacetic acid 440 microliters of bromoform were added at −5° C. to a mixture of 4.26 mg of lithium bromide, 598 mg of potassium hydroxide and 5 ml of water and then, a solution of 825 mg of a 4-cyano-2,3-bis-[(2-methoxy-ethoxy)-methoxy]-benzaldehyde (preparation given hereafter) in 5 ml of dioxane was added dropwise. The mixture was stirred for 72 hours at 0° C. to −5° C. and was poured into a stirred mixture at 0° C. to −5° C. of 15 ml of ethyl acetate and 11 ml of hydrochloric acid. Extraction was carried out with ethyl acetate and the extracts were washed, dried and evaporated to dryness under reduced pressure. The oil obtained was used as is for the following step.

STEP B: Diphenylmethyl [4-cyano-2,3-bis-[(2-methoxy-ethoxy)-methoxy]-phenyl]-bromoacetate The product of Step A was dissolved in 10 ml of methylene chloride and 470 mg of diphenyl diazomethane were added. Evaporation was carried out followed by chromatography on silica (eluant: cyclohexane-ethyl acetate (2-1)) to obtain 450 mg of the desired product.

NMR Spectrum: 3.31 (s), 3.37 (s): (OCH$_3$'s: 3.43 (m), 3.61 (m), 3.77 (m), 4.05 (m) central CH$_2$'s: 5.18 (d), 5.25 (d), 5.29 (AB), OCH$_2$O's, 6.02 (s): =CH—X.

STEP C: Diphenylmethyl 4-cyano-[2,3-bis]-[(2-methoxy-ethoxy)-methoxy]-phenyl]-phthalimidoxy-acetate 326 mg of N-hydroxyphthalimide and 196 mg of potassium acetate were added to a solution of 820 mg of the product of Step B in 13 ml of dimethylformamide and the mixture was stirred for 3 hours at ambient temperature and evaporated to dryness. Chromatography on silica (eluant: cyclohexane-ethyl acetate (1-1)) yielded 640 mg of the desired product which was used as is for the following step.

STEP D: Diphenylmethyl 4-cyano-[2,3-bis]-[(2-methoxy-ethoxy)-methoxy]-phenyl]-aminoxy-acetate Using the procedure of Step D of Example 1, 640 mg of the product of Step C and 50 microliters of hydrazine hydrate were reacted to obtain 320 mg of the expected product.

STEP E: [[[1-[4-cyano-2,3-bis-[(2-methoxy-ethoxy)-methoxy]-phenyl]-2-oxo-2-(diphenylmethoxy)-ethyl]-oxy]-imino]2-[(triphenylmethyl)-amino]-thiazole-4-yl-acetic acid Using the procedure of Step E of Example 1, 320 mg of the product of Step C and 234 mg of triphenylamino-thiazol-4-yl acetic acid were reacted to obtain 550 mg of the desired product.

NMR Spectrum CDCl₃ ppm 3.32 (s), 3.37 (s): OCH₃'s; 3.48 (t) 3.60 (t) 3.75 (m) 4.03 (m): central CH₂'s; 5.13 (AB) 5.24 (AB), O—CH₂—O's; 6.27 (s):

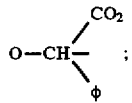

6.74 (s): H₅ thiazole; 6.29 (s): —CO₂—CH—Co₂; 7.09 to 7.32: aromatic H's; 2.60 mobile H: NH STEP F: 4-methoxy-benzyl-7β-[[[[[1-[4-cyano-2,3,-bis-[(2-methoxy-ethoxy)-methoxy]-phenyl]-2-oxo-2-(diphenylmethoxy)-ethyl]-oxy]-amino][2-(triphenylmethyl)-amino]-thiazol-4-yl]-acetamido]-3-[(Z)-3-chloro-1-propenyl]-8-oxo-5-thia-1-azabicyclo-oct-2-en-2 carboxylate Using the procedure of Step F of Example 1, 550 mg of the product of Step E were reacted to obtain after chromatography on silica (eluant: methylene chloride-ethyl acetate (8-2)), 580 mg of the desired product.

STEP G: 4-methoxy-benzyl 7β-[[[[[1-[4-cyano-2,3-bis-[(2-methoxy-ethoxy)-methoxy]-phenyl]-2-oxo-2-(diphenylmethoxy)-ethyl]-oxy]-imino][2-(triphenylmethyl)-amino]-thiazol-4-yl]-acetamido]-3-[(Z)-3-iodo-1-propenyl]-8-oxo-5-thia-1-azabicyclo-oct-2-en-2-carboxylate Using the procedure of Step G of Example 1, 580 mg of the product of Step F were reacted to obtain 615 mg of the desired product.

NMR Spectrum: CDCl₃ 3.25 (s), 3.27 (s), 3.37 (s), 3.2 to 3.6 (m): OCH₃'s and CH₂S's; 3.44 (m), 3.60 (m), 3.80 (m): central CH₂'s; 4.01 (m): CH₂—I; 4.93 (d): H₆; 5.17 to 5.38 (m): O—CH₂—O's; 5.78 (dd, 5.86 (dd): H₇; 6.12 (m): CH=CH—CH₂; 6.43, 6.46 (s): O—CH—o; 6.75 (s), 6.76 (s): H₅ thiazole; 6.83 to 7.45 (m): aromatic H's, HC=, CO₂—CH—φ₂; 7.82, 8.15 (d): mobile H: CONH.

STEP H: 1-[3-[7β-[[[[1-[4-cyano-2,3-bis-[(2-methoxy-ethoxy)-methoxy]-phenyl]-2-oxo-2-(diphenylmethoxy)-ethyl]-oxy]-imino][2-(triphenylmethyl)-amino]-thiazol-4-yl]-acetamido]-2-[(4-methoxy-benzyloxy)-carbonyl]-8-oxo-5-thia-1-azabicyclo[4.2.0][oct-2-en-3-yl]-2-propenyl]-thieno-(2,3-b) pyridinium iodide Using the procedure of Step H of Example 1, 615 mg of the product of Step G and 290 microliters of thieno-(2,3-b)-pyridine were reacted to obtain after chromatography on silica (eluant: methylene chloride-methanol (9-1)), 300 mg of the desired product.

NMR Spectrum: CDCl₃ ppm 3.20 (s), 3.26 (s), 3.35 (s), 3.37 (s): the CH₃O's; 3.43 (m), 3.50 (m), 3.78 (m), 4.02 (m): central CH₂'s; 3.80, 3.81 (s): φ—O—CH₃; 4.93 (d,d) H₆; 5.76, 5.84 (m): H₇; 5.71, 5.96 (m): C—CH₂—N⁺; 6.40, 6.45 (s):

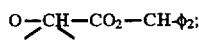

6.91 (m) =CH—CH₂ (E); 6.73, 6.74 (s): H₅ thiazole; 6.94 (m): aromatic H, —O—CH—φ₂, CH=CH— (ΔE); 7.05 to 7.45: the aromatic H's.

STEP I: Internal salt of (6R-(3-(E) 6α,7β-(Z)))-7-(3-(7-(((2-amino-4-thiazolyl) (carboxy-(4-cyano-2, 3-dihydroxyphenyl)-methoxy)-imino)-acetamido)-2-carboxy-8-oxo-5-thia-1-azabicyclo[4.2.0]oct-2-en-3-yl)-2-propenyl)-thieno-(2,3-b) pyridinium Using the procedure of Step I of Example 1, 292 mg of the product of Step H were reacted to obtain 176 mg of the desired product.

NMR Spectrum: DMSO 5.18 (d,d): H₆; 5.82 (m): H₇; 5.68 (d): =C—C₂—N⁺; 5.93 (s,d): O—CH—o; 6.29 (m): CH₂—CH=CH— (ΔE); 6.79 (s,d): H₅ thiazole; 6.94 (d,d), 7.03 (d): aromatic H; 7.89 (d) H₃', 8.28 H₂', 8.15 H₅', 9.22 H₄': thieno pyridine; 9.54, 9.69: CO—NH—CH; 10.33: mobile H.

PREPARATION EXAMPLE 30

4-cyano-2,3-bis-[(2-methoxy-ethoxy)-methoxy]-benzaldehyde

STEP A: 1,4-dicyano-2,3-dihydroxyphenyl 46 g of sodium ethylate were added to a mixture of 400 ml of tetrahydrofuran, 50 g of dicyanoethylsulfide and 52 g of diethyloxalate and the mixture was stirred for one hour and concentrated under reduced pressure. The residue was taken up in 600 ml of water and 250 ml of ethyl acetate and washed with ethyl acetate. The aqueous phase was acidified with concentrated hydrochloric acid and extraction was carried out with ethyl acetate. The extracts were evaporated to dryness under reduced pressure and the dry extract was taken up in 400 ml of nitromethane, followed by separation and washing with water to obtain 12.46 g of the desired product with a Rf=0.31 in CH₂Cl₂—MeOH 85-15.

STEP B: 1,4-dicyano-2,3-dimethoxy phenyl

A mixture of 1 g of the product of Step A, 60 ml of acetone, 3.15 g of potassium acetate and 1.5 ml of dimethyl sulfate was stirred for 16 hours at reflux, then cooled, filtered and evaporated to dryness under reduced pressure. The residue was chromatographed on silica (eluant: methylene chloride-hexane (9-1)) to obtain 820 mg of the desired product.

IR Spectrum: (CHCl₃) conjugated CN 2240 cm⁻¹ aromatic 1595–1555 cm⁻¹

STEP C: 4-cyano-2,3-dimethoxy benzaldehyde 900 ml of toluene were added to a solution of 15.70 g of the product of Step B and 61 ml of a 1.5M solution of diisobutyl aluminium hydride in toluene were added over 15 minutes at −74° C. The mixture was stirred for 30 minutes at −70° C. to −74° C. and 20 ml of acetone were added slowly. The mixture was stirred for 10 minutes and then was poured into 700 ml of 1N hydrochloric acid and 200 ml of ethyl acetate. The mixture was stirred for 30 minutes at ambient temperature, followed by decanting and extracting with ethyl acetate. The extracts were dried and evaporated to dryness to obtain 15.5 g of the desired product. 4.9 g of a previous product were added to the dry extract and the 20.4 g of crude product was chromatographed on silica three times, eluting with toluene-ethanol (95-5) to obtain 7.5 g of the desired product.

NMR Spectrum: CDCl₃ 4.06, 4.10: the O—CH₃'s; 7.38 (d) 7.60 (d): aromatic 2H, ortho coupling; 10.42 (s): CHO.

STEP D: 4-cyano-2,3-bis-[(2-methoxy-ethoxy)-methoxy]-benzaldehyde 124 ml of a molar solution of boron tribromide were added at −70° C. to a solution of 5.9 g of the product of Step C in 150 ml of methylene chloride and the mixture was stirred for 72 hours at ambient temperature, then cooled to −30° C. 30 ml of methanol were added slowly and the mixture was stirred for 30 minutes followed by evaporation to dryness under reduced pressure. The residue was taken up in 200 ml of ethyl acetate, washed with water, dried and evaporated to dryness under reduced pressure to obtain 6.4 g of residue to which was added 190 ml of methylene chloride. After cooling to 0° C., 21 ml of diisopropyl ethyl amine and 141 ml of methoxy ethoxy methyl chloride were added and the mixture was stirred for 3 hours at ambient temperature. The solution was washed with N hydrochloric acid, N sodium hydroxide and water, dried and evaporated to dryness. The residue was chromatographed on silica (eluant: methylene chloride-ethyl acetate (9-1)) to obtain 4.93 g of the desired product.

NMR Spectrum: CDCl₃ 3.35, 3.38 (s): the O—CH₃'s; 3.53, 3.62, 3.88, 4.08 (m): central CH₂'s; 5.33, 5.39 (s): O—CH₂—O; 7.45 (dd=J=8 and 0.5 Hz): H₆; 7.67 (d, J=8 Hz): H₅; 10.39 (d,J=0.5 Hz): CHO.

EXAMPLE 31

Internal salt of (6R-(3-(E) 6α,7β-(Z)))-7-(3-(7-(((2-amino-4-thiazolyl) (carboxy-(4-cyano-2,3-dihydroxy-phenyl)-methoxy)-imino)-acetamido)-2-carboxy-8-oxo-5-thia-1-azabicyclo[4.2.0]oct-2-en-3-yl)-2-propenyl)-quinolinium STEP A: 1-[3-[7β-[[[[1-[4-cyano-2,3-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl] quinolinium iodide Using the procedure of Step H of Example 1, 615 mg of the product of Step G of Example 30 and 200 microliters of quinoline were reacted to obtain after chromatography on silica (eluant: methylene chloride-methanol (91-9)), 145 mg of the desired product.

STEP B: Internal salt of (6R-(3-(E) 6α,7β-(Z)))-7-(3-(7-(((2-amino-4-thiazolyl) (carboxy-(4-cyano-2,3-dihydroxy-phenyl)-methoxy)-imino)-acetamido)-2-carboxy-8-oxo-5-thia-1-azabicyclo[4,2,0]oct-2-en-3-yl)-2-propenyl) quinolinium Using the procedure of Step I of Example 1, 230 mg of the product of Step A were reacted to obtain 137 mg of the desired product.

NMR Spectrum: DMSO 3.30 to 3.8 (m): CH₂—S; 5.15 (d): H₆; 5.60 (dd): H₇; 5.91, 5.93 (s):

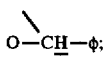

5.90 (m): CH₂—N⁺; 6.37 (m): HC=CH—CH₂; 6.93 (d, J=16) HC=CH—CH₂; 6.78, 6.94 (d): H₅', H₆'; 7.01 (s): H thiazole; 8.08, 8.28 (t): H₆", H₇"; 8.23 (dd) (J=6 and 8 Hz): H₃"; 8.51 (d) 8.55 (dd): H₅" and H₄" or H₈"; 9.34 (d, J=8 Hz) H₄" or H₈"; 9.55 (d, J=6 Hz): H₂"; 9.52 (d) 9.68 (d): HC—NH—CO.

EXAMPLE 32

Internal salt of (6R-(3-(E) 6α,7β-(Z)))-7-(3-(7-(((2-amino-4-thiazolyl) (carboxy-(5-cyano-3,4-dihydroxy-phenyl)-methoxy)-imino)-acetamido)-2-carboxy-8-oxo-5-thia-1-azabicyclo[4.2.0]oct-2-en-3-yl)-2-propenyl)-thieno-(2,3-b)-pyridinium (RS isomer)

STEP A: 1-[3-[7β-[[[[1-[5-cyano-3,4-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4,2,0] [oct-2-en-3-yl]-2-propenyl)-thieno-(2,3-b)-pyridinium iodide (RS isomer)

Using the procedure of Step H of Example 2, 1.5 g of the product of Step G of Example 2 and 1.35 g of thieno-[2,3-b]-pyridine were reacted to obtain 1.22 g of the expected product (R/S mixture).

NMR Spectrum: CDCl₃ 300 MHz 3.27 (s), 3.29 (s), 3.35 (s), 3.36 (s): the C=OMe's; 3.80 (s), 3.81 (s): the =C—OMe's; 3.30 to 4.10: central CH₂'s and CH₂S's; approx. 5.00 to 5.11: the H₆'s; approx. 5.20 to 5.40: the O—CH₂—O's; 6.76 (s) and 6.77 (s): H₅ thiazoles; approx. 6.90 to 7.50: COOCHo₂ and C₆H₅'s; 9.58 (d) resolved: the H₆"s; 7.52 to 8.90 the other quinoline H's; 8.22 and 8.34 (d): the =C—NH—CH's.

STEP B: Internal salt of (6R-(3-(E) 6α,7β (Z)))-7-(3-(7-(((2-amino-4-thiazolyl) (carboxy-(5-cyano-3,4-dihydroxy-phenyl)-methoxy)-imino)-acetamido)-2-carboxy-8-oxo-5-thia-1-azabicyclo[4,2,0]oct-2-en-3-yl)-2-propenyl)-thieno-(2,3-b)-pyridinium (R/S mixture)

Using the procedure of Step I of Example 1, 1.2 g of the product of Step A were reacted to obtain 730 mg of the desired product.

NMR Spectrum: DMSO 300 MHz 5.17 (d) resolved): H₆; 5.40 (s):

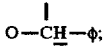

5.68 (d): CH₂—N⁺; 5.79 (m): H₇; 6.87 (m): =C—CH=CH—CH₂ (ΔE); 6.77 (s) and 6.79 (s): H₅ thiazole; 7.12 and 7.17: aromatic and =C—CH=CH—; 7.89 (d): H₃'; 8.28 (d): H₂'; 8.15 (dd): H₅'; 9.09 (d): H₄'; 9.23 (d) resolved H₆'; 9.68 (d) resolved: NH; 10.38: mobile H; 7.39 (m): NH₂.

EXAMPLE 33

Internal salt of (6R-(3-(E) 6α,7β-(Z)))-7-(3-(7-(((2-amino-4-thiazolyl) (carboxy-(5-cyano-3,4-dihydroxy-phenyl)-methoxy)-imino)-acetamido)-2-carboxy-8-oxo-5-thia-1-azabicyclo[4,2,0]oct-2-en-3-yl)-2-propenyl)-thieno-(2,3-b)-pyridinium (S isomer)

240 mg of the product were chromatographed on a microbondapack column, eluant: water, acetonitrile 82/18 (pH=2.7) to obtain 45 mg of the desired product.

NMR Spectrum: DMSO 300 MHz 5.15 (d, J=5): H$_6$; 5.40 (s): O—C$\underline{H}$—φ; 5.67 (d): =CH—CH$_2$—N$^+$; 5.80 (dd, J=5 and 8): H$_7$; 6.25 (m): =C$\underline{H}$—CH$_2$; 6.79 (s): H$_5$ thiazole; 7.13 (m): aromatic and =C$\underline{H}$—CH (ΔE); 7.89 (d, J=6): 8.28 (d, J=6): H$_3$' and H$_2$'; 8.15 (m): H$_5$'; 9.09 (d, J=8): H$_4$'; 9.22 (d, J=6): H$_6$'; 9.62 (d, J=8): =C—N$\underline{H}$—CH; 10.34, 10.43: OH; 7.33: the NH$_2$'s.

EXAMPLE 34

Internal salt of (6R-(3-(E) 6α,7β-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo[4.2.0]oct-2-en-3-yl)-2-propenyl)-imidazo-(1,2-a)-pyridinium STEP A: [[[1-[3-chloro-4,5-bis-[(2-methoxy-ethoxy)-methoxy]-phenyl]-2-oxo-2-(diphenylmethoxy)-ethyl]-oxy]-imino] [2-[(triphenylmethyl)-amino]-thiazol-4-yl]-acetic acid Using the procedure of Step E of Example 1, 2.56 g of the product of Step D of Example 4 and 1.84 g of oxo-[2-[(triphenylmethyl)-amino]-thiazol-4-yl]-acetic acid (Belgium Patent Application No. 864,828) were reacted to obtain after chromatography on silica (eluant: methylene chloride-methanol (97-3)), 3.34 g of the desired product with a Rf=0.54 (CH$_2$Cl$_2$—MeOH (9-1)).

STEP B: 4-methoxy-benzyl 7β-[[[[[1-[3-chloro-4,5-bis-[(2-methoxy-ethoxy)-methoxy]-phenyl]-2-oxo-2-(diphenyl-methoxy)-ethyl]-oxy]-imino] [2-(triphenylmethyl)-amino]-thiazol-4-yl]-acetamido]-3-[(Z)-3-chloro-1-propenyl]-8-oxo-5-thia-1-azabicyclo[4.2.0]oct-2-en-2-carboxylate Using the procedure of Step F of Example 1, 1.42 g of 4-methoxy-benzyl 7β-amino-3-[(Z)-3-chloro-1-propenyl]-8-oxo-5-thia-1-azabicyclo[4.2.0]oct-2-en-2-carboxylate hydrochloride (EP 0,333,154) and 3.34 g of the product of Step A to obtain 2.88 g of the desired product with a Rf=0.44 (CH$_2$Cl$_2$—ACOEt (8-2)).

STEP C: 4-methoxy-benzyl 7β-[[[[[1-[3-chloro-4,5-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-3-[(Z)-3-iodo-1-propenyl]-8-oxo-5-thia-1-azabicyclo[4.2.0]oct-2-en-2-carboxylate Using the procedure of Step G of Example 1, 1.88 g of the product of Step B were reacted to obtain 1.75 g of the desired product with a Rf=0.52 (CH$_2$Cl$_2$—ACOEt (8-2)).

STEP D: 1-[3-[7β-[[[[[1-[3-chloro-4,5-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxybenzyloxy-carbonyl]-8-oxo-5-thia-1-azabicyclo[4.2.0,]oct-2-en-3-yl]-2-propenyl]-(1,2-a)-pyridinium iodide Using the procedure of Step H of Example 1, 876 mg of the product of Step C and 0.308 ml of imidazo-[1,2-a]-pyridine were reacted to obtain after chromatography on silica (eluant: methylene chloride-methanol (97-3)) 450 mg of the desired product.

NMR Spectrum (CDCl$_3$ 300 MHz 3.25, 3.29 (s); 3.35, 3.36 (s): the OCH$_3$'s; 3.43, 3.55, 3.72, 4.01 (m): the central CH$_2$'s and CH$_2$S's; 3.78 (s,d) φ—O—Me; 4.94 (d,d) and 5.83 (m): H$_6$ and H$_7$ (cis); 5.17 to 5.35 and 5.43 (d,t): OCH$_2$O, CO$_2$CH$_2$—φ, NCH$_2$—CH=; 5.94 (s): O—C$\underline{H}$—φ; 6.25 (m): =C$\underline{H}$—CH$_2$ (ΔE); 6.76 (s): H$_5$ thiazole; 6.89 —C$\underline{H}$—φ$_2$; 6.85 to 7.40: φ—C, aromatic, CH=C$\underline{H}$—C= (ΔE); 7.85 (d,d) H$_5$', H$_6$'; 8.05 (d,d): H$_4$'; 8.38 (d,d): H$_3$'; 8.64 (d,d): H$_1$'; 9.11 (d,d): H$_7$'; 7.97 to 8.19 (d) the NH's.

STEP E: Internal salt of (6R-(3-(E) 6α,7β-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo 4.2.0]oct-2-en-3-yl)-2-propenyl)-imidazo-(1,2-a)-pyridinium Using the procedure of Step I of Example 1, 489 mg of the product of Step D were reacted to obtain 187 mg of the expected product.

NMR Spectrum: DMSO 300 MHz 3.62: CH$_2$S; 5.29 (m): N$^+$—CH$_2$—CH=; 5.34 (s,d):

O—C$\underline{H}$—φ;

6.22 (m): =C$\underline{H}$—CH$_2$ (E); 6.77 (s): H$_5$ thiazole; 6.85 (s); 6.90: —C$\underline{H}$—φ$_2$, aromatic and C$\underline{H}$=CH—CH$_2$ (ΔE); 7.33: NH$_2$ and φ—C; 5.13 and 5.75: H$_6$–H$_7$; 7.58 (t): 8.06 (t): H$_5$'–H$_6$'; 8.28 (m): 8.44 (sl): H$_3$'–H$_2$', 8.96 (d): H$_4$'; 9.59 (d,d): H$_7$'; 9.29 (sl), 13.03, 13.66: mobile H.

EXAMPLE 35

Internal salt of (6R-(3-E) 6α,7β-(Z)))-1-(3-(7-(((2-amino-4-thiazolyl) (carboxy-(3-chloro-4,5-dihydroxy-phenyl)-methoxy)-imino)-acetamido-2-carboxy-8-oxo-5-thia-1-azabicyclo[4.2.0]oct-2-en-3-yl)-2-propenyl)-4-methylthio pyridinium STEP A: 1-[3-[7β-[[[[[1-[3-chloro-4,5-bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxy-benzyloxy-carbonyl]-8-oxo-5-thia-1-azabicyclo[4.2.0]oct-2-en-3-yl]-2-propenyl]-4-methylthio pyridinium iodide Using the procedure of Step H of Example 1, 875 mg of the product of Step C of Example 34 and 385 mg of 4-S-methyl thiopyridine were reacted to obtain after chromatography on silica (eluant: methylene chloride methanol (97-3 then 90-10)), 389 mg of the desired product.

NMR Spectrum: CDCl$_3$ 300 MHz 2.61, 2.63: S—CH$_3$; 3.25, 3.28, 3.36, 3.37: the OCH$_3$'s; 3.78 (s): 3.79 (s): the oOMe's; 3.44, 3.58, 3.72, 4.01: the central CH$_2$'s and CH$_2$—S's; 4.97 (d,d): H$_6$; 5.05 to 5.35: OCH$_2$O, CO$_2$C$\underline{H}_2$—φ, CH$_2$N$^+$ (1H); 5.56 (m); 5.85: CH$_2$N$^+$ (1H); 6.24, 6.39 (m): CH=C$\underline{H}$CH$_2$ (ΔE); 6.78 (sl): H$_5$ thiazole; 6.89 (sl): CO$_2$C$\underline{H}_2$—φ; 7 to 7.40: oC, aromatic and =C—C$\underline{H}$=CH— (ΔE); 7.66 (d,d) and 8.90 (m) thiopyridinium.

STEP B: Internal salt of (6R-(3-(E) 6α,7β-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo[4.2.0]oct-2-en-3-yl)-2-propenyl)-4-methylthio pyridinium Using the procedure of Step I of Example 1, 389 mg of the product of Step A were reacted to obtain 174.7 mg of the desired product.

NMR Spectrum: DMSO 300 MHz 2.72: SCH$_3$; 3.49 (s); 3.549 (d); 3.71 (d): CH$_2$S; 5.13, 5.17 (d): H$_6$ (cis); 5.76 (m):

H₇ (cis); 5.23 (m): N⁺—CH₂; 6.24: =C<u>H</u>—CH₂ (ΔE); 6.77 and 6.78 (s): H₅ thiazole; 6.85 to 7.02: aromatic and =CH—C<u>H</u>=; 7.95, 8.70: pyridinium; 9.30 (sl); 9.62 (d,d); 9.96 (ml): the mobile H's; 7.34: NH₂.

EXAMPLE 36

Internal salt of (6R-(3-(E) 6α,7β-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo[4.2.0]oct-2-en-3-yl)-2-propenyl) quinolinium STEP A: 1-[3-[7β-[[[[[1-[3-chloro-4,5-bis-[(2-methoxy-ethoxy)-methoxy]-phenyl]-2-oxo-2-(diphenylmethoxy)-ethyl]-oxy]-imino]2-[(triphenylmethyl)-amino]-thiazol-4-yl]-acetamido]-2-[(4-methoxy-benzyloxy-carbonyl]-8-oxo-5-thia-1-azabicyclo[4,2,0]oct-2-en-3-yl]-2-propenyl] quinolinium iodide Using the procedure of Step H of Example 1, 900 mg of the product of Step C of Example 34 and 0.366 ml of quinoline where reacted to obtain after chromatography on silica (eluant: methylene chloride-methanol (97.3)), 384 mg of the desired product.

NMR Spectrum: CDCl₃ 300 MHz 3.24 s), 3.29 (s), 336 (s,d): the O—CH₃'s; 3.78 (s): φ—OMe; 3.40 (m), 3.58 (m), 3.71 (m), 4.00 (m): the central CH₂'s; 5.07 and 5.26, CO₂CH₂φ and O—CH₂—O; 4.94 (s): H₆; 5.04 (m), H₇; 6.00 to 6.20: =CH—CH₂—N⁺; 5.99 (s) resolved: φ—C<u>H</u>—O; 6.38 (m), 6.55 (m): =C<u>H</u>—CH₂ (ΔE); 6.75 (s) resolved: H₅ thiazole; 6.85 to 7.40; aromatics and =C—C <u>H</u>=CH—CH₂; 7.91 (m), 8.08 to 826 (m), 8.42 (m), 8.95 (m), 10.49 (d): quinoline and mobile H.

STEP B: Internal salt of (6R-(3-(E) 6α,7β-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo[4,2,0]oct-2-en-3-yl)-2-propenyl) quinolinium Using the procedure of Step I of Example 1, 384 mg of the product of Step A were reacted to obtain 192 mg of the desired product.

NMR Spectrum: DMSO 300 MHz 3.35 to 3.70: CH₂S; 5.11 (d, J=5); 5.15 (d, J=5): H₆; 5.32 (o) 5.34 (s):

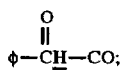

5.74 (m): H₇: 5.89 (m): =CH—C<u>H</u>₂—N; 6.36 (m): =C <u>H</u>—CH₂; 6.75 to 7.00 (m): other CH=, aromatic and H₅ thiazole; 7.33: mobile H's, 8.07, 8.26, 8.52, 9.33: quinoline; 9.57, 9.29, 9.60, 9.91 (m) 13.00 (eq) 13.70 (m): mobile H's.

EXAMPLE 37

Internal salt of (6R-(3-(E) 6α,7β-(Z)))-1-(3-(7-(((2-amino-4-thiazolyl) (carboxy)-3,4-dihydroxy-2-fluorophenyl)-methoxy)-imino)-acetamido)-2-carboxy-8-oxo-5-thia-1-azabicyclo[4.2.0]oct-2-en-3-yl)-2-propenyl)-quinolinium STEP A: 1α-(hydroxy)-2-fluoro-(3,4-bis-[(2-methoxy-ethoxy)-methoxy]phenyl]-acetic acid Using the procedure of Step A of Example 1, 15.5 g of 2-fluoro-3,4-bis-[(2-methoxy-ethoxy]-methoxy]-benzaldehyde were reacted to obtain 20.7 g of the desired product which was used as is for the following step.

STEP B: Diphenylmethyl [2-fluoro-(3,4-bis-[(2-methoxy-ethoxy]-methoxy]-phenyl]-hydroxy acetate Using the procedure of Step B of Example 1, 20.6 g of the product of Step A and 9.08 g of diphenyl diazometane were reacted to obtain after chromatography on silica (eluant: cyclohexane-ethyl acetate (7-3)), 3.2 g of the desired product.

IR Spectrum: CHCl₃
OH 3600 cm⁻¹ and 3530 cm⁻¹
C=O 1733 cm⁻¹
Aromatics 1620, 1603, 1588, 1498 cm⁻¹

STEP C: Diphenylmethyl [2-fluoro-(3,4-bis-[(2-methoxy-ethoxy)-methoxy]-phenyl]-phthalimidoxy acetate Using the procedure of Step C of Example 1, 3.2 g of the product of Step B were reacted to obtain after chromatography on silica, (eluant: methylene chloride-acetone (95-5)), 2.9 g of the desired product.

IR Spectrum (CHCl₃
C=O 1794, 1754, 1737 cm⁻¹
Aromatics 1619, 1597, 1498 cm⁻¹

STEP D: Diphenylmethyl aminoxy-[2-fluoro-(3,4-bis-[(2-methoxy-ethoxy)-methoxy]-phenyl]-acetate Using the procedure of Step D of Example 1, 1.05 g of the desired product were obtained.

IR Spectrum: CHCl₃
O—NH₂ 3340 cm⁻¹
C=O 1744 cm⁻¹
starting NH₂⁺ 1620, 1580, 1498 cm⁻¹
Aromatic STEP E: [[[1-[2-fluoro-(3,4-bis-[(2-methoxy-ethoxy)-methoxy]-phenyl]-2-oxo-2-(diphenylmethoxy)-ethyl]-oxy]-imino]-[2-[(triphenyl)-amino]-thiazol-4-yl acetic acid Using the procedure of Step E of Example 1, 1.05 g of the product of Step D and 0.777 g of oxo-[2-[(triphenylmethyl) -amino]-thiazol-4-yl acetic acid (Belgium Application No. 864,828) were reacted to obtain 1.74 g of the desired product which was used as is for the following step.

STEP F: 4-methoxy-benzyl 7β-[[[[[1-[2-fluoro-3,4-bis-[(2-methoxy-ethoxy)-methoxy]-phenyl]-2-oxo-2-(diphenylmethoxy)-ethoxy]-oxy]-imino] [2-(triphenylmethyl)-amino]-thiazol-4-yl]-acetamido]-3-[(Z) 3-chloro-1-propenyl-8-oxo-5-thia-1-azabicyclo[4,2,0]oct-2-en-2-carboxylate Using the Procedure of Step F of Example 1, 1.74 g of the product of Step E and 0.784 g of 4-methoxy-benzyl 7β-amino-3-[(Z)-3-chloro-1-propenyl]-8-oxo-5-thia-1-azabicyclo[4,2,0]oct-2-en-2-carboxylate were reacted to obtain after chromatography on silica (eluant: methylene chloride-ethyl acetate (8-2)), 1.7 g of the desired product which was used as is for the following step.

STEP G: 4-methoxy-benzyl 7β-[[[[[1-[2-fluoro-(3, 4-bis-[(2-methoxy-ethoxy)-methoxy]-phenyl]-2-oxo-2-(diphenyl-methoxy-ethyl]-oxy]-imino]-[2-[(triphenylmethyl)-amino]-thiazol-4-yl]-acetyl]-amino]-3-[(Z)-3-iodo-1-propenyl-8-oxo-5-thia-1-azabicyclo[4,2,0]oct-2-en-2-carboxylate Using the procedure of Step G of Example 1, 840 mg of the product of Step F were reacted to obtain 814 mg of the desired product with a Rf=0.45 (CH₂Cl₂—ACOEt (8-2)).

71

STEP H: 1-[3-[7β-[[[[[1-[2-fluoro-(3,4-bis-[(2-methoxy-ethoxy]-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4.2.0]oct-2-en-3-yl]-2-propenyl quinolinium iodide Using the procedure of Step H of Example 1, 814 mg of the product of Step G and 0.337 ml of quinoline were reacted to obtain after chromatography on silica (eluant: methylene chloride-methanol (98-2) 368 mg of the expected product.

NMR Spectrum: $CDCl_3$ 300 MHz 3.31 to 3.35: the O—$CH_3$'s; 3.45 (d, J=16): $CH_2S$; 3.51, 3.81, 3.94: the central $CH_2$'s; 3.79 (s) 3.80 (s): the Oφ—O—$CH_3$'s; 4.91 (m): $H_6$; 5.15 to 5.30: CO—$CH_2$—φ, O—$CH_2$—O; 5.83: $H_7$; 6.05 (ml): =C—$\underline{CH}_2$—$N^+$; 6.31, and 6.35 (m): the O—$\underline{CH}$—φ's; 6.49 (ml): $CH_2$—$\underline{CH}$—CH; 6.72, 6.75: $H_5$ thiazole; 6.87 to 7.40: aromatics, $CO_2$—$\underline{CH}φ_2$, CH=C $\underline{H}$—C; 7.90 to 8.20: quinoline, 8.40 (d,d): $H_4'$; 8.90 (d,d): $H_2'$.

STEP I: Internal salt of (6R-(3-(E) 6α,7β-(Z)))-1-(3-(7-(((2-amino-4-thiazolyl((carboxy-(3,4-dihydroxy-2-2-fluoro-phenyl)-methoxy)-imino)-acetamido)-2-carboxy-8-oxo-5-thia-1-azabicyclo[4, 2,0]oct-2-en-3-yl)-2-propenyl) quinolinium Using the procedure of Step I of Example 1, 357 mg of the product of Step H were reacted to obtain 176.9 mg of the desired product.

NMR Spectrum: DMSO 300 MHz 5.14: the $H_6$'s, 5.41 (s) resolved: O—$\underline{CH}$—φ; 5.70 to 5.90: $CH_2N^+$ and $H_7$; 6.54 (d, J=8.5) and 6.70 to 6.80: aromatic and $H_5$ thiazole; 6.37 (m): —CH=$\underline{CH}$—$CH_2$ (ΔE); 6.97 (d,d): —$\underline{CH}$=CH—$CH_2$; 7.34 (l): $NH_2$; 8.07 to 9.58: quinoline; 9.16, 9.49, 9.69: mobile H's.

PREPARATION OF EXAMPLE 37

2-fluoro-3,4-bis-[(2-methoxy-ethoxy)-methoxy] benzaldehyde

STEP A: 2-fluoro-3,4-bis-dihydroxy-benzaldehyde

A mixture of 74.3 g of hexamethylenetetramine and 125 ml of trifluoroacetic acid was stirred for 2 hours at 80° C. and then a solution of 34 g of 3-fluorocatechol in 130 ml of trifluoroacetic acid was added. The mixture was stirred for 2 hours at 80° C. and for 16 hours at ambient temperature. The trifluoroacetic acid was distilled at reduced pressure end the residue was taken up in water and neutralized by the addition of potassium carbonate until a pH of 7 was achieved. After filtration and extraction with ether, the extracts were dried and evaporated to dryness under reduced pressure to obtain 39 g of the product which was used as is for the following step.

STEP B: 2-fluoro-3,4-bis-[(2-methoxy-ethoxy)-methoxy]-benzaldehyde 261 ml of N-ethyl diisopropylamine were added to a solution of 39 g of the product of Step A in 390 ml of acetonitrile and the mixture was cooled to −5° C. 113 ml of (2-methoxyethoxy) methyl chloride were added slowly and the mixture was stirred for 16 hours at −5° C. The acetonitrile was evaporated and the residue was taken up in 250 ml of methylene chloride, then washed with N hydrochloric acid, with water, with N sodium hydroxide and then with water, followed by drying, filtering and evaporating to dryness under reduced pressure to obtain 49.5 g of product which was chromatographed on silica (eluant: methylene chloride-acetone (96-4)) to obtain 10.4 g of the desired product.

NMR Spectrum: $CDCl_3$ 200 MHz 3.37, 3.3 8 (s): the $OCH_3$'s; 5.24 (s); 5.37 (s): the O—$CH_2$—O's; 3.56 (m), 3.83 (m), 4.00 (m): the central $CH_2$'s; 10.26 (s): CHO; 7.03 (dd J=1,5–9): $H_4$; 7.59 (dd J=7,5–9): $H_3$.

EXAMPLE 38

Internal salt of (6R-(3-(E) 6α,7β (Z)))-1-(3-(7-(((2-amino-4-thiazolyl) (carboxy-(3,4-dihydroxy-2-fluorophenyl)-methoxy)-imino)-acetamido)-2-carboxy-8-oxo-5-thia-1-azabicyclo[4,2,0]oct-2-en-3-yl)-2-propenyl)-imidazo(1,2-a)pyridinium

STEP A: 1-[3-[7β-[[[[[1-[2-fluoro-(3,4-bis-[(2-methoxy-ethoxy]-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl-imidazo (1,2-a)pyridinium iodide Using the procedure of Step H of Example 1, 704.5 g of the product of Step G of Example 37 and 0.25 ml of imidazo(1,2-a) pyridine were reacted to obtain after chromatography on silica (eluant: methylene chloride-methanol (95-5), 275 mg of the expected product.

NMR Spectrum: $CDCl_3$ 400 MHz 3.32, 3.33 (s); the —$OCH_3$'s; 3.46, 3.47 (d): $CH_2S$; 3.78 (m): the o—O—$CH_3$'s; 3.53, 3.81, 3.95: the central $CH_2$'s; 4.82: $H_6$; 5.78: $H_7$; 5.00 to 5.32: $OCH_2$—, $CO_2CH_2$φ, =CH—$CH_2N^+$; 5.40: the other H of $CH_2N^+$; 6.32, 67.37 (s) O—CH—φ; 6.28 (m): $CH_2$—$\underline{CH}$=CH (ΔE); 6.74 (s) 6.76 (s): $H_5$ thiazole; 6.8 to 7.40: oC, CO$\underline{CH}$—$o_2$, aromatic, =CH—C $\underline{H}$=CH (ΔE); 7.84 (m) to 9.13 (5H) imidazo pyridinium.

STEP B: Internal salt of (6R-(3-(E) 6α,7β (Z)))-1-(3-(7-(((2-amino-4-thiazolyl) (carboxy-(3,4-dihydroxy-2-fluoro-phenyl)-methoxy)-imino)-acetamido)-2-carboxy-8-oxo-5-thia-1-azabicyclo[4, 2,0]oct-2-en-3-yl)-2-propenyl)-imidazo(1,2-a) pyridinium Using the procedure of Step I of Example 1, 275 mg of the product of Step A were reacted to obtain 116.2 mg of the desired product.

NMR Spectrum: DMSO 300 MHz 3.60: $CH_2S$; 5.11, 5.14 (d): $H_6$; 5.75 (dd) 5.79 (dd): $H_7$; 5.30 (m): $CH_2N^+$; 5.64, 5.65 (s): O—$\underline{CH}$—φ; 6.25 (m): CH=$\underline{CH}$—; 6.91, 6.93 (d): C $\underline{H}$=CH—$CH_2$; 6.57, 6.74 (m): $H_5$" and $H_6$"; 6.77 (s) 6.79 (s): $H_5$ thiazole; 7.57, 8.05 (dd): $H_5'$ and $H_6'$; 8.22 (d) 8.98 (dd): $H_4'$, $H_7'$; 8.30 8.46 (m): $H_2'$, $H_3'$; 9.48 (d) 9.55 (d): CH—NH—C=O; 7.32, 9.13, 9.64 (m): mobile H's.

EXAMPLE 39

Internal salt of (6R-(3-(E) 6α,7β (Z)))-1-(3-(7-(((2-amino-4-thiazolyl) (carboxy-(2,5-difluoro-3,4-dihydroxyphenyl)-methoxy)-imino)-acetamido)-2-carboxy-8-oxo-5-thia-1-azabicyclo[4,2,0]oct-2-en-3-yl)-2-propenyl)-imidazo(1,2-a)pyridinium

STEP A: Diphenylmethyl [2,5-difluoro-3,4-bis-dihydroxy]-phenylhydroxy acetate Using the procedure of Step B of Example 1, 3.30 g of [2,5-difluoro-3,4-bis-dihydroxy]-phenyl hydroxy acetic acid and 2.77 g of diphenyl diazomethane were reacted to obtain after chromatography on silica (eluant: cyclohexane-acetone (6-4)), 3.75 g of the desired product.

IR Spectrum:
Complex absorptions OH/NH region
C=O 1752 cm$^{-1}$
Aromatic 1630–1535–1485 cm$^{-1}$ STEP B: Diphenylmethyl [2,5-difluoro-3,4-bis-[(2-methoxy-ethoxy)-methoxy)-phenyl]-hydroxy-acetate 2.96 g of diisopropylethylamine and 10 ml of methylene chloride were added to a solution of 4.21 g of the product of Step A in 45 ml of methylene chloride and the mixture was cooled to –5° C. 2.71 g of methoxy-ethoxymethyl chloride and 5 ml of methylene chloride were added slowly and the mixture was stirred for 30 minutes at –5° C. and poured into 30 ml of 0.1N hydrochloric acid. The mixture was decanted and washed with a saturated solution of sodium bicarbonate (pH 8), drying, filtering and concentrating to dryness under reduced pressure to obtain 6.9 g of product which was chromatographed on silica (eluant: methylene chloride-ethyl acetate (85-15)) to obtain 3.577 g of the desired product.

IR Spectrum: CHCl$_3$
approx. 3600 cm$^{-1}$ (f)–3530 cm$^{-1}$ complex: OH
1734 cm$^{-1}$: C=O
1624–1600–1589–1492 cm$^{-1}$: aromatic.

NMR Spectrum $19_F$
140.6 F$^2$, J$_{F1-F4}$=14, J$_{F1H5}$=6.5
135.2 F$^5$, J$_{F4-H5}$=11.

STEP C: Diphenylmethyl 2,5-difluoro-3,4-bis-[(2-methoxy-ethoxy)-methoxy)-phenyl]-phthalimidoxy acetate Using the procedure of Step C of Example 1, 4.419 g of product of Step B and 1.41 g of hydroxyphthaliide and 4.12 g of triphenyl-phosphine were reacted to obtain after chromatography on silica (eluant: methylene chloride-acetone (97-3) then cyclohexane-ethyl acetate (1-1)), and 2.56 g of the desired product.

NMR Spectrum: CDCl$_3$ 300 MHz 3.33 (s), 3.36 (s): OCH$_3$; 3.50 (m), 3.91 (m): O—CH$_2$—CH$_2$—O; 5.20 (A,B system), 5.26 (A,B system): OCH$_2$O; 6.26 (s):

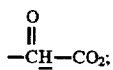

6.94 (s): CO$_2$CH Ph$_2$—; 7.15, 7.3 (m); 7.76 (m): aromatic H's.

STEP D: Diphenylmethyl aminoxy-[2,5-difluoro-3,4-bis-[(2-methoxy-ethoxy)-methoxy)-phenyl]-acetate Using the procedure of Step D of Example 1, 2.537 g of the product of Step C and 0.21 ml of hydrazine hydrate were reacted to obtain after chromatography on silica (eluant: cyclohexane-ethyl acetate (1-1)), 1.67 g of the desired product is obtained.

NMR Spectrum $^{19}$F: CDCl$_3$
135.5 (dd) F$_5$
139.8 (dd) F$_2$
J$_{F5-F2}$=14
J$_{F5-H6}$=10.5
J$_{F2-H6}$=6

STEP E: [[[1-[2,5-difluoro-3,4-bis-[(2-methoxy-ethoxy)-methoxy)-phenyl]-2-oxo-2-(diphenylmethoxy)-ethyl]-oxy]-imino] [2-[(triphenylmethyl)-amino]-thiazol-4-yl] acetic acid Using the procedure of Step E of Example 1, 909 mg of the product of Step D and 652 mg of oxo-[2-[(triphenylmethyl)-amino]-thiazol]-4-yl]-acetic acid Belgian Application No. 864,828) were reacted to obtain after chromatography on silica (eluant: methylene chloride-methanol (96-4)), 1.138 g of the desired product is obtained.

IR Spectrum:
=C—NH+approx. 3405 cm$^{-1}$
general absorption OH/NH
C=O 1740–1727 cm$^{-1}$
C=N
Aromatic+1615–1597–1526–1495 cm$^{-1}$
Heteroaromatic STEP F: 4-methoxy benzyl 7β-[[[[1-[2,5-difluoro-3,4-bis[(2-methoxy-ethoxy)-methoxy]-phenyl]-2-oxo-2-(diphenyl-methoxy)-ethyl]-oxy]-imino] [2-[(triphenylmethyl)-amino]-thiazol-4-yl]-acetyl]-amino]-3-[(Z)-3-chloro-1-propenyl]-8-oxo-5-thia-1-azabicyclo[4,2,0]oct-2-en-2-carboxylate Using the procedure of Step F of Example 1, 1.12 g of the product of Step E were reacted to obtain after chromatography on silica (eluant: methylene chloride-ethyl acetate (9-1)), 979 mg of the expected product.

NMR Spectrum: CDCl$_3$ 400 MHz 3.08, 3.20, 3.40: CH$_2$S; 3.34, 3.35 (s): the C—O—CH$_3$'s; 3.54, 3.92 (m): the central CH$_2$'s; 3.80, 3.81 (s): Ar—O—CH$_3$; 3.70, 4.00: CH=C H$_2$Cl; 4.95, 5.03: H$_6$ cephalo; 5.16, 5.25: OCH$_2$O, CO$_2$C H$_2$Ar; 5.75 (m): =CH—CH$_2$ (ΔZ); 5.85, 6.00: H$_7$ cephalo, =CH—CH$_2$; 6.26 (d, J=11) 6.35 (m): C—C H=CH—CH$_2$Cl, ArCHO ; 6.70, 678 (m): H$_5$ thiazole; approx. 7.00 to 7.35: aromatic H's; 7.30, 8.30: NH—CH.

STEP G: 4-methoxy-benzyl 7β-[[[[1-[2,5-difluoro-3,4-bis-[(2-methoxy-ethoxy)-methoxy]-phenyl]-2-oxo-2-(diphenyl-methoxy)-ethyl]-imino] [2-(triphenylmethyl)-amino]-thiazol-4-yl]-acetamido]-3-[(Z)-3-iodo-1-propenyl]-8-oxo-5-thia-1-azabicyclo[4,2,0]oct-2-en-2-carboxylate Using the procedure of Step G of Example 1, 969 mg of the product of Step F were reacted to obtain 725 mg of the expected product.

STEP H: 1-[3-[7β-[[[[1-[2,5-difluoro-3,4-bis-[(2-methoxy-ethoxy)-methoxy]phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl]-imidazo (1,2-a)pyridinium iodide Using the procedure of Step H of Example 1, 717 mg of the product of Step G and 313 mg of imidazo(1,2-a)pyridine were reacted to obtain after chromatography on silica (eluant: methylene chloride-methanol (95-5)), 350 mg of the desired product.

NMR Spectrum: CDCl$_3$ 400 MHz 3.32, 3.33, 3.34 (s): C—O—CH$_3$; 3.53, 3.92 (m): central CH$_2$'s; 3.30, 3.80: CH$_2$S; 3.79, 3.80 (s): Ar—O—CH$_3$; 4.94 (dd): H$_6$ cephalo; 5.80, 5.88 (d) after exchange: H$_7$ cephalo; (td); 6.31 (td): =CH—CH$_2$N$^+$; 6.31 (s) 6.37 (s): Ar—CH—CO$_2$; 7.84, 8.18 (d): CO—NH—CH; 7.86, 8.02 (m): heterocycle; 8.32 to 9.18: imidazopyridine; 6.75, 7.45 (m): aromatic, H$_5$ thiazole, CH—CH—CH$_2$, CO$_2$—CH—φ$_2$; 5.18, 5.30, 5.43: CH$_2$—N$^+$, OCH$_2$O,

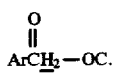

STEP I: Internal salt of (6R-(3-(E) 6α,7β (Z)))-1-(3-(7-(((2-amino-4-thiazolyl) (carboxy-(2,5-difluoro-3,4-dihydroxyphenyl)-methoxy)-imino)-acetamido)-2-carboxy-8-oxo-5-thia-1-azabicyclo[4,2,0]oct-2-en-3-yl)-2-propenyl)-imidazo(1,2-a) pyridinium Using the procedure of Step I of Example 1, 344 mg of the product of Step H were reacted to obtain 170 mg of the expected product.

NMR Spectrum: DMSO 300 MHz 5.16 (dd):L $H_6$ cephalo; 5.77 (m): $H_7$cephalo; 5.29 (m): $CH_2$—$N^+$; (s,d):

6.70 (dd): aromatic H coupled with 2F. 6.80 (s,d): $H_5$ thiazole; 6.87 (dd): CH=CH—$CH_2$ (ΔE) 7.33 (sl): $NH_2$; 8.28, 8.44 (m): $H_2'$ and $H_3'$; 7.18 to 8.96 (4H) imidazopyridine; 9.03, 9.63 (d): C—NH—CH; 9.84 other mobile H's.

PREPARATION OF EXAMPLE 39

2,5-difluoro-3,4-dihydroxy]-phenyl hydroxy-acetic acid

STEP A: 2,5-difluorophenol 325 ml of n-butyl lithium in a 1.6M solution with hexane were added at −65° C. to a solution of 62.19 g of 1,4-difluorobenzene in 500 ml of tetrahydrofuran and the mixture was stirred for 150 minutes. Then, a solution of 53.8 g of trimethylborate in 250 ml of ether was added over 30 minutes at −65° C. and the mixture was stirred for 90 minutes, allowing the temperature to rise to −15° C. The mixture was stirred for 15 minutes and 350 ml of 10% hydrochloric acid were added. After decanting, the residue was washed with water, dried and evaporated to dryness under reduced pressure to obtain 63.5 g of product which was taken up in 400 ml of toluene. After heating to 108° C., 180 ml of 30% hydrogen peroxide were added dropwise and heating was continued for 2 hours at 90° C. The medium was allowed to cool and was filtered. The filtrate was decanted and the organic phase was washed with water, then with a 10% solution of ferrous ammonium sulfate, then with water. The organic phase was extracted twice with 300 ml of 2N sodium hydroxide and acidification was carried out with concentrated, hydrochloric acid, followed by extraction with methylene chloride. The extracts were dried and evaporated to dryness under reduced pressure to obtain the desired product.

NMR Spectrum: $CDCl_3$ 5.21 (sl): OH; 6.55 (dddd): $H_4$, $JH_4$—$H_2$=9, $JH_4$—$F_2$=3.5, $JH_4$—$H_6$=3, $JH_4F_5$=8; 6.74 (ddd): $H_6$, $JH_6$—$H_4$=3, $JH_6$—$F_2$=7; 7.01 (ddd); $H_3$, $JH_3H_4$=9, $JH_3$—$F_2$=10, JH—$F_5$=5.

STEP B: 2,5-difluoroanisole 35.0 g of the product of Step A, 350 ml of acetone, 44.6 g of potassium carbonate and 407 g of dimethyl sulfate (neutralized on potassium bicarbonate) and was allowed to return to ambient temperature. Water was added and extraction was carried out with ether. The extracts were washed, dried and concentrated to dryness under reduced pressure to obtain 39.8 g of the desired product.

NMR Spectrum: $^{19}F$ $CDCl_3$ 188 MHz
119.1 (dddd) $F_5$
144.1 (dddd) $F_2$ $J_{F2\text{-}F5}$=15
$J_{F5\text{-}H3}$=5 $J_{F2\text{-}H3}$=10.5
$J_{F5\text{-}H4}$=8 $J_{F2\text{-}H4}$=3.5
$J_{F5\text{-}H6}$=10 $J_{F2\text{-}H6}$=7

STEP C: 3,6-difluoroguaiacol

Using the procedure of Step A, 55.15 g of the product of Step B and 220 ml of n-butyl lithium, 1,6M in hexane, 36.4 g of trimethyl borate and 200 ml of 30% hydrogen peroxide were reacted to obtain 44.7 g of the desired product.

NMR Spectrum: $CDCl_3$ 200 MHz
4.02 (d, J=2) $OCH_3$
5.56 (sl) OH
6.57 (ddd) $H_4$
6.75 (dt) $H_5$
$J_{H5\text{-}H4}$=9.5; $J_{H5\text{-}F3}$=5; $J_{H5\text{-}F\text{-}6}$=9.5; $J_{H4\text{-}F3}$=10.5; $J_{H4\text{-}F6}$=5.

STEP D: 3,6 difluorocatechol

Using the procedure of Step B of Preparation 1, 21.15 g of the product of Step C and 260 ml of a molar solution of boron tribromide were reacted to obtain 17.62 g of the desired product.

STEP E: 2,5-difluoro-3,4-dihydroxy]-phenyl-hydroxy-acetic acid 7.69 g of sodium hydroxide dissolved in 80 ml of water were added at +10° C. to a solution of 11.7 g of the product of Step D and 7.37 g of monohydrated glyoxylic acid in 40 ml of water and the mixture was stirred for 30 minutes at 10° C. then for 3 hours 30 minutes at ambient temperature. 0.74 g of monohydrated glyoxylic acid were added and the mixture was stirred for one hour at ambient temperature. Concentrated hydrochloric acid was added until a pH of 1 was achieved. Extraction was carried out with ethyl acetate, and the extracts were dried, filtered and concentrated to dryness under reduced pressure to obtain 17.0 g of the desired product.

IR Spectrum: Nujol
Complex absorption OH/NH region
C=O 1700 $cm^{-1}$
Aromatic 1640, 1612, 1526, 1488 $cm^{-1}$

EXAMPLE 40

Internal salt (6R-(3-(E) 6α,7β (Z)))-1-(3-(7-(((2-amino-4-thiazolyl) (carboxy-(2-chloro-4,5-dihydroxy-3-methoxy-phenyl)-methoxy)-imino)-acetamido)-2-carboxy-8-oxo-5-thia-1-azabicyclo[4,2,0]oct-2-en-3-yl)-2-propenyl)-imidazo(1,2-a) pyridinium STEP A: [2-chloro-4,5-bis-[(2-methoxy-ethoxy)-methoxy]-3-methoxy]benzaldehyde and 2-chloro-3,4-bis-[(2-methoxy-ethoxy)-methoxy]-5-methoxy benzaldehyde 2.17 g of 3,4-bis-[(2-methoxy-ethoxy)-methoxy]-5-methoxy benzaldehyde and 21.7 ml of methylene chloride and 4 ml of a solution of 1.76 g of calcium hypochlorite (at 65%) in 10 ml of water were stirred for 20 minutes at 0° to +5° C. Extraction was carried out with methylene chloride and the extracts were washed with water, dried and evaporated to dryness under reduced pressure to obtain 2.34 g of a mixture of isomers (7/3).

NMR Spectrum: CDCl₃ 250 MHz 3.37: the OCH₃'s; 3.7 to 4.1: the central CH₂'s; 5.29 to 5.33: OCH₃; 3.91: OCH₃; 7.54 and 7.30: H₆; 10.38 and 10.40: CHO.

STEP B: [2-chloro-4,5-bis-[(2-methoxy-ethoxy)-methyl]-3-methoxy-styryl carboxylate and corresponding 5-methoxy isomer 2.97 ml of triethylamine, then a solution of 6.72 g of the mixture of isomers of Step A dissolved in 60 ml of tetrahydrofuran were added to a stirred mixture, a +5° to +10° C. of 2.162 g of lithium bromide with 60 ml of tetrahydrofuran and 4.03 ml of triphenylphosphoro-acetate. The mixture was stirred for 16 hours at ambient temperature and concentrated to dryness under reduced pressure. The residue was taken up in methylene chloride, washed with 1N hydrochloric acid, then with water, dried and evaporated to dryness under reduced pressure to obtain 8.9 g of the expected product (mixture of 2 isomers 7/3).

NMR Spectrum: CDCl₃ 250 MHz 1.35 (t,d) 4.28 (q,d): CO₂Et; 3.37, 3.38: the OCH₃'s; 3.57 (m); 3.84 to 4.04 (m): the central CH₂'s; 3.88 (s); 3.86 (s): OCH₃; 5.24 to 5.23: the OCH₂'S; 6.34 (d), 6.38 (d): CH=CH—CO₂; 8.03, 8.05 (d): —CH=CH—CO₂; 6.93, 7.30: aromatic H.

STEP C: [2-chloro-4,5-bis-[(2-methoxy-ethoxy)-methoxy]-3-methoxy]styrol and corresponding 5-methoxy isomer 11.7 ml of a molar solution of diisobutyl aluminium hydride in hexane were added to a solution cooled to −70° C. of 2.83 g of the isomer mixture of Step B in 20 ml of methylene chloride. The mixture was stirred for 20 minutes, at −70° C. and 2 ml of water were added. The mixture was stirred for 30 minutes at 20° C., followed by drying, filtering and evaporation to dryness under reduced pressure to obtain 1.95 g of the desired product (mixture of isomers 7/3)

NMR Spectrum: CDCl₃ 250 MHz 3.37, 3.38: the OCH₃'s; 3.54, 3.84, 3.97 (m): the central CH₂'s; 3.87 (s): OCH₃ (in position 3); 4.34 (d): —CH₂—OH; 6.29 (t): CH=C HCH₂; 6.93 (d): —CH=CH—CH₂; 7.19 (s): aromatic H.

STEP D: [2-chloro-4,5-bis-[(2-methoxy-ethoxy)-methoxy]-3-methoxy] (1,2-epoxy) styrol (isomer A) and [2-chloro-3,4-bis-[(2-methoxy-ethoxy)-methoxy]-5-methoxy] (1,2-epoxy) styrol (isomer B)

A solution of 2.79 g of m-chloroperbenzoic acid in 50 ml of methylene chloride was added at +5° C. to a solution of 4.78 g of the isomer mixture of Step C in 50 ml of methylene chloride and the mixture was stirred for 16 hours at 20° C. 20 ml of a saturated solution of sodium bicarbonate and 50 ml of methylene chloride were added, followed by decanting, washing with water, drying and evaporating to dryness under reduced pressure. The residue was chromatographed on silica (eluant: methylene chloride-acetone 85-15) to obtain 2.12 g of isomer A product and 716 mg of isomer B.

NMR Spectrum: CDCl₃ 250 MHz 3.07 (t,d):

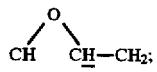

3.37, 3.38 (s): the OCH₃'s; 3.57, 3.83, 3.93 (m): the central CH₂'s; 3.88 (s): OCH₃ (in position 3); 3.83, 4.06 (ddd): —C H₂OH; 4.19 (d, J=2):

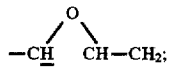

5.2, 5.26 (s): the OCH₂'s; 1.94 (d,d, J=5.5, 7.5): OH.

STEP E: Diphenylmethyl [[2-chloro-4,5-bis-[(2-methoxy-ethoxy)-methoxy]-3-methoxy]-phenyl]-chloroacetate a) Opening of the epoxide A solution prepared at +5° C. of 1.306 g of copper chloride, 20 ml of tetrahydrofuran and 1 g of lithium chloride was stirred for 5 minutes and then, 2.055 g of the isomer A epoxid of Step D dissolved in 10 ml of tetrahydrofuran were added to this solution at 20° C. The mixture was stirred for 5 hours at 20° C. and 10 ml of water were added, followed by decanting, washing, drying and evaporating to dryness under reduced pressure to obtain 2.09 g of intermediate diol.

b) Oxidation 9 ml of water and 3.79 g of sodium periodate and 50 mg of hydrated ruthenium chloride (with 35/40% Ru) were added at +5° C. to +10° C. to a solution of 2.035 g of the diol above with 6 ml of. carbon tetrachloride and 6 ml of acetonitrile. The mixture was stirred for one hour at 20° C. and 20 ml of methylene chloride and 10 ml of water were added, followed by decanting, washing, drying and evaporating to dryness under reduced pressure to obtain 1.8 g of the intermediary acid.

c) Esterification:

790 mg of diphenyl diazomethane were added to a solution of 1.8 g of the above product in 20 ml of methylene chloride and the mixture was stirred for one hour at 20° C. and concentrated to dryness under reduced pressure. After chromatography on silica (eluant: methylene chloride (9-1)), 1.525 g of the desired product was obtained.

NMR Spectrum CDCl₃ 250 MHz 3.34, 3.37: the OCH₃'s; 3.47, 3.57, 3.74, 3.97 (m): the central CH₂'s; 3.87 (s): 3-methoxy; 5.12, 5.24: the OCH₂'s; 5.94:

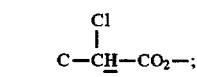

6.89 (s): CO₂—CH

STEP F: Diphenylmethyl aminoxy-[[2-chloro-4,5-bis-[(2-methoxy-ethoxy)-methoxy]-3-methoxy]-acetate a) Phthalimidoxylation 1.48 g of the product of Step E, 7.5 ml of dimethylformamide with 363 mg of potassium acetate and 604 mg of N-hydroxyphthalimide were stirred together for 5 hours.

b) Hydrazinolysis

180 μl of hydrazine hydrate were added at 20° C. and after the mixture was stirred for 20 minutes at 20° C., the phthalylhydrazide was separated out and washed with acetonitrile. The organic fractions were evaporated to dryness to obtain after chromatography on silica (eluant: methylene chloride-ethyl acetate (3-1)), 1.11 g of the desired product.

NMR Spectrum: CDCl₃ 250 MHz 3.33, 3.37 (s): the OCH₃'s; 3.44, 3.57, 3.71, 3.97 (m): the central CH₂'s; 3.88 (s): 3-methoxy; 5.09 and 5.23: the OCH₂'s; 5.73 (s):

5.84: NH₂; 6.91 (s); 6.94: CO₂CH—o₂; 7.07 to 7.35: aromatics.

STEP G: [[[1-[2-chloro-4,5-bis-[(2-methoxy-ethoxy)
-methoxy]-3-methoxy]-phenyl]-2-oxo-2-
(diphenylmethoxy)-ethyl]-oxy]-imino] [2-[
(triphenylmethyl)-amino]-thiazol-4-yl]-acetic acid Using the procedure of Step E of Example 1, 1.1 g of the product of Step F and 835 mg of oxo-[2-[(triphenylmethyl)-amino]-thiazol-4-yl]-acetic acid (Belgian Application No. 864,828) were reacted. The product was not isolated and was used as is for the following step.

STEP H: 4-methoxy-benzyl 7β-[[[[[1-[2-chloro-4,5-
bis-[(2-methoxy-ethoxy)-methoxy]-3-methoxy]-
phenyl]-2-oxo-2-(diphenyl-methoxy)-ethoxy]-oxy]-
imino] [2-(triphenylmethyl)-amino]-thiazol-4-yl]-
acetamido]-3-[(Z)-3-chloro-1-propenyl]-8-oxo-5-
thia-1-azabicyclo[4.2.0]oct-2-en-2-carboxylate Using the procedure of Step F of Example 1, the crude product of Step G and 781 mg of 4-methoxy-benzyl 7β-amino-3[(Z)-3-chloro-1-propenyl]-8-oxo-5-thia-1-azabicyclo[4.2.0]oct-2-en-2-carboxylate hydrochloride (EP 0,333,154) were reacted to obtain after chromatography on silica, (eluant: methylene chloride-ethyl acetate (9-1)), 1.36 g of the desired product.

NMR Spectrum: CDCl₃ 300 MHz 3.25, 3.29, 3.36, 3.37, 3.81: the OCH₃'s; 3.20 to 4.0: —SCH₂—, C—CH₂Cl, the central CH₂'s; 4.94 (d) to 5.25: CO₂CHϕ2, NH—CH—C H—S, the OCH₂O's; 5.75 (m): —CH=CH—CH₂ (Z); 5.9 (m): NH—CH—CH—S; 6.28 (d): —CH=CH—CH₂ (ΔZ); 6.8 to 7.15: aromatics+H₅ thiazole.

STEP I: 4-methoxy-benzyl 7β-[[[[[1-[2-chloro-4,5-
bis-[(2-methoxy-ethoxy)-methoxy]-3-methoxy]-
phenyl]-2-oxo-2-(diphenyl-methoxy)-ethyl]-oxy]-
imino] [2(triphenylmethyl)-amino]-thiazol-4-yl]-
acetamido]-3-[(Z)-3-iodo-1-propenyl]-8-oxo-5-thia-
1-azabicyclo[4.2.0]oct-2-en-2-carboxylate Using the procedure of Step G of Example 1, 1.33 g of the product of Step H were reacted to obtain after chromatography on silica (eluant: methylene chloride-ethyl acetate (9-1)), 990 mg of the desired product.

NMR Spectrum: CDCl₃ 400 MHz 3.24 (s); 3.26 (s); 3.35 (s); 3.36 (s): the 2 OCH₃'s; 3.2 to 4.0 (m): —SCH₂—C and the central CH₂'s; 3.8 (s,d) 3.85, 3.88 (s): the 2 =C—OCH₃'s; 4.9 to 5.07 (m) 5.18 to 5.25 (m): the O—C H₃'s; 4.97, 5.02 (d): CH—CH—S—; 5.87 (ddd) NH—C H—CH—S—; 6.51, 6.53 (s): =NH—O—CH=; 6.79, 6.80 (s): H₅ thiazole; 6.84 to 7.37 (m): aromatics other CH=C and CO₂—CH—ϕ₂; 7.78, 8.3 (d):

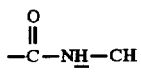

STEP J: 1-[3-7β-[[[[[1-[2-chloro-4,5-bis-[(2-
methoxy-ethoxy)-methoxy]-3-methoxy]-phenyl]-2-
oxo-2-(diphenyl-methoxy)-ethyl]-oxy]-imino]-[2-
(triphenylmethyl)-amino]-thiazol-4-yl]acetamido]-2-
[(4-methoxy-benzyloxy)-carbonyl]-8-oxo-5-thia-1-
azabicyclo [4,2,0]oct-2-en-3-yl]-2-propenyl]-
imidazo(1,2-a)-pyridinium iodide Using the procedure of Step H of Example 1, 735 mg of the product of Step I and 260 microliters of imidazo(1,2-a) pyridine were reacted to obtain 750 mg of the expected product.

NMR Spectrum: CDCl₃ 300 MHz 3.14 to 3.38: —S—CH₂—C=, the

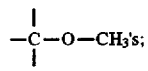

3.78, 3.79, 3.85, 3.87: =C—OCH₃; 3.3 to 4.0: the central CH₂'s; 4.9 to 5.02: NH—CH—CH—S—; 5.8 (m): =NH—CH—CH—S; 6.27 (m): —CH=CH—CH₂ (ΔE); 6.53, 6.54:

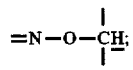

6.76 to 7.3: CO₂—CH—ϕ₂, —CH=CH₂ and the aromatics; 7.6 to 91.0: imidazopyridine.

STEP K: Internal salt of (6R-(3-(E) 6α,7β (Z)))-1-
(3-(7-(((2-amino-4-thiazolyl) (carboxy-(2-chloro-4,
5-dihydroxy-3-methoxy-phenyl)-methoxy)-imino)-
acetamido)-2-carboxy-8-oxo-5-thia-1-azabicyclo[4,
2,0]oct-2-en-3-yl)-2-propenyl)-imidazo(1,2-a)
pyridinium Using the procedure of Step I of Example 1, 750 mg of the product of Step J were reacted to obtain 463 mg of the desired product.

NMR Spectrum: DMSO 300 MHz 5.12 (d,d): =NH—CH—CH—S—; 528 to 5.3: =CH—CH—₂—N⁺; 5.74 (m): =NH—CH—CH—S; 5.75: =N—O—CH—; 6.23 (m): =C—CH=CH—; 6.78 (s): H₅ thiazole; 6.84 (d, J=15): =C—CH=CH— (ΔE); 7.36: NH₂; 7.58 to 8.93: imidazopyridine; 9.55: mobile H's.

EXAMPLE 41

Internal salt of (6R-(3-(E) 6α,7β (Z)))-1-(3-(7-(((2-
amino-4-thiazolyl) (carboxy-(2-chloro-3,4-
dihydroxy-5-methoxy-phenyl)-methoxy)-imino)-
acetyl)-amino)-2-carboxy-8-oxo-5-thia-1-azabicyclo
[4,2,0]oct-2-en-3-yl)-2-propenyl)-imidazo(1,2-a)
pyridinium Using the procedure of Steps E to K of Example 40, isomer B of Step D of Example 40 were reacted to obtain the desired product.

NMR Spectrum: DMSO 300 MHz 3.5 to 3.7 (m): S—CH₂—C=; 3.73, 3.74 (s): OCH₃; 5.18: NH—CH—C H—S; 5.29: —CH₂N⁺; 5.79 (ddd): NH—CH—CH—; 5.83, 5.85 (s): =N—O—CH=; 6.25 (m): CH=CH—; 6.6 (s): 6.78 (s): 6.82 (s): aromatic, H₅ thiazole; 6.88 (d,d J=16): —CH=CH—CH₂ (ΔE); 7.58 to 8.96 96H) imidazopyridine.

EXAMPLE 42

Internal salt of (6R-(3-(E) 6α,7β (Z)))-1-(3-(7-(((2-
amino-4-thiazolyl) (carboxy-(2-chloro-4,5-
dihydroxy-3-methoxy-phenyl)-methoxy)-imino)-
acetamido)-2-carboxy-8-oxo-5-thia-1-azabicyclo[4,
2,0]oct-2-en-3-yl)-2-propenyl) quinolinium STEP A: 1-[3-[7β-[[[[[1-[2-chloro-4,5-bis-[(2-
methoxy-ethoxy)-methoxy]-3-methoxy]-phenyl]-2-
oxo-2-(diphenyl-methoxy)-ethyl]-oxy]-imino] [2-
(triphenylmethyl)-amino]-thiazol-4-yl]-acetamido]-
2-[(4-methoxy-benzyloxy)-carbonyl]-8-oxo-5-thia-1-
azabicyclo[4,2,0]oct-2-en-3-yl]-2-propenyl]
quinolinium iodide Using the procedure of Step J of Example 40, 700 mg of the product of Step I of Example 40 and 282 microliters of quinoline were reacted to obtain 706 mg of the desired product.

STEP B: Internal salt of (6R-(3-(E) 6α,7β (Z)))-1-(3-(7-(((2-amino-4-thiazolyl) (carboxy-(2-chloro-4,5-dihydroxy-3-methoxy-phenyl)-methoxy)-imino)-acetamido)- 2-carboxy-8-oxo-5-thia-1-azabicyclo[4,2,0]oct-2-en-3-yl)-2-propenyl) quinolinium Using the procedure of Step K of Example 40, 690 mg of the product of Step A were reacted to obtain 434 mg of the desired product.

NMR Spectrum: DMSO 300 MHz 3.4 to 3.8 (m): S—CH$_2$—; 3.65, 3.73 (s): =C—OCH$_3$; 5.1, 5.14 (d): —NH—CH—C$\underline{\text{H}}$—; 5.73: —NH—C$\underline{\text{H}}$—CH—; 5.75 (s): =N—O—C$\underline{\text{H}}$=; 5.89 (m): —CH—CH—CH$_2$; 6.75, 6.76, 6.78, 6.79 (s): H$_5$ thiazole, aromatic H; 6.35 (m): —CH=C$\underline{\text{H}}$—C (ΔE); 6.97 (dl J=16): —CH=CH—C (ΔE); 8.07 to 9.58 (7H) quinoline; 9.53: —NH—C$\underline{\text{H}}$—CH—; 7.35, 9.24, 13.0: mobile H's.

EXAMPLE 43

Internal salt of (6R-(3-(E) 6α,7β (Z)))-1-(3-(7-(((2-amino-4-thiazolyl) (carboxy-(2-chloro-3,4-dihydroxy-5-methoxy-phenyl)-methoxy)-imino)-acetamido)-2-carboxy-8-oxo-5-thia-1-azabicyclo[4,2,0]oct-2-en-3-yl)-2-propenyl) quinolinium STEP A: 1-[3-[7β-[[[[[1-[2-chloro-3,4-dihydroxy-5-methoxy]-phenyl]-2-oxo-2-(diphenylmethoxy)-ethyl]-oxy]-imino][2-(triphenylmethyl)-amino]-thiazol]-4-yl]-acetamido]-2-[(4-methoxy-benzyloxy)-carbonyl]-8-oxo-5-thia-1-azabicyclo[4,2,0]oct-2-en-3-yl]-2-propenyl] quinolinium iodide Using the procedure of Step J of Example 40, 450 mg of the product of Step E of Example 41 were reacted to obtain 440 mg of the desired product.

STEP B: Internal salt of (6R-(3-(E) 6α,7β (Z)))-1-(3-(7-(((2-amino-4-thiazolyl) (carboxy-(2-chloro-3,4-dihydroxy-5-methoxy-phenyl)-methoxy)-imino)-acetamido)-2-carboxy-8-oxo-5-thia-1-azabicyclo[4,2,0]oct-2-en-3-yl)-2-propenyl) quinolinium Using the procedure of Step K of Example 40, 440 mg of the product of Step A were reacted to obtain 256 mg of the desired product.

NMR Spectrum: DMSO 300 MHz 3.48 to 3.84 (m): S—CH$_2$; 3.71, 3.73 (s): =C—OCH$_3$; 5.17 (d,d): —NH—CH—C$\underline{\text{H}}$—C; 5.8 (m): —NH—C$\underline{\text{H}}$—CH—; 5.82, 5.84 (s): N—O—C$\underline{\text{H}}$=; 5.88 (m): —CH=CH—CH$_2$—; 6.38 (d,m): CH=C$\underline{\text{H}}$—CH$_2$; 6.97 (d,d) (dJ=16): —C$\underline{\text{H}}$=CH— (ΔE); 6.59 (s): 6.77 (s): 6.81 (s): H$_5$ thiazole, aromatic; 8.06 to 9.58: quinoline (7H); 9.53, 9.64 (d): C—NH—; 7.54 (m): 9.25 (m); 13.70 (m): mobile H's.

EXAMPLE 44

Internal salt of (6R-(3-(E) 6α,7β-Z(S*)))-1-(3-(7-(((2-amino-4-thiazolyl) (carboxy-( 3,4-dihydroxy-5-fluorophenyl)-methoxy)-imino)-acetamido)-2-carboxy-8-oxo-5-thia-1-azabicyclo[4,2,0]oct-2-en-3-yl)-2-propenyl) quinolinium 10 mg of the product of Example 3 were chromatographed on a MICROBONDAPACK C$_{18}$ column (eluant: water (at pH 2.7 with trifluoroacetic acid)—acetonitrile containing 0.025% trifluoroacetic acid 86-14 to obtain 1.5 mg of the expected (S) isomer and 1.5 mg of (R) isomer.

NMR Spectrum: DMSO 400 MHz 3.40 to 3.60 (m): CH$_2$S; 5.13 (d, J=5): H$_6$; 5.77 (dd, J=5 and 8): H$_7$ (d, after exchange); 5.32 (s) φ—CH—O; 5.87 (m): CH$_2$N$^+$; 6.31 (m): CH=C$\underline{\text{H}}$—CH$_2$; 7.00 (d, J=16): C$\underline{\text{H}}$=CH—CH$_2$; 6.77 (s): H$_5$ thiazole; 6.72 (m): H$_4$', H$_6$'; 7.25 (s): mobile 2H's; 8.06 (dd, J=7 and 8) and 8.28 (ddl) J=7 and 9): H$_6$", H$_7$"; 8.22 (dd J=6 and 8): H$_3$"; 8.50 (d, J=8) and 8.55 (d, J=9): H$_4$" and H$_5$"; 9.33 (d, J=8): H$_8$"; 9.57 (d, J=6): H$_2$".

EXAMPLE 45

Internal salt of (6R-(3-(E) 6α,7β-(Z(R*)))-1-(3-(7-((2-amino-4-thiazolyl) (carboxy-(3,4-dihydroxy-5-fluorophenyl)-methoxy)-imino)-acetamido)-2-carboxy-8-oxo-5-thia-1-azabicyclo[4,2,0]oct-2-en-3-yl)-2-propenyl) quinolinium R isomer isolated during the chromatography in Example 44.

NMR Spectrum: DMSO 400 MHz 3.39 to 3.75 (m): CH$_2$S; 5.16 (d, J=5): H$_6$; 5.32 (s) o—CH—O; 5.74 (dd, J=5 and 8); H$_7$; 5.88 (m): CH$_2$N$^+$; 6.36 (dt): CH=C$\underline{\text{H}}$—CH$_2$; 6.99 (d, J=16) C$\underline{\text{H}}$=CH—CH$_2$; 6.73 (m) (3H): H$_5$ thiazole and H$_2$' and H$_6$'; 7.26 (s): mobile 2H's; 8.07 (t, J=8) and 8.28 (t, J=8): H$_6$" and H$_7$"; 8.22 (dd, J=6 and 8): H$_3$"; 8.50 (d, J=8) and 8.55 (d, J=9): H$_5$" and H$_4$"; 9.33 (d, J=8): H$_8$"; 9.59 (d, J=6): H$_2$"; 9.59 (d, m): CONH—CH; 9.14 (s): mobile 1H.

EXAMPLE 46

Internal salt of [[6R-[3-(E) 6α,7β (Z)(S*)-1]]-1-[3-7-[[(2-amino-4-thiazolyl) [carboxy-(2,5-dichloro-3,4-dihydroxy-phenyl)-methoxy]-imino]-acetamido]-2-carboxy-8-oxo-5-thia-1-azabicyclo[4,2,0]oct-2-en-3-yl]-2-propenyl]-4-(methylthio) pyridinium corresponding to resolved isomer of the compound of Example 14

NMR Spectrum: DMSO 300 MHz 2.71 (s): φ—SMe; approx. 3.57: =C—CH$_2$S; 5.15 to 5.25: H$_6$ and N$^+$-C$\underline{\text{H}}_2$—CH=; approx. 5.80 (sl): O—CH-o and H$_7$; 6.25 (m): =C$\underline{\text{H}}$—CH$_2$; approx. 6.98 (d): =C—C$\underline{\text{H}}$=CH; 6.81 (s): H$_5$ thiazole; 7.00: H$_6$; 7.32 (l) 2H: NH$_2$; 7.96, 8.70 (d): H pyridine; 9.58 (d): C—NH—CH; 9.84 (s) 9.92 (s): the OH's; 13.28, 13.78: the other mobile H's

EXAMPLE 47

Internal salt of (6R-(3-(E) 6α,7β-(Z)-(S*)))-1-(3-(7-(((2-amino-4-thiazolyl) (carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-imidazo(1,2-a) pyridinium NMR Spectrum DMSO 300 MHz 5.15 (d, J=5): H$_6$; 5.29 (m): C$\underline{\text{H}}$—N$^+$; 5.79 (s): O—C$\underline{\text{H}}$—φ; 5.79 (dd, d after exchange): H$_7$; 6.24 (dt, J=15.5 and 6.5): —C$\underline{\text{H}}$—CH$_2$, approx. ¾H; 6.81 (s) 6.99 (s): H$_5$ thiazole, aromatic 1H; 6.86 (d, J=15.5) =C—C$\underline{\text{H}}$=CH; 7.58 (t): 8.06 (t): H$_5$', H$_6$'; 8.20 (d): H$_7$'; 8.96 (d): H$_4$'; 8.28 (d): 8.44 (d): H$_2$', H$_3$'; 9.56 (d): CH—N$\underline{\text{H}}$—CO; 7.35 (m): approx. 2H; 9.87 (sl): 1H; 9.96 (sl): 1H; mobile H.

EXAMPLE 48

Internal salt of (6R-(3-(E) 6α,7β-(Z) (R*)))-1-(3-(7-((2-amino-4-thiazolyl) (carboxy-(2,5-dichloro-3,4-dihydroxy-phenyl)-methoxy)-imino)-acetamido)-2-carboxy-8-oxo-5-thia-1-azabicyclo[4,2,0]oct-2-en-3-yl)-2-propenyl)-imidazo[1,2-a-)pyridinium.

NMR Spectrum: DMSO 300 MHz 5.15 (d, J=5): H$_6$; 5.27 (m): C$\underline{\text{H}}_2$—N$^+$; 5.78 (d, J=5): H$_7$; 5.81 (s): O—C$\underline{\text{H}}$—φ, approx. 1.7H; 6.24 (dt, J=16 and 6): =C<u>H</u>—CH₂, approx. 0.85H; 6.84 (s): 6.99 (s): approx. 1.7H, H₅ and aromatic 1H; 6.85 (d, J=16): =C—C<u>H</u>=CH; 7.57 (dd, J=6 and 7): H₅'; 8.05 (dd, J=7 and 8.5): H₆'; 8.17 (d, J=8.5): H₇'; 8.94 (d, J=6): H₄'; 8.26 (d, J=2): 8.42 (d, J=2) H₂', H₃'.

Using the procedure described in the previous examples and starting with appropriate intermediates the following products were obtained:

EXAMPLE 49

Internal salt of (6R-(3-(E) 6α,7β-(Z)))-1-(3-(7-(((2-amino-4-thiazolyl) (carboxy-(2,3-dihydroxy-4-methoxy-phenyl)-methoxy)-imino)-acetamido)-2-carboxy-8-oxo-5-thia-1-azabicyclo[4.2.0]oct-2-en-3-yl)-2-propenyl) quinolinium NMR Spectrum DMSO 300 MHz 3.52 (d) 3.70: CH₂S; 3.72, 3.74: C—OMe; 5.15 (d, resolved): H₆; 5.57 (dd) 5.80 (m): H₇; 5.83, 5.87:

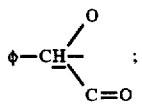

5.70 to 6.0: CH₂—N⁺; 6.42 (d, resolved): 6.75 (d, resolved) aromatic H; 6.40 (m) 6.99 (d, resolved, J approx. 16): ethylene (ΔE); 6.78, 6.82: H₅ thiazole; 8.07 (t): 8.26: aH₃', H₆', H₇'; 8.53 (d): 8.56 (d): 9.34 (d): H₄', H₅'; 9.53 (d): H₈'; 9.45 (d): 9.56 (d):

7.45 and 8.84: mobile H.

EXAMPLE 50

Internal salt of (6R-(3-(E) 6α,7β-(Z)))-7-(3-(7-(((2-amino-4-thiazolyl) (carboxy-(2,3-dihydroxy-4-methoxy-phenyl)-methoxy)-imino)-acetamido)-2-carboxy-8-oxo-5-thia-1-azabicyclo(4.2.0]oct-2-en-3-yl)-2-propenyl)-thieno(2,3-b)pyridinium NMR Spectrum: DMSO 400 MHz 3.54 (d) approx. 3.68 (d): =C—CH₂S; 5.18 (m): the H₆'s; 5.76 (m): 5.96 (m): H₇; 5.72 (s): 5.74 (s): the φ—OMe's; 5.67 (m): C<u>H</u>₂—CH=; 5.83 (s): 5.87 (s): C—C<u>H</u>—φ; approx. 6.8 (s) resolved: the H thiazoles; 6.42 (m): 6.73 (m): H₅, H₆; 6.30 (m): 7.15 (d) resolved: =C—CH=C<u>H</u>—CH (ΔE); 7.88 (d): H₃'; 8.29 (d): H₂'; 8.15 (m): H₅'; 9.08 (d): H₄'; 9.22 (d): H₆'; 9.44 (d): 9.53 (d): =C—N<u>H</u>—CH; 7.44 (m): 8.60 to 8.90: mobile H₅.

EXAMPLE 51

Internal salt of (6R-(3-(E) 6α,7β (Z)))-1-(3-(7-(((2-amino-4-thiazolyl) (carboxy-(2,3-dihydroxy-4-methoxy-phenyl)-methoxy)-imino)-acetamido)-2-carboxy-8-oxo-5-thia-1-azabicyclo[4.2.0]oct-2-en-3-yl)-2-propenyl)-imidazo(1,2-a)pyridinium NMR Spectrum: DMSO 300 MHz 7.35 (m): 8.69 (m): 8.82 (m): mobile H's; 3.52 (m) approx. 3.70 (m): CH₂S; 3.74 (s): 3.75 (s): C<u>H</u>₃O—φ; 5.15 (d, resolved): H₆; 5.74 (dd, d after exchange): 5.81 (dd, d after exchange): H₇; 5.29 (m): C<u>H</u>₂—N⁺: 5.83 (s): 5.86 (s): O—C<u>H</u>—φ; 6.25 (m): 6.90 (d, resolved): CH=C<u>H</u>—CH₂; 6.43 (d): H₆'; 6.72 to 6.80 (m): H₅' and H₅ thiazole; 7.58 (t): H₅"; 8.06 (t): H₆"; 8.21 (d): 8.96 (d): H₄", H₇"; 8.29 (sl): H₃"; 8.44 (sl): H₂"; 9.44 (d): 9.54 (d): CO—N<u>H</u>—CH.

EXAMPLE 52

Internal salt of (6R-(3-(E) 6α,7β (Z)))-1-(3-(7-(((2-amino-4-thiazolyl) (carboxy-(2,3,4-trihydroxy-phenyl)-methoxy)-imino)-acetamido)-2-carboxy-8-oxo-5-thia-1-azabicyclo[4.2.0]oct-2-en-3-yl)-2-propenyl)-imidazol(1,2-a)pyridinium NMR Spectrum: DMSO 300 MHz 3.54 (m): CH₂S; 5.15 (d): H₆; 5.82 (m): H₇ and O—C<u>H</u>—φ; 5.28 (m): =CH—C<u>H</u>₂—N⁺; 6.26 (m): C<u>H</u>=; 6.5 to 7.4 (m): aromatic 6H; 7.58 (t): H₅'; 8.06 (t): H₆'; 8.20 (d): 8.96 (d): H₄', H₇'; 8.29 (sl): 8.44 (sl): H₂', H₃'; 9.41 (d): 9.53 (d): CO—N<u>H</u>—CH; 8.68 (m): 9.27 (m): 7.36 (m): mobile H's.

EXAMPLE 53

Internal salt of (6R-(3-(E) 6α,7β (Z)))-1-(3-(7-(((2-amino-4-thiazolyl) (carboxy-(2,3-difluoro-4,5-dihydroxy-phenyl)-methoxy)-imino)-acetamido)-2-carboxy-8-oxo-5-thia-1-azabicyclo[4.2.0]oct-2-en-3-yl)-2-propenyl)-imidazo(1,2-a)pyridinium NMR Spectrum: DMSO 300 MHz approx. 3.70: CH₂S; 5.09 (d): 5.14 (d): H₆; 5.29 (m): CH₂—N⁺; 5.58 (s): 5.59 (s): O—CH—φ; 5.72 (m): H₇; 6.22 (m): CH=C<u>H</u>—CH₂; 6.68 (m): H₆'; 6.77 (s): 6.789 (s): H₅ thiazole; 6.85 (d, J=16): =C—C<u>H</u>=CH; 7.58 (t): 8.06 (t): H₅", H₆"; 8.19 (d): 8.96 (d): J₄", H₇"; 8.28 (s): 8.44 (sl): H₂", H₃"; 7.32 (m): 9.5 to 9.9 (m): mobile H's.

EXAMPLE 54

Internal salt of (6R-(3-(E) 6α,7β (Z)))-1-(3-(7-(((2-amino-4-thiazolyl) (carboxy-2,3-difluoro-4,5-dihydroxy-phenyl)-methoxy)-imino-acetamido)-2-carboxy-8-oxo-5-thia-1-azabicyclo[4.2.0]oct-2-en-3-yl)-2-propenyl) quinolinium NMR Spectrum: DMSO 300 MHz 3.45 (m):L CH₂S; 5.09 (d): 5.14 (d): H₆; 5.72 (m): H₇; 5.58 (s): 5.59 (s): O—C HCO; 5.88 (m): C<u>H</u>—N⁺; 6.34 (m): CH=C<u>H</u>—CH₂; 6.94 (d, J=16): 6.97 (d, J=16): C<u>H</u>—=CH—CH₂; 6.67 (m): H₆"; 6.76 (s): 6.77 (s): H₅ thiazole; 8.07 (m): 8.26 (m): 8.53 (m): 9.34 (d): 9.57 (d): quinoline; 7.32 (m): 9.5 to 9.9 (mn): mobile H's.

EXAMPLE 55

Internal salt of (6R-(3-(E) 6α,7β (Z)))-1-(3-(7-(((2-amino-4-thiazolyl) (carboxy-(2,5-difluoro-3,4-dihydroxy-phenyl)-methoxy)-imino)-acetamido)-2-carboxy-8-oxo-5-thia-1-azabicyclo[4.2.0]oct-2- 3-yl)-2-propenyl) pyridinium NMR Spectrum: DMSO 300 MHz 3.58 (m): CH₂S; 5.18 (d,d): H₆; 5.79 (m): H₇; 5.41 (sl): CH₂N⁺; 5.64 (s): 5.65 (s): O—C<u>H</u>—C=; 6.30 (m): CH=CH—CH₂; 7.02 (dd, J=16): C<u>H</u>=—CH—CH₂; 6.70 (dd): H₆'; 6.78 (s): 6.80 (s): H₅ thiazole; 8.18 (m): H₃", H₅"; 8.63 (m): H₄"; 9.05 (d): H₂", H₆"; 9.35 (d): 9.62 (d): CO—N<u>H</u>CH; 7.33 (m): 9.80 (m): mobile H.

EXAMPLE 56

Internal salt of (6R-3-(E) 6α,7β (Z)))-1-(3-(7-(((2amino-4-thiazolyl) (carboxy-(2,5-difluoro-3,4-dihydroxy-phenyl)-methoxy)-imino)-acetamido)-2-carboxy-8-oxo-5-thia-1-azabicyclo[4.2.0]oct-2-en-3-yl)-2-propenyl)-6,7-dihydro-5H-pyrindinium NMR Spectrum: DMSO (300 MHz) 2.24 (m): CH₂ in position 6'; 3.14 (m)–3.37 (m): CH₂ in position 5' and 7';

3.56 (m): CH₂S; 5.15 (d)–5.18 (d): H₆; 5.79 (m): H₇; 5.33 (d): =CH—C<u>H</u>₂—N⁺; 5.63 (s)–5.65 (s): O—C<u>H</u>—φ; 6.23 (m): CH=C<u>H</u>—CH₂; 6.85 (d)–6.88 (d, J=16): C<u>H</u>=CH—CH₂; 6.71 (dd, J=10.5 and 6): H₆'; 6.78 (s)–6.81 (s): H₅ thiazole; 7.91 (m): H₃'; 8.43 (d, J=8): H₄'; 8.76 (d, J=6): H₂'; 9.54 (d)–9.63 (d): CH—N<u>H</u>—CO; 7.35 (m)–9.85 (m): mobile H's.

EXAMPLE 57

Internal salt of (6R -(3 (E) 6α,7β (Z)))-1 (3-(7-(((2-amino-4-thiazolyl) (carboxy-(2,5-difluoro-3-4-dihydroxy-phenyl)-methoxy)-imino)-acetamido)- 2-carboxy-8-oxo-5-thia-1-azabicyclo[4,2,0]oct-2-en-3-yl)-2-propenyl) quinolinium NMR Spectrum: DMSO (300 MHz) 3.4 to 3.7 (m): CH₂S; 5.15 (dd): H₆; 5.79 (m): H₇; 5.62 (s)–5.64(s): —O—C<u>H</u>—φ; 5.89 (m): =CH—C<u>H</u>₂—N⁺; 6.37 (m): CH=C<u>H</u>—CH₂; 6.97 (dd, J=15.5): C<u>H</u>=CH—CH₂; 6.76 (s)–6.80 (s): H₅ thiazole; 6.70 (dd, J=11 and 6): H₆"; 8.07 (m)–8.27 (m)–8.53 (m)–9.34 (d): quinoline; 9.58 (d): H₂; 9.53 (d)–9.62 (d): CO—N<u>H</u>—CH; 7.30 (m)–9.83 (m): mobile H.

EXAMPLE 58

Internal salt of (6R-(3-(E) 6α,7β (Z)))-3-(3-(7-(((2-amino-4-thiazolyl) (carboxy-2,5-difluoro-3,4-dihydroxy-phenyl)-methoxy)-imino)-acetamido)-2-carboxy-8-oxo-5-thia-1-azabicyclo[4,2,0]oct-2-en-3-yl)-2-propenyl) thiazolium NMR Spectrum: DMSO (300 MHz) 3.50 to 3.75 (m): CH₂S; 5.16 to 5.19 (d): H₆; 5.81 (mi): H₇; 5.33 (m): =CH—C<u>H</u>₂—N⁺; 5.63 (s)–5.65 (s): O—C<u>H</u>—φ; 6.26 (m) CH=C<u>H</u>—CH₂; 6.71 (dd, J=6 and 11): H₆"; 6.78 (s)–6.81 (s): H₅ thiazole; 8.37 (m)–8.51 (m): H₄', H₅'; 10.20 (sl): H₂'; 7.30 (m): 9.5 to 9.9 (m)–13.25 (m)–13.75 (m): mobile H's.

EXAMPLE 59

Internal salt of (6R -(3-(E)6α,7β (Z)))-2-(3-(7-(((2-amino-4-thiazolyl) (carboxy-(2,5-difluoro-3,4-dihydroxy-phenyl)-methoxy)-imino)-acetamido)-2-carboxy -8-oxo-5-thia-1-azabicyclo[4,2,0]oct-2-en-3-yl)-2-propenyl)isoquinolinium NMR Spectrum: DMSO (300 MHz) 3.50 to 3.75 (m): CH₂S; 5.18 (dd): H₆; 5.80 (m) H₇; 5.53 (d): =CH—C<u>H</u>₂—N⁺; 5.63 (s)–5.65 (s): O—C<u>H</u>—φ; 6.37 (m): CH=C<u>H</u>—CH₂; 7.09 (dd, J=15.5): C<u>H</u>=CH—CH₂; 6.71 (dd, J-11 and 6): H₆"; 6.78 (s)–6.80 (s): H₅ thiazole; 8.09 (t)–8.28 (t): H₆', H₇; 8.37 (d)–8.53 (d): H₅', H₈'; 8.61 (d)–8.74 (d): H₃', H₄'; 10.06 (s): H₁'; 7.35 (m)–9.84 (m): mobile H's; 9.56 (d)–9.65 (d): CH—N<u>H</u>—CO.

EXAMPLE 60

Internal salt of (6R-(3-(E) 6α,7β-(Z))) 1-(3-(7-(((2-amino 4-thiazolyl) (carboxy (2,5-difluoro 3,4-dihydroxy phenyl) methoxy) imino) acetamido) 2-carboxy 8-oxo 5-thia 1-azabicyclo[4,2,0] oct-2-en-3-yl) 2-propenyl) 4-(methylthio) pyridinium NMR Spectrum:(DMSO) 300 MHz 2.71 (s): φSMe; 3.54 (d), 3.66 (d); C<u>H</u>—S; 5.17 (m): les H₆; 5.22 (s,l): =CH—C<u>H</u>₂—N⁺; 5.63 (s) resolved: OC<u>H</u>—φ; 5.79 (m): les H₇; 6.26 (m) CH=C<u>H</u>—C₂ ΔE; 6.98 (d,J=16) resolved: C<u>H</u>=CH—CH₂; 6.71 (dd, J=6 et 11): H difluorophenyl; 6.78 (s) resolved: H₅ thiazole; 7.30 (s,l): NH₂; 7.95 (d), 8.70 (d): methylthiopyridinium; 9.62–9.67 (d), 9.85: H mobile; 19,49.

EXAMPLE 61

Internal salt of (6R-(3-(E) 6α,7β-(Z)))4-(3-(7-(((2-amino 4-thiazolyl) (carboxy (2,5-difluoro 3,4-dihydroxy phenyl) methoxy)imino) acetamido) 2-carboxy 8-oxo 1-azabicyclo 5-thia 1-azabicyclo[4,2,0] oct-2-en-3-yl) 2-propenyl) 2-amino thiazolo (5,4-b)-pyridinium NMR Spectrum: (DMSO) 300 MHz ~3.60: CH₂S; 5.19 (d) resolved: H₆; 5.81 (d): H₇; 5.47 (d): =CH—C<u>H</u>₂—N⁺; 5.63 (s): O—C<u>H</u>—φ; 6.21 (m) CH=C<u>H</u>—CH₂. 7.08 (d) resolved J=16: C<u>H</u>=CH—CH₂; 6.78 (s): H₅ thiazole; 6.70 (dd, J=6 et 11): H₆"; 7.83 (m): H₅"; 8.29 CH—N<u>H</u>—CO; 8.73 (s), 9.84 (m), 7.33 (m): H mobile.

EXAMPLE 62

Internal salt of (6R-(3-(E) 6α,7β-(Z)))7-(3-(7-(((2-amino 4-thiazolyl) (carboxy (2,5-difluoro 3,4-dihydroxy phenyl) methoxy)imino) acetamido) 2-carboxy 8-oxo 5-thia 1-azabicyclo[4,2,0]oct-2-en-3-yl) 2-propenyl)thieno (2,3,-b)-pyridinium NMR Spectrum: (DMSO) 3,4 to 3,8 : CH₂S; 5,18 (d, resolved): H₆; 5.81 (dd, resolved): H₇; 5,66 (m) 3H =CH—C<u>H</u>₂—N⁺ et O—C<u>H</u>—φ; 6.30 (m) CH=C<u>H</u>—CH₂, 7,14 (d, resolved, J=16: C<u>H</u>=CH—CH₂; 6.70 (dd, J=6 et 11): H₆"; 6,77 (s), 6,81 (s): H₅ thiazole; 7.89 (d, J=6): H₃'; 8.28 (d, J=6): H₂'; 8,16 (m): H₅'; 9,09 (d, J=8): H₄'; 9,23 (d, J=6): H₆'; 9,35 (d), 9,65 (d): CO—N<u>H</u>—CH; 7,32 (m), 9,83 (m): H mobile.

EXAMPLE 63

Internal salt of (6R-(3-(E) 6α,7β-(Z)))7-(3-(7-(((2-amino 4-thiazolyl) (carboxy (3,4-dihydroxy 2,5-difluorophenyl) methoxy)imino) acetamido) 2-carboxy 8-oxo 5-thia 1-azabicyclo[4,2,0]oct-2-en-3-yl) 2-propenyl) imidazo (2,1-b)-thiazolium

EXAMPLE 64

Internal salt of (6R-(3-(E) 6α,7β-(Z)))3-(3-(7-(((2-amino 4-thiazolyl) (carboxy (3,4-dihydroxy 2,5-difluorophenyl) methoxy)imino) acetamido) 2-carboxy 8-oxo 5-thia 1-azabicyclo[4,2,0]oct-2-en-3-yl) 2-propenyl) 1-methyl 1H-benzimidazolium

EXAMPLE 65

Internal salt of (6R-(3-(E) 6α,7β-(Z)))7-(3-(7-(((2-amino 4-thiazolyl) (carboxy (3,4-dihydroxy 2,5-difluorophenyl) methoxy)imino) acetamido) 2-carboxy 8-oxo 5-thia 1-azabicyclo[4,2,0]oct-2-en-3-yl) 2-propenyl) 4-methylthieno (2,3-b)-pyridinium In addition to the compounds described above, the following products constitute compounds which can be obtained by the methods of the invention.

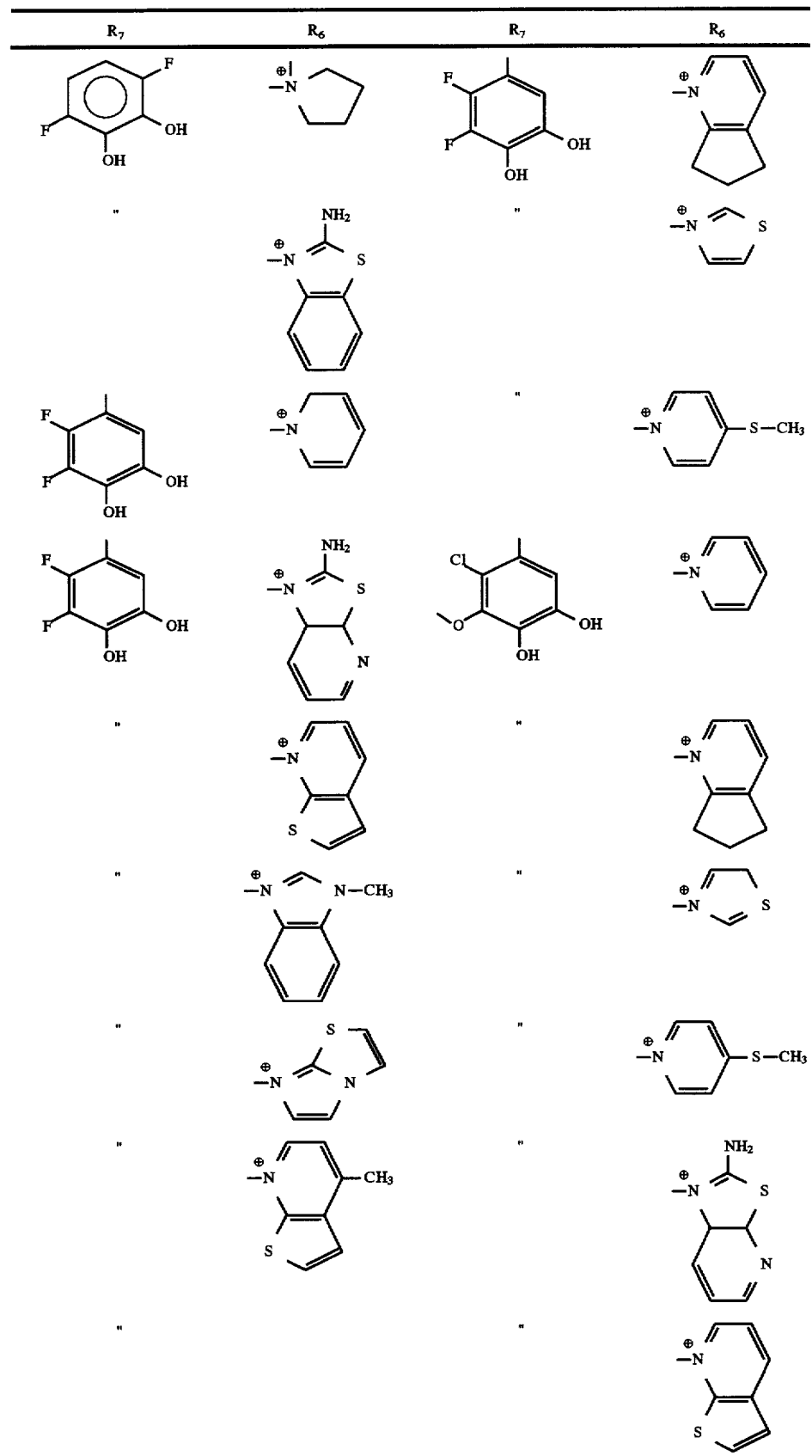

| $R_7$ | $R_6$ | $R_7$ | $R_6$ |
|---|---|---|---|
| " | 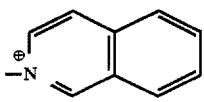 | " | 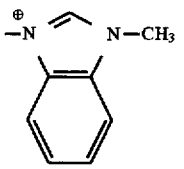 |
| " | | " | 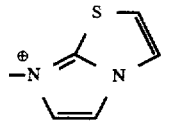 |
| " | | " | 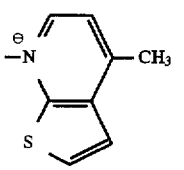 |
| 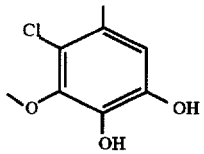 |  | 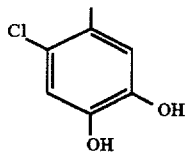 | 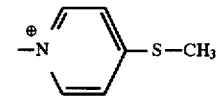 |
| " | 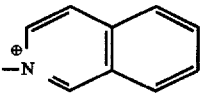 | " | 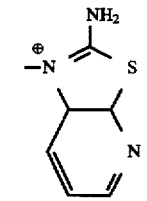 |
| " | 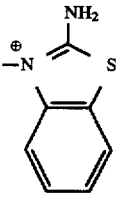 | " | 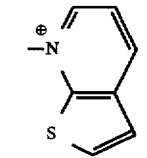 |
| 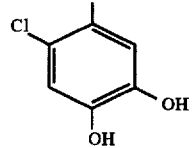 | 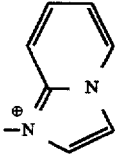 | " | 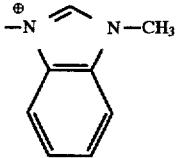 |
| " | 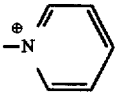 | " | 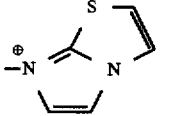 |
| " | 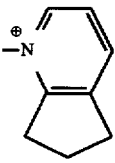 | " | 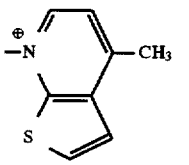 |

| $R_7$ | $R_6$ | $R_7$ | $R_6$ |
|---|---|---|---|
| " | 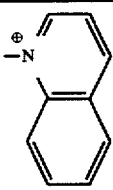 | " | 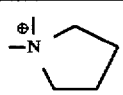 |
| " | 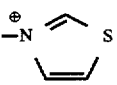 | " | 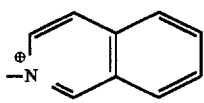 |
| | | " | 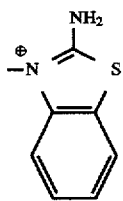 |
| 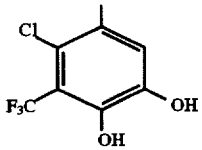 | 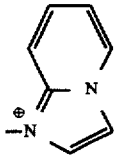 | 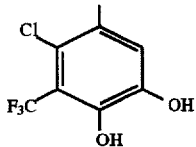 | 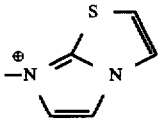 |
| " | 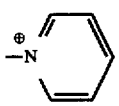 | " | 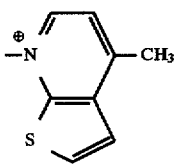 |
| " | 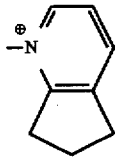 | " | 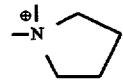 |
| " | 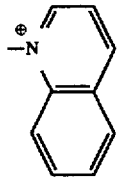 | " | 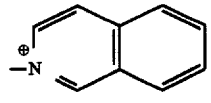 |
| " | 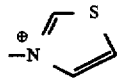 | " | 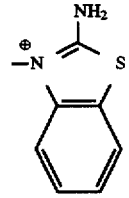 |
| " | 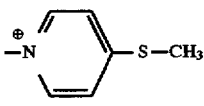 | 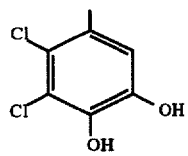 | 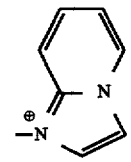 |

-continued

| R₇ | R₆ | R₇ | R₆ |
|---|---|---|---|

| R7 | R6 | R7 | R6 |
|---|---|---|---|
| " | 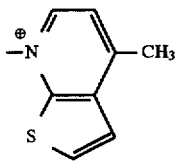 | " | 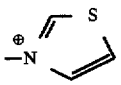 |
| " | 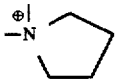 | " | 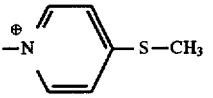 |
| " | 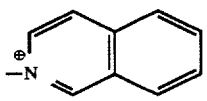 | " | 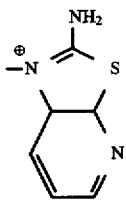 |
| 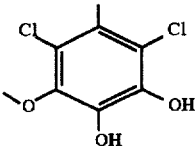 | 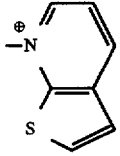 | 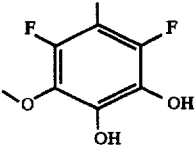 | 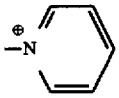 |
| " | 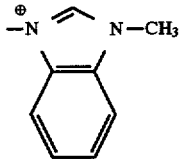 | " | 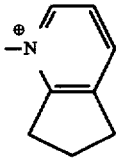 |
| " | 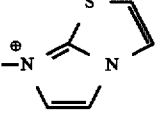 | " | 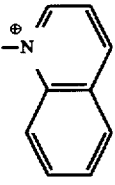 |
| " | 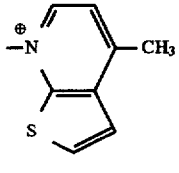 | " | 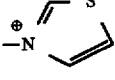 |
| " | 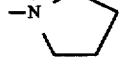 | " | 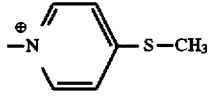 |
| " | 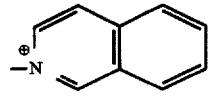 | " | 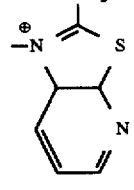 |

-continued
| $R_7$ | $R_6$ | $R_7$ | $R_6$ |
|---|---|---|---|
| " | 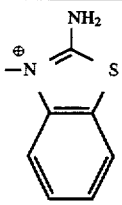 | " | 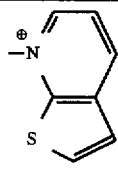 |
| 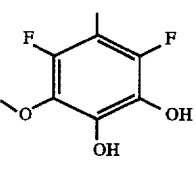 | 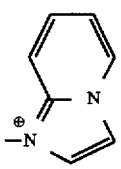 | " | 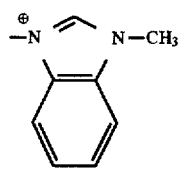 |
| | | " | 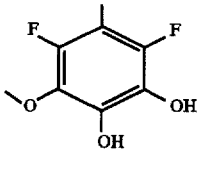 |
| 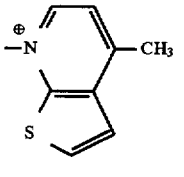 | 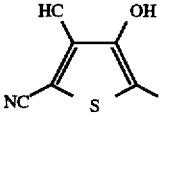 | 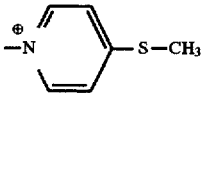 | 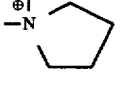 |
| " | 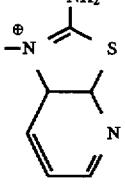 | " | 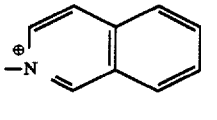 |
| " | 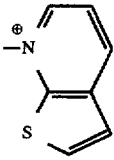 | " | 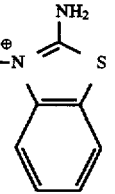 |
| " | 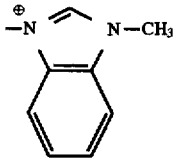 | " | 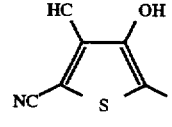 |
| 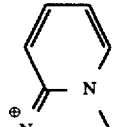 | 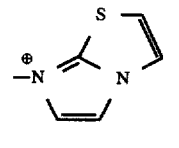 | " | 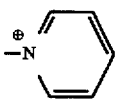 |
| " | 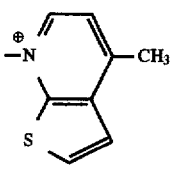 | | |

-continued
| R₇ | R₆ | R₇ | R₆ |
|---|---|---|---|
| " | 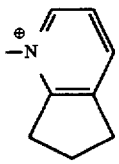 | " | 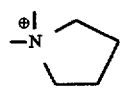 |
| " | 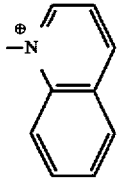 | " | 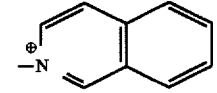 |
| " | 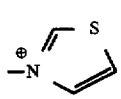 | " | 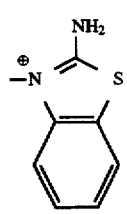 |
| 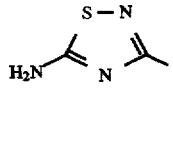 | 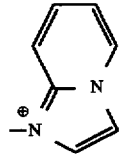 | 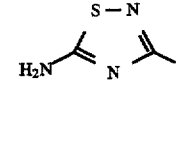 | 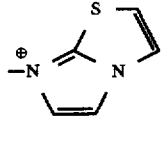 |
| " | 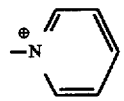 | " | 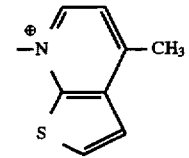 |
| " | 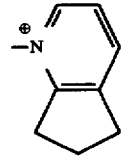 | " | 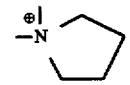 |
| " | 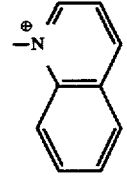 | " | 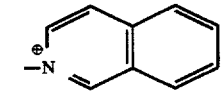 |
| " | 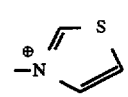 | " | 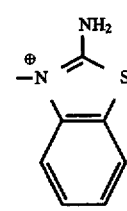 |

-continued
| R7 | R6 | R7 | R6 |
|---|---|---|---|
| 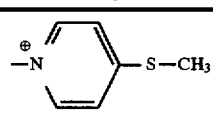 | 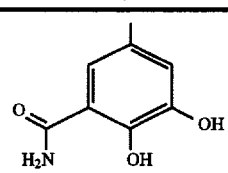 | 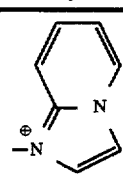 | 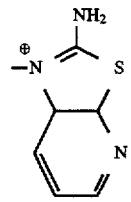 |
| " | 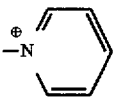 | " | 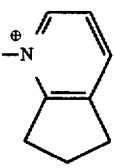 |
| " | 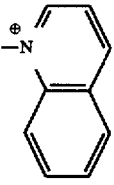 | " | 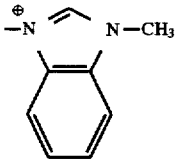 |
| " | 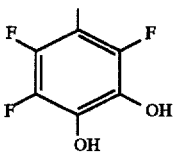 | " | 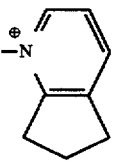 |
| 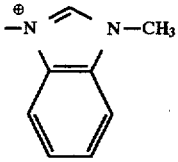 | 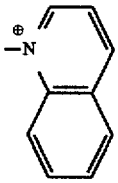 | 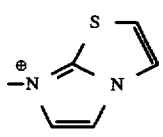 | 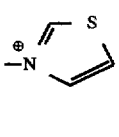 |
| " | 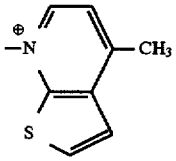 | " | 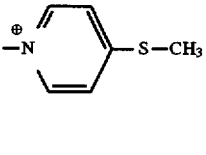 |
| " | 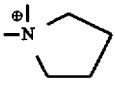 | " | 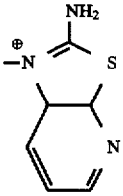 |

-continued

| R₇ | R₆ | R₇ | R₆ |
|---|---|---|---|

EXAMPLE 66

Internal salt of [6R-(3-(E) 6α.7β-(Z))]-1-(3-(7-[((2-amino-4-thiazolyl)-((carboxy-(2,3-difluoro-4,5-dihydroxy-phenyl)-methoxy)-imino)-acetamido]-2-carboxy-8-oxo-5-thia-1-azabicyclo[4.2.0]oct-2-en-3-yl)-2-propenyl)-imidazo(1,2-a) pyridinium

Stage A

1-[3-[7β-[[[[[1-[2,3-difluoro-4,5bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxy benzyloxy)-carbonyl]-8-oxo-5-thia-1-azabicyclo[4,2,0]oct-2-en-3-yl]-2-propenyl]-imidazo(1,2-a) pyridinium iodide Using the procedure of Stage H of Example 1, 600 mg of the iodated derivative obtained below and 0.215 ml of imidazo(1.2-a) pyridine were reacted to obtain after chromatograph on silica (eluant methylene chloride-methanol (95-5)), 534 mg of the desired product.

NMR spectrum: CDCl$_3$ 300 MHz 3.17 (s), 3.25 (s), 3.35 (s), 3.36 (s): the OMe's; 3.78, 3.79: the Φ-OMe's; 3.30 to 4.00: —O—CH$_2$—CH$_2$—O and =C—CH$_2$S; 4.93 (m): H$_6$; 5.76 to 5.89: H$_7$; 4.98 to 5.35: O—CH$_2$—O and COOCH$_2$—Φ; 6.28 (m): =CH—CH$_2$ΔE; 6.34 (s), 6.36 (s): C—C—Φ; 6.76 (s), 6.77 (s): H$_5$ thiazole; 6.85 to 7.35: the phenyls, COOCH—Φ$_2$; 7.87 (m) 1H, 8.04 (t) 1H, 8.39 (d) resolved 1H, 8.61 (d) resolved 1H, 9.09 (t) 1H: imidazopyridine; 7.73, 8.19:

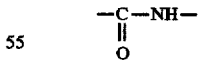

Stage B

Internal salt of (6R-(3-(E) 6α,7β-(Z)))-1-(3-(7-((2-amino-4-thiazolyl)-((carboxy-(2,3-difluoro-4,5-dihydroxy-phenyl)-methoxy)-imino)-acetamido]-2-carboxy-8-oxo-5-thia-1-azabicyclo[4,2,0]oct-2-en-3-yl)-2-propenyl)-imidazo(1,2-a) pyridinium Using the procedure of Stage I of Example 1 191 mg of the product of Stage A and 2 ml of trifluoroacetic acid with 10% anisole were reacted to obtain 66 mg of the expected product.

NMR spectrum: DMSO (300 MHz) ~3.70: $CH_2S$; 5.09 (d)–5.14 (d): $H_5$; 5.29 (m): $CH_2$—N⊕; 5.58 (s)–5.59 (S): O—CHΦ; 5.72 (m): $H_7$; 6.22 (m): CH=C$\underline{H}$—$CH_2$; 6.68 (m): $H_6$'; 6.77 (s)–6.78 (s): $H_5$ thiazole; 6.85 (d, J=16): =C—C$\underline{H}$=CH—; 7.58 (t)–8.06 (t): $H_5$", $H_6$"; 8.19 (d)–8.96 (d): $H_4$", $H_7$"; 8.28 (m)–8.44 (sl): $H_2$", $H_3$"; 7.32 (m), 9.5 to 9.9 (m): mobile H's.

Preparation of 4-methoxybenzyl 7β-[[[[1-[2,3-difluoro-4,5bis-[(2-methoxyethoxy)-methoxy]-phenyl]-2-oxo-2-(diphenylmethoxy)-ethyl]-oxy]-imino]-[2-(triphenylmethyl)-amino] thiazol-4-yl]-acetamido)-3-[(Z) 3-iodo-1-propenyl]-8-oxo-5-thia-1-azabicyclo[4.2.0]oct-2-en-2-carboxylate used at the start of Example 53.

Stage A 2,3-difluoro 6-methoxy phenol

Using the procedure of Example 39, 125 g of 3,4-difluoroanisole (commercial) and 500 ml of a 1.6M solution of N-butyllithium in hexane were reacted at −72° C., and then 92.4 ml of trimethylborate, 500 ml of hydrochloric acid and 120 g of intermediate compound were reacted and the product was reacted with 440 ml of 30% hydrogen peroxide to obtain 82.4 g of the expected product melting at 46.6° C.

Stage B 2,3-difluoro-4-hydroxy-5-methoxy-benzaldehyde 47 g of the product of Stage A in solution in 100 ml of ethanol were added dropwise over approximately 15 minutes to a solution of 62 g of dimethylamine (in aqueous solution at 40%), 375 ml of formalin and 290 ml of ethanol. The reaction mixture was refluxed for 3 hours and the solvent was eliminated. The residue was taken up in 400 ml of ether and filtered to obtain 51.3 g of intermediate methylated dimethylamino which was dissolved in 500 ml of a methylene chloride-methanol mixture (50-50). Then, 250 ml of methyl iodide were added and the mixture was stirred for 16 hours at ambient temperature, followed by filtering to obtain 88 g of the intermediate quaternary amine melting at 140° C. This intermediate product was heated for 3 hours at reflux in a mixture of 250 ml of acetic acid, 250 ml of water and 150 g of hexamethylene tetramine. 63 ml of concentrated hydrochloric acid were added, followed by stirring for 20 minutes at reflux, cooling the reaction medium and extracting with ethyl acetate to obtain 33.2 g of the expected aldehyde.

Stage C 2,3-difluoro-4,5bis[(2-methoxyethoxy)-methoxy]-benzaldehyde

Using the procedure of Stage C of Preparation 3, 36.6 g of the product of Stage B, 214 ml of diisopropylethylamine and 92 ml of chloro(2-methoxy ethoxy) methane were reacted to obtain 65.4 g of the expected product with a Rf=0.4 (methylene chloride-acetone 9-1).

Stage D

[2,3-difluoro-4,5-bis[(2-methoxyethoxy)-methoxy]-styryl-carboxylate

Using the procedure of Stage B of Example 40, 65.4 g of the aldehyde of Stage C were reacted to obtain 103 g of crude product which was chromatographed on silica (eluant: methylene chloride-ethyl acetate 9-1) to obtain 44.3 g of the expected product.

Stage E

[2,3-difluoro-4,5-bis[(2-methoxyethoxy)-methoxy]-styrol

Using the procedure of Stage C of Example 40, 44.3 g of the ester of Stage D and 230 ml of a molar solution of diisobutyl-aluminum hydride in hexane were reacted to obtain 32 g of the expected product.

Stage F

[2,3-difluoro 4,5-bis[(2-methoxyethoxy) methoxy] (1,2-epoxy) styrol

Using the procedure of Stage D of Example 40, 32 g of the product of Stage E were reacted to obtain 33.5 g of the expected product with a Rf=0.14 ($CH_2Cl_2$—AcOEt 8-2).

Stage G diphenylmethyl [[2,3-difluoro-4,5-bis[(2-methoxyethoxy)-methoxy]-phenyl]-chloro-acetate Using the procedure of Stage E of Example 40, 33.5 g of the epoxide of Stage F were reacted to obtain 15.6 g of the intermediate diol. 32.78 g of sodium periodate and 424 mg of hydrated ruthenium chloride were reacted with 16.6 g of chlorodiol prepared in an identical manner to obtain 15.6 g of the intermediate acid which was reacted with 7.5 g de diphenyldiazomethane to obtain 21 g of the expected product with Rf=0.4 ($CHCl_2$—AcOEt 8-2).

Stage H diphenylmethylaminoxy [[2,3-difluoro-4,5-bis[(2-methoxyethoxy)-methoxy]-phenyl]-acetate Using the procedure of Stage F of Example 40, 20 g of the chlorinated derivative of Stage G were reacted to obtain 13 g of the expected product with a Rf=0.2 (AcOEt—$CH_2Cl_2$ 1-3).

Stage I

[[1-[2,3-difluoro-4,5bis-[(2-methoxy ethoxy)-methoxy]-phenyl]-2-oxo-2-(diphenylmethoxy)-ethyl]-oxy]-imino]-[2-[(triphenylmethyl)-amino]-thiazol-4-yl]-acetic acid Using the procedure of Stage E of Example 1, 12 g of the product of Stage H and 9.45 mg of oxo [2-((triphenylmethyl) amino] thiazol-4-yl] acetic acid (described in Belgian Application No. 864828) were reacted to obtain the product which was not isolated and treated as is in the following stage.

Stage J 4-methoxy-benzyl7β-[[[[1-[2,3-difluoro-4,5bis-[(2-methoxyethoxy)-methoxy]-phenyl]-2-oxo-2-(diphenylmethoxy)-ethyl]-oxy]-imino]-[2-(triphenylmethyl)-amino] thiazol 4-yl]acetamido]-3-(Z) 3-chloro-1-propenyl]-8-oxo-5-thia-1-azabicyclo [4,2,0]oct-2-en-2-carboxylate Using the procedure of Stage F of Example 1, the crude product of Stage I and 12.89 g of 4-methoxy-benzyl 7β-amino 3-[(Z) 3-chloro-1-propenyl]-8-oxo-5-thia-1-azabicyclo[4,2,0]oct-2-en-2-carboxylate hydrochloride (EP 0,33,154) were reacted to obtain after chromatography on silica, (eluant: methylene chloride-ethyl acetate (9-1)). 14 g of the desired product with a Rf=0.23 ($CH_2Cl_2$—AcOEt 9-1).

Stage K 4-methoxy-benzyl7β-[[[[1-[2,3-difluoro-4,5bis-[(2-methoxy ethoxy)-methoxy]-phenyl]-2-oxo-2-(diphenylmethoxy) ethyl]-oxy]-imino]-[2-(triphenylmethyl)-amino]-thiazol-4-yl]acetamido]-3-[(Z) 3-iodo-1-propenyl]-8-oxo-5-thia-1-azabicyclo [4,2,0]oct-2-en-2-carboxylate Using the procedure of Stage G of Example 1, 6 g of the product of Step J were reacted to obtain after chromatography on silica (eluant: methylene chloride-ethyl acetate (9-1)) 5 g of the desired product with a Rf=0.27 (CHCl₂—AcOEt 9-1).

EXAMPLE 67

Internal salt of (6R-(3-(E) 6α,7β-(Z)))-1-(3-(7-((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)quinolinium Using the procedure of Stages A and B of Example 66, 750 mg of the iodated derivative prepared above and the appropriate amine were reacted to obtain 420 mg of the intermediate quaternary salt which was reacted with 4 ml of trifluoroacetic acid with 10% anisole to obtain 220 mg of the expected product.

NMR spectrum: DMSO (300 MHz) 3.45 (m): CH₂S; 5.09 (d)–5.14 (d): H₆; 5.72 (m): H₇; 5.58 (s)–5.59 (s): O—CH—CO; 5.88 (m): CH₂—N⁺; 6.34 (m): CH=CH—CH₂; 6.94 (d, J=16)–6.97 (d, J=16): CH=CH—CH₂; 6.67 (m): H₆"; 6.76 (s)–6.77 (s): H₅ thiazole; 8.07 (m)–8.26 (m)–8.53 (m)–9.34 (d)–9.57 (d): quinoline; 7.32 (m)–9.5 to 9.9 (m): mobile H's.

EXAMPLE 68

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-axo-5-thia-1-azabicyclo[4,2,0]oct-2-en-3-yl)-2-propenyl)-pyridinium Stage A 1-[3-[7β-[[[[1-[2,5-difluoro-3,4bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0]oct-2-en-3-yl]-2-propenyl] pyridinium iodide 713 mg of 4-methoxybenzyl 7β-[[[[1-[2,5-difluoro-2,4bis-[(2-methoxy-ethoxy)-methoxy]-phenyl]-2-oxo-2-(diphenyl-methoxy)-ethyl]-oxy]-imino]-[2-(triphenylmethyl)amino]-thiazol-4-yl]-acetamido]-3-[(Z) 3-iodo-1-propenyl]-8-oxo-5-thia-1-azabicyclo[4,2,0]oct-2-en-2-carboxylate of Stage G of Example 39 were mixed with 205 mg of pyridine and 10 ml of methylene chloride. The solvent was evaporated and the mixture was stirred for 1 hour. After taking up in ether and stirring for 1 hour, the crystallized product was separated out, washed with ether and dried for 16 hours under reduced pressure to obtain after chromatography on silica (eluant: methylene chloride-methanol (95-5)), 106 mg of the desired product with Rf=0.2.

NMR spectrum: CDCl₃ 400 MHz 3.33–3.34 (s): C—O—CH₃; 3.54–3.92 (m): central CH₂'s; 3.30–3.80: CH₂S; 3.79 (s): Ar—O—CH₃; 4.97 (dd): H₆ cephalo; 5.80–5.91 (d) after exchange: H₇ cephalo; 6.28 (m)–6.47 (dt): =CH—CH₂N⁺; 6.32 (s)–6.38 (s):

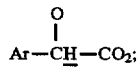

7.94–8.24 (d): CO—NH—CH; 8.02 to 9.23: pyridine; 6.75–7.40 (m): aromatic, CH=CH—CH₂, CO₂—CH—Φ₂; 5.55–5.75: CH₂—N⁺; 5.24 (m): OCH₂O.

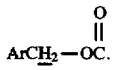

Stage B

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4,2,0]oct-2-en-3-yl)-2-propenyl)-pyridinium 98 mg of the product of Stage A in 3 ml of trifluoroacetic acid with 10% anisole were stirred for 2 hours at ambient temperature. The solution was poured into 75 ml of ether and stirred for 1 hour. The crystallized product was separated out, washed with ether and dried for 16 hours under reduced pressure to obtain 46 mg of the expected product.

NMR spectrum: DMSO (400 MHz) 3.58 (m): CH₂S; 5.18 (d,d): H₆; 5.79 (m): H₇; 5.41 (sl): CH₂N⁺; 5.64 (s)–5.65 (s): O—CH—C=; 6.30 (m): CH=CH—CH₂; 7.02 (dd, J=16): CH=CH—CH₂; 6.70 (dd): H₆'; 6.78 (s)–6.80 (s): H₅ thiazole; 8.18 (m): H₃", H₅"; 8.63 (m): H₄"; 9.05 (d): H₂", H₆"; 9.35 (d)–9.62 (d): CO—NHCH; 7.33 (m)–9.80 (m): mobile H.

EXAMPLE 69

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4,2,0]oct-2-en-3-yl)-2-propenyl)-6,7-dihydro-5H-pyrindinium Stage A 1-[3-[7β-[[[[1-[2,5-difluoro-3,4bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0]oct-2-en-3-yl]-2-propenyl]-6,7-dihydro-5H-pyrindinium iodide Using the procedure of Stage A of Example 68, 2.008 g of the iodated derivative and 843 mg of 2,3-cyclopentenopyridine were reacted to obtain 1.7 g of the expected product with a Rf=0.2 (methylene chloride-methanol 95-5).

Stage B

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)- 2-carboxy-8-oxo-5-thia-1-azabicyclo[4,2,0]oct-2-en-3-yl)-2-propenyl)-6,7-dihydro-5H-pyrindinium Using the procedure of Stage B of Example 68, 656 mg of the product of Stage A and 7 ml of trifluoroacetic acid with 10% anisole were reacted to obtain the expected product.

NMR spectrum: DMSO (300 MHz) 2.24 (m): CH₂ in position 6'; 3.14 (m)–3.37 (m): CH₂ in position 5' and 7'; 3.56 (m): CH₂S; 5.15 (d)–5.18 (d): H₆; 5.79 (m): H₇; 5.33 (d): =CH—CH₂—N⁺; 5.63 (s)–5.65 (s): O—CH—Φ; 6.23 (m): CH=CH—CH₂; 6.85 (d)–6.88 (d, J=16): C H=CH—CH₂; 6.71 (dd, J=10.5 and 6): H₆"; 6.78 (s)–6.81 (s): H₅ thiazole; 7.91 (m): H₃'; 8.43 (d, J=8): H₄'; 8.76 (d, J=6): H₂'; 9.54 (d)–9.63 (d): CH—NH—CO; 7.35 (m)–9.85 (m): mobile H's

EXAMPLE 70

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-quinolinium

Stage A

1-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4.2.0]oct-2-en-3-yl]-2-propenyl]-quinolinium iodide Using the procedure of Stage A of Example 68, 940 mg of the iodated derivative and 430 mg of quinoline were reacted to obtain 821 mg of the expected product with a Rf=0.2 (methylene chloride-methanol 95-5).

NMR spectrum: CDCl₃ 300 MHz 3.32–3.34–3.35 (s): C—O—CH₃; 3.54–3.91 (m): central CH₂'s and CH₂S; 3.79 (s): Ar—O—CH₃; 4.93 (dd): H₆ cephalo; 5.80–5.87 (m): H₇ cephalo; 6.35 (m)–6.56 (m): CH—CH—CH₂; 6.31 (s)–6.37 (s):

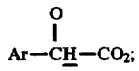

Ar—CH—CO₂;

7.93 to 8.96: quinoline; 6.85–7.40 (m): aromatic, C H=CH—CH₂, CO₂—CH—Φ₂; 5.15–5.30: OCH₂O,

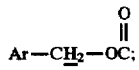

Ar—CH₂—OC;

5.95–6.05: CH₂—N⁺; 6.85–7.40: H₅ thiazole.

Stage B

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-quinolinium Using the procedure of Stage B of Example 68, 802 mg of the product of Stage A and 10 ml of trifluoroacetic acid with 10% anisole were reacted to obtain 437 mg of the expected product.

NMR spectrum: DMSO (300 MHz) 3.4 to 3.7 (m): CH₂S; 5.15 (dd): H₆; 5.79 (m): H₇; 5.62 (s)–5.64 (s): —O—C H—Φ; 5.89 (m): =CH—CH₂—N⁺; 6.37 (m): CH=C H—CH₂; 6.97 (dd, J=15.5): CH=CH—CH₂; 6.76 (s)–6.80 (s): H₅ thiazole; 6.70 (dd, J=11 and 6): H₆"; 8.07 (m)–8.27 (m)–8.53 (m)–9.34 (d): quinoline; 9.58 (d): H₂'; 9.53 (d)–9.62 (d): CO—NH—CH; 7.30 (m)–9.83 (m): mobile H.

EXAMPLE 71

Internal salt of (6R-(3-(E) 6α,7β-(Z)))-3-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-thiazolium

Stage A

3-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-yl]-acetamido]-2-[4-methoxybenzyloxy)-carbonyl]-8-oxo-5-thia-1-azabicyclo[4.2.0]oct-2-en-3-yl]-2-propenyl]-thiazolium iodide Using the procedure of Stage A of Example 68, 856 mg of the iodated derivative and 285 mg of thiazole were reacted to obtain 516 mg of the expected product with a Rf=0.2 (methylene chloride-methanol 95-5).

NMR spectrum: CDCl₃ 300 MHz 3.32–3.36 (s): the C—O—CH₃'s; 3.54–3.92 (m): the central CH₂'s and CH₂S; 3.78 (s): Ar—O—CH₃; 4.97 (m): H₆ cephalo; 5.25 (m): OCH₂O, CO₂CH₂Ar; 5.39 (m)–5.57 (m): CH₂N⁺; 5.74–5.90 (m): H₇ cephalo, 6.10–6.32 (m): =C H—CH₂N⁺; 6.32 (s)–6.38 (s): ArCHO; 6.87 (s)–6.90 (s): CO₂—CH—Φ₂; 6.76–6.78 (s): H₅ thiazole; 6.95 to 7.36: aromatic H's; 7.91: NH—CH—; 8.21–10.90–10.94: H' of the thiazole.

Stage B

Internal salt of (6R-(3-(E) 6α,7β-(Z)))-3-(3-(7-(((2-amino-4-thiazolyl)-((carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-thiazolium Using the procedure of Stage B of Example 68, 504 mg of the product of Stage A and 8 ml of trifluoroacetic acid with 10% anisole were reacted to obtain 238 mg of the expected product.

NMR spectrum: DMSO (300 MHz) 3.50 to 3.75 (m): CH₂S; 5.16 to 5.19 (d): H₆; 5.81 (m): H₇; 5.33 (m): =CH—CH₂—N⁺; 5.63 (s)–5.65 (s): O—CH—Φ; 6.26 (m): CH=CH—CH₂; 6.96 (dd, J=16): CH=CH—CH₂; 6.71 (dd, J=6 and 11): H₆"; 6.78 (s)–6.81 (s): H₅ thiazole; 8.37 (m)–8.51 (m): H₄', H₅'; 10.20 (sl): H₂'; 7.30 (m): 9.5 to 9.9 (m)–13.25 (m)–13.75 (m): mobile H's.

EXAMPLE 72

Internal salt of (6R-(3-(E) 6α,7β-(Z)))-2-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-isoquinolinium

Stage A

2-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetyl]-amino]-2-[[(4-methoxybenzyloxy)-carbonyl]-8-oxo-5-thia-1-azabicyclo[4.2.0]oct-2-en-3-yl]-2-propenyl]-isoquinolinium iodide Using the procedure of Stage A of Example 68, 856 mg of the iodated derivative and 369 mg of isoquinoline were reacted to obtain the 827 mg of the expected product with a Rf=0.2 (methylene chloride-methanol 95-5).

NMR spectrum: DMSO 300 MHz 3.31 (s)–3.32 (s)–3.33 (s)–3.39 (s): C—CH$_3$; 3.79 (s): Ar—O—CH$_3$; 3.44–4.00: OCH$_2$CH$_2$O and CH$_2$S; 5.24 (m): OCH$_2$O and CO$_2$—CH$_2$—Ar; 4.95 (dd): H$_6$ cephalo; 5.63 (m): H$_7$ cephalo; 5.88 (m): CH$_2$—N$^\oplus$; 6.32 (s)–6.38 (s):

ArCH:

6.36 (m)–6.56 (m): CH—CH$_2$N$^\oplus$; 6.75 (s)–6.77 (s): H$_5$ thiazole; 6.88–7.40: CH=CH—CH$_2$. CO$_2$CH—Φ$_2$ and aromatic H's; 7.90–8.70 and 10.93 (s)–10.98 (s): pyridine.

Stage B

Internal salt of (6R-(3-(E) 6α,7β-(Z)))-2-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-isoquinolinium Using the procedure of Stage B of Example 68, 807 mg of the product of Stage A and 10 ml of trifluoroacetic acid with 10% anisole were reacted to obtain 402 mg of the expected product.

NMR spectrum: DMSO (300 MHz) 3.53 to 3.75 (m): CH$_2$S; 5.18 (dd): H$_6$; 5.80 (m): H$_7$; 5.53 (d): =CH—CH$_2$—N$^\oplus$; 5.63 (s)–5.65 (s): O—CH—Φ; 6.37 (m): CH=CH—CH$_2$; 7.09 (dd, J=15.5): CH=CH—CH$_2$; 6.71 (dd, J=11 and 6): H$_6$''; 6.78 (s)–6.80 (s): H$_5$ thiazole; 8.09 (t)–8.28 (t): H$_6'$, H$_7'$; 8.37 (d)–8.53 (d): H$_5'$, H$_8'$; 8.61 (d)–8.74 (d): H$_3'$, H$_4'$; 10.06 (s): H$_1'$; 7.35 (m)–9.84 (m): mobile H's; 9.56 (d)–9.65 (d): CH—NH—CO.

EXAMPLE 73

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-4-(methylthio)-pyridinium Stage A 1-[3-[7β-[[[[[1-[2,5-difluoro-3,4bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0] oct-2-en-3-yl]-2-propenyl]-4-(methylthio)-pyridinium iodide Using the procedure of Stage A of Example 68, 855 mg of the iodated derivative and 371 mg of 4-methylthiopyridine were reacted to obtain 807 mg of the expected product with a Rf=0.2 (methylene chloride-methanol 95-5).

NMR spectrum: CDCl$_3$ 400 MHz 2.60 (s)–2.62 (s): CH$_2$S; 3.33–3.34 (s): the C—O—CH$_3$'s; 3.45–3.60–3.92 (m): the central CH$_2$'s; 3.79 (s): Ar—O—CH$_3$; 4.96 (m): H$_6$ cephalo; 5.24 (m): OCH$_2$O, CO$_2$CH$_2$Ar; 5.36 (m)–5.55 (m): CH$_2$N$^\oplus$; 5.78–5.91: H$_7$ cephalo, 6.17–6.50 (m): CH—CH$_2$ (ΔE); 6.33 (s)–6.38 (s):

Ar—CH:

6.75 (s)–6.77 (s): H$_5$ thiazole; 6.76: H$_6$ fluorophenyl; 6.90–7.40: aromatic H; CH=CH—CH$_2$; 7.63 (t)–8.89 (dd): pyridine; 7.88 (d)–8.82 (d): CONHCH.

Stage B

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-4-(methylthio)-pyridinium Using the procedure of Stage B of Example 68, 790 mg of the product of Stage A and 10 ml of trifluoroacetic acid with 10% anisole were reacted to obtain 408 mg of the expected product.

NMR spectrum: (DMSO) 300 MHz 2.71 (s): ΦSMe; 3.54 (d), 3.66 (d): CH—S; 5.17 (m): the H$_6$'s; 5.22 (s,l): —CH—CH—N$^+$; 5.63 (s) resolved: OCH—Φ; 5.79 (m): the H$_7$'s; 6.26 (m) CH=CH—CH$_2$ΔE, 6.98 (d, J=16) resolved: CH=CH—CH$_2$; 6.71 (dd, J=6 and 11): H$_6$''; 6.78 (s) resolved: H$_5$ thiazole; 7.30 (s,l): NH$_2$, 7.95 (d), 8.70 (d): N—S; 9.62–9.67 (d), 9.85: the mobile H's; 19.49.

EXAMPLE 74

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-1-azabicyclo-5-thia-1-azabicyclo[4,2,0]oct-2-en-3-yl)-2-propenyl)-2-amino-thiazolo(5,4-b)-pyridinium Stage A 1-[3-[7β-[[[[1-[2,5-difluoro-3,4bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0]oct-2-en-3-yl]-2-propenyl]-2-amino-thiazolo (5,4-b) pyridinium iodide Using the procedure of Stage A of Example 68, 579 mg of the iodated derivative and 417 mg of 2-triphenyl-methylamino-thiazolo (5,4-b) pyridine in 4 ml of methylene chloride in the presence of 0.2 ml of ethanol were reacted and the reaction mixture was stirred for 30 hours at 25° C. to obtain 328 mg of the expected product with a Rf=0.25 (methylene chloride-methanol 90-10).

NMR spectrum: CDCl$_3$ 300 MHz 3.32–3.33–3.34 (s): COCH$_3$; 3.2 to 3.5: CH$_2$S; 3.54 (m)–3.92 (m): the central CH$_2$'s; 3.78 (s)–3.79 (s): Ar—O—CH$_3$; 5.01 (d, resolved): H$_6$; 5.88 (dd)–6.03 (dd): H$_7$; 5.24 (m): CH$_2$—N$^\oplus$ and O—CH$_2$—O; 6.05 (m): CH=CH—CH$_2$; 6.33 (s)–6.39 (s):

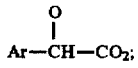
Ar—CH—CO$_2$:

6.75-7.15: aromatic H's, CH=CH—CH$_2$, H$_5$ thiazole, CO$_2$—CH—Φ$_2$; 7.45 (d)–8.49 (d): CONHCH; 7.75 to 8.63: 2-amino thiazolo (5,4-b) pyridine.

Stage B

Internal salt of (6R-(3-(E) 6α,7β-(Z)))-4-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4,2,0]oct-2-en-3-yl)-2-propenyl)-2-amino-thiazolo (5,4-b)-pyridinium Using the procedure of Stage B of Example 68, 314 mg of the product of Stage A and 5 ml of trifluoroacetic acid with 10% anisole were reacted to obtain 126 mg of the expected product.

NMR spectrum: (DMSO) 300 MHz ~3.60: $CH_2$; 5.19 (d) resolved: $H_6$; 5.81 (d): $H_7$; 5.47 (d): =CH—$\underline{CH}_2$—$N^+$; 5.63 (s), 5.65 (s): O—$\underline{CH}$—Φ; 6.21 (m): CH=$\underline{CH}$—$CH_2$; 7.08 (d) resolved J=16: $\underline{CH}$=CH—$CH_2$; 6.78 (s): $H_5$ thiazole; 6.70 (dd, J=6 and 11): $H_6''$; 7.83 (m): $H_5'$; 8.29 (d, J=8): $H_4'$; 8.64 (d, J=6): $H_6'$; 9.55 (d), 9.64 (d): CH—$\underline{NH}$—CO; 8.73 (s), 9.84 (m), 7.33 (m): mobile H.

EXAMPLE 75

Internal salt of (6R-(3-(E) 6α,7β-(Z)))-7-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-thieno (2,3-b) pyridinium Stage A 7-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4.2.0]oct-2-en-3-yl]-2-propenyl]-thieno (2,3-b) pyridinium iodide Using the procedure of Stage A of Example 68, 894 mg of the iodated derivative and 440 mg of thieno (2,3-b) pyridine were reacted to obtain 754 mg of the expected product with a Rf=0.2 (methylene chloride-methanol 95-5).

NMR spectrum: $CDCl_3$ 300 MHz 3.32–3.33–3.34–3.35 (s): $COCH_3$; 3.4–3.6: $CH_2S$; 3.79 (s)–3.81 (s resolved): Ar—O—$CH_3$; 3.54 (m)–3.92 (m): $OCH_2CH_2O$; 4.98 (d, resolved)–5.02 (d, resolved): $H_6$ cephalosporin; 5.17–5.35 (m); $OCH_2O$, $CO_2\underline{CH}_2Ar$; 5.82 (dd)–5.91 (dd): $H_7$ cephalosporin; 5.24 (m): 6.32 (s)–6.38 (s):

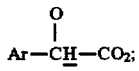

Ar—C$\underline{H}$—CO$_2$;

5.6–6.55: (complex m): C$\underline{H}$=; 6.7–8.35 (complex m): aromatic H's, $CO_2$—CH—$Ph_2$; 8.58 (m)–8.80 (m): aromatic H's; 9.72 (m): mobile H's.

Stage B:

Internal salt of (6R-(3-(E) 6α,7β-(Z)))-7-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl)-thieno (2,3-b) pyridinium Using the procedure of Stage B of Example 68, 736 mg of the product of Stage A and 10 ml of trifluoroacetic acid with 10% anisole were reacted to obtain 322 mg of the expected product.

NMR spectrum: (DMSO) 3.4 to 3.8: $CH_2S$; 5.18 (d, resolved): $H_6$; 5.81 (dd, resolved): $H_7$; 5.66 (m) 3H=CH—$\underline{CH}_2$—$N^⊕$ and O—$\underline{CH}$—Φ; 6.30 (m): CH=$\underline{CH}$—$CH_2$; 7.14 (d, resolved, J=16): $\underline{CH}$=CH—$CH_2$; 6.70 (dd, J=6 and 11): $H_6''$; 6.77 (s), 6.81 (s): $H_5$ thiazole; 7.89 (d, J=6): $H_3'$; 8.28 (d, J=6): $H_2'$; 8.16 (m): $H_5'$; 9.09 (d, J=8): $H_4'$; 9.23 (d, J=6): $H_6'$; 9.55 (d), 9.65 (d): CO—$\underline{NH}$—CH; 7.32 (m), 9.83 (m): mobile H's.

EXAMPLE 76

Internal salt of (6R-(3-(E) 6α,7β-(Z)))-7-(3-(7-(((2-amino-4-thiazolyl)-(carboxy-(3,4-dihydroxy-2,5-difluorophenyl)-methoxy)-imino)-acetamido)-2-carboxy-8-oxo-5-thia-1-azabicyclo[4.2.0]oct-2-en-3-yl)-2-propenyl)-imidazo (2,1-b)-thiazolium Stage A 7-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxybenzyloxyy)-carbonyl]-8-oxo-5-thia-1-azabicyclo[4.2.0]oct-2-en-3-yl]-2-propenyl]-imidazo (2,1-b) thiazolium iodide Using the procedure of Stage A of Example 68, 553.5 mg of the iodated derivative and 355 mg of imidazo (2,1-b) thiazole were reacted to obtain the 494 mg of the expected product with Rf=0.2 (methylene chloride-methanol 95-5).

NMR spectrum: $CDCl_3$ 300 MHz 3.32–3.34: $CH_3O$; 3.54 (m)–3.92 (m): $OCH_2CH_2O$, $CH_2S$; 3.79 (t): $\underline{CH}_3OAr$; 5.04 (m): $H_6$ cephalosporin; 5.81 (m)–5.91 (m): $H_7$ cephalosporin; 6.00–6.35: =$\underline{CH}$—$CH_2$ ΔE; 6.33 (s)–6.38 (s):

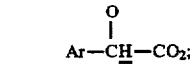

Ar—C$\underline{H}$—CO$_2$;

5.24 (m): Ar$\underline{CH}_2OCO$; 6.76 (s)–6.7 (s): $H_5$ thiazole; 6.87 (s)–6.90 (s): $CO_2$—CH—$Ph_2$; 6.75–7.50: aromatic H (phenyl), CH=CH—$CH_2$ ΔE, 1H of the imidazo (2,1-b) thiazole; 8.02 (m)–8.31 (m)–8.37 (m): 3H of the imidazothiazole; 7.96 (d)–8.24 (d): CON$\underline{H}$—CH.

Stage B

Internal salt of (6R-(3-(E) 6α,7β-(Z)))-7-(3-(7-(((2-amino-4-thiazolyl)-(carboxy-(3,4-dihydroxy-2,5-difluorophenyl)-methoxy-imino)-acetamido)- 2-carboxy-8-oxo-5-thia-1-azabicyclo[4.2.0]oct-2-en-3-yl)-2-propenyl)-imidazo (2,1-b)-thiazolium Using the procedure of Stage B of Example 68, 477 mg of the product of Stage A and 5 ml of trifluoroacetic acid with 10% anisole were reacted to obtain 238 mg of the expected product.

NMR spectrum: DMSO 300 MHz 3.55–3.80: $CH_2S$; 5.11–5.20 $H_6$ and CH—$\underline{CH}_2$—$N^⊕$; 5.81 (m): $H_7$; 6.80 (s, resolved): $H_5$ of the thiazole; 6.74 (dd): $H_6'$ of the fluorophenyl; 7.08 (d, resolved): C$\underline{H}$=CH—$CH_2$; 7.31 (sl): $NH_2$; 7.73–8.03–8.23–8.28: imidazo (2,1-b) thiazole; 9.56 (d)–9.65 (d): CO—NH; 9.80–9.85: mobile H's.

EXAMPLE 77

Internal salt of (6R-(3-(E) 6α,7β-(Z)))-3-(3-(7-(((2-amino-4-thiazolyl)-(carboxy-(3,4-dihydroxy-2,5-difluorophenyl)-methoxy)-imino)-acetamido)-2-carboxy-8-oxo-5-thia-1-azabicyclo[4.2.0]oct-2-en-3-yl)-2-propenyl)-1-methyl-1H-benzimidazolium Stage A 3-[3-[7β-[[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamino]-2-[(4-methoxybenzyloxy)-carbonyl]-8-oxo-5-thia-1-azabicyclo[4.2.0]oct-2-en-3-yl]-2-propenyl]1-methyl-1H-benzimidazolium iodide Using the procedure of Stage A of Example 68, 513 mg of the iodated derivative and 337 mg of 1-methyl benzimidazole were reacted to obtain 472 mg of the expected product with a Rf=0.2 (methylene chloride-methanol 95-5).

NMR spectrum: CDCl₃ 300 MHz 3.33: C$\underline{H}_3$O—C; 3.54 (m)–3.75 (m): CH₂S; OCH₂CH₂O; 3.91 (m): C$\underline{H}_3$OAr; 4.24 (s, resolved): CH₃N<; 4.99 (d): H₆ cephalosporin; 5.23 (m): OCH₂O, CO₂C$\underline{H}_2$Ar, 1H of CH₂N⊕; 5.42 (m): 1H of CH₂N⊕; 5.89 (m): H₇ cephalosporin; 6.21–6.51: =C$\underline{H}$—CH₂; 6.32 (s)–6.37 (s):

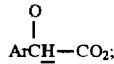

6.76 (s, resolved): H₅ thiazole; 6.90 (s): CO₂C$\underline{H}$Ph₂; ~6.91 (masked): fluorophenyl; 7.0–7.7: aromatic H's (except H₂'): C$\underline{H}$=CH—CH₂; 11.00 (s, resolved): H₂' of 1-methylbenzimidazole.

Stage B

Internal salt of (6R-(3-(E) 6α,7β-(Z)))-3-(3-(7-(((2-amino-4-thiazolyl)-(carboxy-(3,4-dihydroxy-2,5-difluorophenyl)-methoxy)-imino)-acetamido)-2-carboxy-8-oxo-5-thia-1-azabicyclo[4.2.0]oct-2-en-3-yl)-2-2-propenyl)-1-methyl-1H-benzimidazolium Using the procedure of Stage B of Example 68, 455 mg of the product of Step A and 5 ml of trifluoroacetic acid with 10% anisole were reacted to obtain 213 mg of the expected product.

NMR spectrum: DMSO 300 MHz 3.5–3.7: CH₃S; 4.09 (s): N—CH₃; 5.18 (d, resolved): H₆; 5.89 (m): H₇; 5.64 (s, resolved): OCHΦ; 6.79 (s, resolved): H₅ thiazole; 6.26 (m): CH=C$\underline{H}$—CH₂; 6.70: H of the fluorophenyl; 7.09 (d, resolved): C$\underline{H}$=CH—CH₂; 7.30 (sl): NH₂; 6.71 (m)–8.02 (m): aromatic H's; 9.55 (d)–9.65 (d): NH—CO; 9.71: H benzimidazole; 9.85: mobile H's.

EXAMPLE 78

Internal salt of (6R-(3-(E) 6α,7β-(Z)))-7-(3-(7-(((2-amino-4-thiazolyl)-(carboxy-(3,4-dihydroxy-2,5-difluorophenyl)-methoxy)-imino)-acetamido)-2-carboxy-8-oxo-5-thia-1-azabicyclo[4.2.0]oct-2-en-3-yl)-2-propenyl)-4-methyl-thieno (2,3-b)-pyridinium Stage A 7-[3-[7β-[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0]oct-2-en-3-yl]-2-propenyl]-4-methyl-thieno (2,3-b) pyridinium iodide Using the procedure of Stage A of Example 68, 398 mg of the iodated derivative and 405 mg of 4-methyl thieno (2,3-b) pyridine were reacted to obtain 257 mg of the expected product with Rf=0.4 (methylene chloride-methanol 90-10).

NMR spectrum: CDCl₃ 300 MHz 2.93 (s, resolved): 4-methyl pyridine; 3.33–3.34: C$\underline{H}_3$O—C; 3.55 (m)–3.93 (m): OCH₂CH₂O; 3.80 (s): C$\underline{H}_3$OAr; ~3.45–3.75: CH₂; 4.98 (d, resolved): H₆ cephalosporin; 5.24: OCH₂O, CO₂C$\underline{H}_2$Ar; 5.56–5.75–5.90: CH—CH₂N⊕; 5.84 (m): H₇ cephalosporin; 6.31 (s)–6.36 (s):

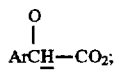

6.25–6.53: =CH—CH₂ ΔE; 6.75 (s)–6.77 (s): H₅ thiazole; 6.70–7.40: aromatic H's, C$\underline{H}$=CH—CH₂ E and H of the fluorophenyl; 7.66 (d, resolved)–7.84 (m)–8.24 (d)–9.62 (d, resolved): thieno (2,3-b) pyridine.

Stage B

Internal salt of (6R-(3-(E) 6α,7β-(Z)))-7-(3-(7-(((2-amino-4-thiazolyl)-(carboxy-(3,4-dihydroxy-2,5-difluorophenyl)-methoxy)-imino)-acetamido)-2-carboxy-8-oxo-5-thia-1-azabicyclo[4.2.0]oct-2-en-3-yl)-2-propenyl)-4-methyl-thieno (2,3-b)-pyridinium Using the procedure of Stage B of Example 68, 241 mg of the product of Stage A and 4 ml of trifluoroacetic acid with 10% anisole were reacted to obtain 132 mg of the expected product.

NMR spectrum: DMSO 300 MHz 2.91 (s): 4-methylpyridine; 5.17 (m): H₆ cephalosporin; 5.62 (m): CH₂N⁺ and Ar—CH—CO₂; 5.80 (m): H₇ cephalosporin; 6.28 (m): CH=C$\underline{H}$—CH₂; 6.70 (m): H of the fluorophenyl; 6.77 (s)–6.80 (s): H₅ thiazole; 7.12: C$\underline{H}$=CH—CH₂; 7.32 (m): NH₂; 7.97: aromatic H's; 8.26 (d)–9.08 (d): thieno (2,3-b) pyridine; 9.54 (s)–9.64 (s): NH—CO; 9.82: mobile H's.

EXAMPLE 79

Internal salt of (6R-(3-(E) 6α,7β-(Z)))-1-(3-(7-(((2-amino-4-thiazolyl)-(carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl) 1-methyl-pyrrolidinium Stage A 1-[3-[7β-[[[[1-[2,5-difluoro-3,4bis-[(2-methoxyethoxy)-methoxy]-phenyl]-2-oxo-2-(diphenylmethoxy)-ethyl]-oxy]-imino]-[2-(triphenylmethyl)-amino]-thiazol-4-yl]-acetamido]-2-[(4-methoxybenzyloxy)-carbonyl]-8-oxo-5-thia-1-azabicyclo[4,2,0]oct-2-en-3-yl]-2-propenyl]-1-methyl-pyrrolidinium iodide Using the procedure of Stage A of Example 68, 256 mg of the iodated derivative in 5 ml of ether and 1 ml of methylene chloride were reacted and homogenization was carried out using ultrasound and 0.10 ml of 1-methyl pyrrolidine were added to obtain 208 mg of the expected product with Rf=0.2 (methylene chloride-methanol 95-5).

NMR spectrum: CDCl₃ 300 MHz. 2.25 (l):

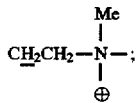

3.67 (l): CH₂—C$\underline{H}_2$—⊕N—Me; 3.21 (s, resolved): CH₃—N₊<; 3.33–3.35: CH₃—C—O; 3.55–4.00: OCH₂CH₂O, CH₂S; 3.80 (s): C$\underline{H}_3$OAr; 4.24 (m)–4.50 (m): =CH—C $\underline{H}_2$N⊕; 5.00 (d, resolved: H₆ cephalosporin; 5.25 (m): OCH₂O, CO₂C$\underline{H}_2$Ar; 5.78 (dd)–5.92 (dd): H₇ cephalosporin; 6.05 (m)–6.19 (m): =C$\underline{H}$—CH₂ ΔE; 6.77 (s, resolved): H₅ thiazole; 6.91 (m): CO₂C$\underline{H}$Ph₂, H of the fluorophenyl; 7.00–7.40: aromatic H's. C$\underline{H}$=CH—CH$_2$; 7.96(d) 8.20 (d): CON$\underline{H}$CH. 6.36 (s, resolved):

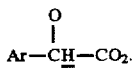

Ar—C$\underline{H}$—CO$_2$.

Stage B

Internal salt of (6R-(3-(E) 6α,7β-(Z)))-1-(3-(7-(((2-amino-4-thiazolyl) ((carboxy-(2,5-difluoro-3,4-dihydroxyphenyl)-methoxy)-imino)-acetamido)-2-carboxy-8-oxo-5-thia-1-azabicyclo[4.2.0]oct-2-en-3-yl)-2-propenyl-1-methyl-pyrrolidinium Using the procedure of Stage B of Example 68, 295 mg of the product of Stage A and 5 ml of trifluoroacetic acid with 10% anisole were reacted to obtain 130 mg of the expected product.

NMR spectrum: DMSO 300 MHz 2.09 (sl): pyrrolidine; 2.96 (s)–2.99 (s): methyl pyrrolidine; 4.01 (m)–4.10 (m): pyrrolidine and CH$_2$—N$^\oplus$; 5.21 (m): H$_6$ cephalosporin; 5.45–5.95: H$_7$ cephalosporin; 5.63 (s)–5.64 (s): Ar—C$\underline{H}$—CO$_2$; 6.16 (m): CH=C$\underline{H}$—CH$_2$; 6.73 (dd): H of the fluorophenyl; 6.80–6.87: H$_5$ thiazole; 7.04 (d, J=15): C$\underline{H}$=CH—CH$_2$; 7.30 (l): NH$_2$; 9.67–9.89: mobile H's.

EXAMPLE 80

Internal salt of (6R-(3-(E) 6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4.2.0]oct-2-en-3-yl)-2-propenyl)-6,7-dihydro-pyrindinium Using the procedure of Stages A and B of Example 68, 700 mg of the iodated derivative prepared above and the appropriate amine were reacted to obtain 604 mg of the intermediate quaternary salt, 600 mg of which were reacted with 6 ml of trifluoroacetic acid with 10% anisole to obtain 323 mg of the expected product.

NMR spectrum: DMSO 300 MHz. 2.24 (m)–3.14–3.34 (m): indane; 3.53 (dl)–3.74 (dl): the CH$_2$S's; 5.10 (m)–5.16 (m): H$_6$; 5.58 (s)–5.60 (s): O—C$\underline{H}$—CO; 5.72 (m): H$_7$; 6.68 (m): fluorophenyl; 6.77 (s)–6.78 (s): H$_5$ thiazole; 6.86 (dl): CH=C$\underline{H}$—CH$_2$; 7.91 (dd)–8.43 (d)–8.75 (d): pyrindane.

EXAMPLE 81

Internal salt of (6R-(3-(E) 6α,7β-(Z)))-2-(3-(7-(((2-amino-4-thiazolyl)-(carboxy-(2,3-difluoro-4,5-dihydroxy-phenyl)-methoxy)-imino)-acetamido)-2-carboxy-8-oxo-5-thia-1-azabicyclo[4.2.0]oct-2-en-3-yl)-2-propenyl)-isoquinolinium Using the procedure of Stages A and B of Example 68, 700 mg of the iodated derivative prepared above and the appropriate amine were reacted to obtain 584 mg of the intermediate quaternary salt, 580 mg of which were reacted with 6 ml of trifluoroacetic acid with 10% anisole to obtain 312 mg of the expected product.

NMR spectrum: DMSO 300 MHz. 3.45 (m): the CH$_2$S's; 5.09 (m)–5.15 (d, resolved): H$_6$; 5.58 (s)–5.60 (s): C—C$\underline{H}$—CO; 5.56 (d, resolved): CH$_2$—N$^\oplus$; 5.75 (m): H$_7$; 6.69 (m): fluorophenyl; 6.78 (s): H$_5$ thiazole; 6.54 (m): CH=C$\underline{H}$—CH$_2$; 7.09 (d, resolved): C$\underline{H}$=CH—CH$_2$; 8.09 to 10.06: isoquinoline.

EXAMPLE 82

Internal salt of (6R-(3-(E) 6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4.2.0]oct-2-en-3-yl)-2-propenyl)-1-methyl-pyrrolidinium Using the procedure of Stages A and B of Example 68, 923 mg of the iodated derivative prepared above and the appropriate amine were reacted to obtain 661 mg of the intermediate quaternary salt, 652 mg of which were reacted with 6 ml of trifluoroacetic acid with 10% anisole to obtain 317 mg of the expected product.

NMR spectrum: DMSO 300 MHz. 2.10 (sl)–3.45-(sl): pyrrolidine; 2.99 (sl): N$^\oplus$—CH$_3$; 3.45 (m): the CH$_2$S's; 5.12 (d)–5.16 (d): H$_6$; 5.58 (s)–5.60 (s): O—C$\underline{H}$—CO; 4.10 (sl): CH$_2$—N$^\oplus$; 5.75 (m): H$_7$; 6.69 (m): H of the fluorophenyl; 6.68 (s, resolved): H$_5$ thiazole; 6.12 (m): CH=C$\underline{H}$—CH$_2$; 7.03 (d, resolved): C$\underline{H}$=CH—CH$_2$.

EXAMPLE 83

Internal salt of (6R-(3-(E) 6α,7β-(Z)))-7-(3-(7-(((2-amino-4-thiazolyl)-(carboxy-(2,3-difluoro-4,5-dihydroxyphenyl)-methoxy)-imino)-acetamido)- 2-carboxy-8-oxo-5-thia-1-azabicyclo[4.2.0]oct-2-en-3-yl)-2-propenyl)-thieno (2,3-b) pyridinium Using the procedure of Stages A and B of Example 68, 700 mg of the iodated derivative prepared above and the appropriate amine were reacted to obtain 565 mg of the intermediate quaternary salt, 537 mg of which were reacted with 6 ml of trifluoroacetic acid with 10% anisole to obtain 290 mg of the expected product.

NMR spectrum: DMSO 300 MHz. 3.54 (d)–3.76 (d): the CH$_2$S's; 5.11 (d)–5.16 (d): H$_6$; 5.58 (s)–5.59 (s): O—C$\underline{H}$—CO; 5.67 (m): CH$_2$—N$^\oplus$; 5.74 (m): H$_7$; 6.68 (m): fluorophenyl; 6.77 (s, resolved): H$_5$ thiazole; 6.22 (m): CH=C$\underline{H}$—CH$_2$; 7.13 (d, resolved, J=15): C$\underline{H}$=CH—CH$_2$; 7.89–8.14–8.28–9.28–9.71: thieno (2,3-b) pyridine.

EXAMPLE 84

Internal salt of (6R-(3-(E) 6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4.2.0]oct-2-en-3-yl)-2-propenyl)-4-methylthio pyridinium.

Using the procedure of Stages A and B of Example 68, 800 mg of the iodated derivative prepared above and the appropriate amine were reacted to obtain 660 mg of the intermediate quaternary salt, which was reacted with 6 ml of trifluoroacetic acid with 10% anisole to obtain 305 mg of the expected product.

NMR spectrum: DMSO 300 MHz. 3.72 (s): CH$_3$—S—; 3.47 (d)–3.69 (d): the CH$_2$S's; 5.11 (d)–5.16 (d): H$_6$; 5.58 (s)–5.60 (s): O—C$\underline{H}$—CO; 5.22 (m): CH$_2$—N$^\oplus$; 5.74 (m): H$_7$; 6.69 (m): H of the fluorophenyl; 6.78 (s, resolved): H$_5$ thiazole; 6.22 (m): CH=C$\underline{H}$—CH$_2$; 6.96 (d, resolved): C$\underline{H}$=CH—CH$_2$; 7.95 (d)–8.69 (s, resolved): pyridine.

EXAMPLE 85

Internal salt of (6R-(3-(E)-6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4.2.0]oct-2-en-3-yl)-2-propenyl)-pyridinium Using the procedure of Stages A and B of Example 68, 700 mg of the iodated derivative prepared above and the appropriate amine were reacted to obtain 563 mg of intermediate quaternary salt, 546 mg of which were reacted with 6 ml of trifluoroacetic acid with 10% anisole to obtain 280 mg of the expected product.

NMR spectrum: DMSO 300 MHz. 3.45 (m): the CH$_2$S's; 5.11 (d)–5.16 (d): H$_6$; 5.58 (s)–5.60 (s): O—C$\underline{H}$—CO; 5.41

(sl): $CH_2$—$N^{\oplus}$; 5.74 (m): $H_7$; 6.69 (m): H of the fluorophenyl; 6.78 (s, resolved): $H_5$ thiazole; 6.27 (m): CH=C H—$CH_2$; 7.00 (d, resolved, J=15.5): CH=CH—$CH_2$; 8.04 (t)–8.18 (t)–9.75 (sl): pyridine; 9.57 (m)–9.27 (s)–9.77 (s)–9.88 (s): mobile H's.

EXAMPLE 86

Internal salt of (6R-(3-(E)-6α,7β-(Z)))-3-(3-(7-(((2-amino-4-thiazolyl)-(carboxy-(2,3-difluoro-4,5-dihydroxyphenyl)-methoxy)-imino)-acetamido)- 2-carboxy-8-oxo-5-thia-1-azabicyclo[4,2,0]oct-2-en-3-yl)-2-propenyl)-1-methyl-1H-benzimidazolium Using the procedure of Stages A and B of Example 68, 700 mg of the iodated derivative prepared above and the appropriate amine were reacted to obtain 447 mg of the intermediate quaternary salt, 440 mg of which were reacted with 6 ml of trifluoroacetic acid with 10% anisole to obtain 247 mg of the expected product.

NMR spectrum: DMSO 300 MHz. 4.09: N—$CH_3$ (1-methyl 1H-benzimidazole); 3.54 (d)–3.76 (d): the $CH_2S$'s; 5.11 (d)–5.14 (d, resolved): $H_6$; 5.58 (s)–5.59 (s): O—CH—CO; 5.30 (m): $CH_2$—$N^{\oplus}$; 5.74 (m): $H_7$; 6.68 (m): fluorophenyl; 6.77 (s)–6.78 (s): $H_5$ thiazole; 6.22 (m): CH=CH—$CH_2$; 7.08 (d, resolved): CH=CH—$CH_2$; 7.7 (m)–8.02 (m)–9.70 (s): benzimidazole; 9.6 (m) to 9.90: mobile H's.

EXAMPLE 87

Internal salt of (6R-(3-(E)-6α,7β-(Z)))-7-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-imidazo-(2,1-b)-thiazolium Using the procedure of Stages A and B of Example 68, 500 mg of the iodated derivative prepared above and the appropriate amine were reacted to obtain 130 mg of the intermediate quaternary salt: 330 mg of the product prepared in an identical manner were reacted with 5 m of trifluoroacetic acid with 10% anisole to obtain 174 mg of the expected product.

NMR spectrum: DMSO 300 MHz. 3.54 (d)–3.76 (d): the $CH_2S$'s; 5.11 (d)–5.14 (d, resolved): $H_6$; 5.58 (s)–5.59 (s): O—CH—CO; 5.30 (m): $CH_2$—$N^{\oplus}$; 5.74 (m): $H_7$; 6.68 (m): fluorophenyl; 6.77 (s)–6.78 (s): $H_5$ thiazole; 6.22 (m): CH=CH—$CH_2$; 7.08 (d, resolved): CH=CH—$CH_2$; 7.23 (d)–8.03 (s)–8.23 (s)–8.28 (d, resolved): imidazo (2,1-b) thiazole; 9.68 (m) to 9.90: mobile H's.

EXAMPLE 88

Internal salt of (6R-(3-(E)-6α,7β-(Z)))-3-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-thiazolium Using the procedure of Stages A and B of Example 68, 450 mg of the iodated derivative prepared above and the appropriate amine were reacted to obtain 130 mg of the intermediate quaternary salt, which was reacted with 5 ml of trifluoroacetic acid with 10% anisole to obtain 63 mg of the expected product.

NMR spectrum: DMSO 300 MHz. 3.54; (d)–3.76 (d): the $CH_2S$'s; 5.13 (d, resolved): $H_6$; 5.58 (s)–5.59 (s): O—C H—CO; 5.33 (m): $CH_2$—$N^{\oplus}$; 5.74 (m): $H_7$; 6.68 (m): fluorophenyl; 6.79 (s, resolved): $H_5$ thiazole; 6.22 (m): CH=CH—$CH_2$; 7.08 (d, resolved): CH=CH—$CH_2$; 8.36 (m)–8.03 (s)–8.51 (M)–10.2 (s): thiazole; 9.67 (m) to 9.87: mobile H's.

EXAMPLE 89

Internal salt of (6R-(3-(E)-6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-5,6,7,8-tetrahydro quinolinium Using the procedure of Stages A and B of Example 68, 300 mg of the iodated derivative prepared above and the appropriate amine were reacted to obtain 212 mg of the intermediate quaternary salt. 230 mg of identical product were reacted with 5 ml of trifluoroacetic acid with 10% anisole to obtain 143 mg of the expected product.

NMR spectrum: DMSO 300 MHz. 1.77 (m)–1.91 (m)–2.96 (m)–3.12 (m)–5.38 (m): $CH_2$ quinoline; 3.3 to 3.8 (m): the $CH_2S$'s; 5.09 (d)–5.15 (d): $H_6$; 5.58 (s)–5.60 (s): O—CH—CO; 5.38 (m): $CH_2$—$N^{\oplus}$; 5.74 (m): $H_7$; 6.69 (m): fluorophenyl; 6.77 (s)–6.78 (s): $H_5$ thiazole; 6.22 (m): CH=CH—$CH_2$; 6.73 (m): CH=CH—$CH_2$; 7.92 (m)–8.35 (d)–8.85 (d): CH-quinoline; 7.31 (m)–9.58 (d, resolved): mobile H's.

EXAMPLE 90

Internal salt of (6R-(3-(E)-6α,7β-(Z)))-1-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-5,6,7,8,9,10,11,12, 13,14-decahydrocyclododeca b) pyridinium Using the procedure of Stages A and B of Example 68, 300 mg of the iodated derivative prepared above and the appropriate amine were reacted to obtain 212 mg of the intermediate quaternary salt, 200 mg of which were reacted with 5 ml of trifluoroacetic acid with 10% anisole to obtain 60 mg of the expected product.

NMR spectrum: DMSO 300 MHz. 1.42–1.54–1.74–2.50–3.14–3.87: cyclododecane; 3.3 to 3.8 (m): the $CH_2S$'s; 5.10 (d)–5.15 (d): $H_6$; 5.58 (s)–5.60 (s): O—CH—CO; 5.38 (m): $CH_2$—$N^{\oplus}$; 5.73 (m): $H_7$; 6.69 (m): fluorophenyl; 6.77 (s)–6.78 (s): $H_5$ thiazole; 6.22 (m): CH=CH—$CH_2$; 6.73 (m): CH=CH—$CH_2$; 5.13 (d)–7.97 (t)–8.87 (d): pyridine; 9.58 (d, resolved): CH—NH—CO.

EXAMPLE 91

Internal salt of (6R-(3-(E)-6α,7β-(Z)))-5-amino-2-(3-(7-(((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-1-(3-methoxypropyl)-1H-pyrazolium Using the procedure of Stages A and B of Example 68, 300 mg of the iodated derivative prepared above and the appropriate amine were reacted to obtain 279 mg of the intermediate quaternary salt, 66 mg of which were reacted with 1 ml of trifluoroacetic acid with 10% anisole to obtain 17 mg of the expected product.

NMR spectrum: DMSO 300 MHz. 3.54 (d)–3.76 (d): the $CH_2S$'s; 5.11 (d): $H_6$; 5.60 (d): O—CH—CO; 4.98 (t): $CH_2$—$N^{\oplus}$; 4.73 (t): $H_7$; 6.69 (m): fluorophenyl; 6.79 (s, resolved): H₅ thiazole; 6.05 (m): CH=C$\underline{H}$—CH₂; 6.69 (m): C$\underline{H}$=CH—CH₂; 1.77 (sl)–4.17 (t)–3.40 (s): methoxypropyl; 7.30–7.33 (s): NH₂; 5.86 (d)–8.10 (sl): pyrazole; 9.58: C—$\underline{NH}$—CH.

EXAMPLE 92

Internal salt of (6R-(3-(E)-6α,7β-[Z,(S*)]-1-(3-(7-((2-amino-4-thiazolyl)-(carboxy-(2,3-difluoro-4,5-dihydroxyphenyl)-methoxy)-imino)-acetamido)-2-carboxy-8-oxo-5-thia-1-azabicyclo[4,2,0]oct-2-en-3-yl)-2-propenyl)-quinolinium Using the procedure of Stages A and B of Example 68, 4.14 g of the iodated derivative prepared below and the appropriate amine were reacted to obtain 2.79 g of the intermediate quaternary salt, which was reacted with 70 ml of trifluoroacetic acid with 10% anisole to obtain the expected product.

NMR spectrum: DMSO 300 MHz. 3.45 (m): the CH₂S's; 5.08 (s): H₆; 5.57 (s): O—C$\underline{H}$—CO; 5.88 (m): CH₂—N⊕; 5.73 (dd): H₇; 6.67 (m): fluorophenyl; 6.32 (m): CH=C$\underline{H}$—CH₂; 6.95 (d): C$\underline{H}$=CH—CH₂; 8.07 (t) 1H-9.34 (d) 1H-9.57 (d) and 8.20 to 8.33 (2H)-8.53 (m) 2H: quinoline.

Preparation of 4-methoxybenzyl-7β-[[[[[1-[2,3-difluoro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z) (S*)3-iodo-1-propenyl]-8-oxo-5-thia-1-azabicyclo[4,2,0]oct-2-en-2-carboxylate.

Stage A

[[1-(2,3-difluoro-4,5bis[(2-methoxyethoxy)-methoxy]-phenyl]-2-oxo-2-(diphenylmethoxy)-ethyl]-oxy]-imino]-[2-(triphenyl-methyl)-amino]-thiazol-4-yl]-acetic acid The aminoxy derivative of Stage H of the preparation of Example 68 was subjected to a high performance liquid chromatography, followed by stirring for 2 hours under a nitrogen atmosphere and at ambient temperature with 5.39 g of the appropriate enantiomer and 3.87 g of oxo [2-[(triphenylmethyl)-amino]-thiazol-4-yl]-acetic acid in the present of 60 ml of methanol. Then, the solvent was eliminated to obtain 8.3 g of the expected product.

Stage B 4-methoxybenzyl-7β-[[[[[1-[2,3-difluoro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z) (S*)]-3-chloro-1-propenyl]-8-oxo-5-thia-1-azabicyclo[4,2,0]oct-2-en-2-carboxylate 3.67 g of 4-methoxybenzyl-7β-amino-3-[(Z) 3-chloro-1-propenyl]-8-oxo-5-thia-1-azabicyclo[4,2,0]oct-2-en-2-carboxylate hydrochloride (prepared as described in Application EP 0,333,154) and 2.04 g of N-ethyl dimethylaminopropyl carbodiimide (EDAC) were added to a solution of 8.29 g of the product of Stage A in 60 ml of methylene chloride and the mixture was cooled to 5° C. The mixture was stirred for 15 minutes at 0° C., then for 1 hour while allowing the temperature to rise to 20° C. The reaction mixture was poured into a saturated aqueous solution of sodium chloride, followed by decanting. The organic phase was dried and the solvent was eliminated under reduced pressure. The residue was chromatographed on silica (eluant: CH₂Cl₂-AeOEt 9-1) to obtain 8.16 g of the expected product.

Stage C 4-methoxybenzyl-7β-[[[[[1-[2,3-difluoro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z) (S*)] 3-iodo-1-propenyl]-8-oxo-5-thia-1-azabicyclo[4,2,0]oct-2-en-2-carboxylate 2.2 g of sodium and 1 crystal of iodine were added to solution of 6.63 g of the product of Stage B in 66 ml of acetone and the mixture was stirred for 1 hour at ambient temperature. After evaporating to dryness under reduced pressure, the dry exact was taken up in methylene chloride, washed with a 10% solution of sodium thiosulfate then with salt water, followed by drying, then evaporating to dryness under reduced pressure to obtain 6.64 g of the expected product which was used as is for the following stage.

EXAMPLE 93

Internal salt of (6R-(3-(E)-6α,7β-[(Z) (S*)]-1-(3-(7-(((2-amino-4-thiazolyl)-(carboxy-(2,3,4-trihydroxyphenyl)-methoxy)-imino)-acetamido)-2-carboxy-8-oxo-5-thia-1-azabicyclo[4,2,0]oct-2-en-3-yl)-2-propenyl)-thieno (2,3-b) pyridinium Using the procedure of Stages A and B of Example 68, 4.14 g of the iodated derivative prepared above and the appropriate amine were reacted to obtain 2.15 g of the intermediate quaternary salt, which was reacted with 50 ml of trifluoroacetic acid with 10% anisole to obtain the expected product.

NMR spectrum: DMSO 300 MHz. 3.54 (d)–3.76 (d): the CH₂S's; 5.11 (d): H₆; 5.58 (s): O—C$\underline{H}$—CO; 5.67 (m): CH₂—N⊕; 5.76 (m): H₇; 6.67 (dd, J=6.5 and 2): chlorophenyl; 6.78 (s): H₅ thiazole; 6.22 (m): CH=C$\underline{H}$—CH₂; 7.11 (d, J=16): C$\underline{H}$=CH—CH₂; 7.89 (d)–8.28 (d)-and 8.15 (t)–9.28 (d)–9.71 (d): thieno (2,3-b) pyridine.

EXAMPLE 94

Internal salt of (6R-(3-(E)-6α,7β-[(Z) (S*)]-1-(3-(7-(((2-amino-4-thiazolyl)-(carboxy-(2,5-difluoro 3,4 dihydroxyphenyl)-methoxy)-imino)-acetyl)-amino)-2-carboxy-8-oxo-5-thia-1-azabicyclo[4,2,0]oct-2-en-3-yl)-2-propenyl)-quinolinium The iodated derivative of Stage A of Example 72, was subjected to a high performance liquid chromatography and the 2 enantiomers were separated. The operation was carried out as in Stage B of Example 70 with 1.53 g of the appropriate enantiomer and 16.5 ml of trifluoroacetic acid with 10% anisole to obtain 645 mg of the expected product.

NMR spectrum: DMSO 300 MHz. 5.14 (m): H₆; 5.63 (s)–5.64 (s): O—C$\underline{H}$—CO; 5.89 (m): CH₂—N⊕; 5.81 (m): H₇; 6.31 (m): CH=C$\underline{H}$—CH₂; 6.36 (m): C$\underline{H}$=CH—CH₂; 6.69 (dd): difluorophenyl; 8.07 (t)–8.26 (m)–8.53 (m)–9.34 (d)–9.58 (d): quinoline.

EXAMPLE 95

Internal salt of (6R-(3-(E)-6α,7β-[Z]-1-(3-(7-(((2-amino-4-thiazolyl)-(carboxy-(2,3-dichloro 4,5 dihydroxyphenyl)-methoxy)-imino)-acetyl amino)-2-carboxy-8-oxo-5-thia-1-azabicyclo-[4,2,0]oct-2-en-3-yl)-2-propenyl)-quinolinium Using the procedure of Stages A and B of Example 68, 850 mg of the iodated derivative prepared below and 0.34 ml of quinoline were reacted to obtain 850 mg of the intermediate quaternary salt, 810 mg of which were reacted with 8 ml of trifluoroacetic acid with 10% anisole to obtain 390 mg of the expected product.

NMR spectrum: DMSO 300 MHz. 3.4–3.7: the $CH_2S$'s; 5.72 (d): $H_6$; 5.07 (d)–5.14 (d): $H_7$; 5.75–5.76 (s): O—C$\underline{H}$—CO; 5.88 (m): $CH_2$—$N^{\oplus}$; 6.33 (m): CH=C$\underline{H}$—$CH_2$; 6.78 (s)–6.79 (s): $H_5$ thiazole; 6.93 (s)–6.95 (s): fluorophenyl; 6.97 (m): C$\underline{H}$=CH—$CH_2$; 8.07 and 8.26 (d)–8.51 (d) and 8.55 (d)–9.34 (d)–9.58 (d): quinoline.

Preparation of 4-methoxybenzyl-7β-[[[[1-[2,3-dichloro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z) 3-iodo-1-propenyl]-8-oxo-5-thia-1-azabicyclo[4.2.0]oct-2-en-2-carboxylate.

Stage A 2,3-dichloro-4,5bis-[(2-methoxyethoxy)-methoxy]-benzaldehyde

Using the procedure of Stage B of Preparation 3, 2.21 g of 2,3-dichloro-4-hydroxy-5-methoxy-benzaldehyde were reacted to obtain 1.4 g of dimethylated product which was reacted with 1.7 ml of chloro (2-methoxyethoxy) methane to obtain 2.6 g of the expected product with a Rf=0.25 ($CH_2Cl_2$—AcOEt 9-1).

Stage B 2,3-dichloro-4,5bis-[(2-methoxyethoxy)-methoxy]-styryl carboxylate

Using the procedure of Stage B of Example 40, 27.5 g of Stage A, 6.78 g of lithium bromide, 13.8 ml of triphenyl phosphonacetate and 10.36 ml of triethylamine were reacted to obtain 31.5 g of the expected product melting at<45° C.

Stage C 2,3-dichloro-4,5bis-[(2-methoxyethoxy)-methoxy]-styrol

Using the procedure of Stage C of Example 40, 20 g of ester of Step B and 88 ml of diisobutylaluminium hydride were reacted to obtain 17.9 g of the expected product melting at 60° C.

Stage D 2,3-dichloro-4,5bis-[(2-methoxyethoxy)-methoxy]-(1,2-epoxy) styrol

Using the procedure of Stage D of Example 40, 13.2 g of thee allylic alcohol of Step C and 10.3 g of m-chloro perbenzoic acid were reacted to obtain 13.7 g of the expected product with a Rf=0.25 (AcOEt-cyclohexane 6-4).

Stage E diphenylmethyl-2,3-dichloro-4,5-bis-[2-methoxyethoxy)-methoxy]-phenyl-chloro-acetate.

a) Opening the epoxide

Using the procedure of Example 40, 427 mg of the epoxide, 295 mg of cupric chloride and 184 mg of lithium chloride were reacted to obtain 410 mg of intermediate diol melting at 68° C.

b) Oxidation

Using the procedure of Example 40, 1.06 mg of the diol, 1.97 g of sodium periodate and 32 mg of ruthenium chloride were reacted to obtain 1.01 g of the desired product.

c) Esterification 8 ml of diphenyldiazomethane were reacted with the above product as indicated in Example 40, to obtain 1.52 g of the expected product with Rf=0.25 (cyclohexane-AcOEt 5-5).

Stage F diphenylmethylaminoxy-2,3-dichloro-4,5-bis-[(2-methoxy-ethoxy)-methoxy]-phenyl-acetate a) Phthalimidoxylation 7.30 g of the product of Stage E, 60 ml of dimethylformamide, 1.27 of potassium acetate and 2.13 g of N-hydroxyphthalimide were stirred for 3 hours to obtain 8.95 g of intermediate product.

b) Hydrazinolysis

Using the procedure of Example 40, 640 mg of the product above and 0.088 ml of hydrazine hydrate were reacted to obtain 505 mg of the expected product with a Rf=0.15 ($CH_2Cl_2$—AcOEt 9-1).

Stage G

[[1-[2,3-dichloro-4,5-bis-[(2-methoxy-ethoxy)-methoxy]-phenyl]-2-oxo-2-(diphenylmethoxy)-ethyl]-oxy]-imino]-2-[(triphenylmethyl)-amino]-thiazol]-4-yl]-acetic acid Using the procedure of Stage E of Example 1, 5.56 g of the product of Stage F and 3.8 g of oxo-[2-[(triphenylmethyl)-amino]-thiazol]-4-yl]-acetic acid (described in Belgian Application No. 864828) were reacted to obtain 8.9 g of the expected product.

Stage H 4-methoxybenzyl-7β-[[[[1-[2,3-dichloro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z)-3-chloro-1-propenyl]-8-oxo-5-thia-1-azabicyclo[4.2.0] oct-2-en-2-carboxylate Using the procedure of stage F of Example 1, 1.28 g of the product of Stage G and 0.605 g of 4-methoxybenzyl-7β-amino-3-[(Z)-3-chloro-1-propenyl]-8-oxo-5-thia-1-azabicyclo[4.2.0] oct-2-en-2-carboxylate (EP 0,333,154) were reacted to obtain after chromatography on silica, (eluant: methylene chloride-ether (8-2)), 1.27 g of the desired product with a Rf=0.25 ($CH_2Cl_2$-ether 9-1).

EXAMPLE 96

Internal salt of (6R-(3-(E)-6α,7β-[(Z)]-1-(3-(7-(((2-amino-4-thiazolyl)-(carboxy-(2,3-dichloro-4,5-dihydroxyphenyl)-methoxy)-imino)-acetamido)-2-carboxy-8-oxo-5-thia-1-azabicyclo[4.2.0]oct-2-en-3-yl)-2-propenyl)-imidazo-(1,2-a)-pyridinium Using the procedure of Stages A and B of Example 68, 700 mg of the iodated derivative prepared below and 0.25 ml of imidazo (1,2-a) pyridine were reacted to obtain 550 mg of the intermediate quaternary salt of which were reacted with 5 ml of trifluoroacetic acid with 10% anisole to obtain 210 mg of the expected product.

NMR spectrum: DMSO 300 MHz. 3.4–3.7: the $CH_2S$'s; 5.04–5.08 (d): $H_7$; 5.29 (m): $CH_2$—$N^{\oplus}$; 5.72 (d): $H_6$; 5.77 (s): O—C$\underline{H}$—CO; 6.20: CH=C$\underline{H}$—$CH_2$; 6.79–6.80 (s): $H_5$ thiazole; 6.87 (d, resolved): C$\underline{H}$=CH—$CH_2$; 6.94 (s)–6.95 (s): chlorophenyl; 7.58 (t)–8.05–8.19–8.36–8.28 and 8.44: imidazo (1,2-a) pyridine.

EXAMPLE 97

Internal salt of (6R-(3-(E)-6α,7β-[(Z)]-1-(3-(7-(((2-amino-4-thiazolyl)-(carboxy-(2,3-dichloro-4,5-dihydroxyphenyl)-methoxy)-imino)-acetamido)-2-carboxy-8-oxo-5-thia-1-azabicyclo[4.2.0]oct-2-en-3-yl)-2-propenyl)-6,7-dihydro-5H-pyrindinium Using the procedure of Stages A and B of Example 68, 850 mg of the iodated derivative prepared above and 0.34 ml of cyclopentylpyridine were reacted to obtain 730 mg of the intermediate quaternary salt, 710 mg of which were reacted with 0.7 ml of trifluoroacetic acid with 10% anisole to obtain 318 mg of the expected product.

NMR spectrum: DMSO 300 MHz. 2.24–3.15 and 3.35: indane; 3.4–3.7: the $CH_2S$'s; 5.09–5.16: $H_7$; 5.33 (d): $CH_2$—$N^\oplus$; 5.74: $H_6$; 5.77–5.78: O—C$\underline{H}$—CO; 6.13: CH=C$\underline{H}$—$CH_2$; 6.79–6.80: $H_5$ thiazole; 6.87 (d, resolved): C$\underline{H}$=CH—$CH_2$; 6.95 (s)–6.96 (s): chlorophenyl; 7.82–8.43–8.76 (d): pyridine.

EXAMPLE 98

Internal salt of (6R-(3-(E)-6α,7β-[(Z)]-7-(3-(7-(((2-amino-4-thiazolyl)-(carboxy-(2,3-dichloro-4,5-dihydroxyphenyl)-methoxy)-imino)-acetamido)-2-carboxy-8-oxo-5-thia-1-azabicyclo[4,2,0]oct-2-en-3-yl)-2-propenyl)-thieno (2,3-b)-pyridinium Using the procedure of Stages A and B of Example 68, 710 mg of the iodated derivative prepared above and 325 mg of thienopyridine were reacted to obtain 740 mg of the intermediate quaternary salt, 700 mg of which were reacted with 7 ml of trifluoroacetic acid with 10% anisole to obtain 265 mg of the expected product.

NMR spectrum: DMSO 300 MHz. 3.67: $CH_2$—$N^\oplus$; 5.10–5.17 (d): $H_7$; 5.77: $H_6$ and O—C$\underline{H}$—CO; 6.26 (m): CH=C$\underline{H}$—$CH_2$; 6.78 (s): $H_5$ thiazole; 6.84 (s): chlorophenyl; 7.13 (d, J=15.5): C$\underline{H}$=CH—$CH_2$; 7.88 (d)–8.15 (d)–8.28 (d)–9.08 (d)–9.22 (d): thienopyridine.

EXAMPLE 99

Internal salt of (6R-(3-(E)-6α,7β-[(Z)[-1-(3-(7-(((2-amino-4-thiazolyl)-(carboxy-(2,6-dichloro-3,4-dihydroxyphenyl)-5-methoxyphenyl)-methoxy)-imino)-acetamido)-2-carboxy-8-oxo-5-thia-1-azabicyclo[4,2,0]oct-2-en-3-yl)-2-propenyl)-quinolinium Using the procedure of Stages A and B of Example 68, 450 mg of the iodated derivative prepared below and 386 mg of quinoline were reacted to obtain 434 mg of the intermediate quaternary salt, 427 mg of which were reacted with 4 ml of trifluoroacetic acid with 10% anisole to obtain 195 mg of the expected product.

NMR spectrum: DMSO 300 MHz. 3.52: the $CH_2S$'s; 3.71 (s): methoxyphenyl; 5.17 (m): $H_6$; 5.69–5.76: $H_7$; 5.88 (m): $CH_2$—$N^\oplus$; 6.17–6.20 (s): O—C$\underline{H}$—CO; 6.38 (m): CH=C$\underline{H}$—$CH_2$; 6.72 (s)–6.78 (s): $H_5$ thiazole; 6.97: C$\underline{H}$=CH—$CH_2$; 8.06–8.26–8.53 and 9.47: quinoline.

Preparation of 4-methoxybenzyl-7β-[[[[[1-[2,6-dichloro-4,5bis-[(2-methoxy-ethoxy)-methoxy]-3-methoxy]-phenyl]-2-oxo-2-(diphenyl-methoxy)-ethyl]-oxy]-imino]-[2-(triphenylmethyl)-amino]-thiazol-4-yl]-acetamido]-3-[(Z)3-iodo-1-propenyl]-8-oxo-5-thia-1-azabicyclo[4,2,0]oct-2-en-2-carboxylate.

Stage A 2,6-dichloro-3,4,5-trimethoxy-benzaldehyde 442 ml of as solution of chlorine (37.13 g) in acetic acid were added to 50 g of trimethoxy aldehyde in 200 ml of acetic acid. After stirring for 16 hours at ambient temperature, 500 ml of water were added and the mixture was stirred for 1 hour, followed by filtering. The precipitate was taken up in cyclohexane dried and the solvent was eliminated under reduced pressure to obtain 37.1 g of the expected product melting at 76° C.

Stage B diphenylmethylaminoxy [2,6-dichloro-3-methoxy-4,5-bis-[2-methoxy ethoxy)-methoxy]-phenyl]-acetate Using the procedure of Stages B to F of Example 40 the aldehyde obtained in Stage A above was reacted to obtain the expected product.

Stage C

[[[1-[2,6-dichloro-3-methoxy-4,5bis-[(2-methoxy-ethoxy)-phenyl]-2-oxo-2-(diphenylmethoxy)-ethyl]-oxy]-imino]-[2-[triphenylmethyl-amino]-thiazol]-4-yl]-acetic acid 1 g of the product of Stage B was mixed with 10 ml of methanol and after 617 mg of oxo-2-[triphenylmethyl-amino]-thiazol]-4-yl]-acetic acid (described in Belgian Patent Application No. 864828) were added, the mixture was stirred for 2 hours. The solvent was eliminated under reduced pressure and the residue was taken up in 20 ml of methylene chloride, followed by washing with a 0.1N-hydrochloric acid solution, drying, filtering and evaporating the solvent under reduced pressure to obtain 1.517 g of the expected product with a Rf=0.5 (AcOEt-EtOH 7-3).

Stage D 4-methoxybenzyl-7β-[[[[[2,6-dichloro-3-methoxy-4,5bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-3-[(Z)-3-chloro-1-propenyl]-8-oxo-5-thia-1-azabicyclo[4,2,0]oct-2-en-2-carboxylate 0.677 g of 4-methoxybenzyl-7β-amino-3-[(Z) 3-chloro-1-propenyl]-8-oxo-5-thia-1-azabicyclo [4,2,0]oct-2-en-2-carboxylate (described in European Patent Application No. 0,333,154), and 1.48 g of the product of Stage C in 10 ml of methylene chloride were stirred cooled to 5° C. and then, 0.327 g of 1-(3-dimethylaminopropyl)-3-ethyl carbodiimide (EDAC) were added. The mixture was stirred for 30 minutes and then the reaction mixture was treated with 10 ml of potassium hydrogenophosphate in 20 ml of methylene chloride, followed by decanting, washing and drying and evaporating the solvents to obtain 1.90 g of the expected product with a Rf=0.30 [eluant: methylene chloride-ethyl acetate (90-10)].

Stage E 4-methoxybenzyl-7β-[[[[[2,6-dichloro-3-methoxy-4,5bis-[(2-methoxy-ethoxy)-methoxy]-phenyl]-2-oxo-2-(diphenyl-methoxy)-ethyl]-oxy]-imino]-[2-(triphenylmethyl)-amino]-thiazol-4-yl]-acetamido]-3-[(Z)-3-iodo-1-propenyl]-8-oxo-5-thia-1-azabicyclo [4,2,0]oct-2-en-2-carboxylate 1.18 g of the product of Stage D in 11 ml of acetone and 0.471 g of sodium iodide in the presence a crystal of iodine were stirred for one hour at ambient temperature. After elimination of the solvent, the residue was taken up in methylene chloride and the organic phase is washed and dried. The solvent was eliminated and the residue was chromatographed on silica (eluant: methylene chloride-methanol 9-1) to obtain 0.908 g of iodated product with a Rf=0.30 (eluant: methylene chloride-methanol 90-10).

EXAMPLE 100

Internal salt of (6R-(3-(E)-6α,7β-[(Z)]-7-(3-(7-(((2-amino-4-thiazolyl)-(carboxy-(2,6-dichloro-3,4-dihydroxy)-5-methoxyphenyl)-methoxy)-imino)-acetamido)-2-carboxy-8-oxo-5-thia-1-azabicyclo[4,2,0]oct-2-en-3-yl)-2-propenyl)-thieno-(2,3-b)-pyridinium Using the procedure of Stages A and B of Example 68, 450 mg of the iodated derivative prepared above and 404 mg of thieno-(2.3-b) pyridine were reacted to obtain 423 mg of the intermediate quaternary salt, 415 mg of which were reacted with 4 ml of trifluoroacetic acid with 10% anisole to obtain 193 mg of the expected product.

NMR spectrum: DMSO 300 MHz. 3.56: the $CH_2S$'s; 5.19 (d, d): $H_6$; 5.67 (m): $CH_2$—$N^{\oplus}$; 6.17–6.19 (s): O—C$\underline{H}$—CO; 6.30 (m): C$\underline{H}$=CH—$CH_2$; 7.13 (d): C$\underline{H}$=CH—$CH_2$; 7.88–8.27 and 8.14–9.08–9.21 (d): thieno (2.3-b) pyridine.

EXAMPLE 101

Internal salt of (6R-(3-(E)-6α.7β-[(Z)]-1-(3-(7-(((2-amino-4-thiazolyl)-(carboxy-(2-chloro-3.4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-6.7-dihydro-5H-pyrindinium.

Using the procedure of Stages A and B of Example 68, 1 g of the 2-chloro-5-methoxy iodated derivative obtained as indicated below and 405 mg of cyclopentenopyridine were reacted to obtain 1.14 g of the intermediate quaternary salt, 1.13 g of which were reacted with 11.3 ml of trifluoro-acetic acid with 10% anisole to obtain 682 mg of the expected product.

NMR spectrum: DMSO 300 MHz. 2.23 (m)–3.14 and 3.36 (m): indane; 3.54 (d, resolved): the $CH_2S$'s; 3.73 (s)–3.75 (S): $CH_3$—O—Φ; 5.2 (d, resolved): $H_6$; 5.33 (dl): $CH_2$—$N^{\oplus}$; 5.83 (m): $H_7$; 5.84 (s)–5.86 (s): O—C$\underline{H}$—CO; 6.25 (m): C$\underline{H}$=C$\underline{H}$—$CH_2$; 6.6 (s): chlorophenyl; 6.8 (s): $H_5$ thiazole; 7.91 (m)–8.42 and 8.76 (d): pyridine.

Preparation or 4-methoxybenzyl-7β-[[[[1-[2-chloro-3.4bis-[(2-methoxy-ethoxy)-methoxy]-5-methoxy]-phenyl]-2-oxo-2-(diphenyl-methoxy)-ethyl]-oxy]-imino]-[2-(triphenylmethyl)-amino]-thiazol-4-yl]-acetamido]-3-[(Z)-3-iodo-1-propenyl]-8-oxo-5-thia-1-azabicyclo[4.2.0]oct-2-en-2-carboxylate.

Using the procedure of the preparation of Example 40, Stage E, the [2-chloro-3,4-bis-[(2-methoxy ethoxy)-methoxy]-5-methoxy-(1,2-epoxy)-styrol (isomer B) of Stage D was reacted to obtain the desired product.

EXAMPLE 102

Internal salt of (6R-(3-(E)-6α.7β-[(Z)]-2-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-isoquinolinium Using the procedure of Stages A and B of Example 68, 1 g of the 2-chloro-5-methoxy iodated derivative obtained above and 439 mg of isoquinoline were reacted to obtain 1.03 g of the intermediate quaternary salt, 1.02 g of which were reacted with 10.2 ml of trifluoroacetic acid with 10% anisole to obtain 645 mg of the expected product.

NMR spectrum: DMSO 300 MHz. 3.5 to 3.9: the $CH_2S$'s; 3.73 (s)–3.75 (s): $CH_3$—O—Φ; 5.21 (m): $H_6$; 5.52 (dl): $CH_2$—$N^{\oplus}$; 5.31 (m): $H_7$; 5.8 (s)–5.85 (s): O—C$\underline{H}$—CO; 6.38 (m): CH=CH$CH_2$; 6.8 (s)–6.83 (s): $H_5$ thiazole; 8.09 (t)–8.28–8.61 (d)–8.74 (d)–8.37 (d)–8.54 (d) and 10.06 (s): isoquinoline.

EXAMPLE 103

Internal salt of (6R-(3-(E)-6α.7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-1-methyl pyrrolidinium.

Using the procedure of Stages A and B of Example 68, 1 g of the 2-chloro-5-methoxy iodated derivative above and 362 ml of N-methyl-pyrrolidine were reacted to obtain 940 mg of the intermediate quaternary salt, 930 mg of which were reacted with 9.5 ml of trifluoroacetic acid with 10% anisole to obtain 570 mg of the expected product.

NMR spectrum: DMSO 300 MHz. 2.09 (m)–2.98 (m)–3.4 (m): 1-methyl pyrrolidine; 3.75 (s)–3.76 (s): $CH_3$—O—Φ; 5.22 (d, resolved): $H_6$; 4.09 (dl): $CH_2$—$N^{\oplus}$; 5.84 (m): $H_7$; 5.86 (s)–5.88 (s): O—C$\underline{H}$—CO; 6.18 (m): CH=C$\underline{H}$—$CH_2$; 6.62 (s)–6.63 (s): chlorophenyl; 6.84 (s)–6.87 (s): $H_5$ thiazole; 7.02 (dl, J=15.5): C$\underline{H}$=CH—$CH_2$.

EXAMPLE 104

Internal salt of (2(E)-3-(6R-6α.7β[(Z)]-N(2-amino-2-oxoethyl)-3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4.2.0]oct-2-en-3-yl)-N,N-dimethyl-2-propen-1-aminium Using the procedure of Stages A and B of Example 68, 1 g of the 2-chloro-5-methoxy iodated derivative above and 69.4 mg of dimethylaminoacetamide were reacted to obtain 968 mg of the intermediate quaternary salt, 957 mg of which were reacted with 9.6 ml of trifluoroacetic acid with 10% anisole to obtain 698 mg of the expected product.

NMR spectrum: DMSO 300 MHz. 3.18 (s): $N^{\oplus}(CH_3)_2$; 3.5 to 3.95 (m): the $CH_2S$'s; 3.75 (s)–3.76 (s): $CH_3$—O—Φ; 5.23 (d, resolved): $H_6$; 3.18 (s): $CH_2$—$N^{\oplus}$; 5.83 (m): $H_7$; 5.86 (s)–5.88 (s): O—C$\underline{H}$—CO; 6.14 (m): CH=C$\underline{H}$—$CH_2$; 6.61 (s)–6.62 (s): chlorophenyl; 6.83 (s)–6.86 (s): $H_5$ thiazole; 7.02: C$\underline{H}$=CH—$CH_2$; 7.67 (sl)–7.93 (sl): CON$H_{2;\ 9.541}$ (d)–9.65 (d): CO—$\underline{NH}$—CH.

EXAMPLE 105

Internal salt of (6R-(3-(E)-6α.7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-pyridinium.

Using the procedure of Stages A and B of Example 68, 1 g of the 2-chloro-5-methoxy iodated derivative above and 275 mg of pyridine were reacted to obtain 1.02 g of the intermediate quaternary salt, 1.01 g of which were reacted with 10 ml of trifluoroacetic acid with 10% anisole to obtain 560 mg of the expected product.

NMR spectrum: DMSO 300 MHz. 3.5 to 3.8: the $CH_2S$'s; 3.73 (s)–3.75 (s): $CH_3$—O—Φ; 5.2 (d, resolved): $H_6$; 5.41 (d): $CH_2$—$N^{\oplus}$; 5.8: $H_7$; 5.85 (s)–5.86 (s): O—C$\underline{H}$—CO; 6.31 (m): CH=C$\underline{H}$—$CH_2$; 7.0: C$\underline{H}$=CH—$CH_2$; 8.18 (m)–8.63 (t)–9.05 (m): pyridine.

EXAMPLE 106

Internal salt of (6R-(3-(E)-6α.7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-4-(methylthio)-pyridinium Using the procedure of Stages A and B of Example 68, 1 g of the 2-chloro-5-methoxy iodated derivative above and 500 mg of methylthio pyridine were reacted to obtain 1.003 mg of the intermediate quaternary salt, 998 mg of which were reacted with 10 ml of trifluoroacetic acid with 10% anisole to obtain 656 mg of the expected product.

NMR spectrum: DMSO 300 MHz. 2.71 (s): S—$CH_3$; 3.54 (d)–3.67 (m): the $CH_2$S's; 3.73 (s)–3.76 (s): $CH_3$—O—Φ; 5.21: $H_6$; 5.81: $CH_2$—$N^\oplus$ and $H_7$; 6.99 (d, J=15.5): CH=C$\underline{H}$—$CH_2$; 6.81 (s)–6.83 (s): chlorophenyl; 6.61 (s): $H_5$ thiazole; 7.95 (d)–8.69 (d): pyridine.

EXAMPLE 107

Internal salt of (6R-(3-(E)-6α,7β-[(Z)]-3-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-1-methyl-1H-benzimidazolium Using the procedure of Stages A and B of Example 68, 1 g of the 2-chloro-5-methoxy iodated derivative above and 360 mg of methylimidazobenzene were reacted to obtain 1.04 g of the intermediate quaternary salt, 1.03 g of which were reacted with 10 ml of trifluoroacetic acid with 10% anisole to obtain 648 mg of the expected product.

NMR spectrum: DMSO 300 MHz. 3.55 (d, resolved) –3.67 (m): the $CH_2$S's; 3.72 (s)–3.74 (s): $CH_3$—O—φ; 5.20 (m): $H_6$; 5.20 (d): $CH_2$—$N^\oplus$; 5.80 (m): $H_7$; 5.83 (s)–5.85 (s): O—C$\underline{H}$—CO; 6.27 (m)–7.08 (d, resolved): CH=C$\underline{H}$—$CH_2$; 6.8 (s)–6.84: chlorophenyl; 6.6 (m): $H_5$ thiazole; 7.71 (m)–8.03–9.7 (s, resolved): benzimidazole.

EXAMPLE 108

Internal salt of (6R-(3-(E)-6α,7β-[(Z)]-7-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-thieno-(2,3-b)-pyridinium Using the procedure of Stages A and B of Example 68, 1 g of the 2-chloro-5-methoxy iodated above and 400 μl of thieno (2,3-b) pyridine were reacted to obtain 991 mg of the intermediate quaternary salt, 976 mg of which were reacted with 10 ml of trifluoroacetic acid with 10% anisole to obtain 683 mg of the expected product.

NMR spectrum: DMSO 300 MHz. 3.58 (d): the $CH_2$S's; 3.74 (m): $CH_3$—O—Φ; 5.21 (m): $H_6$; 5.68 (d): $CH_2$—$N^\oplus$; 5.84 (m): $H_7$; 6.30 (m): CH=C$\underline{H}$—$CH_2$; 6.84 (s)–6.88: chlorophenyl and $H_5$ thiazole; 7.89 (d)–8.29 (d)–8.15 (dd) –9.09 (d)–9.21 (d): thieno pyridine.

EXAMPLE 109

Internal salt of (6R-(3-(E)-6α,7β-[(Z)]-3-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-thiazolium Using the procedure of Stages A and B of Example 68, 1 g of the 2-chloro-5-methoxy iodated above and 250 μl of thiazole were reacted to obtain 924 mg of intermediate quaternary salt, which was reacted with 9.3 ml of trifluoroacetic acid with 10% anisole to obtain 617 mg of the expected product.

NMR spectrum: DMSO 300 MHz. 3.60 (d, resolved) –3.79 (masked): the $CH_2$S's; 3.75 (s, resolved): $CH_3$—O—Φ; 5.21 (d, resolved): $H_6$; 5.33 (s): $CH_2$—$N^\oplus$; 5.82 (m): $H_7$; 5.85 (s)–5.87: O—C$\underline{H}$—CO; 6.25 (m): CH=C$\underline{H}$—$CH_2$; 6.67 (s): chlorophenyl; 6.84 (s)–6.87: $H_5$ thiazole; 8.37 (m)–8.52 (d)–10.21: thiazole.

EXAMPLE 110

Internal salt of (6R-(3-(E)-6α,7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-3-(aminocarbonyl)-pyridinium Using the procedure of Stages A and B of Example 68, 1 g of the 2-chloro-5-methoxy iodated above and 360 mg of nicotinamide were reacted to obtain 993 mg of intermediate quaternary salt, 980 mg of which were reacted with 10 ml of trifluoroacetic acid with 10% anisole to obtain 611 mg of the expected product.

NMR spectrum: DMSO 300 MHz. 3.55 to 3.8: the $CH_2$S's and $CH_3$—O—Φ; 5.21 (m): $H_6$; 5.47 (d): $CH_2$—$N^\oplus$; 5.83 (m): $H_7$; 5.88 (s, resolved): O—C$\underline{H}$—CO; 6.32 (m): CH=C$\underline{H}$—$CH_2$; 6.60 (s): chlorophenyl; 6.87 (s, resolved): $H_5$ thiazole; 8.29 (dd)–8.97 (d)–9.17 (d)–9.47 (s): 3-aminocarbonyl pyridine.

EXAMPLE 111

Internal salt of (6R-(3-(E)-6α,7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-pyridazinium Using the procedure of Stages A and B of Example 68, 735 mg of the 2-chloro-5-methoxy iodated derivative above and 60 mg of pyridazine were reacted to obtain 730 mg of intermediate quaternary salt, 720 mg of which were reacted with 7.2 ml of trifluoroacetic acid with 10% anisole to obtain 470 mg of the expected product.

NMR spectrum: DMSO 300 MHz. 3.5 to 3.7: the $CH_2$S's; 3.74 (s)–3.75 (s): $CH_3$—O—φ; 5.22 (d, resolved): $H_6$; 5.61 (d): $CH_2$—$N^\oplus$; 5.82 (m): $H_7$; 5.84 (s)–5.86 (s): O—C$\underline{H}$—CO; 6.30 (m): CH=C$\underline{H}$—$CH_2$; 6.61 (s): chlorophenyl; 6.82 (s)–6.85 (s): $H_5$ thiazole; 8.63 (m)–8.75 (m)–9.65 (m) 2H: pyridazine.

EXAMPLE 112

Internal salt of (6R-(3-(E)-6α,7β-[(Z)]-1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2.0]oct-2-en-3-yl)-2-propenyl)-3-carboxy pyridinium Using the procedure of Stages A and B of Example 68, 735 g of the 2-chloro-5-methoxy iodated derivative above and 150 mg of diphenylmethyl ester of nicotinic acid were reacted to obtain 480 mg of intermediate quaternary salt, 470 mg of which were reacted with 4.17 ml of trifluoroacetic acid with 10% anisole to obtain 243 mg of the expected product.

NMR spectrum: DMSO 300 MHz. 3.4 to 3.80 (m complex): the $CH_2$S's; 3.74 (s)–3.75 (s): $CH_3$—O—φ; 5.21 (dd): $H_6$; 5.5 (m): $CH_2$—$N^\oplus$; 5.82 (m): $H_7$; 5.83 (s)–5.85 (s): O—C$\underline{H}$—CO; 6.31 (m): CH=C$\underline{H}$—$CH_2$; 6.79 (sl)–6.82 (sl): chlorophenyl; 6.61 (s): $H_5$ thiazole; 8.29 (m)–9.0 (d)–9.22 (d)–9.58 (s): 3-carboxy pyridine.

EXAMPLE 113

Internal salt of (2-(E)-3-(6R-6α,7β-[(Z)]3-(7-(((2-amino-4-thiazolyl)-(carboxy-(2-chloro-3,4-dihydroxy)-5-methoxy-phenyl)-methoxy)-imino)-acetamido)-2-carboxy-8-oxo-5-thia-1-azabicyclo[4,2.0]oct-2-en-3-yl)-N,N-dimethyl-N-(2-hydroxy-2-oxoethyl)-2-propen-1-aminium Using the procedure of Stages A and B of Example 68, 800 g of the 2-chloro-5-methoxy iodated derivative above and 177 mg of diphenylmethyl ester of N,N-dimethyl glycine were reacted to obtain 928 mg of intermediate quaternary salt, 875 mg of which were reacted with 8.8 ml of trifluoroacetic acid with 10% anisole to obtain 426 mg of the expected product.

NMR spectrum: DMSO 300 MHz. 3.17 (s): $(CH_3)_2N^{\oplus}$; 3.76 (s): $CH_3$—O—Φ; 4.27 (s): $\underline{CH}_2$—$N^{\oplus}$—$\underline{CH}_2$—CO; 5.22 (m): $H_6$; 4.27 (s): $CH_2$—$N^{\oplus}$; 5.82 (m): $H_7$; 5.86 (s)–5.87 (s): O—$\underline{CH}$—CO; 6.16 (m): CH=$\underline{CH}$—$CH_2$; 6.61 (s)–6.62 (s): chlorophenyl; 6.8 (s)–6.85 (s): $H_5$ thiazole.

Preparation of the diphenylmethyl ester of N,N-dimethyl glycine 2. g of N,N-dimethyl-glycine were dissolved in 19.4 ml of N hydrochloric acid and then after 76.3 ml of a 0.38M/l solution of diphenyl diazomethane in either were added, 24 ml of methanol were added. The mixture was stirred for 1 hour at ambient temperature, followed by alkalinizing to a pH=10 by the addition of 32 ml of N-sodium hydroxide. The mixture was stirred for 5 minutes and after-extracting with ether, drying and elimination the solvent under reduced pressure, the residue was chromatographed on silica (eluant: $CHCl_2$ with 10% ethyl acetate then 8% methanol) to obtain 2.173 g of the expected product.

EXAMPLE 114

Internal salt of (6R-(3-(E)-6α,7β-[(Z)] 1-(3-(7-(((2-amino-4-thiazolyl)-(carboxy-(2-chloro-3,4-dihydroxy)-5-methoxy-phenyl)-methoxy)-imino)-acetamido)-2-carboxy-8-oxo-5-thia-1-azabicyclo[4,2,0]oct-2-en-3-yl)-2-propenyl-4-(2-(2-methyl-5-nitro-1H-imidazol-1-yl)-ethyl-pyridinium Using the procedure of Stages A and B of Example 68, 735 mg of the 2-chloro-5-methoxy iodated derivative above and 117 mg of 4-(2-(2-methyl-5-nitro-(1H)-imidazol-1-yl)-ethyl)-pyridine were reacted to obtain 768 mg of intermediate quaternary salt, 758 mg of which were reacted with 7.6 ml of trifluoroacetic acid with 10% anisole to obtain 503 mg of the expected product.

NMR spectrum: DMSO 300 MHz. 2.34 (s): $CH_3$ 2-methylimidazole; 338 (t): Φ—$\underline{CH}_2$—$CH_2$; 3.59 (m): the $CH_2S$'s; 3.75 (m): $CH_3$—O—Φ; 4.64: $CH_2$—C$\underline{H}_2$-imidazole; 5.21 (d, resolved): $H_6$; 5.36 (dt): $CH_2$—$N^{\oplus}$; 5.83 (m): $H_7$; 5.83 (s)–5.85: O—$\underline{CH}$—CO; 6.27 (m): CH=$\underline{CH}$—$CH_2$; 6.61 (s): chlorophenyl; 6.8 (s)–6.83: $H_5$ thiazole; 8.06 (d)–8.98 (d): pyridine; 8.08 (s): CH imidazole.

EXAMPLE 115

Internal salt of (6R-(3-(E)-6α,7β-[(Z)] 1-(3-(7-(((2-amino-4-thiazolyl)-(carboxy-(2-chloro-3,4-dihydroxy)-5-methoxyphenyl)-methoxy)-imino)-acetamido)-2-carboxy-8-oxo-5-thia-1-azabicyclo[4,2,0]oct-2-en-3-yl)-2-propenyl)-4-(3-(1-methyl-pyridinium-4-yl)-propyl)-pyridinium Using the procedure of Stages A and B of Example 68, 200 mg of the 2-chloro-5-methoxy iodated derivative above and 46 mg of 4-(3-(1-methyl pyridini-4-yl) pyridine were reacted to obtain 128 mg of intermediate quaternary salt, 120 mg of which were reacted with 1.2 ml of trifluoroacetic acid with 10% anisole to obtain 77 mg of the expected product.

NMR spectrum: DMSO 300 MHz. 2.08 (m)–2.94 (m): propyl pyridine; 3.5 (m): the $CH_2S$'s; 3.73 (s)–3.74 (s): $CH_3$—O—Φ; 4.29 (s): 1-$CH_3$-pyridine; 5.2 (d, resolved): $H_6$; 5.35 (d): $CH_2$—$N^{\oplus}$; 5.81 (m): $H_7$; 5.82 (s)–5.84 (s): O—$\underline{CH}$—CO; 6.3 (m): CH=$\underline{CH}$—$CH_2$; 8.0 (d)–8.06 (dt) –8.88 (d)–8.95 (d): pyridine.

Preparation of 4-(3-(1-methylpyridin-4-yl)-propyl)-pyridine 378 mg of trimethylene bipyridine were dissolved in 3.8 ml of methylene chloride and then 118 µl of methyl iodide were added. The mixture was stirred for 2 hours at ambient temperature, followed by filtering and evaporating the solvent under reduced pressure. The residue was chromatographed on silica (eluant: methylene chloride-methanol 92-8) to obtain 170 mg of the expected product.

EXAMPLE 116

Internal salt of (6R-(3-(E)-6α,7β-[(Z)] 1-(3-(7-(((2-amino-4-thiazolyl)-(carboxy-(-4,5-dihydroxy)-3-fluorophenyl)-methoxy)-imino)-acetamido)-2-carboxy-8-oxo-5-thia-1-azabicyclo[4,2,0]oct-2-en-3-yl)-2-propenyl)-imidazo (1,2-a)-pyridinium Using the procedure of Stages H and I of Example 3, 700 mg of the iodated derivative of Stage G of Example 3 and 254 ml of imidazo (1,2-a) pyridine were reacted to obtain 713.5 mg of intermediate quaternary salt, 703 mg of which were reacted with 7 ml of trifluoroacetic acid with 10% anisole to obtain 364 mg of the expected product.

NMR spectrum: DMSO 300 MHz. 3.69 (m): the $CH_2S$'s; 5.15 (m): $H_6$; 5.29 (masked): $CH_2$—$N^{\oplus}$; 5.77 (m): $H_7$; 5.53 (d, resolved): O—$\underline{CH}$—CO; 6.24 (m): $\underline{CH}$=CH—$CH_2$; 6.73 to 6.76 3H (s): $H_5$ thiazole and fluorophenyl; 6.88 (d, resolved): CH=$\underline{CH}$—$CH_2$; 7.05 (t)–8.05 (t)–8.18 (d)–8.95 (d)–8.28 (m)–8.43 (sl): imidazopyridine.

EXAMPLE 117

Internal salt of (6R-(3-(E)-6α,7β-[(Z)] 1-(3-(7-(((2-amino-4-thiazolyl)-(carboxy-(4,5-dihydroxy)-3-fluorophenyl)-methoxy)-imino)-acetamido)-2-carboxy-8-oxo-5-thia-1-azabicyclo[4,2,0]oct-2-en-3-yl)-2-propenyl)-6,7-dihydro-5H-pyrindinium Using the procedure of Stages H and I of Example 3, 700 mg of the product of Stage G of Example 3 and 293 ml of cyclopentyl (b) pyridine were reacted to obtain 668.4 mg of intermediate quaternary salt, 657 mg of which were reacted with 7 ml of trifluoroacetic acid with 10 anisole to obtain 369 mg of the expected product.

NMR spectrum: DMSO 300 MHz. 2.23 (m)–3.14 (m)–3.36 (m): indane; 3.53 (dl)–3.74 (dl): the $CH_2S$'s; 5.16 (resolved): $H_6$; 5.3 to 5.35: $CH_2$—$N^{\oplus}$ and O—$\underline{CH}$—CO; 5.76 (m): $H_7$; 6.22 (m): $\underline{CH}$=CH—$CH_2$; 6.73 to 6.80: $H_5$ thiazole and fluorophenyl; 6.87 (d,l): CH=$\underline{CH}$—$CH_2$; 7.91 (dd)–8.42 (d)–8.95 (d): pyridine.

EXAMPLE 118

Internal salt of (6R-(3-(E)-6α,7β-[(Z)] 1-(3-(7-(((2-amino-4-thiazolyl)-(carboxy-(2-chloro-4,5-dihydroxyphenylmethoxy)-imino)-acetamido)-2-carboxy-8-oxo-5-thia-1-azabicyclo[4,2,0]oct-2-en-3-yl)-2-propenyl)-imidazo (1,2-a)-pyridinium Using the procedure of Stages A and B of Example 68, 685 mg of the iodated derivative obtained below and 246 ml of imidazo (1,2-a) pyridine were reacted to obtain 541 mg of intermediate quaternary salt, 657 mg of which were reacted with 5 ml of trifluoroacetic acid with 10% anisole to obtain 304 mg of the expected product.

NMR spectrum: DMSO 300 MHz. 3.69 (m): the CH$_2$S's; 5.13 (d, resolved): H$_6$; 5.21 (s): O—C$\underline{H}$—CO; 5.29 (sl): CH$_2$—N$^\oplus$; 5.75 (m): H$_7$; 6.22 (m): CH=C$\underline{H}$—CH$_2$; 6.75 to 6.92: C$\underline{H}$=CH—CH$_2$, chlorophenyl and H$_5$ thiazole; 8.28 (sl)–8.44 (sl): imidazole; 7.58 (t)–8.06 (t)–8.20 (d)–8.96 (d): pyridine.

Preparation of 4-methoxybenzyl-7β-[[[[1-(2-chloro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z)-3-iodo-1-propenyl]-8-oxo-5-thia-1-azabicyclo[4,2,0]oct-2-en-2-carboxylate.

Stage A 2-chloro-4,5-dihydroxy-benzaldehyde

Using the procedure of Preparation 4, Stage A, 37.3 g of 2-chloro-vaniline were reacted to obtain 32.7 g of expected product is obtained.

Stage B 2-chloro,4,5-bis-[2-methoxyethoxy)-methoxy]-benzaldehyde

Using the procedure of Preparation 4, Stage B, 32.7 g of the product of Stage A and 79 ml of diisopropylethylamine were reacted to obtain 50.7 g of the expected product.

Stage C 2-chloro-4,5-bis-[(2-methoxyethoxy)-methoxy]-styryl-carboxylate

Using the procedure of stage B of Example 40, 50.7 g of the product of Stage B were reacted to obtain 60.2 g of the expected crude product.

Stage D 2-chloro-4,5-bis-[(2-methoxyethoxy)-methoxy]-styrol

Using the procedure of Stage C of Example 40, 60.8 g of the ester of Stage C and 293 ml of a molar solution of diisobutyl-aluminum hydride in hexane were reacted to obtain 18.5 g of the expected product.

Stage E 2-chloro-4,5-bis-[(2-methoxyethoxy)-methoxy]-(1,2-epoxy)-styrol 19 g of vanadylacetylacetonate in solution of 50 ml of methylene chloride were cooled to 0° C. and 3.5 ml of terbutyl hydroperoxide in a toluene solution (3M/l) were added over 30 minutes. The mixture was stirred for 20 minutes at 0° C. and 2.63 g of the product of Stage D in solution in 10 ml of methylene chloride were added. The reaction mixture was stirred for 3 hours at ambient temperature and 30 ml of water were added. The organic phase was separated and the solvent was eliminated under reduced pressure. The residue was chromatographed on silica (eluant: methylene chloride-acetone 8-2) to obtain 21.8 g of the expected product with a Rf=0.35 (CH$_2$Cl$_2$-acetone 8-2).

Stage F diphenylmethyl-[2-chloro-4,5-bis-[(2-methoxyethoxy)-methoxy]-phenyl-chloro-acetate Using the procedure of Stage E of Example 40, 18 g of the epoxide of Stage E above were reacted to obtain 15.67 g of chlorodiol which was oxidized with 30.56 g of sodium periodate and 400 mg of hydrated ruthenium chloride to obtain 13.59 g of acid which was reacted with 6.36 g of diphenyldiazomethane to obtain 18.8 g of the expected product with a Rf=0.3 (CH$_2$Cl$_2$—AcOEt 9-1).

Stage G diphenylmethylaminoxy-[2-chloro-4,5-bis-[(2-methoxy-ethoxy)-methoxy]-phenyl]-acetate Using the procedure of Stage F of Example 40, 18.8 g of the ester of Stage F above 7.33 g of N-hydroxy phthalimide and then 2.36 ml of hydrazine hydrate were reacted to obtain after chromatographing on silica (eluant: methylene chloride-ethyl acetate 6-4), 11.45 g of the expected product with a Rf=0.3 (CH$_2$Cl$_2$—AcOEt 9-1).

Stage H

[[1-[2-chloro-4,5bis-[(2-methoxyethoxy)-methoxy]-phenyl-2-oxo-2-(diphenylmethoxy)-ethyl]-oxy]-imino]-[2-[(triphenyl-methyl)-amino]-thiazol-4-yl] acetic acid Using the procedure of Stage E of Example 1, 11.45 g of the product of Stage G and 9.03 g of oxo-[2-((triphenylmethyl)-amino]-thiazol-4-yl]-acetic acid (described in Belgian Application No. 864828) were reacted to obtain 18.77 g of the expected product with a Rf=0.3 (CH$_2$Cl$_2$—MeOH 6-4).

Stage I 4-methoxybenzyl-7β-[[[[1-[2-chloro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z)-3-chloro-1-propenyl]-8-oxo-5-thia-1-azabicyclo[4,2,0]oct-2-en-2-carboxylate Using the procedure of Stage F of Example 1, the product of Stage H and 8.2 g of 4-methoxybenzyl-7β-amino-3-[(Z)-3-chloro-1-propenyl]-8-oxo-5-thia-1-azabicyclo[4,2,0]oct-2-en-2-carboxylate hydrochloride (EP 0,333,154) were reacted to obtain after chromatography on silica, (eluant: methylene chloride-ethyl acetate (9-1)), 5.34 g of the desired product with a Rf=0.25 (CH$_2$Cl$_2$—AcOEt 9-1).

Stage J 4-methoxybenzyl-7β-[[[[1-[2-chloro-4,5bis-[(2-methoxy-ethoxy)-methoxy]-phenyl]-2-oxo-2-(diphenylmethoxy)-ethyl]-oxy]-imino]-[2-(triphenylmethyl)-amino]-thiazol-4-yl]-acetamido]-3-[(Z)-3-iodo-1-propenyl]-8-oxo-5-thia-1-azabicyclo[4,2,0]oct-2-en-2-carboxylate Using the procedure of Stage G of Example 1, 1.3 g of Stage I were reacted to obtain after chromatography on silica, (eluant: methylene chloride-ethyl acetate (9-1)), 731 mg of the desired product with a Rf=0.1 (CH$_2$Cl$_2$—AcOEt 9-1).

EXAMPLE 119

Internal salt of (6R-(3-(E)-6α,7β-[(Z)] 1-(3-(7-(((2-amino-4-thiazolyl)-(carboxy-(2-chloro-4,5-dihydroxyphenyl)-methoxy)-imino)-acetamido)-2-carboxy-8-oxo-5-thia-1-azabicyclo[4,2,0]oct-2-en-3-yl)-2-propenyl)-6,7-dihydro-5H-pyrindinium Using the procedure of Stages A and B of Example 68, 685 mg of cyclopenta (b) pyridine were reacted to obtain 500 mg of intermediate quaternary salt, 657 mg of which was reacted with 5 ml of trifluoroacetic acid with 10% anisole to obtain 278 mg of the expected product.

NMR spectrum: DMSO 300 MHz. 2.24 (m)–3.14 (t): indane; 3.53 (dl)–3.74 (dl): the CH$_2$S's; 5.13 (d)–5.16 (m): H$_6$; 5.33 (d): CH$_2$—N$^\oplus$; 5.71 (s): O—C<u>H</u>—CO; 5.76 (m): H$_7$; 6.21 (m): CH=C<u>H</u>—CH$_2$; 6.78 (s)–6.80 (s)–6.92 (s): chlorophenyl and H$_5$ thiazole; 6.84 (d, J=16): C<u>H</u>=CH—CH$_2$; 7.91 (dd)–8.43 (d)–8.74 (d): pyridine.

EXAMPLE 120

Internal salt of (6R-(3-(E)-6α,7β-[(Z)] 2-(3-(7-(((2-amino-4-thiazolyl)-(carboxy-(2-chloro-4,5-dihydroxyphenyl)-methoxy)-imino)-acetamido)-2-carboxy-8-oxo-5-thia-1-azabicyclo[4,2,0]oct-2-en-3-yl)-2-propenyl)-isoquinolinium.

Using the procedure of Stages A and B of Example 68, 260 mg of the iodated derivative above and 108 ml of isoquinoline were reacted to obtain 84 mg of intermediate quaternary salt, which was reacted with 2 ml of trifluoroacetic acid with 10% anisole to obtain 39 mg of the expected product.

NMR spectrum: DMSO 300 MHz. 3.45 (m): the CH$_2$S's; 5.14 (d, resolved): H$_6$; 5.57 (d, resolved): CH$_2$—N$^\oplus$; 5.71 (s): O—C<u>H</u>—CO; 5.76 (m): H$_7$; 6.57 (m): CH=C<u>H</u>—CH$_2$; 6.78 (s, resolved): H$_5$ thiazole; 6.92 (d): chlorophenyl; 7.10 (d, resolved): C<u>H</u>=CH—CH$_2$; 8.09 (t)–8.28 (t)–8.31 (d)–8.38 (d)–8.67 (d)–8.74 (dd)–10.06 (sl): isoquinoline.

EXAMPLE 121

Internal salt of (6R-(3-(E)-6α,7β-[(Z)] 1-(3-(7-(((2-amino-4-thiazolyl)-(carboxy-(2-chloro-4,5-dihydroxyphenyl)-methoxy)-imino)-acetamido)-2-carboxy-8-oxo-5-thia-1-azabicyclo[4,2,0]oct-2-en-3-yl)-2-propenyl)-quinolinium.

Using the procedure of Stages A and B of Example 68, 703 mg of the iodated derivative above and 288 ml of quinoline were reacted to obtain 529.5 mg of intermediate quaternary salt, which were reacted with 15 ml of trifluoroacetic acid with 10% anisole to obtain 273 mg of the expected product.

NMR spectrum: DMSO 300 MHz. 3.45 (m): the CH$_2$S's; 5.12 (d, resolved): H$_6$; 5.70 (s): O—C<u>H</u>—CO; 5.70 (m): H$_7$; 5.70 to 5.90: CH$_2$—N$^\oplus$; 6.34 (m): CH=C<u>H</u>—CH$_2$; 6.75 to 6.96: H$_5$ thiazole, chlorophenyl and C<u>H</u>=CH—CH$_2$; 8.06 (m)–8.25 (m)–8.34 (m)–9.34 (d)–9.56 (m): quinoline.

PREPARATION OF EXAMPLE 122 diphenylmethyl-[5-cyano-3,4-bis-[2-methoxy-ethoxy)-methoxy]-thienyl-chloro-acetate.

Stage A 3,4-bis-[2-methoxy-ethoxy)-methoxy]-5-cyano-2-ethoxycarbonyl-thiophene 92 g of 3,4-dihydroxy-5-cyano-2-ethoxycarbonyl-thiophene (described in Japanese Application No. J57116064) and 860 ml of methylene chloride were mixed together under an inert gas atmosphere at 0° C. and then 153 ml of diisopropylethylamine, then 102 ml of methoxy-ethoxymethyl chloride were added slowly. After 45 minutes, the reaction mixture was washed with a 0.1N solution hydrochloric acid, then with a 1M solution of sodium bicarbonate and finally with water saturated with sodium chloride. After drying and evaporating the solvent, 161 g of the expected product were obtained which was used as in the following stage:

NMR spectrum (CDCl$_3$, 300 MHz, ppm): 1.36 (t), 4.34 (q) CO$_2$Et; 3.36 (s), 3.38 (s) 2-OCH$_3$; 3.50 to 3.63 (m) (4H), 3.94 (m) (4H) O—(CH$_2$)$_2$—O; 5.36 (s), 5.42 (s)

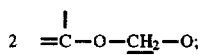

IR Spectrum (CHCl$_3$) Absorptions at 2225 cm$^{-1}$ (conjugated C=N); 1720 cm$^{-1}$ (C=O); 1554, 1490 cm$^{-1}$ (conjugated system).

Stage B 3,4-bis-[2-methoxy-ethoxy)-methoxy]-5-cyano-2-hydroxymethyl-thiophene

A mixture of 161 g of the product of Stage A and 1 liter of tetrahydrofuran was stirred under an inert gas atmosphere and 262 g of lithium triterbutoxy alumino hydride were added at 5° C. over 5 hours. The temperature was allowed to rise and the reaction mixture was stirred for 36 hours. The suspension was concentrated and poured into a mixture of 1.2 liters of a saturated aqueous solution of ammonium chloride, 1.5 liters of water and 0.5 liter of ethyl acetate. The mixture was stirred for 18 hours, followed by filtering. The filtrate was washed with a saturated aqueous solution of sodium chloride, dried and the solvent was evaporated off to obtain 108 g of the expected product which was used as is for the following stage.

Stage C 3,4-bis-[2-methoxy-ethoxy)-methoxy]-5-cyano-2-formyl-thiophene 450 ml of methylene chloride were added to the 108 g of the alcohol of Stage B and after the reaction mixture was cooled to 5° C., then 497 g of manganese dioxide were added slowly. After total disappearance of the starting product, filtration was carried out and the filter was rinsed with ethyl acetate. The filtrate was concentrated to dryness and the residue was chromatographed on silica, eluting with methylene chloride-ethyl acetate mixtures 98/2, 97/3, 96/4 to obtain 67 g of expected product.

NMR spectrum (CDCl$_3$, 300 MHz, ppm): 3.35 (s) (3H), 3.38 (s) (3H) the O—CH$_3$'s; 3.58 (m) (4H), 3.93 (m) (4H) the O—(CH$_2$)$_2$—O's; 5.37 (s) (2H), 5.44 (s) (2H) the O—CH$_2$—O's; 10.04 (s) (1H) CHO IR Spectrum (CHCl$_3$) Absorptions at 2220 cm$^{-1}$ (C=N); 1670 cm$^{-1}$ (C=O, conjugated aldehyde); 1582, 1550, 1485 cm$^{-1}$ (heterocycle).

Stage D diphenylmethyl-[5-cyano-3,4-bis[2(2-methoxyethoxy)-methoxy]-thienyl-chloroacetate 63.6 g of the product of Stage C, 1 liter of toluene, 15.8 g of malodinitrile and a 4 Å molecular sieve 1.8 ml of piperidine were added. The mixture was stirred for 40 minutes and 74 ml of terbutylhydroperoxide in a 3M solution in toluene were added to the reaction mixture over 5 minutes without exceeding 11° C. After 20 minutes, the mixture was filtered, the filter was rinsed with ethyl acetate and the solvent was evaporated to obtain 82 g of an oil of a dicyanoepoxide. The product was taken up in 1.8 liters of tetranhydrofuran and 240 ml of 1N hydrochloric acid were added to the solution over about 7 minutes followed by stirring at ambient temperature for 1 hour.

870 ml of a solution of 0.38 mol/l of diphenyldiazomethane in ethyl ether were added to the reaction mixture over about 12 minutes which was then stirred for 2 hours at ambient temperature. Extraction with ethyl ether was followed by washing with 1N sodium hydroxide then with water saturated with sodium chloride. The organic phase was dried and the solvent was evaporated. The residue was chromatographed on silica eluting with cyclohexane-ethyl acetate mixtures (4/1), (3/1) then (2/1) to obtain 68 g of the expected product.

NMR spectrum (CDCl$_3$, 250 MHz, ppm): 3.31 (s) (3H), 3.36 (s) (3H) the O—CH$_3$'s; 3.48 (m), 3.58 (m), 3.82 (m), 3.92 (m) (8H) the O—(CH$_2$)$_2$—O's; 5.17 (syst. AB), 5.41 (s) (2H) the O—CH$_2$—O's; 5.98 (s) (1H)

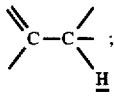

6.91 (s) (1H) CO$_2$—CH—Φ$_2$; 7.34 (m) (10H) the phenyls.

IR spectrum (CHCl$_3$) Absorptions at 2221 cm$^{-1}$ (C≡N); 1746 cm$^{-1}$ (C=O), 1603, 1589, 1496 cm$^{-1}$ (aromatic-heteroatom).

EXAMPLE 122

Internal salt of (6R-[(3-(E)-6α,7β-[(Z)]]-1-[3-[7-[[2-amino-4-thiazolyl)-[carboxy-5-cyano-3,4-dihydroxy-2-thienyl)-methoxy]-imino]-acetamido)-2-carboxy-8-oxo-5-thia-1-azabicyclo[4.2.0]oct-2-en-3-yl)-2-propenyl)-quinolinium.

Stage A diphenylmethyl-[5-cyano-3,4bis-[(2-methoxyethoxy) -methoxy]-thienyl]-phthalimidoxy-acetate 13.1 g of N-hydroxy phthalimide, 6.55 g of sodium bicarbonate and 400 ml of water were mixed together and after the mixture was stirred for 2 hours, 25 g of diphenylmethyl [5-cyano-3,4bis-[(2-methoxy-ethoxy)-methoxy]-thienyl-chloroacetate in 400 ml of dichloroethane were added. 0.89 g of triethyl benzylammonium chloride were added and the mixture was stirred for 13 hours at ambient temperature, followed by extraction with dichloroethane. The organic phase was washed with water with sodium chloride added to it, dried and the solvent was evaporated. The residue was purified by chromatography on silica eluting with a cyclohexane-ethyl acetate mixture (6-4), then (1-1) to obtain 15.4 g of the expected product.

NMR spectrum (CDCl$_3$, 300 MHz, ppm): 3.28 (s) (3H), 3.36 (s) (3H) —O—CH$_3$; 3.46 (m) (2H), 3.58 (m) (2H), 3.78 to 3.95 (m) (4H) —O—(CH$_2$)$_2$—O; 5.21 (AB) (2H), 5.37 (AB) (2H) O—CH$_2$—O; 6.26 (s) (1H)

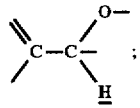

6.96 (s) (1H) —CO$_2$—CH—Φ$_2$; 7.2 to 7.4 (m) (10H), 7.75 (m) (4H) phthalimide H.

IR Spectrum (CHCl$_3$) Absorptions at 2222 cm$^{-1}$: —C≡N; 1796 and 1740 cm$^{-1}$ C=O, 1610–1580 cm$^{-1}$ and 1496 cm$^{-1}$: conjugated system+aromatic.

Stage B diphenylmethylaminoxy-[5-cyano-3,4bis-[(2-methoxyethoxy)-methoxy]-thienyl]-acetate 5.06 g of the product of Stage A were dissolved under a nitrogen atmosphere in 72 ml of methanol and the mixture was cooled to −11° C. Then, 0.35 ml of hydrazine hydrate were added and the same temperature is maintained for 15 minutes after which, another 0.02 ml of hydrazine hydrate were added. After 30 minutes, another 0.04 ml were added to the reaction mixture and stirred for 45 minutes to obtain the expected product in solution, which is used as is for the following stage.

Stage C

[[[2-[5-cyano-3 4-bis-[(2-methoxy-ethoxy)-methoxy]-thienyl]-2-oxo-2-(diphenylmethoxy)-ethyl-oxy-imino]-[2-triphenylmethyl)-amino]-thiazol-4-yl]-acetic acid 3 g of oxo-[2-triphenylmethyl)-amino]-thiazol-4-yl]-acetic acid (described in Belgian Patent Application No. 864828) were added to the solution of Stage B and the temperature was allowed to rise. 10 ml of methylene chloride were added then the crystals formed were separated. The filtrate was concentrated to dryness and the residue was chromatographed on silica eluting with methylene chloride-methanol mixture (95-5) to obtain a total of 5.5 g of the crude expected product.

Stage D 4-methoxybenzyl-7β-[[[[2-[5-cyano-3,4bis-[2-methoxy-ethoxy)-methoxy]-thienyl]-2-oxo-2-(diphenylmethoxy)-ethyl]-oxy]-imino]-[2-(triphenylmethyl)-amino]-thiazol-4-yl]-acetamido]-3-[(Z)-3-chloro-1-propenyl]-8-oxo-5-thia-1-azabicyclo[4.2.0]oct-2-en-2-carboxylate 2.44 g of 4-methoxybenzyl-7β-amino-3-[(Z)-3-chloro-1-propenyl]-8-oxo-5-thia-1-azabicyclo[4.2.0]oct-2-en-2-carboxylate hydrochloride (described in European Patent Application No. 0.333,154), 5.5 g of the product of Stage C and 60 ml of methylene chloride were mixed together at 0° C. and then, 1.75 g of 1-(3-dimethylamino-propyl)-3-ethyl-carbodiimide (EDC) were added. The mixture was stirred for 45 minutes while allowing the temperature to rise. The reaction medium was treated with 100 ml of 0.5M potassium hydrogenophosphate and then washed with a sodium chloride solution. After drying, the solvent was evaporated to obtain 8.5 g of the expected product with a Rf=0.42 [eluant: methylene chloride-ethyl acetate (9-1)] which can be purified by chromatography on silica eluting with a cyclohexane-ethyl acetate mixture (1-1).

NMR spectrum (CDCl$_3$, 300 MHz, ppm): 3.20 3.34 —O—CH$_3$, S—CH$_2$—; 3.43 (m), 3.59 (m), 3.92 (m), 3.45 3.90, 4.14 (m) (1H) —O—CH$_2$—CH$_2$—O, —CH—CH$_2$—X 5.02 (m) H$_6$; 5.86 (m) H$_7$; 5.40 to 5.50 o—CH—OCO, O—CH$_2$—O; 5.78 (m) CH$_2$—CH=CH—(ΔZ); 6.20 to 6.35 CH$_2$—CH=CH—(ΔZ); 6.77 (s/d) H$_5$ thiazole; 6.91 (m) (4H) Aromatics, —CO$_2$—CH—Φ, NH—CO—

IR Spectrum (CHCl$_3$) Absorptions at 3404 cm$^{-1}$: =C—NH—; 2221 cm$^{-1}$: —C≡N; 1791, 1730 and 1684 cm$^{-1}$: β-lactame; 1613, 1587, 1526, 1517 and 1496 cm$^{-1}$: aromatic C=C, heteroatom and amide II.

Stage E 4-methoxybenzyl-7β-[[[[2-[5-cyano-3,4bis-[2-methoxy-ethoxy)-methoxy]-thienyl]-2-oxo-2-(diphenylmethoxy)-ethyl]-oxy]-imino]-[2-(triphenylmethyl)-amino]-thiazol-4-yl]-acetamido]-3-[(Z)-3-iodo-1-propenyl]-8-oxo-5-thia-1-azabicyclo [4.2.0]oct-2-en-2-carboxylate 1.5 g of the product after chromatography in Stage D, 20 ml of acetone and 0.5 g of sodium iodide were stirred for 70 minutes at ambient temperature in the presence of 30 mg of iodine. After elimination of the solvent, the residue was taken up in methylene chloride and the organic phase was washed with a sodium thiosulfate solution then with a sodium chloride solution and dried. The solvent was eliminated and the residue was chromatographed on silica eluting with a cyclohexane-ethyl acetate mixture (1-1) to obtain 0.9 g of the expected iodated product.

Stage F

1-[3-[7β-[[[[[2-[5-cyano-3,4-bis-[(2-methoxy-ethoxy)-methoxy]-thienyl]-2-oxo-2-(diphenylmethoxy)-ethyl]-oxy]-imino]-[2-(triphenylmethyl)-amino]-thiazol-4-yl]-acetamido]-2-[(4-methoxy benzyloxy)-carbonyl]-8-oxo-5-thia-1-azabicyclo[4.2.0]oct-2-en-3-yl]-2-propenyl]-quinolinium iodide 0.450 g of the product of Stage E were dissolved in 5 ml of methylene chloride and 185 µl of quinoline were added with stirring and the solvent was evaporated. The mixture was stirred for 80 minutes, followed by taking up in ether, crystallizing, separating and chromatographing on silica eluting with a methylene chloride-methanol mixture (95-5) to obtain 0.260 g of the expected product with a Rf=0.37 [eluant: methylene chloride-methanol (90-10)].

Stage G

Internal salt of [6R-[3-(E)-6α,7β-(Z)]]-1-[3-[7-[[2-amino-4-thiazolyl)-[carboxy-(5-cyano-3,4-dihydroxy-2-thienyl)-methoxy]-imino]-acetamido]-2-carboxy-8-oxo-5-thia-1-azabicyclo[4.2.0]oct-2-en-3-yl]-2-propenyl]-quinolinium A mixture of 0.255 g of the product of Stage F and 3 ml of trifluoroacetic acid containing 10% anisole was stirred at ambient temperature for 2 hours and 45 minutes. After adding isopropyl ether, filtering, washing and drying for 16 hours under reduced pressure at ambient temperature, 0.118 g of the desired internal salt were isolated.

NMR analysis of the proton (DMSO 300 MHz in ppm) R/S structure; Δ3 syn; ΔE/ΔZ mixture ~70/30. 5.18 (m) and 5.30 (m) (1H): H$_6$; 5.65/5.90 (<4H):

H$_7$, O—CH—[thienyl ring with S]

=CH—$\underline{CH}_2$—N$^+$ and =CH—CH$_2$ (ΔZ) 6.39 (m) (0.7H): C=$\underline{CH}$—CH$_2$ (E); 6.61 (d, J=11) (0.3H): C=$\underline{CH}$—CH$_2$ (Z); 6.70 (s) and 6.74 (s) (1H): H$_5$ thiazole; 6.95 (d, J=15.5): =C—$\underline{CH}$—CH (ΔE); 8.07 (m) (1H), 8.29 (m) (2H), 8.51 (m) (2H), 9.34 (m) (1H) and 9.57 (m) (1H): H of the quinolinium; 11.6 (l): =C—NH—CH.

IR Spectrum (nujol) General absorption OH/NH, 2215 cm$^{-1}$. Conjugated C=N, 1778 cm$^{-1}$, β-lactame, 1672 cm$^{-1}$; other C=O.

PREPARATION OF EXAMPLE 123 diphenylmethyl-α-bromo-[5-(terbutoxy-carbonyl)-amino]-3-(1,2,4-thiadiazole)-acetate Stage A diphenylmethyl-[5-(terbutoxy-carbonyl)-amino]-3-(1,2,4-thiadiazole)-acetate 7.25 g of [5-(terbutoxycarbonyl)-amino-3-(1,2,4-thiadiazole acetic acid were mixed at ambient temperature with 90 ml of methylene chloride and 49 ml of methanol. The solution was cooled to 0° C. and 93.3 ml of diphenyl-diazomethane in a 0.3M solution in ether were added dropwise. The reaction medium was allowed to return to ambient temperature over 2 hours 30 minutes and the solvents were evaporated under reduced pressure to obtain 13.66 g of crude product which was chromatographed on silica (eluant: methylene chloride-acetonitrile 98-2) to obtain 8.38 g of the expected product.

NMR Spectrum (CDCl$_3$ 300 MHz in ppm) 1.52 (s) terbutyl 4.06 (s) CH$_2$—CO$_2$ 6.92 (m) CH$_2$—$\underline{CH}$—Φ$_2$ 7.26 (s) phényls 10.20 (sl) NH Stage B diphenylmethyl-α-bromo-[5-(terbutoxycarbonyl) amino]-3-(1,2,4-thiadiazole)-acetate 146 mg of bromine (47 µl) were added to 390 mg of the ester of Stage A in solution in 6 ml of acetic acid and the mixture was stirred for 2 hours 30 minutes at ambient temperature. The solvent was evaporated and the residue was taken up in methylene chloride, washed with an aqueous solution of sodium bicarbonate at 10%, dried and the solvents were evaporated to obtain 390 mg of the crude product which was chromatographed on silica (eluant: methylene chloride) to obtain 190 mg of the expected product.

NMR Spectrum (CDCl$_3$ 250 MHz in ppm) 1.55 terbutyl 6.95 phényls 7.2 to 7.4 —$\underline{CH}$—Br 9.23 NH

EXAMPLE 123

Internal salt of (6R-[(3-(E)-6α,7β-[(Z)]]-1-[3-[7-[[2-amino-4-thiazolyl)-[carboxy-(5-amino-1,2,4-thiadiazol-3-yl)-methoxy]-imino]-acetamido)-2-carboxy-8-oxo-5-thia-1-azabicyclo[4.2.0]oct-2-en-3-yl)-2-propenyl]-quinolinium Stage A diphenylmethyl-α-phthalimidoxy-[5-(terbutoxy-carbonyl)-amino]-3-(1,2,4-thiadiazole)-acetate 130 mg of sodium bicarbonate and 252 mg of hydroxy-phthalimide in 3 ml of water were stirred for one hour under an inert atmosphere and then 390 mg of the bromo ester of Preparation above then 17.6 mg of triethylbenzylammonium chloride were added dropwise. Vigorous stirring was carried out for 20 hours. 10 to 20 ml of methylene chloride were added, followed by decanting, extracting with methylene chloride, drying and evaporating the solvent to obtain 426 mg of crude product. The latter was purified by chromatography on silica (eluant: methylene chloride-ethyl acetate 98-2) to obtain 169 mg of the expected product.

NMR Spectrum (CDCl$_3$ 300 MHz in ppm) 1.56 (s) terbutyl 5.98 (s) —CH—COO 7.07 (s) CH—Φ$_2$ 7.15 to 7.35 phényl 7.72 (m)–7.76 (m) phthalimide 8.53 (sl) —NH—

Stage B diphenylmethyl-α-aminoxy-[5-terbutoxycarbonyl)-amino]-3-(1,2,4-thiadiazole)-acetate 58 mg of the phthalimido ester of Stage A in 1 ml of methylene chloride were cooled to 0° C. under an inert atmosphere and then 5.5 µl of hydrazine hydrate were added. The mixture was stirred for 30 minutes, followed by filtration. The precipitate was rinsed with methylene chloride and the solvent was evaporated under reduced pressure at ambient temperature to obtain 58 mg of crude product which was chromatographed on silica (eluant: cyclohexane-ethyl acetate 7-3) to obtain 26 mg of the expected product.

NMR Spectrum (CDCl₃ 300 MHz in ppm) 1.55 (sl) terbutyl 6.22 (s) —CH—COO 6.90 to 7.30 phényls 6.96 or 7.10 O—CH—Φ3.10 mobile H's Stage C 1-[3-[7-[[2-(triphenylmethyl)-amino]-4-thiazolyl]-(2-diphenylmethoxy)-carbonyl]-[5-(terbutoxycarbonyl)-amino]-(1,2,4-thiadiazol-3-yl)-methoxy]-imino]-acetamido]-2-[(4-methoxy)-benzyloxycarbonyl]-8-oxo-5-thia-1-azabicyclo-[4.2.0]oct-2-en-3-yl]-2-propenyl]-quinolinium iodide 65.4 mg of 1-[3-[7β-[oxo-(2-(triphenylmethyl)-amino]-4-thiazolyl]-acetamido]-2-[(4-methoxy)-benzyloxycarbonyl]-8-oxo-5-thia-1-azabicyclo-[4.2.0]oct-2-en-3-yl]-2-propenyl]-quinolinium iodide, 1 ml of methanol and 0.3 ml of methylene chloride were mixed together under an inert atmosphere chloride were mixed together under an inert atmosphere at ambient temperature and 36 mg of the aminoxy derivative of Stage B in 0.5 ml of methylene chloride were added. Then 12.5 mg of toluene sulfonic acid were added and the mixture was stirred for 20 hours at ambient temperature. The solvent was evaporated under reduced pressure at ambient temperature and the residue was taken up in ether. After stirring for 15 minutes, the precipitate was filtered and dried under reduced pressure for one hour to obtain 83 mg of crude product which was used as is for the rest of the synthesis.

Stage D

Internal salt of (6R-[(3-(E)-6α,7β-[(Z)]]-1-[3-[7-[[(2-amino-4-thiazolyl)-[carboxy-(5-amino-1,2,4-thiadiazol-3-yl)-methoxy]-imino]-acetamido)-2-carboxy-8-oxo-5-thia-1-azabicyclo [4.2.0]oct-2-en-3-yl)-2-propenyl]-quinolinium 83 mg of the crude product of Stage C in 0.8 ml of a solution of trifluoroacetic acid with 10% anisole were stirred for 3 hours at ambient temperature. Filtration was carried out, followed by rinsing with trifluoroacetic acid. Then, about 2 ml of ethyl ether were added and the mixture was stirred for 30 minutes. After filtering and rinsing with ether, the precipitate was dried under reduced pressure for 16 hours at ambient temperature to obtain 34 mg of the expected crude product.

NMR Spectrum (CDCl₃ 300 MHz in ppm) 5.26 (d) H₆ 5.48 (d,d) after exchange 6.53 (d) H₇ 6.09 (dt) ΔE CH=CH—CH₂ 6.53 CH=CH—CH₂ 6.75 (s) H₅ of the thiazole 9.73 (d, mobile) —NH—

In addition to the products described above in the Examples, the following products constitute products which can be obtained by the methods of the invention:

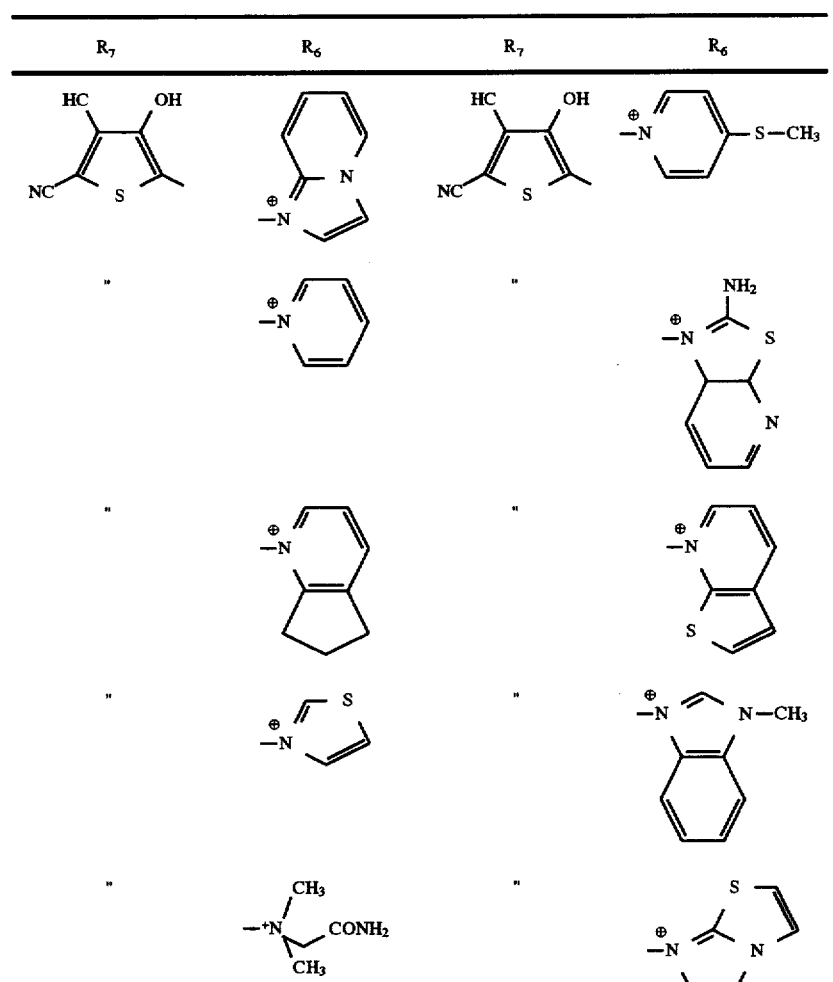

-continued
| R₇ | R₆ | R₇ | R₆ |
|---|---|---|---|
| " | 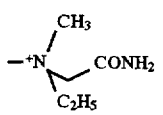 | " | 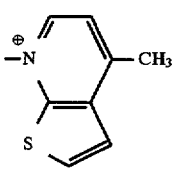 |
| | | " | 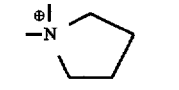 |
| | | " | 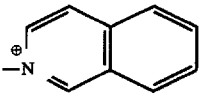 |
| | | " | 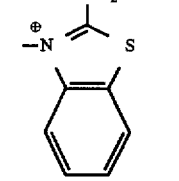 |
| 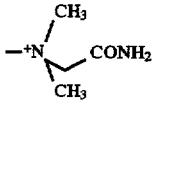 | 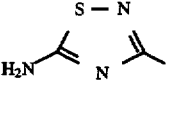 | 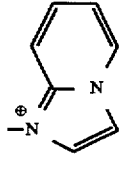 | 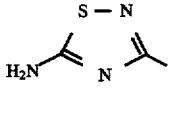 |
| " | 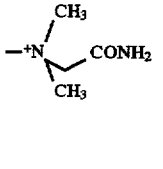 | " | 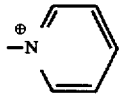 |
| " | 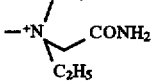 | " | 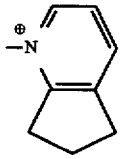 |
| " | 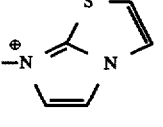 | " | 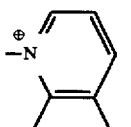 |
| " | 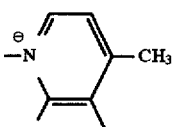 | " | 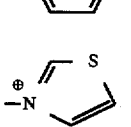 |
| " | 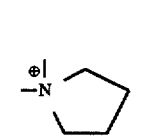 | " | 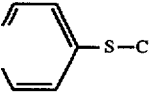 |

| R7 | R6 | R7 | R6 |
|---|---|---|---|

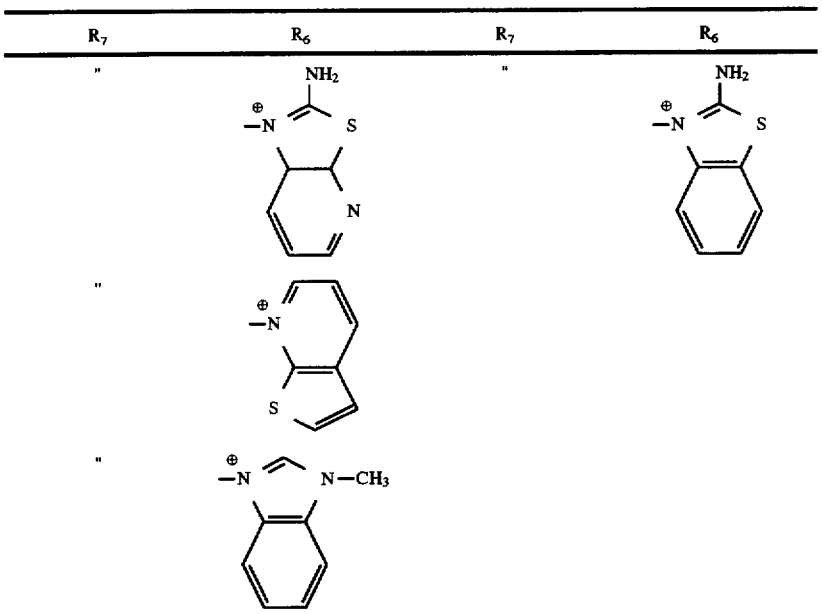

EXAMPLE 124

The following preparations for injections were made containing 500 mg of the product of Example 2 or 121 and sufficient sterile aqueous excipient for 5 ml

PHARMACOLOGICAL STUDY

In vitro activity, method of dilutions in liquid medium

A series of tubes was prepared in which an equal amount of sterile nutritional medium was distributed and increasing amounts of the test product was distributed into each tube. Then, each tube was seeded with a bacterial strain and after incubation in an oven for twenty four hours at 37° C. The growth inhibition was evaluated by transillumination which allowed the minimal inhibiting concentrations (M.I.C.) to be determined, expressed in ug/ml (TABLE I).

In vitro activity, method of dilutions in solid medium

A series of dishes was prepared in which an equal amount of sterile nutritional medium was distributed containing increasing amounts of the test product. Then, each dish was seeded with several bacteria strains and after incubation in an oven for 24 hours at 37° C., the growth inhibition was evaluated by the absence of any bacterial development, which allowed the minimal inhibiting concentrations (M.I.C.) to be determined expressed in micrograms/ml. The results were expressed in M.I.C. 90 which is the minimum concentration of antibiotic allowing the growth of the strains studied to be inhibited by 90° (TABLE II).

TABLE II

| | $MIC_{90}$ | | | |
|---|---|---|---|---|
| Product of example | oracillin-sensitive penicillin-resistants Staphylococci aureus (20 strains) | Enterobacteria producing cephalosporinases (20 strains) | Enterobacteria producting β lactamase with enlarged spectrum (16 strains) | Pseudomonas Aeruginosa (39 strains) |
| 39 | 2,5 | 0,3 | 2,5 | 0,08 |
| 43 | 0,3 | 2,5 | 1,2 | 1,2 |
| 27 | 5 | 0,3 | 10 | 0,08 |

Activity in vitro, method of dilutions in solid medium

A series of dishes were prepared in which an equal quantity of sterile nutritive medium was distributed containing increasing quantities of the product to be studied and then each dish was seeded with several bacterial strain. After incubation for 24 hours in an oven at 37° C., the growth inhibition was evaluated by the absence of any bacterial development which allowed the minimum inhibiting concentrations (MIC) expressed in micrograms/cm$^3$ to be determined. The results are expressed in $MIC_{50}$ and $MIC_{90}$ which is the minimum concentration of antibiotic inhibiting the growth of the strains studied by 50 and 90%. The following results were obtained:

| Strains | < > | MIC₅₀ | MIC₉₀ |
|---|---|---|---|
| Penicillin-sensitive *Staphylococcus aureus* (14 strains) | 0.04–0.15 | 0.15 | 0.15 |
| Penicillin-resistant *Staphylococcus aureus* (21 strains) | 0.08–1.2 | 0.15 | 0.15 |
| Streptococci group D (10 strains) | 2.5–20 | 2.5 | 5 |
| Enterobacteria producing β-lactamases | < > | MIC₅₀ | MIC₉₀ |
| Chromosomal Plasmidic | 0.15–5 | 1.2 | 5 |
| SHV-2 (13 strains) | 0.08–1.2 | 0.3 | 1.2 |
| SHV-4 (29 strains) | 0.6–20 | 2.5 | 5 |
| TEM-3 (35 strains) | 0.15–20 | 1.2 | 2.5 |

Various modifications of the products and methods of the invention may be made without departing from the spirit or scope thereof. It is to be understood that the invention is intended to be limited only as defined in the appended claims.

What we claim is:

1. A compound having a structural formula selected from the group consisting of

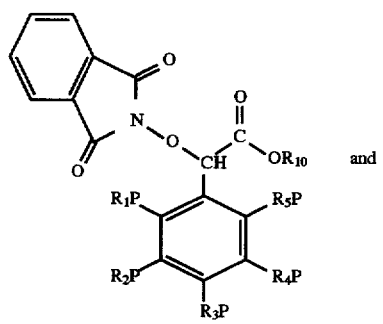  V

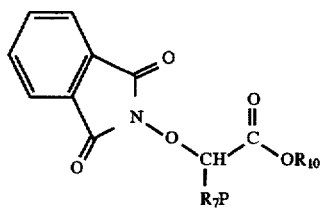  III' wherein $R_{1p}$, $R_{2p}$, $R_{3p}$ and $R_{5p}$ are individually selected from the group consisting of hydrogen, halogen, hydroxy, protected hydroxy, alkyl of 1 to 4 carbon atoms optionally substituted with at least one halogen, alkoxy of 1 to 4 carbon atoms alkylthio of 1 to 4 carbon atoms, —NO₂, —CN, —NH₂, protected amino, mono- and dialkylamino of 1 to 4 carbon toms, carbamoyl, (alkylamino) carbonyl of 2 to 5 carbon atoms, (dialkylamino) carbonyl of 3 to 9 carbon atoms, carboxy, alkoxycarbonyl of 2 to 5 carbon atoms, acyloxy of 1 to 8 carbon atoms and

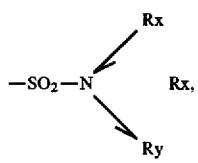

and Ry are individually hydrogen or alkyl of 1 to 4 carbon atoms, $R_{4p}$ is selected from the group consisting of —OH, protected hydroxy and acyloxy of 1 to 8 carbon atoms, with the proviso that when $R_{3p}$ is —OH or acyloxy of 1 to 8 carbon atoms, at least one of $R_{1p}$, $R_{2p}$ and $R_{5p}$ is other than hydrogen, wherein $R_{10}$ is the remainder of an easily cleavable ester and $R_{7p}$ is K or L, in which the hydroxy or amino are protected

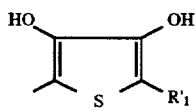  K

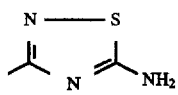  L wherein $R'_1$ is selected from the group consisting of alkyl of 1 to 4 carbon atoms, —CN, carboxy and alkoxy carbonyl of 1 to 4 alkoxy carbon atoms.

* * * * *